(12) United States Patent
Boojamra et al.

(10) Patent No.: US 7,842,672 B2
(45) Date of Patent: Nov. 30, 2010

(54) PHOSPHONATE INHIBITORS OF HCV

(75) Inventors: Constantine G. Boojamra, San Francisco, CA (US); James M. Chen, San Ramon, CA (US); Alan X. Huang, San Mateo, CA (US); Choung U. Kim, San Carlos, CA (US); Kuei-Ying Lin, Sunnyvale, CA (US); Richard L. Mackman, Millbrae, CA (US); David A. Oare, Belmont, CA (US); Jason K. Perry, San Francisco, CA (US); Oliver L. Saunders, San Mateo, CA (US); Sundaramoorthi Swaminathan, Burlingame, CA (US); Lijun Zhang, Palo Alto, CA (US)

(73) Assignee: Gilead Sciences, Inc., Foster City, CA (US)

( * ) Notice: Subject to any disclaimer, the term of this patent is extended or adjusted under 35 U.S.C. 154(b) by 639 days.

(21) Appl. No.: 11/825,395

(22) Filed: Jul. 6, 2007

(65) Prior Publication Data

US 2008/0107628 A1 May 8, 2008

Related U.S. Application Data

(60) Provisional application No. 60/819,489, filed on Jul. 7, 2006, provisional application No. 60/832,905, filed on Jul. 24, 2006.

(51) Int. Cl.
*A01N 43/04* (2006.01)
*A61K 31/70* (2006.01)

(52) U.S. Cl. .............. 514/43; 514/45; 514/46; 514/47; 514/48; 514/49; 514/50; 514/51; 514/52

(58) Field of Classification Search ............... None
See application file for complete search history.

(56) References Cited

U.S. PATENT DOCUMENTS

| | | | |
|---|---|---|---|
| 4,968,788 A | 11/1990 | Farquhar | |
| 5,663,159 A | 9/1997 | Starrett, Jr. et al. | |
| 5,688,778 A * | 11/1997 | Kim et al. ............ | 514/81 |
| 5,798,340 A | 8/1998 | Bischofberger et al. | |
| 6,018,049 A | 1/2000 | Hajima et al. | |
| 6,127,121 A | 10/2000 | Meyer, Jr. et al. | |
| 6,143,877 A | 11/2000 | Meyer et al. | |
| 2002/0103378 A1 | 8/2002 | Ellis | |
| 2004/0023921 A1 | 2/2004 | Hong et al. | |
| 2004/0100960 A1 | 5/2004 | Mehta | |
| 2004/0147464 A1 | 7/2004 | Roberts et al. | |
| 2005/0215511 A1 | 9/2005 | Roberts et al. | |
| 2005/0215513 A1 | 9/2005 | Boojamra et al. | |

FOREIGN PATENT DOCUMENTS

| EP | 398231 | 11/1990 |
|---|---|---|
| EP | 0 632 048 | 3/2001 |
| WO | WO 95/07920 | 3/1995 |
| WO | WO 96/15111 | 5/1996 |
| WO | WO 01/38584 | 5/2001 |

(Continued)

OTHER PUBLICATIONS

Charubala et al. (2002) "Inhibition of HIV-1 Replication by Chemically Synthesized, Nuclease-Resistant, Nontoxic (2'-5')-Oligoadenylate Agonists," *Helvetica Chimica Acta* 85:2284-2299.

Kim et al. (1991) "Regiospecific and Highly Stereoselective Electrophilic Addition to Furanoid Glycals: Synthesis of Phosphonate Nucleotide Analogues with Potent Activity Against HIV," *J Org. Chem.* 56:2642-2647.

(Continued)

*Primary Examiner*—Patrick T Lewis
(74) *Attorney, Agent, or Firm*—John S. Ward

(57) ABSTRACT

A compound of Formula I, Formula II, Formula III, or Formula IV:

Formula I

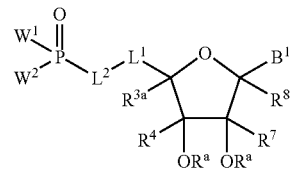

Formula II

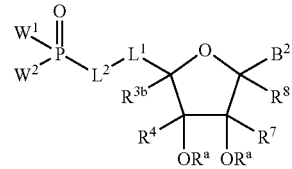

Formula III

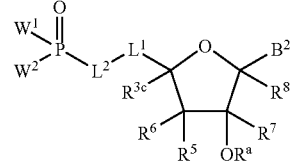

Formula IV
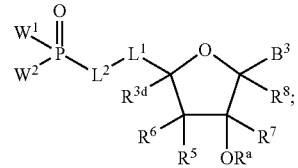

or a pharmaceutically acceptable salt, solvate, and/or ester thereof, therapeutic compositions containing such compounds, and therapeutic methods that include the administration of such compounds.

107 Claims, No Drawings

FOREIGN PATENT DOCUMENTS

| | | |
|---|---|---|
| WO | WO-01/60379 | 8/2001 |
| WO | WO-02/057287 | 7/2002 |
| WO | WO-03/026589 | 4/2003 |
| WO | WO 03/061385 | 7/2003 |
| WO | WO 03/062257 | 7/2003 |
| WO | WO-03/072757 | 9/2003 |
| WO | WO 03/073989 | 9/2003 |
| WO | WO-2004/028481 | 4/2004 |
| WO | WO-2004/096233 | 11/2004 |
| WO | WO-2004/096235 | 11/2004 |
| WO | WO-2004/096286 | 11/2004 |
| WO | WO 2005/021568 | 3/2005 |
| WO | WO-2005/123087 | 12/2005 |
| WO | WO 2005/123087 | 12/2005 |
| WO | WO 2006/000922 | 1/2006 |
| WO | WO 2006/002231 | 1/2006 |
| WO | WO-2006/050161 | 5/2006 |

OTHER PUBLICATIONS

Meier et al. (1991) "O-Alkyl-5', 5'-Dinucleoside-Phosphates as Combined Prodrugs of Antiviral and Antibiotic Compounds," *Bioorganic & Medicinal Chemistry Letters* 1(10)327-330.

Stuyver et al. (2003) "Ribonucleoside Analogue that Blocks Replication of Bovine Viral Diarrhea and Hepatitis C Viruses in Culture," *Antimicrobial Agents and Chemotherapy* 47(1):244-254.

Zhang et al. (2001) "Novel Synthesis of [33 p]-(2-Chloroethyl)phosphonic Acid," *J Org. Chem.* 66:327-329.

Alexander et al. "Preparation of 9-(2-Phosphonomethoxyethyl) Adenine Esters as Potential Prodrugs" 59:1853; Collect Czech Chem Commun., 1994.

Anan'eva et al."(2-Iodoethyl)Phosphonic Derivatives." 53(3):480-483; J. Gen. Chem. USSR., 1983.

Anderson et al. "2-Chloro-4(R),5(R)-dimethyl-2-oxo-1,3,2-dioxaphospholane, a New Chiral Derivatizing Agent." 49:1304-1305; J Org Chem., 1984.

Bai et al. "Structural Specificity of Mucosal-Cell Transport and Metabolism of Peptide Drugs: Implication for Oral Peptide Drug Delivery." 9:969-979;Pharm Res., 1992.

Balsiger et al. "Synthesis of Potential Anticancer Agents. XVIII. Analogs of Carbamoyl Phosphate." 24:434-436; J Org Chem., 1959.

Balthazor et al. "Nickel-Catalyzed Arbuzov Reaction: Mechanistic Observations." 45:5425-5426;J Org Chem., 1980.

Benzaria et al. "Synthesis, in Vitro Antiviral Evaluation, and Stability Studies of Bis(S-acyl-2-thioethyl) Ester Derviatives . . . " 39:4958-4965; J Med Chem., 1996.

Beusen et al. "Solid-State Nuclear Magnetic Resonance Anlysis of the Conformation of an Inhibitor Bound to Thermolysin." 38: 2742-2747; J Med Chem., 1995.

Bhuta et al. "Analogues of Chloramphenicol: Circular Dichroism Spectra, Inhibition of Ribosomal Peptidyltransferase, and Possible . . . " 23(12):1299-1305;J Med Chem., 1980.

Burger et al. "Monoesters and Ester-amidates of Aromatic Phosphonic Acids." 79:3575-3579; J Am Chem Soc.,1957.

Campagne et al. "(1H-Benzotriazol-1-yloxy)tris(dimethylamino) phosphonium Hexafluorophosphate-and . . . " 60(16):5214-5223;J Org Chem., 1995.

Campagne et al. "Synthesis of Mixed Phosphonate Diester Analogues of Dipeptides Using BOP or PyBOP Reagents." 34:6743-6744; Tet Lett., 1993.

Campbell et al. "The Synthesis of Phosphonate Esters, an Extension of the Mitsunobu Reaction." 57:6331-6335; J Org Chem., 1992.

Casteel et al. "Steric and Electronics Effects in the Aryl Phosphate to Aryiphosphonate Rearrangement." 691-693;Synthesis., 1991.

Cavalier et al. "New Highly Diastereoselective Synthesis of Phosphoramidates. A Route to Chiral Methyl p-Nitrophenyl Alkylphosphonates." 1:73-75; Synlett., 1998.

Chen et al "Design, Synthesis, and Biochemical Evaluation of Phosphonate and Phosphonamidate Analogs of Glutathionylspermidine . . . " 40(23):3842-3850;J Med Chem.,1997.

Clayton et al. "BRL.8988 (Talampicillin), a Well-Absorbed Oral Form of Ampicillin." 5(6):670-671;Antimicro AG & Chemo., 1974.

Coe et al. "Synthesis of Some Mimics of Nucleoside Triphosphates." pp. 312-314; J. Chem. Soc. Chem. Commun.., 1991.

Corey et al "Selective Cleavage of Allyl Ethers Under Mild Conditions by Transition Metal Reagants." 38(18):3224;J Org Chem., 1973.

Davies et al. "Dinucleotide Analogues as Inhibitors of Thymidine Kinase, Thyidylate Kinase, and Ribonucleotide Reductase." 31(7)1 305-1308;J Med Chem.,1988.

Efimov et al. "Synthesis of DNA Analogues with Novel Carboxamidomethyl Phosphonamide and Glycinamide Internucleoside Linkages." 8:1013-1018; Bioorg Med Chem Lett., 1998.

Eliel et al., p. 322-381; Stereochem Org Comp., 1994.

Fasman et al., pp. 385-394; Practical Handbook of Biochem and Molec Biol.,1989.

Freeman et al."3 Prodrug Design for Phosphantes and Phosphonates" 34:112-147; Progress in Medicinal Chemistry., 1997.

Galeotti et al. "A Straightforward Synthesis of -Amino Phosphonate Monoesters Using BroP or TPyCIU." 37(23):3997-3998; Tet Lett., 1996.

Greene et al. "Protection for the Amino Acids." 7:309-405; Protective Groups in Organic Synthesis (2nd Ed.) (John Wiley & Sons).,1991.

Griffin et al. "D-Glucopyranose 5-Deoxy-6-phosphonic Acid." 78(10):2336-2338; J Am Chem Soc.,1956.

Hakimelahi et al. "Design, Synthesis, and Structure-Activity Relationship of Novel Dinucleotide Analogs as Agents against Herpes, . . . " 38:4648-4659, J. Med Chem., (1995).

Jacob III, Peyton "Resolution of ( )-5-Bromonornicotine. Synthesis of (R)- and (S)- Nornicotine of High Enantiomeric Purity." 47:4165-4167; J Org Chem., 1982.

Khandazhinskaya et al."Carbocyclic Dinucleoside Polyphosphonates: Interactions with HIV reverse Transcriptase and Antiviral Activity." 45:1284-1291;J Med Chem., 2002.

Kunz et al. "71. Synthesis of the Glycopeptide Partial Sequence A 80-A84 of Human Fibroblast Interferon." 68:618-622;Helvetica Chimica Acta., 1985.

Lochmuller et al. "Chromatographic Resolution of Enantiomers Selective Review." 113:283-302;J Chromatog., 1975.

Lohmann et al."Replication of Subgenomic Hepatitis C Virus RNA's in a Hepatoma Cell Line." 285:110-113; Science., 1999.

Lu et al. "Palladium-Catalyzed Reaction of Aryl Polyfluoroalkanesulfonates with 0,0-Dialkyl Phosphonates." p. 726-727;Synthesis., 1987.

Maffre-Lafon et al."Solid Phase Synthesis of Phosphonopeptides from Fmoc Phosphonodipeptides." 35:4097-4098;Tet Lett., 1994.

Maynard et al. "Organophosphorus Compounds II. Preparation of Phosphonic Acid Esters Using the Dicyclohexylcarbodi-Imide Reagent." 16:609-612;Aust J Chem., 1963.

McKenna et al. "Functional Selectivity in Phosphonate Ester Dealkylation with Bromotrimethylsilane." p. 739;JCS Chem Com., 1979.

Melvin, L.S "An Efficient Synthesis of 2-Hydroxyphenylphosphonates." 22:3375-3376; Tet Lett., 1981.

Mikhailopulo et al. "Pyrophosphoryl Derivatives of 1-(2-Deoxy-3-O-Phosphonomethyl-B- and—-D-erythro-Pentofuranosyl) Thymin." 19(10-12):1885-1909; Nucls & Nuclt.,2000.

Mitsunobu, Oyo "The use of Diethyl Azodicarboxylate and Triphenlyphosphine in Synthesis and Transformation of Natural Products." 1-28; Synthesis., 1981.

Morgan et al. "Structure-Based Design of an Inhibitor of the Zinc Peptidase Thermolysin." 116(8):3251-3260; J Am Chem Soc., 1994.

Morr et al. "Formation of Phostonic Acids During the Reduction of Azidonucleosidephosphonic Acids." 42:8841-8843; Tet Lett., 2001.

Musiol et al. "On the Synthesis of Phosphonamidates Peptides." 59(21):6144-6146;J Org Chem., 1994.

Ohashi et al. "Synthesis of Phosphonosphingoglycolipid Found in Marine Snail Turbo Cornutus." 29:1189-1192;Tet Lett., 1988.

Okamoto "Optical resolution of dihydropyridine enantiomers by High-performance liquid chromatography using phenycarbamates ." 513:375-378;Journal of Chromatography.,1990.

Paquette, Leo A. "Three-Membered Rings with One Hetero Atom." Chptr:1;Principals of Modern Heterocyclic Chemistry., 1968.

Paquette, Leo A. "The Four-Membered Heterocycles." Chptr:3;Principals of Modern Heterocyclic Chemistry., 1968.

Paquette, Leo A. "Furan, Pyrrole, and Thiophene." Chptr:4;Principals of Modern Heterocyclic Chemistry., 1968.

Paquette, Leo A. "The Azoles." Chptr:6;Principals of Modern Heterocyclic Chemistry., 1968.

Paquette, Leo A. "The Pyridine Group." Chptr:7; Principals of Modern Heterocyclic Chemistry., 1968.

Paquette, Leo A. "The Diazines and S-Triazine." Chptr:9; Principals of Modern Heterocyclic Chemistry., 1968.

Patois et al. "2-Alkyl-5,5-dimethyl-1,3,2-dioxaphosphorinan-2-ones—Lithiated Carbanions Synthesis, Stability, and . . . "p. 1577-1581;J Chem Soc Perkin Trans 1., 1990.

Petrakis et al. "Palladium-Catalyzed Substitutions of Triflates Derived from Tyrosine-Containing Peptides and Simpler Hydroxyarenes." 109:2831-2833; J Am Chem Soc., 1987.

Pungente, Weiler "Synthesis and Stereochemical Elucidation of a 14-Membered Ring Phosphonate." 3(5):643-646;Org Lett., 2001.

Quast et al. "Herstellung von Methylphosphonsaure-dichlorid." 490; Synthesis., 1974.

Ramasamy et al. "Monocyclic L-Nucleosides with Type 1 Cytokine-Inducing Activity." 43:1019-1028;J Med Chem., 2000.

Redmore, Derek "Phosphorus Derivatives of Nitrogen Heterocycles, 2. Pyridinephosphonic Acid Derivatives." 35(12):4114-4117;J Org Chem., 1970.

Roach et al. "Fluorescence Detection of Alkylphosphonic Acids Using p-(9-Anthroyloxy)phenacyl BromideFluorescence Detection of Alkylphosphonic." 59:1056-1059;Anal Chem.,1987.

Rosenberg et al. "Synthesis of Potential Prodrugs and Metabolites of 9-(S)-(3-Hydroxy-2-Phosphonylmethoxypropyl)Adenines." 52:2792-2800; Collect Czech Chem Commun., 1987.

Rubira et al. "Synthesis and NMR Conformational Studies of Stable Analogues of 2-Deoxy-D-ribose-1-Phosphate." 54:8223-8240;Tetrahedron., 1998.

Saady et al. "Selective Monodeprotection of Phosphate, Phosphite, Phosphonate, and Phosphoramide Benzyl Esters." 60:2946-2947;J Org Chem., 1995.

Sakamoto et al. "Studies on Prodrugs. II. Preparation and Characterization of (5-Substituted 2-Oxo-1,3-dioxolen-4-yl)methyl Est." 32(6):2241-2248; Chem Pharm Bull.,1983.

Serafinowska et al."Synthesis and in Vivo Evaluation of Prodrugs of 9-[2-(Phosphonomethoxy)ethoxy]adenine." 38:1372-1379; J Med Chem.,1995.

Siddiqui et al. "A 4'-C-Ethynyl-2',3'-Dideoxynucleoside Analogue Highlights the Role of the 3'-OH in Anti-HIV Active 4'-C-Ethynyl-2'-deox." 47:5041-5048;J Med Chem., 2004.

Silverberg et al. "A Simple, Rapid and Efficient Protocol for the Selective Phosphorylation of Phenols with Dibenzyl Phosphite." 37:771-774; Tet Lett.,1996.

Skwarczynski et al."Alkylation of Potassium 1-(N-Benzyloxycarbonylamino)Alkylphosphonates and Phosphinates in the Presence . . . " 25(22):3565-3571;Synthetic Comm., 1995.

Spatola et al. "Peptide Backbone Modifications: A Structure-Activity Analysis of Peptides . . . "p. 267-357;Chem. and Biochem. of Amino Acids, Peptides, and Proteins., 1983.

Stowell et al. "The Mild Preparation of Synthetically Useful Phosphonic Dicholrides: Application to the Synthesis of Cyclic Phospho." 31(23):3261-3262; Tetrahedron., 1990.

Stuttgart, Georg Thieme "An Overview." p. 1-20;Protecting Groups.,1994.

Stuttgart, Georg Thieme "Hydroxyl Protecting Groups." p. 21-94;Protecting Groups.,1994.

Stuttgart, Georg Thieme "Diol Protecting Groups." p. 95-117;Protecting Groups.,1994.

Stuttgart, Georg Thieme "Carboxyl Protecting Groups." p. 118-154;Protecting Groups.,1994.

Stuttgart, Georg Thieme "Carbonyl Protecting Groups." p. 155-184; Protecting Groups.,1994.

Sun et al. "A General Synthesis of Dioxolenone Prodrug Moieties." 43:1161-1164; Tet Lett.,2002.

Szabo et al."Solid Phase Synthesis of 5'-Methylenephosphonate DNA." 14(3-5):871-874;Nucls & Nuclt., 1995.

Tann et al. "Fluorocarbohydrates in Synthesis. An Efficient Synthesis of 1-(2-Deoxy-2-fluoro-B-D-arabinofuranosyl)-5-iodouracil . . . " 50:3644-3647;J Org Chem., 1985.

Thomson et al. "Synthesis and Bioactivation of Bis(aroyloxymethyl)and Mono(aroyloxymethyl) Esters of Benzylphosphonate . . . " 19:2303-2308; J Chem Soc Perkin Comm I., 1993.

Van Der Laan et al. "Optimization of the Binding Properties of PNA-(5')-DNA Chimerae." 8:663-668;Bioorg Med Chem Lett., 1998.

Van Der Laan et al. "An Approach Towards the Synthesis of Oligomers Containing a N-2 Hydroxyethyl-aminomethylphosphonate . . . " 37(43):7857-7860; Tet Lett., 1996.

Vieira de Almeida et al. "Synthesis of Deoxy Phosphatidylinositol Analogues and Phosphonate Isosters . . . " 55:12997-13010; Tetrahedron., 1999.

Watanabe et al. "Dibenzyl Phosphorofluoridate, A New Phosphorylating Agent." 29:5763-5764;Tet Lett., 1988.

Wissner et al. "Analogues of Platelet Activating Factor. 6 Mono-and bis-aryl Phosphate Antagonists of Platelet Activating Factor." 35:1650-1662;J Med Chem., 1992.

Yamauchi et al. "Synthesis of Peptides Analogs Containing(2-aminoethyl)phosphonic acid . . . " 49(7):1158-1163; J Org Chem., 1984.

* cited by examiner

PHOSPHONATE INHIBITORS OF HCV

This application claims priority to U.S. Ser. No. 60/819,489, filed Jul. 7, 2006, and U.S. Ser. No. 60/832,905, filed Jul. 24, 2006, both of which are hereby incorporated by reference in their entireties.

FIELD OF THE INVENTION

This application relates generally to compounds and pharmaceutical compositions useful for the treatment of infection by, but not limited to, RNA viruses. In particular, these derivatives are intended for the treatment of infection by the Hepatitis C virus (HCV).

BACKGROUND OF THE INVENTION

Hepatitis C virus (HCV) is the major cause of non-A non-B hepatitis worldwide. Infection with HCV can progress to chronic liver disease (chronic hepatitis C), which can then progress to serious conditions such as liver cirrhosis, hepatocellular carcinoma and terminal liver disease leading to death.

The current standard-of-care treatment for HCV infection is interferon-α (or its PEG-derivatized equivalent) in combination with ribavirin, a regimen that produces sustained virologic response in only 40% of people infected with the HCV genotype 1. This regimen has significant side effects, leading an unacceptable number of patients to discontinue treatment (*Hepatology*, 2002, 2, 205). There is a clear need for novel therapies that are both more effective, and more tolerable to treat patients.

Therefore, a need exists for the development of effective antiviral agents for treatment of HCV infection that overcomes the limitations of existing pharmaceutical therapies.

SUMMARY OF THE INVENTION

The present application is directed to compounds and pharmaceutical compositions for treating HCV, e.g., by inhibiting HCV NS5b polymerase.

In one embodiment, the present application provides for compounds having a structure according to Formula I, Formula II, Formula III or Formula IV:

Formula I
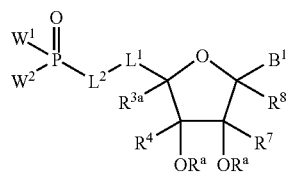

Formula II
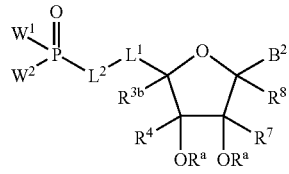

Formula III
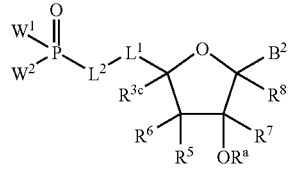

Formula IV
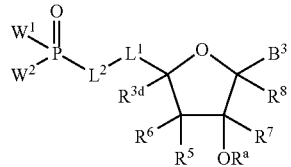

or a pharmaceutically acceptable salt, solvate, and/or ester thereof, wherein:

$L^1$ is —O—, —S—, or —N($R^{11}$)—;

$L^2$ is —C($R^{10}$)$_2$—;

each $R^{3a}$ is $CH_2R^9$, alkenyl, substituted alkenyl, alkynyl, or substituted alkynyl;

each $R^{3b}$ is $CH_2R^9$, alkenyl, substituted alkenyl, alkynyl, or substituted alkynyl wherein $R^9$ is not H;

each $R^{3c}$ is $CH_2R^9$, alkenyl, substituted alkenyl, alkynyl, or substituted alkynyl wherein $R^9$ is not H, OH, or F;

each $R^{3d}$ is H, $CH_2R^9$, alkenyl, substituted alkenyl, alkynyl, or substituted alkynyl;

each $R^4$ is independently H, $CH_2R^9$, alkenyl, substituted alkenyl, alkynyl, or substituted alkynyl;

each $R^5$ and $R^6$ is independently H, N($R^a$)$_2$, $N_3$, CN, $NO_2$, $SR^a$, halogen, $CH_2R^9$, alkenyl, substituted alkenyl, alkynyl, or substituted alkynyl; or $R^5$ and $R^6$ taken together are =O, =$NR^b$, or =$CR^cR^d$; or $R^5$ and $R^6$ taken together with the carbon atom to which they are attached form a 3-7 membered heterocyclic ring wherein one carbon atom in the heterocyclic ring can optionally be replaced with —O—, —S— or —$NR^a$—;

each $R^a$ is independently H, alkyl, substituted alkyl, alkenyl, substituted alkenyl, alkynyl, or substituted alkynyl;

each $R^b$ is independently H, alkyl, substituted alkyl, alkenyl, substituted alkenyl, alkynyl, substituted alkynyl, or $OR^a$;

each $R^c$ and $R^d$ are independently H, alkyl, substituted alkyl, alkenyl, substituted alkenyl, alkynyl, substituted alkynyl, or halo;

each $R^7$ is independently H, $CH_2R^9$, alkenyl, substituted alkenyl, alkynyl, or substituted alkynyl;

each $R^8$ is independently H, $CH_2R^9$, halo, alkyl, substituted alkyl, haloalkyl, —CN, —$N_3$, alkenyl, substituted alkenyl, alkynyl, or substituted alkynyl;

each $R^9$ is independently H, OH, halo, $N_3$, CN, N($R^a$)$_2$, alkyl, substituted alkyl, alkenyl, substituted alkenyl, alkynyl, or substituted alkynyl, wherein one or more of the non-adjacent carbon atoms in the alkyl or substituted alkyl is optionally replaced with —O—, —S— or —$NR^a$—;

each $R^{10}$ is independently H, alkoxy, alkyl, or halo;

each $R^{11}$ is independently H, alkyl, aryl, or substituted aryl;

$B^1$ is a nucleobase selected from

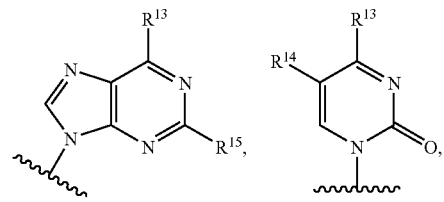

-continued

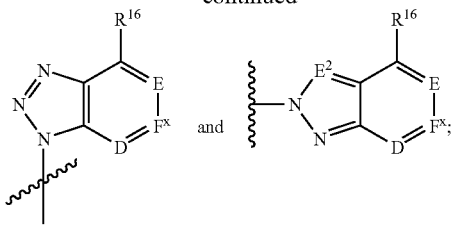

and each $R^{13}$ is independently OH or $NH_2$;
$R^{14}$ is H or $CH_3$;
$R^{15}$ is H, amino, or halo;
$R^{16}$ is H, halo, $OR^{17a}$, $N(R^{20})(R^{21})$, $N(R^{28})N(R^{28})S(O)_2 R^{28}$, alkyl, substituted alkyl, alkenyl, substituted alkenyl, alkynyl, substituted alkynyl, aryl, substituted aryl, heteroaryl, substituted heteroaryl, $S(O)_m R^{28}$, or $S(O)_2 NR^{17a}R^{17b}$, $NR^{17a}R^{17b}$, $N_3$, NO, $NO_2$, formyl, cyano, —C(O)$NR^{17a}R^{17b}$, —C(S)$NR^{17a}R^{17b}$, or —C(O)$OR^{17a}$;
each $R^{17a}$ and $R^{17b}$ are independently H, alkyl substituted alkyl, alkenyl, substituted alkenyl, alkynyl, substituted alkynyl, optionally substituted aryl, optionally substituted heteroaryl, or optionally substituted alkanoyl;
$R^{20}$ is H or $OR^{17a}$;
$R^{21}$ is H, alkyl, substituted alkyl, alkenyl, substituted alkenyl, alkynyl, substituted alkynyl, optionally substituted aryl, cycloalkyl, or arylalkyl; or
$R^{20}$ and $R^{21}$ together with the nitrogen to which they are attached form an optionally substituted 3-7 membered heterocyclic ring wherein one carbon atom of the heterocyclic ring can optionally be replaced with —O—, —S— or —$NR^a$—;
$E^2$ is >N, >C—$R^{25}$ or >C—$R^{30}$;
D, E, and $F^x$ are each independently >N or >C—$R^{21}$;
each $R^{25}$ is independently H, cyano, nitro, azido, optionally substituted ($C_1$-$C_6$)alkyl, optionally substituted ($C_1$-$C_6$) alkenyl, optionally substituted ($C_1$-$C_6$)alkynyl, —NH-CONH$_2$, C(O)$NR^{26}R^{27}$, C(S)$NR^{26}R^{27}$, C(O)$OR^{28}$, hydroxy, $OR^{28}$, $S(O)_m R^{28}$, $S(O)_m NR^{26}R^{27}$, —$NR^{26}R^{27}$, halo, 1,3-oxazol-2-yl, 1,3-oxazol-5-yl, 1,3-thiazol-2-yl, imidazol-2-yl, 2-oxo-[1,3]dithiol-4-yl, furan-2-yl, or 2H-[1,2,3]triazol-4-yl;
each $R^{26}$ and $R^{27}$ is independently H, optionally substituted ($C_1$-$C_6$)alkyl, optionally substituted ($C_1$-$C_6$)alkenyl, optionally substituted ($C_1$-$C_6$)alkynyl, optionally substituted ($C_3$-$C_8$)cycloalkyl, aryl, heteroaryl, optionally substituted heterocycle, hydroxy, optionally substituted ($C_1$-$C_6$)alkoxy; or $R^{26}$ and $R^{27}$ together with the nitrogen to which they are attached form an optionally substituted 3-7 membered heterocyclic ring wherein one carbon atom of the heterocyclic ring can optionally be replaced with —O—, —S— or —$NR^a$—;
each $R^{28}$ is independently H, optionally substituted ($C_1$-$C_6$)alkyl, optionally substituted ($C_1$-$C_6$)alkenyl, optionally substituted ($C_1$-$C_6$)alkynyl, optionally substituted ($C_3$-$C_8$)cycloalkyl, aryl, heteroaryl or heterocycle;
$R^{30}$ is —C≡$CR^{31}$, —CH=$CHR^{32}$, formyl, —CH=$NNHR^{33}$, —CH=N($OR^{33}$), —CH($OR^{34}$), or —B($OR^{33}$);
$R^{31}$ is H, tri($C_1$-$C_6$)alkylsilyl, ($C_1$-$C_6$)alkoxy($C_1$-$C_6$)alkyl, optionally substituted heteroaryl, optionally substituted aryl, carboxy, or ($C_1$-$C_6$)alkoxycarbonyl;
$R^{32}$ is hydrogen or ($C_1$-$C_6$)alkoxy;
$R^{33}$ is H or ($C_1$-$C_6$)alkyl;
$R^{34}$ is ($C_1$-$C_6$)alkyl;
m is 0, 1, or 2;
wherein each aryl or heteroaryl of $R^{26}$, $R^{27}$, $R^{28}$ and $R^{31}$ is independently optionally substituted with one or more ($C_1$-$C_6$)alkyl, ($C_1$-$C_6$)alkoxy, ($C_1$-$C_6$)alkanoyl, ($C_1$-$C_6$) alkanoyloxy, ($C_1$-$C_6$)alkoxycarbonyl, $NR^{35}R^{36}$, —C(=O)$NR^{35}R^{36}$, cyano, halo, hydroxy, nitro, carboxy, ($C_3$-$C_8$)cycloalkyl, ($C_3$-$C_8$)cycloalkoxy, guanidino, trifluoromethoxy, mercapto, $S(O)_m R^{38}$, $S(O)_m NR^{35}R^{36}$ or trifluoromethyl;
$R^{35}$ and $R^{36}$ are each independently H, ($C_1$-$C_6$)alkyl or ($C_1$-$C_6$)alkanoyl;
$R^{38}$ is H, ($C_1$-$C_6$)alkyl or ($C_1$-$C_6$)alkanoyl;
$B^2$ is a nucleobase selected from

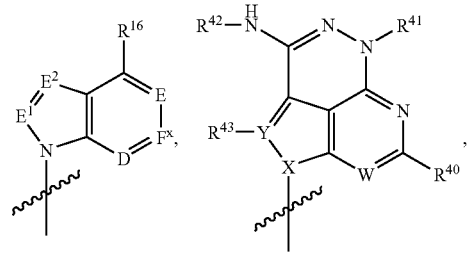

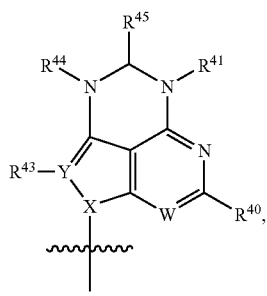

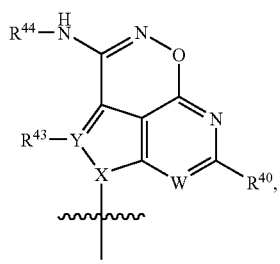

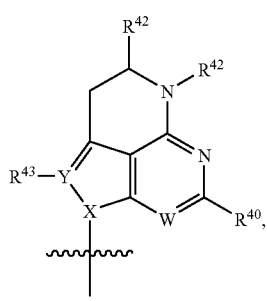

-continued
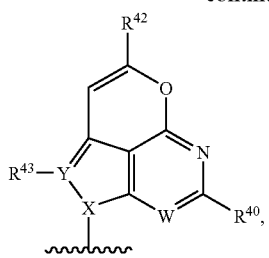
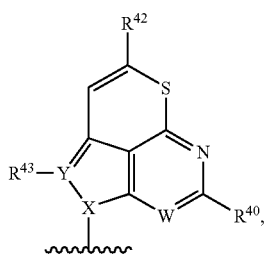
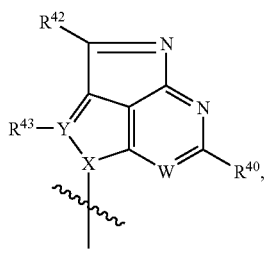
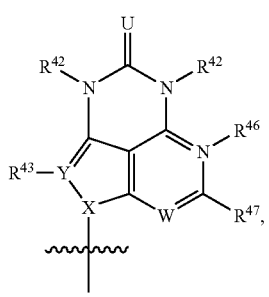
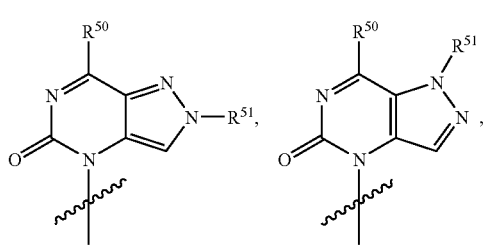
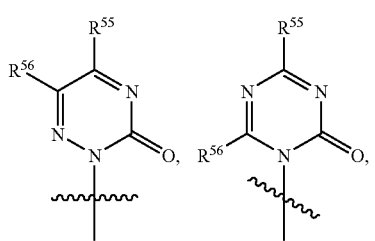
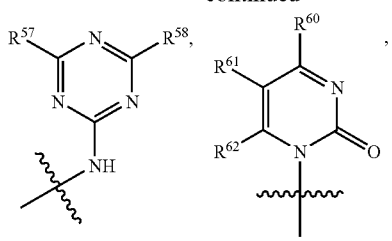
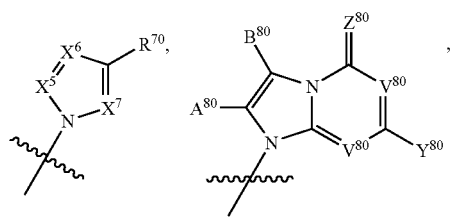
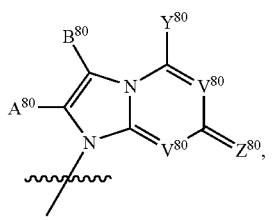
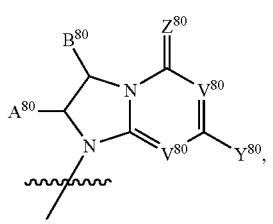
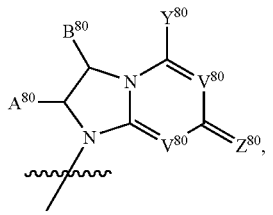
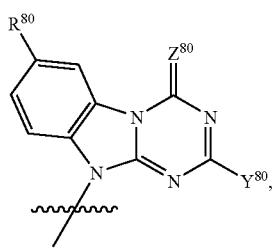
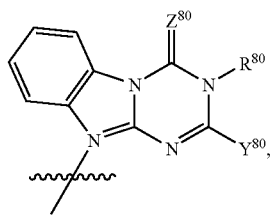 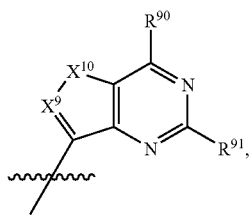

-continued

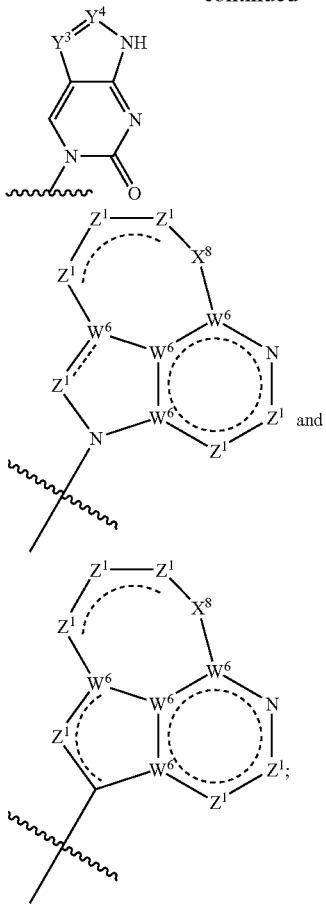

$E^1$ is >N or >C—$R^{25}$, $E^2$, $R^{16}$, E, $F^x$, and D are defined as for $B^1$;

$R^{40}$ is H, $NR^{4a}R^{4b}$, $NHC(O)R^{4b}$, $(C_1-C_6)$alkyl$NR^{4a}R^{4b}$, $NHNH_2$, cyano, $(C_1-C_6)$alkyl, $(C_2-C_6)$alkenyl, $(C_2-C_6)$alkynyl, aryl$(C_1-C_6)$alkyl, heterocycle$(C_1-C_6)$alkyl, halo, $(C_1-C_6)$alkylthio, $(C_1-C_6)$alkoxy, hydroxy, or mercapto;

$R^{41}$ is H, $(C_1-C_6)$alkyl, hydroxy$(C_1-C_6)$alkyl, $(C_2-C_6)$alkenyl, $(C_2-C_6)$alkynyl, heterocycle, aryl, aryl$(C_1-C_6)$alkyl;

each $R^{42}$ is independently H, hydroxy, mercapto,
cyano, —$SNR^{4c}R^{4d}$, —$C(NH)NR^{4c}R^{4d}$, —$C(=NH)NHOH$, —$C(NH)NHOR_{4c}$, —$C(=NH)NHNR^{4c}R^{4d}$, $NHCOR^{4c}$, $SR^{4c}$, $OR^{4c}$, $SOR^{4c}$, $SO_2R^{4c}$, —$C(O)NR^{4c}R^{4d}$, —$C(S)NR^{4c}R^{4d}$, or $R^{4c}$;

$R^{43}$ is H, hydroxy, $NR^{4c}R^{4d}$, $NHC(O)NR^{4c}$, $NHNHR^{4c}$, $(C_1-C_6)$alkyl, $(C_2-C_6)$alkenyl, $(C_2-C_6)$alkynyl, heterocycle, aryl, aryl$(C_1-C_6)$alkyl, halo, $C(O)OR^{4c}$, $C(O)NR^{4c}R^{4d}$, or absent when Y is N;

$R^{4a}$ and $R^{4b}$ are each independently hydrogen, $(C_1-C_6)$alkyl, $(C_2-C_6)$alkenyl, $(C_2-C_6)$alkynyl, heterocycle, or aryl;

$R^{4c}$, and $R^{4d}$ are each independently hydrogen, $(C_1-C_6)$alkyl, $(C_2-C_6)$alkenyl, $(C_2-C_6)$alkynyl, heterocycle, or aryl;

X, Y, and W are each independently N, C, $CR^{4c}$, S or P;

each $R^{44}$ and $R^{45}$ is independently H, hydroxy, mercapto, cyano, —$SNR^{4c}R^{4d}$, —$C(NH)NR^{4c}R^{4d}$, —$C(=NH)NHOH$, —$C(NH)NHOR_{4c}$, —$C(=NH)NHNR^{4c}R^{4d}$, $NHCOR^{4c}$, $SR^{4c}$, $OR^{4c}$, $SOR^{4c}$, $SO_2R^{4c}$, —$C(O)NR^{4c}R^{4d}$, —$C(S)NR^{4c}R^{4d}$, or $R^{4c}$;

$R^{46}$, and $R^{47}$ together with the atoms to which they are attached form a heterocyclic ring;

U is S or O;

wherein each aryl or heterocycle of $R^{40}$, $R^{41}$, $R^{42}$, $R^{43}$, $R^{4a}$, $R^{4b}R^{4c}$, $R^{4d}$, $R^{44}$ and $R^{45}$ is optionally substituted with one or more $(C_1-C_6)$alkyl, $(C_1-C_6)$alkylthio, $(C_1-C_6)$alkoxy, $(C_1-C_6)$alkanoyl, $(C_1-C_6)$alkanoyloxy, $(C_1-C_6)$alkoxycarbonyl, cyano, halo, hydroxy, nitro, carboxy, $(C_3-C_8)$cycloalkyl, $(C_3-C_8)$cycloalkoxy, trifluoromethoxy, mercapto, or trifluoromethyl;

$R^{50}$ is $NR^{5a}R^{5b}$, $ONR^{5a}R^{5b}$, $NR^{5a}NR^{5a}R^{5b}$, $SR^{5b}$, $OR^{5b}$, H, hydroxy, $(C_1-C_6)$alkyl, $(C_1-C_6)$alkenyl, $(C_1-C_6)$alkynyl, or aryl;

$R^{51}$ is $(C_1-C_6)$alkyl, $(C_1-C_6)$alkanoyl, or aryl;

$R^{55}$ is $NR^{5a}R^{5b}$, $ONR^{5a}R^{5b}$, $NR^{5a}NR^{5a}R^{5b}$, $SR^{5b}$, $OR^{5b}$, H, halo, hydroxy, $(C_1-C_6)$alkyl, $(C_2-C_6)$alkenyl, $(C_2-C_6)$alkynyl, or aryl;

$R^{56}$ is H, halo, $(C_1-C_6)$alkyl, $(C_2-C_6)$alkenyl or $(C_2-C_6)$alkynyl;

$R^{57}$ and $R^{58}$ are each independently -L-$R^{5c}$;

each L is independently a direct bond, —N($R^{5a}$)—, O or S;

each $R^{5a}$ and $R^{5b}$ is independently H, hydroxy, $(C_1-C_6)$alkyl, $(C_2-C_6)$alkenyl, $(C_2-C_6)$alkynyl, or aryl;

each $R^{5c}$ is $NR^{5a}R^{5b}$, H, hydroxy, $(C_1-C_6)$alkyl, $(C_2-C_6)$alkenyl, $(C_2-C_6)$alkynyl, or aryl;

wherein each $(C_1-C_6)$alkyl, $(C_2-C_6)$alkenyl, $(C_2-C_6)$alkynyl, or aryl of $R^{50}$, $R^{51}$, $R^{55}$, $R^{56}$, $R^{57}$, $R^{58}$, $R^{5a}$, $R^{5b}$ and $R^{5c}$ is optionally substituted with one or more $(C_1-C_6)$alkyl, $(C_1-C_6)$alkylthio, $(C_1-C_6)$alkoxy, $(C_1-C_6)$alkanoyl, $(C_1-C_6)$alkanoyloxy, $(C_1-C_6)$alkoxycarbonyl, cyano, halo, hydroxy, nitro, carboxy, $(C_3-C_8)$cycloalkyl, $(C_3-C_8)$cycloalkoxy, trifluoromethoxy, mercapto, or trifluoromethyl;

$R^{60}$, $R^{61}$, and $R^{62}$ are each independently H, halo, $NR^{6b}R^{6c}$, hydroxyamino, $NR^{6b}NR^{6b}R^{6c}$, $N_3$, NO, $NO_2$, formyl,
cyano, $C(O)NR^{6b}R^{6c}$, —$C(S)NR^{6b}R^{6c}$, —$C(O)OR^{6b}$, $R^{6b}$, $OR^{6b}$, or $SR^{6b}$;

$R^{6b}$, and $R^{6c}$ are each independently H, $(C_1-C_6)$alkyl, $(C_2-C_6)$alkenyl, $(C_2-C_6)$alkynyl, aryl, $(C_1-C_6)$alkanoyl, or aryl$(C_1-C_6)$alkyl;

wherein each $(C_1-C_6)$alkyl, $(C_2-C_6)$alkenyl, $(C_2-C_6)$alkynyl, or aryl of $R^{6b}$ and $R^{6c}$ is optionally substituted with one or more $(C_1-C_6)$alkyl, $(C_1-C_6)$alkylthio, $(C_1-C_6)$alkoxy, $(C_1-C_6)$alkanoyl, $(C_1-C_6)$alkanoyloxy, $(C_1-C_6)$alkoxycarbonyl, cyano, halo, hydroxy, nitro, carboxy, $(C_3-C_8)$cycloalkyl, $(C_3-C_8)$cycloalkoxy, trifluoromethoxy, mercapto, or trifluoromethyl;

$X^5$, $X^6$, and $X^7$ are each independently N, CH, or C—$R^{7a}$;

$R^{70}$ and $R^{7a}$ are each independently H, halo, $NR^{7b}R^{7c}$, hydroxyamino, $NR^{7b}NR^{7b}R^{7c}$, $N_3$, NO, $NO_2$, formyl,
cyano, —$C(O)NR^{7b}R^{7c}$, —$C(S)NR^{7b}R^{7c}$, —$C(O)OR^{7b}$, $R^{7b}$, $OR^{7b}$, or $SR^{7b}$;

$R^{7b}$, and $R^{7c}$ are each independently H, $(C_1-C_6)$alkyl, $(C_2-C_6)$alkenyl, $(C_2-C_6)$alkynyl, aryl, $(C_1-C_6)$alkanoyl, or aryl$(C_1-C_6)$alkyl;

$A^{80}$, $B^{80}$, and $Y^{80}$, are each independently H, halo, $OR^{80}$, $S(O)_nR^{80}$, $NR^{80}R^{81}$, cyano, trifluoromethyl, $C(W^{80})OR^{80}$, $C(W^{80})SR^{80}$, $C(W^{80})NR^{80}R^{81}$, nitro, azido, carbocyclic, $(C_1-C_6)$alkyl, $(C_2-C_6)$alkenyl, $(C_2-C_6)$alkynyl, aryl, aryl$(C_1-C_6)$alkyl, or heterocycle; or $A^{80}$ and B$^{80}$ taken together with the carbon atoms to which they are attached from a 4-7 membered carbocyclic or heterocyclic ring;

W$^{80}$ is O, S, NR$^{80}$;

n is 0, 1, or 2;

Z$^{80}$ is O, S, NR$^{80}$, or CR$^{80}$R$^{81}$;

each V$^{80}$ is independently N or CR$^{80}$;

each R$^{80}$ and R$^{81}$ is independently H, carbocycle, (C$_1$-C$_6$) alkyl, (C$_2$-C$_6$)alkenyl, (C$_2$-C$_6$)alkynyl, halo, (C$_1$-C$_6$) alkoxy, amino, methylamino, dimethylamino, cyano, (C$_1$-C$_6$)alkanoyl, aryl, aryl(C$_1$-C$_6$)alkyl, an amino acid residue or heterocycle; or R$^{80}$ and R$^{81}$ taken together with the atom(s) to which they are attached form a 3-7 membered carbocyclic or heterocyclic ring;

X$^9$ is CR$^{90a}$ or N;

X$^{10}$ is O, S, or NR$^{91a}$;

R$^{90}$ and R$^{91}$ are each independently H, halo, hydroxy, (C$_1$-C$_6$)alkoxy, NR$^{90b}$R$^{91b}$, aryl, heterocycle; (C$_1$-C$_6$)alkyl, (C$_2$-C$_6$)alkenyl, (C$_2$-C$_6$)alkynyl, (C$_3$-C$_8$)cycloalkyl, aryl(C$_1$-C$_6$)alkyl, S(O)$_m$R$^{90b}$, S(O)$_m$(aryl), or S(O)$_m$NR$^{90b}$R$^{91b}$;

R$^{90a}$ is H, halo, methyl, azido, or amino;

R$^{91a}$ is H, (C$_1$-C$_6$)alkyl or (C$_1$-C$_6$) alkanoyl;

R$^{90b}$ and R$^{91b}$ are each independently H, (C$_1$-C$_6$)alkyl, (C$_3$-C$_8$)cycloalkyl, aryl(C$_1$-C$_6$)alkyl, aryl, (C$_1$-C$_6$) alkanoyl, or aryl-C(O)—;

wherein each (C$_1$-C$_6$)alkyl, (C$_3$-C$_8$)cycloalkyl, aryl(C$_1$-C$_6$)alkyl, aryl, (C$_1$-C$_6$) alkanoyl, aryl-C(O)— and heterocycle of R$^{90}$, R$^{91}$, R$^{91a}$, R$^{90b}$ and R$^{91b}$ are optionally substituted with one to four halo, hydroxy, amino, (C$_1$-C$_6$)alkyl, and (C$_1$-C$_6$)alkoxy;

each Z$^1$ is independently N, C—R$^{9a}$, O, S, NR$^{9b}$, >C=O, >C=S, >C=NR$^{9b}$, >S=O, >S(O)$_2$ or CH—R$^{9a}$; provided that if a Z$^1$ participates in an optional bond represented by a dotted line ▬▬▬ in the formula, then that Z$^1$ is N or C—R$^{9a}$; and provided that if a Z$^1$ does not participate in an optional bond represented by a dotted line ▬▬▬ in the formula, then that Z$^1$ is O, S, NR$^{9b}$, >C=O, >C=S, >C=NR$^{9b}$, >S=O, >S(O)$_2$ or CH—R$^{9a}$;

X$^8$ is O, S, SO, SO$_2$, Se, SeO, SeO$_2$ or NR$^{9b}$;

each W$^6$ is C, CH, or N; wherein if a W$^6$ participates in an optional bond represented by a dotted line ▬▬▬ in the formula, then that W$^6$ is C; and if a W$^6$ does not participate in an optional bond represented by a dotted line ▬▬▬ in the formula, then that W$^6$ is CH, or N;

each R$^{9a}$ is independently H, halo, NR$^{9c}$R$^{9d}$, hydroxyamino, NR$^{9c}$NR$^{9c}$R$^{9d}$, N$_3$, cyano, —C(O)NR$^{9c}$R$^{9d}$, —C(S)NR$^{9c}$R$^{9d}$, —C(S)NR$^{9c}$R$^{9d}$, —C(=NH)OR$^{9c}$, R$^{9c}$, OR$^{9c}$, or SR$^{9c}$;

each R$^{9b}$ is independently H, (C$_1$-C$_6$)alkyl, (C$_2$-C$_6$)alkenyl, (C$_2$-C$_6$)alkynyl, aryl, (C$_1$-C$_6$)alkanoyl, or aryl(C$_1$-C$_6$)alkyl;

R$^{9c}$ and R$^{9d}$ are each independently H, (C$_1$-C$_6$)alkyl, (C$_2$-C$_6$)alkenyl, (C$_2$-C$_6$)alkynyl, aryl, (C$_1$-C$_6$)alkanoyl, or aryl(C$_1$-C$_6$)alkyl;

Y$^3$=Y$^4$ is —N=N—, —CH=N—, —N=CR$^{8a}$—, or —CH=CR$^{8a}$—;

each R$^{8a}$ is independently H, halo, or (C$_1$-C$_6$)alkyl;

B$^3$ is a nucleobase selected from

W$^1$ and W$^2$ are each independently a group of the formula:

wherein:

each Y$^1$ is independently O, S, NR, $^+$N(O)(R), N(OR), $^+$N(O)(OR), or N—NR$_2$;

each Y$^2$ is independently a bond, O, CR$_2$, NR, $^+$N(O)(R), N(OR), $^+$N(O)(OR), N—NR$_2$, S, S—S, S(O), or S(O)$_2$;

M2 is 0, 1 or 2;

each R$^x$ is independently R$^y$, a protecting group, or the formula:

wherein:

M1a, M1c, and M1d are independently 0 or 1;

M12c is 0, 1, 2, 3, 4, 5, 6, 7, 8, 9, 10, 11 or 12; or when taken together, two R$^x$ are optionally substituted C$_2$-C$_4$ alkylene thereby forming a phosphorous-containing heterocycle;

each R$^y$ is independently H, F, Cl, Br, I, OH, R, —C(=Y$^1$)R, —C(=Y$^1$)OR, —C(=Y$^1$)N(R)$_2$, —N(R)$_2$, —$^+$N(R)$_3$, —SR, —S(O)R, —S(O)$_2$R, —S(O)(OR), —S(O)$_2$(OR), —OC(=Y$^1$)R, —OC(=Y$^1$)OR, —OC(=Y$^1$)(N(R)$_2$), —SC(=Y$^1$)R, —SC(=Y$^1$)OR, —SC(=Y$^1$)(N(R)$_2$), —N(R)C(=Y$^1$)R, —N(R)C(=Y$^1$)OR, or —N(R)C(=Y$^1$)N(R)$_2$, amino (—NH$_2$), ammonium (—NH$_3$$^+$), alkylamino, dialkylamino, trialkylammonium, C$_1$-C$_8$ alkyl, C$_1$-C$_8$ alkylhalide, carboxylate, sulfate, sulfamate, sulfonate, C$_1$-C$_8$ alkylsulfonate, C$_1$-C$_8$ alkylamino, C$_1$-C$_8$ alkylhydroxyl C$_1$-C$_8$ alkylthiol, alkylsulfone (—SO$_2$R), sulfonamide (—SO$_2$NR$_2$), alkylsulfoxide (—SOR), ester (—C(=O)OR), amido (—C(=O)NR$_2$), nitrile (—CN), azido (—N$_3$), nitro (—NO₂), $C_1$-$C_8$ alkoxy (—OR), $C_1$-$C_8$ alkyl, $C_1$-$C_8$ substituted alkyl, $C_2$-$C_8$ alkenyl, $C_2$-$C_8$ substituted alkenyl, $C_2$-$C_8$ alkynyl, $C_2$-$C_8$ substituted alkynyl, a protecting group, or $W^3$; or when taken together, two $R^y$ on the same carbon atom forms a carbocyclic ring of 3 to 7 carbon atoms;

each R is independently H, halogen, $C_1$-$C_8$ alkyl, $C_1$-$C_8$ substituted alkyl, $C_2$-$C_8$ alkenyl, $C_2$-$C_8$ substituted alkenyl, $C_2$-$C_8$ alkynyl, $C_2$-$C_8$ substituted alkynyl, $C_6$-$C_{20}$ aryl, $C_6$-$C_{20}$ substituted aryl, $C_2$-$C_{20}$ heterocycle, $C_2$-$C_{20}$ substituted heterocycle or a protecting group;

$W^3$ is $W^4$ or $W^5$;

$W^4$ is R, —C(Y¹)R^y, —C(Y¹)W⁵, —SO₂R^y, or —SO₂W⁵; and $W^5$ is a carbocycle or a heterocycle wherein $W^5$ is independently substituted with 0 to 3 $R^y$ groups.

In another embodiment, the present application provides for a pharmaceutical composition comprising a compound of Formula I, Formula II, Formula III, or Formula IV; or a pharmaceutically acceptable salt, solvate, and/or ester thereof; and a pharmaceutically acceptable carrier or excipient.

In another embodiment, the present application provides for a pharmaceutical composition comprising a compound of Formula I, Formula II, Formula III, or Formula IV; at least one additional therapeutic agent; and a pharmaceutically acceptable carrier or excipient.

In another embodiment, the present application provides for combination pharmaceutical agent comprising:
a) a first pharmaceutical composition comprising a compound of Formula I, Formula II, Formula III, or Formula IV; or a pharmaceutically acceptable salt, solvate, or ester thereof; and
b) a second pharmaceutical composition comprising at least one additional therapeutic agent selected from the group consisting of interferons, ribavirin analogs, NS3 protease inhibitors, alpha-glucosidase 1 inhibitors, hepatoprotectants, non-nucleoside inhibitors of HCV, and other drugs for treating HCV.

In another embodiment, the present application provides for a method of inhibiting HCV polymerase, comprising contacting a cell infected with HCV with an effective amount of a compound of Formula I, Formula II, Formula III, or Formula IV; or a pharmaceutically acceptable salts, solvate, and/or ester thereof.

In another embodiment, the present application provides for a method of inhibiting HCV polymerase, comprising contacting a cell infected with HCV with an effective amount of a compound of Formula I, Formula II, Formula III, or Formula IV; or a pharmaceutically acceptable salts, solvate, and/or ester thereof; and at least one additional therapeutic agent.

In another embodiment, the present application provides for a method of treating HCV in a patient, comprising administering to said patient a therapeutically effective amount of a compound of Formula I, Formula II, Formula III, or Formula IV; or a pharmaceutically acceptable salt, solvate, and/or ester thereof.

In another embodiment, the present application provides for a method of treating HCV in a patient, comprising administering to said patient a therapeutically effective amount of a compound of Formula I, Formula II, Formula III, or Formula IV; or a pharmaceutically acceptable salt, solvate, and/or ester thereof; and at least one additional therapeutic agent.

DETAILED DESCRIPTION

Reference will now be made in detail to certain claims of the invention, examples of which are illustrated in the accompanying structures and formulas. While the invention will be described in conjunction with the enumerated claims, it will be understood that they are not intended to limit the invention to those claims. On the contrary, the invention is intended to cover all alternatives, modifications, and equivalents, which may be included within the scope of the present invention as defined by the claims.

DEFINITIONS

Unless stated otherwise, the following terms and phrases as used herein are intended to have the following meanings:

When trade names are used herein, applicants intend to independently include the tradename product and the active pharmaceutical ingredient(s) of the tradename product.

As used herein, "a compound of the invention" or "a compound of formula (I)" means a compound of formula (I) or a pharmaceutically acceptable salt, solvate, or physiologically functional derivative thereof. Similarly, with respect to isolatable intermediates, the phrase "a compound of formula (number)" means a compound of that formula and pharmaceutically acceptable salts, solvates and physiologically functional derivatives thereof.

"Alkyl" is hydrocarbon containing normal, secondary, tertiary or cyclic carbon atoms. For example, an alkyl group can have 1 to 20 carbon atoms (i.e., $C_1$-$C_{20}$ alkyl), 1 to 10 carbon atoms (i.e., $C_1$-$C_{10}$ alkyl), or 1 to 6 carbon atoms (i.e., $C_1$-$C_6$ alkyl). Examples of suitable alkyl groups include, but are not limited to, methyl (Me, —CH₃), ethyl (Et, —CH₂CH₃), 1-propyl (n-Pr, n-propyl, —CH₂CH₂CH₃), 2-propyl (i-Pr, i-propyl, —CH(CH₃)₂), 1-butyl (n-Bu, n-butyl, —CH₂CH₂CH₂CH₃), 2-methyl-1-propyl (i-Bu, i-butyl, —CH₂CH(CH₃)₂), 2-butyl (s-Bu, s-butyl, —CH(CH₃)CH₂CH₃), 2-methyl-2-propyl (t-Bu, t-butyl, —C(CH₃)₃), 1-pentyl (n-pentyl, —CH₂CH₂CH₂CH₂CH₃), 2-pentyl (—CH(CH₃)CH₂CH₂CH₃), 3-pentyl (—CH(CH₂CH₃)₂), 2-methyl-2-butyl (—C(CH₃)₂CH₂CH₃), 3-methyl-2-butyl (—CH(CH₃)CH(CH₃)₂), 3-methyl-1-butyl (—CH₂CH₂CH(CH₃)₂), 2-methyl-1-butyl (—CH₂CH(CH₃)CH₂CH₃), 1-hexyl (—CH₂CH₂CH₂CH₂CH₂CH₃), 2-hexyl (—CH(CH₃)CH₂CH₂CH₂CH₃), 3-hexyl (—CH(CH₂CH₃)(CH₂CH₂CH₃)₂), 2-methyl-2-pentyl (—C(CH₃)₂CH₂CH₂CH₃), 3-methyl-2-pentyl (—CH(CH₃)CH(CH₃)CH₂CH₃), 4-methyl-2-pentyl (—CH(CH₃)CH₂CH(CH₃)₂), 3-methyl-3-pentyl (—C(CH₃)(CH₂CH₃)₂), 2-methyl-3-pentyl (—CH(CH₂CH₃)CH(CH₃)₂), 2,3-dimethyl-2-butyl (—C(CH₃)₂CH(CH₃)₂), 3,3-dimethyl-2-butyl (—CH(CH₃)C(CH₃)₃), and octyl (—(CH₂)₇CH₃).

"Alkoxy" means a group having the formula —O-alkyl, in which an alkyl group, as defined above, is attached to the parent molecule via an oxygen atom. The alkyl portion of an alkoxy group can have 1 to 20 carbon atoms (i.e., $C_1$-$C_{20}$ alkoxy), 1 to 12 carbon atoms (i.e., $C_1$-$C_{12}$ alkoxy), or 1 to 6 carbon atoms (i.e., $C_1$-$C_6$ alkoxy). Examples of suitable alkoxy groups include, but are not limited to, methoxy (—O—CH₃ or —OMe), ethoxy (—OCH₂CH₃ or —OEt), t-butoxy (—O—C(CH₃)₃ or —OtBu) and the like.

"Haloalkyl" is an alkyl group, as defined above, in which one or more hydrogen atoms of the alkyl group is replaced with a halogen atom. The alkyl portion of a haloalkyl group can have 1 to 20 carbon atoms (i.e., $C_1$-$C_{20}$ haloalkyl), 1 to 12 carbon atoms (i.e., $C_1$-$C_{12}$ haloalkyl), or 1 to 6 carbon atoms (i.e., $C_1$-$C_6$ alkyl). Examples of suitable haloalkyl groups include, but are not limited to, —CF₃, —CHF₂, —CFH₂, —CH₂CF₃, and the like.

"Alkenyl" is a hydrocarbon containing normal, secondary, tertiary or cyclic carbon atoms with at least one site of unsaturation, i.e. a carbon-carbon, sp² double bond. For example, an alkenyl group can have 2 to 20 carbon atoms (i.e., $C_2$-$C_{20}$ alkenyl), 2 to 12 carbon atoms (i.e., $C_2$-$C_{12}$ alkenyl), or 2 to 6 carbon atoms (i.e., $C_2$-$C_6$ alkenyl). Examples of suitable alkenyl groups include, but are not limited to, ethylene or vinyl (—CH═CH$_2$), allyl (—CH$_2$CH═CH$_2$), cyclopentenyl (—C$_5$H$_7$), and 5-hexenyl (—CH$_2$CH$_2$CH$_2$CH$_2$CH═CH$_2$).

"Alkynyl" is a hydrocarbon containing normal, secondary, tertiary or cyclic carbon atoms with at least one site of unsaturation, i.e. a carbon-carbon, sp triple bond. For example, an alkynyl group can have 2 to 20 carbon atoms (i.e., C$_2$-C$_{20}$ alkynyl), 2 to 12 carbon atoms (i.e., C$_2$-C$_{12}$ alkyne), or 2 to 6 carbon atoms (i.e., C$_2$-C$_6$ alkynyl). Examples of suitable alkynyl groups include, but are not limited to, acetylenic (—C≡CH), propargyl (—CH$_2$C≡CH), and the like.

"Alkylene" refers to a saturated, branched or straight chain or cyclic hydrocarbon radical having two monovalent radical centers derived by the removal of two hydrogen atoms from the same or two different carbon atoms of a parent alkane. For example, an alkylene group can have 1 to 20 carbon atoms, 1 to 10 carbon atoms, or 1 to 6 carbon atoms. Typical alkylene radicals include, but are not limited to, methylene (—CH$_2$—), 1,1-ethyl (—CH(CH$_3$)—), 1,2-ethyl (—CH$_2$CH$_2$—), 1,1-propyl (—CH(CH$_2$CH$_3$)—), 1,2-propyl (—CH$_2$CH (CH$_3$)—), 1,3-propyl (—CH$_2$CH$_2$CH$_2$—), 1,4-butyl (—CH$_2$CH$_2$CH$_2$CH$_2$—), and the like.

"Alkenylene" refers to an unsaturated, branched or straight chain or cyclic hydrocarbon radical having two monovalent radical centers derived by the removal of two hydrogen atoms from the same or two different carbon atoms of a parent alkene. For example, and alkenylene group can have 1 to 20 carbon atoms, 1 to 10 carbon atoms, or 1 to 6 carbon atoms. Typical alkenylene radicals include, but are not limited to, 1,2-ethylene (—CH═CH—).

"Alkynylene" refers to an unsaturated, branched or straight chain or cyclic hydrocarbon radical having two monovalent radical centers derived by the removal of two hydrogen atoms from the same or two different carbon atoms of a parent alkyne. For example, an alkynylene group can have 1 to 20 carbon atoms, 1 to 10 carbon atoms, or 1 to 6 carbon atoms. Typical alkynylene radicals include, but are not limited to, acetylene (—C≡C—), propargyl (—CH$_2$C≡C—), and 4-pentynyl (—CH$_2$CH$_2$CH$_2$C≡CH—).

"Amino" refers generally to a nitrogen radical which can be considered a derivative of ammonia, having the formula —N(X)$_2$, where each "X" is independently H, substituted or unsubstituted alkyl, substituted or unsubstituted carbocyclyl, substituted or unsubstituted heterocyclyl, etc. The hybridization of the nitrogen is approximately sp$^3$. Nonlimiting types of amino include —NH$_2$, —N(alkyl)$_2$, —NH(alkyl), —N(carbocyclyl)$_2$, —NH(carbocyclyl), —N(heterocyclyl)$_2$, —NH(heterocyclyl), —N(aryl)$_2$, —NH(aryl), —N(alkyl) (aryl), —N(alkyl)(heterocyclyl), —N(carbocyclyl)(heterocyclyl), —N(aryl)(heteroaryl), —N(alkyl)(heteroaryl), etc. The term "alkylamino" refers to an amino group substituted with at least one alkyl group. Nonlimiting examples of amino groups include —NH$_2$, —NH(CH$_3$), —N(CH$_3$)$_2$, —NH (CH$_2$CH$_3$), —N(CH$_2$CH$_3$)$_2$, —NH(phenyl), —N(phenyl)$_2$, —NH(benzyl), —N(benzyl)$_2$, etc. Substituted alkylamino refers generally to alkylamino groups, as defined above, in which at least one substituted alkyl, as defined herein, is attached to the amino nitrogen atom. Non-limiting examples of substituted alkylamino includes —NH(alkylene-C(O)—OH), —NH(alkylene-C(O)—O-alkyl), —N(alkylene-C (O)—OH)$_2$, —N(alkylene-C(O)—O-alkyl)$_2$, etc.

"Aryl" means an aromatic hydrocarbon radical derived by the removal of one hydrogen atom from a single carbon atom of a parent aromatic ring system. For example, an aryl group can have 6 to 20 carbon atoms, 6 to 14 carbon atoms, or 6 to 12 carbon atoms. Typical aryl groups include, but are not limited to, radicals derived from benzene (e.g., phenyl), substituted benzene, naphthalene, anthracene, biphenyl, and the like.

"Arylalkyl" refers to an acyclic alkyl radical in which one of the hydrogen atoms bonded to a carbon atom, typically a terminal or sp$^3$ carbon atom, is replaced with an aryl radical. Typical arylalkyl groups include, but are not limited to, benzyl, 2-phenylethan-1-yl, naphthylmethyl, 2-naphthylethan-1-yl, naphthobenzyl, 2-naphthophenylethan-1-yl and the like. The arylalkyl group can comprise 6 to 20 carbon atoms, e.g., the alkyl moiety is 1 to 6 carbon atoms and the aryl moiety is 6 to 14 carbon atoms.

"Arylalkenyl" refers to an acyclic alkenyl radical in which one of the hydrogen atoms bonded to a carbon atom, typically a terminal or sp$^3$ carbon atom, but also an sp$^2$ carbon atom, is replaced with an aryl radical. The aryl portion of the arylalkenyl can include, for example, any of the aryl groups disclosed herein, and the alkenyl portion of the arylalkenyl can include, for example, any of the alkenyl groups disclosed herein. The arylalkenyl group can comprise 6 to 20 carbon atoms, e.g., the alkenyl moiety is 1 to 6 carbon atoms and the aryl moiety is 6 to 14 carbon atoms.

"Arylalkynyl" refers to an acyclic alkynyl radical in which one of the hydrogen atoms bonded to a carbon atom, typically a terminal or sp$^3$ carbon atom, but also an sp carbon atom, is replaced with an aryl radical. The aryl portion of the arylalkynyl can include, for example, any of the aryl groups disclosed herein, and the alkynyl portion of the arylalkynyl can include, for example, any of the alkynyl groups disclosed herein. The arylalkynyl group can comprise 6 to 20 carbon atoms, e.g., the alkynyl moiety is 1 to 6 carbon atoms and the aryl moiety is 6 to 14 carbon atoms.

The term "substituted" in reference to alkyl, alkylene, aryl, arylalkyl, alkoxy, heterocyclyl, heteroaryl, carbocyclyl, etc., for example, "substituted alkyl", "substituted alkylene", "substituted aryl", "substituted arylalkyl", "substituted heterocyclyl", and "substituted carbocyclyl" means alkyl, alkylene, aryl, arylalkyl, heterocyclyl, carbocyclyl respectively, in which one or more hydrogen atoms are each independently replaced with a non-hydrogen substituent. Typical substituents include, but are not limited to, —X, —R, —O$^-$;

═O, —OR, —SR, —S$^-$; —NR$_2$, —N$^+$R$_3$,

═NR, —CX$_3$, —CN, —OCN, —SCN, —N═C═O, —NCS, —NO, —NO$_2$,

═N$_2$, —N$_3$, —NHC(═O)R, —C(═O)R, —C(═O)NRR—S(═O)$_2$—, —S(═O)$_2$OH, —S(═O)$_2$R, —OS(═O)$_2$OR, —S(═O)$_2$NR, —S(═O)R, —OP(═O)(OR)$_2$, —P(═O) (OR)$_2$, —P(═O)(O$^-$)$_2$, —P(═O)(OH)$_2$, —P (O)(OR)(O$^-$), —C(═O)R, —C(═O)X, —C(S)R, —C(O)OR, —C(O)O$^-$, —C(S)OR, —C(O)SR, —C(S)SR, —C(O)NRR, —C(S) NRR, —C(═NR)NRR, where each X is independently a halogen: F, Cl, Br, or I; and each R is independently H, alkyl, aryl, arylalkyl, a heterocycle, or a protecting group or prodrug moiety. Alkylene, alkenylene, and alkynylene groups may also be similarly substituted. Unless otherwise indicated, when the term "substituted" is used in conjunction with groups such as arylalkyl, which have two or more moieties capable of substitution, the substituents can be attached to the aryl moiety, the alkyl moiety, or both.

The term "prodrug" as used herein refers to any compound that when administered to a biological system generates the drug substance, i.e., active ingredient, as a result of spontaneous chemical reaction(s), enzyme catalyzed chemical reaction(s), photolysis, and/or metabolic chemical reaction(s). A prodrug is thus a covalently modified analog or latent form of a therapeutically active compound.

One skilled in the art will recognize that substituents and other moieties of the compounds of Formula I-IV should be selected in order to provide a compound which is sufficiently stable to provide a pharmaceutically useful compound which can be formulated into an acceptably stable pharmaceutical composition. Compounds of Formula I-IV which have such stability are contemplated as falling within the scope of the present invention.

"Heteroalkyl" refers to an alkyl group where one or more carbon atoms have been replaced with a heteroatom, such as, O, N, or S. For example, if the carbon atom of the alkyl group which is attached to the parent molecule is replaced with a heteroatom (e.g., O, N, or S) the resulting heteroalkyl groups are, respectively, an alkoxy group (e.g., —OCH$_3$, etc.), an amine (e.g., —NHCH$_3$, —N(CH$_3$)$_2$, etc.), or a thioalkyl group (e.g., —SCH$_3$). If a non-terminal carbon atom of the alkyl group which is not attached to the parent molecule is replaced with a heteroatom (e.g., O, N, or S) the resulting heteroalkyl groups are, respectively, an alkyl ether (e.g., —CH$_2$CH$_2$—O—CH$_3$, etc.), an alkyl amine (e.g., —CH$_2$NHCH$_3$, —CH$_2$N(CH$_3$)$_2$, etc.), or a thioalkyl ether (e.g., —CH$_2$—S—CH$_3$). If a terminal carbon atom of the alkyl group is replaced with a heteroatom (e.g., O, N, or S), the resulting heteroalkyl groups are, respectively, a hydroxyalkyl group (e.g., —CH$_2$CH$_2$—OH), an aminoalkyl group (e.g., —CH$_2$NH$_2$), or an alkyl thiol group (e.g., —CH$_2$CH$_2$—SH). A heteroalkyl group can have, for example, 1 to 20 carbon atoms, 1 to 10 carbon atoms, or 1 to 6 carbon atoms. A C$_1$-C$_6$ heteroalkyl group means a heteroalkyl group having 1 to 6 carbon atoms.

"Heterocycle" or "heterocyclyl" as used herein includes by way of example and not limitation those heterocycles described in Paquette, Leo A.; *Principles of Modern Heterocyclic Chemistry* (W. A. Benjamin, New York, 1968), particularly Chapters 1, 3, 4, 6, 7, and 9; *The Chemistry of Heterocyclic Compounds, A Series of Monographs*" (John Wiley & Sons, New York, 1950 to present), in particular Volumes 13, 14, 16, 19, and 28; and *J. Am. Chem. Soc.* (1960) 82:5566. In one specific embodiment of the invention "heterocycle" includes a "carbocycle" as defined herein, wherein one or more (e.g. 1, 2, 3, or 4) carbon atoms have been replaced with a heteroatom (e.g. O, N, or S). The terms "heterocycle" or "heterocyclyl" includes saturated rings, partially unsaturated rings, and aromatic rings (i.e., heteroaromatic rings). Substituted heterocyclyls include, for example, heterocyclic rings substituted with any of the substituents disclosed herein including carbonyl groups. A non-limiting example of a carbonyl substituted heterocyclyl is:

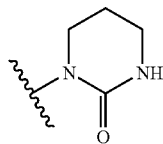

Examples of heterocycles include by way of example and not limitation pyridyl, dihydroypyridyl, tetrahydropyridyl (piperidyl), thiazolyl, tetrahydrothiophenyl, sulfur oxidized tetrahydrothiophenyl, pyrimidinyl, furanyl, thienyl, pyrrolyl, pyrazolyl, imidazolyl, tetrazolyl, benzofuranyl, thianaphthalenyl, indolyl, indolenyl, quinolinyl, isoquinolinyl, benzimidazolyl, piperidinyl, 4-piperidonyl, pyrrolidinyl, 2-pyrrolidonyl, pyrrolinyl, tetrahydrofuranyl, tetrahydroquinolinyl, tetrahydroisoquinolinyl, decahydroquinolinyl, octahydroisoquinolinyl, azocinyl, triazinyl, 6H-1,2,5-thiadiazinyl, 2H,6H-1,5,2-dithiazinyl, thienyl, thianthrenyl, pyranyl, isobenzofuranyl, chromenyl, xanthenyl, phenoxathinyl, 2H-pyrrolyl, isothiazolyl, isoxazolyl, pyrazinyl, pyridazinyl, indolizinyl, isoindolyl, 3H-indolyl, 1H-indazoly, purinyl, 4H-quinolizinyl, phthalazinyl, naphthyridinyl, quinoxalinyl, quinazolinyl, cinnolinyl, pteridinyl, 4aH-carbazolyl, carbazolyl, β-carbolinyl, phenanthridinyl, acridinyl, pyrimidinyl, phenanthrolinyl, phenazinyl, phenothiazinyl, furazanyl, phenoxazinyl, isochromanyl, chromanyl, imidazolidinyl, imidazolinyl, pyrazolidinyl, pyrazolinyl, piperazinyl, indolinyl, isoindolinyl, quinuclidinyl, morpholinyl, oxazolidinyl, benzotriazolyl, benzisoxazolyl, oxindolyl, benzoxazolinyl, isatinoyl, and bis-tetrahydrofuranyl:

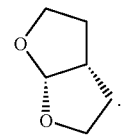

By way of example and not limitation, carbon bonded heterocycles are bonded at position 2, 3, 4, 5, or 6 of a pyridine, position 3, 4, 5, or 6 of a pyridazine, position 2, 4, 5, or 6 of a pyrimidine, position 2, 3, 5, or 6 of a pyrazine, position 2, 3, 4, or 5 of a furan, tetrahydrofuran, thiofuran, thiophene, pyrrole or tetrahydropyrrole, position 2, 4, or 5 of an oxazole, imidazole or thiazole, position 3, 4, or 5 of an isoxazole, pyrazole, or isothiazole, position 2 or 3 of an aziridine, position 2, 3, or 4 of an azetidine, position 2, 3, 4, 5, 6, 7, or 8 of a quinoline or position 1, 3, 4, 5, 6, 7, or 8 of an isoquinoline. Still more typically, carbon bonded heterocycles include 2-pyridyl, 3-pyridyl, 4-pyridyl, 5-pyridyl, 6-pyridyl, 3-pyridazinyl, 4-pyridazinyl, 5-pyridazinyl, 6-pyridazinyl, 2-pyrimidinyl, 4-pyrimidinyl, 5-pyrimidinyl, 6-pyrimidinyl, 2-pyrazinyl, 3-pyrazinyl, 5-pyrazinyl, 6-pyrazinyl, 2-thiazolyl, 4-thiazolyl, or 5-thiazolyl.

By way of example and not limitation, nitrogen bonded heterocycles are bonded at position 1 of an aziridine, azetidine, pyrrole, pyrrolidine, 2-pyrroline, 3-pyrroline, imidazole, imidazolidine, 2-imidazoline, 3-imidazoline, pyrazole, pyrazoline, 2-pyrazoline, 3-pyrazoline, piperidine, piperazine, indole, indoline, 1H-indazole, position 2 of a isoindole, or isoindoline, position 4 of a morpholine, and position 9 of a carbazole, or β-carboline. Still more typically, nitrogen bonded heterocycles include 1-aziridyl, 1-azetedyl, 1-pyrrolyl, 1-imidazolyl, 1-pyrazolyl, and 1-piperidinyl.

"Heterocyclylalkyl" refers to an acyclic alkyl radical in which one of the hydrogen atoms bonded to a carbon atom, typically a terminal or sp$^3$ carbon atom, is replaced with a heterocyclyl radical (i.e., a heterocyclyl-alkylene-moiety). Typical heterocyclyl alkyl groups include, but are not limited to heterocyclyl-CH$_2$—, 2-(heterocyclyl)ethan-1-yl, and the like, wherein the "heterocyclyl" portion includes any of the heterocyclyl groups described above, including those described in *Principles of Modern Heterocyclic Chemistry*. One skilled in the art will also understand that the heterocyclyl group can be attached to the alkyl portion of the heterocyclyl alkyl by means of a carbon-carbon bond or a carbon-heteroatom bond, with the proviso that the resulting group is chemically stable. The heterocyclyl alkyl group comprises 6 to 20 carbon atoms, e.g., the alkyl portion of the arylalkyl group is 1 to 6 carbon atoms and the heterocyclyl moiety is 5 to 14 carbon atoms. Examples of heterocyclylalkyls include by way of example and not limitation 5-membered sulfur, oxygen, and/or nitrogen containing heterocycles such as thiazolylmethyl, 2-thiazolylethan-1-yl, imidazolylmethyl, oxazolylmethyl, thiadiazolylmethyl, etc., 6-membered sulfur, oxygen, and/or nitrogen containing heterocycles such as piperidinylmethyl, piperazinylmethyl, morpholinylmethyl, pyridinylmethyl, pyridizylmethyl, pyrimidylmethyl, pyrazinylmethyl, etc.

"Heterocyclylalkenyl" refers to an acyclic alkenyl radical in which one of the hydrogen atoms bonded to a carbon atom, typically a terminal or sp$^3$ carbon atom, but also a sp$^2$ carbon atom, is replaced with a heterocyclyl radical (i.e., a heterocyclyl-alkenylene-moiety). The heterocyclyl portion of the heterocyclyl alkenyl group includes any of the heterocyclyl groups described herein, including those described in *Principles of Modern Heterocyclic Chemistry*, and the alkenyl portion of the heterocyclyl alkenyl group includes any of the alkenyl groups disclosed herein. One skilled in the art will also understand that the heterocyclyl group can be attached to the alkenyl portion of the heterocyclyl alkenyl by means of a carbon-carbon bond or a carbon-heteroatom bond, with the proviso that the resulting group is chemically stable. The heterocyclyl alkenyl group comprises 6 to 20 carbon atoms, e.g., the alkenyl portion of the heterocyclyl alkenyl group is 1 to 6 carbon atoms and the heterocyclyl moiety is to 14 carbon atoms.

"Heterocyclylalkynyl" refers to an acyclic alkynyl radical in which one of the hydrogen atoms bonded to a carbon atom, typically a terminal or sp$^3$ carbon atom, but also an sp carbon atom, is replaced with a heterocyclyl radical (i.e., a heterocyclyl-alkynylene-moiety). The heterocyclyl portion of the heterocyclyl alkynyl group includes any of the heterocyclyl groups described herein, including those described in *Principles of Modern Heterocyclic Chemistry*, and the alkynyl portion of the heterocyclyl alkynyl group includes any of the alkynyl groups disclosed herein. One skilled in the art will also understand that the heterocyclyl group can be attached to the alkynyl portion of the heterocyclyl alkynyl by means of a carbon-carbon bond or a carbon-heteroatom bond, with the proviso that the resulting group is chemically stable. The heterocyclyl alkynyl group comprises 6 to 20 carbon atoms, e.g., the alkynyl portion of the heterocyclyl alkynyl group is 1 to 6 carbon atoms and the heterocyclyl moiety is 5 to 14 carbon atoms.

"Heteroaryl" refers to an aromatic heterocyclyl having at least one heteroatom in the ring. Non-limiting examples of suitable heteroatoms which can be included in the aromatic ring include oxygen, sulfur, and nitrogen. Non-limiting examples of heteroaryl rings include all of those listed in the definition of "heterocyclyl", including pyridinyl, pyrrolyl, oxazolyl, indolyl, isoindolyl, purinyl, furanyl, thienyl, benzofuranyl, benzothiophenyl, carbazolyl, imidazolyl, thiazolyl, isoxazolyl, pyrazolyl, isothiazolyl, quinolyl, isoquinolyl, pyridazyl, pyrimidyl, pyrazyl, etc.

"Carbocycle" or "carbocyclyl" refers to a saturated (i.e., cycloalkyl), partially unsaturated (e.g., cycloakenyl, cycloalkadienyl, etc.) or aromatic ring having 3 to 7 carbon atoms as a monocycle, 7 to 12 carbon atoms as a bicycle, and up to about 20 carbon atoms as a polycycle. Monocyclic carbocycles have 3 to 6 ring atoms, still more typically 5 or 6 ring atoms. Bicyclic carbocycles have 7 to 12 ring atoms, e.g., arranged as a bicyclo [4,5], [5,5], [5,6] or [6,6] system, or 9 or 10 ring atoms arranged as a bicyclo [5,6] or [6,6] system, or spiro-fused rings. Non-limiting examples of monocyclic carbocycles include cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, and phenyl. Non-limiting examples of bicyclo carbocycles includes naphthyl.

"Arylheteroalkyl" refers to a heteroalkyl as defined herein, in which a hydrogen atom (which may be attached either to a carbon atom or a heteroatom) has been replaced with an aryl group as defined herein. The aryl groups may be bonded to a carbon atom of the heteroalkyl group, or to a heteroatom of the heteroalkyl group, provided that the resulting arylheteroalkyl group provides a chemically stable moiety. For example, an arylheteroalkyl group can have the general formulae -alkylene-O-aryl, -alkylene-O-alkylene-aryl, -alkylene-NH-aryl, -alkylene-NH-alkylene-aryl, -alkylene-S-aryl, -alkylene-S-alkylene-aryl, etc. In addition, any of the alkylene moieties in the general formulae above can be further substituted with any of the substituents defined or exemplified herein.

"Heteroarylalkyl" refers to an alkyl group, as defined herein, in which a hydrogen atom has been replaced with a heteroaryl group as defined herein. Non-limiting examples of heteroaryl alkyl include —CH$_2$-pyridinyl, —CH$_2$-pyrrolyl, —CH$_2$-oxazolyl, —CH$_2$-indolyl, —CH$_2$-isoindolyl, —CH$_2$-purinyl, —CH$_2$-furanyl, —CH$_2$-thienyl, —CH$_2$-benzofuranyl, —CH$_2$-benzothiophenyl, —CH$_2$-carbazolyl, —CH$_2$-imidazolyl, —CH$_2$-thiazolyl, —CH$_2$-isoxazolyl, —CH$_2$-pyrazolyl, —CH$_2$-isothiazolyl, —CH$_2$-quinolyl, —CH$_2$-isoquinolyl, —CH$_2$-pyridazyl, —CH$_2$-pyrimidyl, —CH$_2$-pyrazyl, —CH(CH$_3$)-pyridinyl, —CH(CH$_3$)-pyrrolyl, —CH(CH$_3$)-oxazolyl, —CH(CH$_3$)-indolyl, —CH(CH$_3$)-isoindolyl, —CH(CH$_3$)-purinyl, —CH(CH$_3$)-furanyl, —CH(CH$_3$)-thienyl, —CH(CH$_3$)-benzofuranyl, —CH(CH$_3$)-benzothiophenyl, —CH(CH$_3$)-carbazolyl, —CH(CH$_3$)-imidazolyl, —CH(CH$_3$)-thiazolyl, —CH(CH$_3$)-isoxazolyl, —CH(CH$_3$)-pyrazolyl, —CH(CH$_3$)-isothiazolyl, —CH(CH$_3$)-quinolyl, —CH(CH$_3$)-isoquinolyl, —CH(CH$_3$)-pyridazyl, —CH(CH$_3$)-pyrimidyl, —CH(CH$_3$)-pyrazyl, etc.

The term "optionally substituted" in reference to a particular moiety of the compound of Formula I, II, III, or IV (e.g., an optionally substituted aryl group) refers to a moiety having 0, 1, 2, or more substituents.

"Linker" or "link" means a chemical moiety comprising a covalent bond or a chain of atoms. Linkers include repeating units of alkyloxy (e.g. polyethyleneoxy, PEG, polymethyleneoxy) and alkylamino (e.g. polyethyleneamino, Jeffamine™); and diacid ester and amides including succinate, succinamide, diglycolate, malonate, and caproamide.

The terms such as "oxygen-linked", "nitrogen-linked", "carbon-linked", "sulfur-linked", or "phosphorous-linked" mean that if a bond between two moieties can be formed by using more than one type of atom in a moiety, then the bond formed between the moieties is through the atom specified. For example, a nitrogen-linked amino acid would be bonded through a nitrogen atom of the amino acid rather than through an oxygen or carbon atom of the amino acid.

Certain Y$^1$ and Y$^2$ alternatives are nitrogen oxides such as $^+$N(O)(R) or $^+$N(O)(OR). These nitrogen oxides, as shown here attached to a carbon atom, can also be represented by charge separated groups such as

or

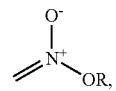

respectively, and are intended to be equivalent to the aforementioned representations for the purposes of describing this invention.

Unless otherwise specified, the carbon atoms of this invention are intended to have a valence of four. In some chemical structure representations where carbon atoms do not have a sufficient number of variables attached to produce a valence of four, the remaining carbon substituents needed to provide a valence of four should be assumed to be hydrogen. For example,

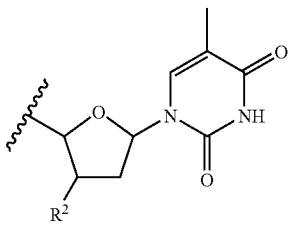

has the same meaning as

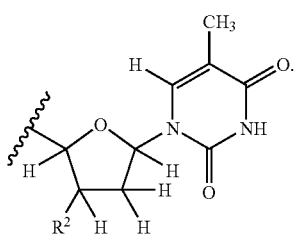

Whenever a compound described herein is substituted with more than one of the same designated group, e.g., "R" or "R¹", then it will be understood that the groups may be the same or different, i.e., each group is independently selected. Wavy lines indicate the site of covalent bond attachments to the adjoining substructures, groups, moieties, or atoms.

The term "chiral" refers to molecules which have the property of non-superimposability of the mirror image partner, while the term "achiral" refers to molecules which are superimposable on their mirror image partner.

The term "stereoisomers" refers to compounds which have identical chemical constitution, but differ with regard to the arrangement of the atoms or groups in space.

"Diastereomer" refers to a stereoisomer with two or more centers of chirality and whose molecules are not mirror images of one another. Diastereomers have different physical properties, e.g., melting points, boiling points, spectral properties, and reactivities. Mixtures of diastereomers may separate under high resolution analytical procedures such as electrophoresis and chromatography.

"Enantiomers" refer to two stereoisomers of a compound which are non-superimposable mirror images of one another.

Stereochemical definitions and conventions used herein generally follow S. P. Parker, Ed., *McGraw-Hill Dictionary of Chemical Terms* (1984) McGraw-Hill Book Company, New York; and Eliel, E. and Wilen, S., *Stereochemistry of Organic Compounds* (1994) John Wiley & Sons, Inc., New York. Many organic compounds exist in optically active forms, i.e., they have the ability to rotate the plane of plane-polarized light. In describing an optically active compound, the prefixes D and L or R and S are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process. The terms "racemic mixture" and "racemate" refer to an equimolar mixture of two enantiomeric species, devoid of optical activity.

"Nucleobase" or "nucleoside base" means any nitrogen-containing heterocyclic moiety capable of forming Watson-Crick hydrogen bonds in pairing with a complementary nucleobase or nucleobase analog, e.g. a purine, a 7-deazapurine, or a pyrimidine. Typical nucleobases are the naturally-occurring nucleobases: adenine, guanine, cytosine, uracil, thymine, and analogs of the naturally-occurring nucleobases, e.g. 7-deazaadenine, substituted 7-deazapurines such as 7-alkynyl, 7-cyano, 7-carboxamido, 7-deazaguanine, 7-deaza-8-azaguanine, 7-deaza-8-azaadenine, inosine, nebularine, nitropyrrole, nitroindole, 2-aminopurine, 2-amino-6-chloropurine, 2,6-diaminopurine, hypoxanthine, pseudouridine, pseudocytosine, pseudoisocytosine, 5-propynylcytosine, isocytosine, isoguanine, 7-deazaguanine, 2-thiopyrimidine, 6-thioguanine, 4-thiothymine, 4-thiouracil, $O^6$-methylguanine, $N^6$-methyladenine, $O^4$-methylthymine, 5,6-dihydrothymine, 5,6-dihydrouracil, 4-methylindole, pyrazine bases including 3-oxo-2-carboxamidopyrazine, 5-fluoro-3-oxo-2-carboxamidopyrazine, 6-fluoro-3-oxo-2-carboxamidopyrazine, pyrazolo[3,4-D]pyrimidines (U.S. Pat. Nos. 6,143,877 and 6,127,121; WO 01/38584), and ethenoadenine (Fasman (1989) in *Practical Handbook of Biochemistry and Molecular Biology*, pp. 385-394, CRC Press, Boca Raton, Fla.).

The invention provides compounds of Formula I, II, III or IV wherein $B^1$, $B^2$, or $B^3$ is a nucleoside base. The compounds may include any nucleoside base, provided the final compound possesses useful therapeutic (e.g. anti-viral) properties. Additional nucleoside bases that can be incorporated into the compounds of this invention are disclosed in United States Patent Application Publication Number 2004/0147464, United States Patent Application Publication Number 2005/0215511, International Patent Application Publication Number WO 03/061385, International Patent Application Publication Number WO 03/062257, International Patent Application Publication Number WO 03/072757, International Patent Application Publication Number WO 03/073989, International Patent Application Publication Number WO 2005/021568, International Patent Application Publication Number WO 2005/123087, International Patent Application Publication Number WO 2006/002231, and International Patent Application Publication Number WO 2006/000922.

In one embodiment, compounds of this invention are of Formula I:

Formula I

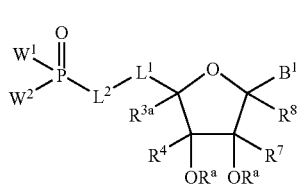

wherein all variables are defined as above for Formula I. In one aspect of this embodiment, each $R^a$ is H. In another aspect of this embodiment, $R^{3a}$ is $CH_2R^9$. In another aspect of this embodiment, $R^{3a}$ is alkenyl or substituted alkenyl. In another aspect of this embodiment, $R^{3a}$ is alkynyl or substituted alkynyl. In another aspect of this embodiment, each $R^{10}$ is H and $L^1$ is O.

In preferred embodiment of Formula I, $B^1$ is

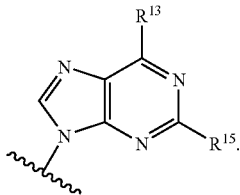

In one aspect of this embodiment, each $R^{10}$ is H, $L^1$ is O, and each $R^a$ is H. In another aspect of this embodiment, $R^{3a}$ is $CH_2R^9$. In another aspect of this embodiment, $R^{3a}$ is alkenyl or substituted alkenyl. In another aspect of this embodiment, $R^{3a}$ is alkynyl or substituted alkynyl. In another aspect of this embodiment, $R^{3a}$ is $CH_2R^9$ and $R^9$ is not H.

In another preferred embodiment of Formula I, $B^1$ is

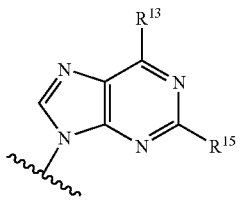

wherein each $R^{10}$ is H, $L^1$ is O, and each $R^a$ is H. In one aspect of this embodiment, $R^{3a}$ is $CH_2R^9$. In another aspect of this embodiment, $R^{3a}$ is alkenyl or substituted alkenyl. In another aspect of this embodiment, $R^{3a}$ is alkynyl or substituted alkynyl. In another aspect of this embodiment, $R^{3a}$ is $CH_2R^9$ and $R^9$ is not H. In another aspect of this embodiment, $R^{13}$ is $NH_2$. In another aspect of this embodiment, $R^{13}$ is $NH_2$ and $R^{15}$ is H. In another aspect of this embodiment, $R^{13}$ is OH. In another aspect of this embodiment, $R^{13}$ is OH and $R^{15}$ is $NH_2$. In another aspect of this embodiment, each $W^1$ and $W^2$ is independently $Y^2$—$R^x$ wherein each $Y^2$ is independently —O— or —N(R)— and $R^x$ is not H. In another aspect of this embodiment, each $W^1$ and $W^2$ is independently $Y^2$—$R^x$ wherein each $Y^2$ is —O— and $R^x$ is not H. In another aspect of this embodiment, each $W^1$ and $W^2$ is independently $Y^2$—$R^x$ wherein each $Y^2$ is independently —N(R)— and $R^x$ is not H.

In another preferred embodiment of Formula I, $B^1$ is

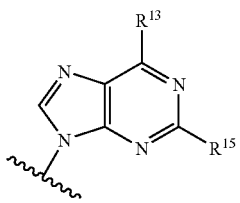

wherein $R^{13}$ is $NH_2$, each $R^{10}$ is H, $L^1$ is O, and each $R^a$ is H. In one aspect of this embodiment, $R^{3a}$ is $CH_2R^9$. In another aspect of this embodiment, $R^{3a}$ is alkenyl or substituted alkenyl. In another aspect of this embodiment, $R^{3a}$ is alkynyl or substituted alkynyl. In another aspect of this embodiment, $R^{3a}$ is $CH_2R^9$ and $R^9$ is not H. In another aspect of this embodiment, $R^{3a}$ is methyl. In another aspect of this embodiment, $R^{3a}$ is ethylenyl. In another aspect of this embodiment, $R^{3a}$ is ethynyl. In another aspect of this embodiment, each $W^1$ and $W^2$ is independently $Y^2$—$R^x$ wherein each $Y^2$ is independently —O— or —N(R)— and $R^x$ is not H. In another aspect of this embodiment, each $W^1$ and $W^2$ is independently $Y^2$—$R^x$ wherein each $Y^2$ is —O— and $R^x$ is not H. In another aspect of this embodiment, each $W^1$ and $W^2$ is independently $Y^2$—$R^x$ wherein each $Y^2$ is independently —N(R)— and $R^x$ is not H.

In another preferred embodiment of Formula I, $B^1$ is

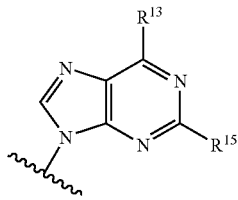

wherein $R^{13}$ is OH, each $R^{10}$ is H, $L^1$ is O, and each $R^a$ is H. In one aspect of this embodiment, $R^{3a}$ is $CH_2R^9$. In another aspect of this embodiment, $R^{3a}$ is alkenyl or substituted alkenyl. In another aspect of this embodiment, $R^{3a}$ is alkynyl or substituted alkynyl. In another aspect of this embodiment, $R^{3a}$ is $CH_2R^9$ and $R^9$ is not H. In another aspect of this embodiment, $R^{3a}$ is methyl. In another aspect of this embodiment, $R^{3a}$ is ethylenyl. In another aspect of this embodiment, $R^{3a}$ is ethynyl. In another aspect of this embodiment, each $W^1$ and $W^2$ is independently $Y^2$—$R^x$ wherein each $Y^2$ is independently —O— or —N(R)— and $R^x$ is not H. In another aspect of this embodiment, each $W^1$ and $W^2$ is independently $Y^2$—$R^x$ wherein each $Y^2$ is —O— and $R^x$ is not H. In another aspect of this embodiment, each $W^1$ and $W^2$ is independently $Y^2$—$R^x$ wherein each $Y^2$ is independently —N(R)— and $R^x$ is not H.

In another preferred embodiment of Formula I, $B^1$ is

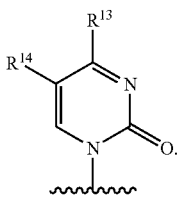

In one aspect of this embodiment, $R^{10}$ is H, $L^1$ is O, and each $R^a$ is H. In another aspect of this embodiment, $R^{3a}$ is $CH_2R^9$. In another aspect of this embodiment, $R^{3a}$ is alkenyl or substituted alkenyl. In another aspect of this embodiment, $R^{3a}$ is alkynyl or substituted alkynyl. In another aspect of this embodiment, $R^{3a}$ is $CH_2R^9$ and $R^9$ is not H.

In another preferred embodiment of Formula I, $B^1$ is

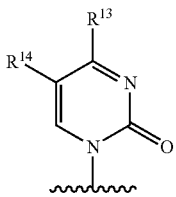

wherein each $R^{10}$ is H, $L^1$ is O, and each $R^a$ is H. In one aspect of this embodiment, $R^{3a}$ is $CH_2R^9$. In another aspect of this embodiment, $R^{3a}$ is alkenyl or substituted alkenyl. In another aspect of this embodiment, $R^{3a}$ is alkynyl or substituted alkynyl. In another aspect of this embodiment, $R^{3a}$ is $CH_2R^9$ and $R^9$ is not H. In another aspect of this embodiment, $R^{13}$ is $NH_2$. In another aspect of this embodiment, $R^{13}$ is $NH_2$ and $R^{14}$ is H. In another aspect of this embodiment, $R^{13}$ is OH. In another aspect of this embodiment, $R^{13}$ is OH and $R^{14}$ is H. In another aspect of this embodiment, each $W^1$ and $W^2$ is independently $Y^2$—$R^x$ wherein each $Y^2$ is —O— and $R^x$ is not H. In another aspect of this embodiment, each $W^1$ and $W^2$ is independently $Y^2$—$R^x$ wherein each $Y^2$ is independently —N(R)— and $R^x$ is not H.

In another preferred embodiment of Formula I, $B^1$ is

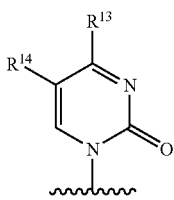

wherein $R^{13}$ is $NH_2$, $R^{14}$ is H, each $R^{10}$ is H, $L^1$ is O, and each $R^a$ is H. In one aspect of this embodiment, $R^{3a}$ is $CH_2R^9$. In another aspect of this embodiment, $R^{3a}$ is alkenyl or substituted alkenyl. In another aspect of this embodiment, $R^{3a}$ is alkynyl or substituted alkynyl. In another aspect of this embodiment, $R^{3a}$ is $CH_2R^9$ and $R^9$ is not H. In another aspect of this embodiment, $R^{3a}$ is methyl. In another aspect of this embodiment, $R^{3a}$ is ethylenyl. In another aspect of this embodiment, $R^{3a}$ is ethynyl. In another aspect of this embodiment, each $W^1$ and $W^2$ is independently $Y^2$—$R^x$ wherein each $Y^2$ is independently —O— or —N(R)— and $R^x$ is not H. In another aspect of this embodiment, each $W^1$ and $W^2$ is independently $Y^2$—$R^x$ wherein each $Y^2$ is —O— and $R^x$ is not H. In another aspect of this embodiment, each $W^1$ and $W^2$ is independently $Y^2$—$R^x$ wherein each $Y^2$ is independently —N(R)— and $R^x$ is not H.

In another preferred embodiment of Formula I, $B^1$ is

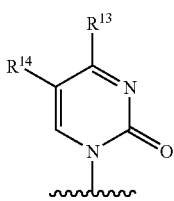

wherein $R^{13}$ is OH, $R^{14}$ is H, each $R^{10}$ is H, $L^1$ is O, and each $R^a$ is H. In one aspect of this embodiment, $R^{3a}$ is $CH_2R^9$. In another aspect of this embodiment, $R^{3a}$ is alkenyl or substituted alkenyl. In another aspect of this embodiment, $R^{3a}$ is alkynyl or substituted alkynyl. In another aspect of this embodiment, $R^{3a}$ is $CH_2R^9$ and $R^9$ is not H. In another aspect of this embodiment, $R^{3a}$ is methyl. In another aspect of this embodiment, $R^{3a}$ is ethylenyl. In another aspect of this embodiment, $R^{3a}$ is ethynyl. In another aspect of this embodiment, each $W^1$ and $W^2$ is independently $Y^2$—$R^x$ wherein each $Y^2$ is independently —O— or —N(R)— and $R^x$ is not H. In another aspect of this embodiment, each $W^1$ and $W^2$ is independently $Y^2$—$R^x$ wherein each $Y^2$ is —O— and $R^x$ is not H. In another aspect of this embodiment, each $W^1$ and $W^2$ is independently $Y^2$—$R^x$ wherein each $Y^2$ is independently —N(R)— and $R^x$ is not H.

In another preferred embodiment of Formula I, $B^1$ is

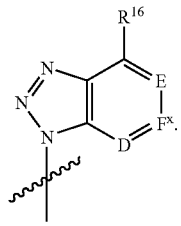

In one aspect of this embodiment, each $R^{10}$ is H, $L^1$ is O, and each $R^a$ is H. In another aspect of this embodiment, $R^{3a}$ is $CH_2R^9$. In another aspect of this embodiment, $R^{3a}$ is alkenyl or substituted alkenyl. In another aspect of this embodiment, $R^{3a}$ is alkynyl or substituted alkynyl. In another aspect of this embodiment, $R^{3a}$ is $CH_2R^9$ and $R^9$ is not H.

In another preferred embodiment of Formula I, $B^1$ is

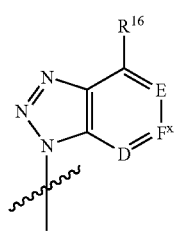

wherein each $R^{10}$ is H, $L^1$ is O, and each $R^a$ is H. In one aspect of this embodiment, $R^{3a}$ is $CH_2R^9$. In another aspect of this embodiment, $R^{3a}$ is alkenyl or substituted alkenyl. In another aspect of this embodiment, $R^{3a}$ is alkynyl or substituted alkynyl. In another aspect of this embodiment, $R^{3a}$ is $CH_2R^9$ and $R^9$ is not H. In another aspect of this embodiment, each E and D is >N. In another aspect of this embodiment, each E and D is >N and $F^x$ is >C—$R^{25}$.

In another preferred embodiment of Formula I, $B^1$ is

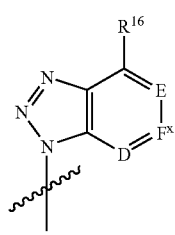

wherein each E and D is >N, each $R^{10}$ is H, $L^1$ is O, and each $R^a$ is H. In one aspect of this embodiment, $R^{3a}$ is $CH_2R^9$. In another aspect of this embodiment, $R^{3a}$ is alkenyl or substituted alkenyl. In another aspect of this embodiment, $R^{3a}$ is alkynyl or substituted alkynyl. In another aspect of this embodiment, $R^{3a}$ is $CH_2R^9$ and $R^9$ is not H. In another aspect of this embodiment, $F^x$ is >C—$R^{25}$.

In another preferred embodiment of Formula I, B$^1$ is

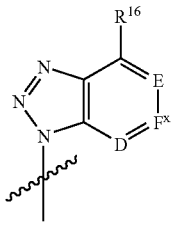

wherein each E and D is >N, F$^x$ is >C—R$^{25}$, each R$^{10}$ is H, L$^1$ is O, and each R$^a$ is H. In one aspect of this embodiment, R$^{3a}$ is CH$_2$R$^9$. In another aspect of this embodiment, R$^{3a}$ is alkenyl or substituted alkenyl. In another aspect of this embodiment, R$^{3a}$ is alkynyl or substituted alkynyl. In another aspect of this embodiment, R$^{3a}$ is CH$_2$R$^9$ and R$^9$ is not H. In another aspect of this embodiment, R$^{3a}$ is methyl. In another aspect of this embodiment, R$^{3a}$ is ethylenyl. In another aspect of this embodiment, R$^{3a}$ is ethynyl. In another aspect of this embodiment, each W$^1$ and W$^2$ is independently Y$^2$—R$^x$ wherein each Y$^2$ is independently —O— or —N(R)— and R$^x$ is not H. In another aspect of this embodiment, each W$^1$ and W$^2$ is independently Y$^2$—R$^x$ wherein each Y$^2$ is —O— and R$^x$ is not H. In another aspect of this embodiment, each W$^1$ and W$^2$ is independently Y$^2$—R$^x$ wherein each Y$^2$ is independently —N(R)— and R$^x$ is not H.

In another preferred embodiment of Formula I, B$^1$ is

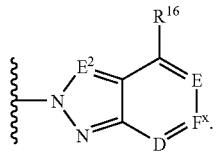

In one aspect of this embodiment, each R$^{10}$ is H, L$^1$ is O, and each R$^a$ is H. In another aspect of this embodiment, R$^{3a}$ is CH$_2$R$^9$. In another aspect of this embodiment, R$^{3a}$ is alkenyl or substituted alkenyl. In another aspect of this embodiment, R$^{3a}$ is alkynyl or substituted alkynyl. In another aspect of this embodiment, R$^{3a}$ is CH$_2$R$^9$ and R$^9$ is not H. In another aspect of this embodiment, each W$^1$ and W$^2$ is independently Y$^2$—R$^x$ wherein each Y$^2$ is independently —O— or —N(R)— and R$^x$ is not H. In another aspect of this embodiment, each W$^1$ and W$^2$ is independently Y$^2$—R$^x$ wherein each Y$^2$ is —O— and R$^x$ is not H. In another aspect of this embodiment, each W$^1$ and W$^2$ is independently Y$^2$—R$^x$ wherein each Y$^2$ is independently —N(R)— and R$^x$ is not H.

In one embodiment, compounds of this invention are of Formula II:

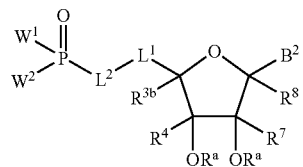

Formula II wherein all variables are defined as above for Formula II. In one aspect of this embodiment, each R$^a$ is H. In another aspect of this embodiment, R$^{3b}$ is CH$_2$R$^9$ wherein R$^9$ is not H. In another aspect of this embodiment, R$^{3b}$ is alkenyl or substituted alkenyl. In another aspect of this embodiment, R$^{3b}$ is alkynyl or substituted alkynyl. In another aspect of this embodiment, each R$^{10}$ is H and L$^1$ is O.

In a preferred embodiment of Formula II, B$^2$ is

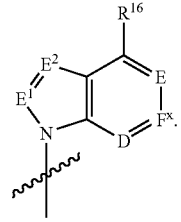

In one aspect of this embodiment, each R$^{10}$ is H, L$^1$ is O, and each R$^a$ is H. In another aspect of this embodiment, R$^{3b}$ is CH$_2$R$^9$ wherein R$^9$ is not H. In another aspect of this embodiment, R$^{3b}$ is alkenyl or substituted alkenyl. In another aspect of this embodiment, R$^{3b}$ is alkynyl or substituted alkynyl.

In another preferred embodiment of Formula II, B$^2$ is

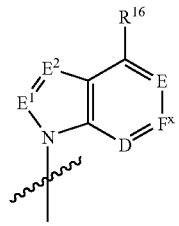

wherein each R$^{10}$ is H, L$^1$ is O, and each R$^a$ is H. In one aspect of this embodiment, R$^{3b}$ is CH$_2$R$^9$ wherein R$^9$ is not H. In another aspect of this embodiment, R$^{3b}$ is alkenyl or substituted alkenyl. In another aspect of this embodiment, R$^{3b}$ is alkynyl or substituted alkynyl. In another aspect of this embodiment, each E$^2$, E, and D is >N. In another aspect of this embodiment, each E$^2$, E, and D is >N and F$^x$ is >C—R$^{25}$. In another aspect of this embodiment, each E$^2$, E, and D is >N and each E$^1$ and F$^x$ is independently >C—R$^{25}$. In another aspect of this embodiment, each E$^1$, E$^2$, E, and D is >N and F$^x$ is >C—R$^{25}$. In another aspect of this embodiment, each E$^1$, E, and D is >N and each E$^2$ and F$^x$ is independently >C—R$^{25}$. In another aspect of this embodiment, each E and D is >N; each E$^1$ and F$^x$ is independently >C—R$^{25}$; and E$^2$ is >C—R$^{30}$.

In another preferred embodiment of Formula II, B$^2$ is

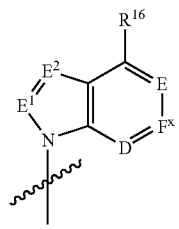

wherein each E$^2$, E, and D is >N, each R$^{10}$ is H, L$^1$ is O, and each R$^a$ is H. In one aspect of this embodiment, R$^{3b}$ is CH$_2$R$^9$ wherein R$^9$ is not H. In another aspect of this embodiment, $R^{3b}$ is alkenyl or substituted alkenyl. In another aspect of this embodiment, $R^{3b}$ is alkynyl or substituted alkynyl. In another aspect of this invention, $F^x$ is >C—$R^{25}$. In another aspect of this invention $E^1$ is >N. In another aspect of this invention, $E^1$ is >C—$R^{25}$.

In another preferred embodiment of Formula II, $B^2$ is

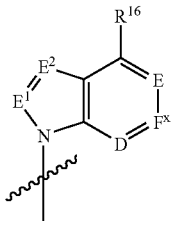

wherein each $E^2$, E, and D is >N, $F^x$ is >C—$R^{25}$, each $R^{10}$ is H, $L^1$ is O, and each $R^a$ is H. In one aspect of this embodiment, $R^{3b}$ is $CH_2R^9$ wherein $R^9$ is not H. In another aspect of this embodiment, $R^{3b}$ is alkenyl or substituted alkenyl. In another aspect of this embodiment, $R^{3b}$ is alkynyl or substituted alkynyl. In another aspect of this embodiment, $E^1$ is >N. In another aspect of this embodiment, $E^1$ is >C—$R^{25}$.

In another preferred embodiment of Formula II, $B^2$ is

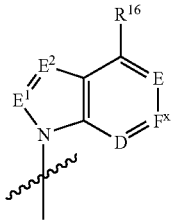

wherein each $E^2$, E, and D is >N, each $E^1$ and $F^x$ is independently >C—$R^{25}$, each $R^{10}$ is H, $L^1$ is O, and each $R^a$ is H. In one aspect of this embodiment, $R^{3b}$ is $CH_2R^9$ wherein $R^9$ is not H. In another aspect of this embodiment, $R^{3b}$ is alkenyl or substituted alkenyl. In another aspect of this embodiment, $R^{3b}$ is alkynyl or substituted alkynyl. In another aspect of this embodiment, each $R^{25}$ is H. In another aspect of this embodiment, $R^{16}$ is $N(R^{20})(R^{21})$. In another aspect of this embodiment, $R^{16}$ is $N(R^{20})(R^{21})$ wherein $R^{20}$ is $OR^{17a}$. In another aspect of this embodiment, $R^{16}$ is $OR^{17a}$. In another aspect of this embodiment, $R^{16}$ is $NH_2$ and each $R^{25}$ is H. In another aspect of this embodiment, $R^{16}$ is $OR^{17a}$ and $F^x$ is >C—$NR^{26}R^{27}$. In another aspect of this embodiment, $R^{16}$ is OH, $E^1$ is >C—$R^{25}$ wherein $R^{25}$ is H, and $F^x$ is >C—$NR^{26}R^{27}$ wherein each $R^{26}$ and $R^{27}$ is H. In another aspect of this embodiment, each $W^1$ and $W^2$ is independently $Y^2$—$R^x$ wherein each $Y^2$ is independently —O— or —N(R)— and $R^x$ is not H. In another aspect of this embodiment, each $W^1$ and $W^2$ is independently $Y^2$—$R^x$ wherein each $Y^2$ is —O— and $R^x$ is not H. In another aspect of this embodiment, each $W^1$ and $W^2$ is independently $Y^2$—$R^x$ wherein each $Y^2$ is independently —N(R)— and $R^x$ is not H.

In another preferred embodiment of Formula II, $B^2$ is

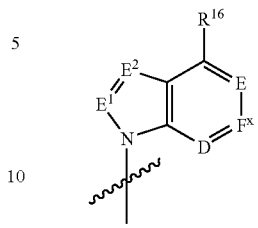

wherein each $E^1$, $E^2$, E, and D is >N, $F^x$ is >C—$R^{25}$, each $R^{10}$ is H, $L^1$ is O, and each $R^a$ is H. In one aspect of this embodiment, $R^{3b}$ is $CH_2R^9$ wherein $R^9$ is not H. In another aspect of this embodiment, $R^{3b}$ is alkenyl or substituted alkenyl. In another aspect of this embodiment, $R^{3b}$ is alkynyl or substituted alkynyl. In another aspect of this embodiment, $R^{16}$ is $N(R^{20})(R^{21})$. In another aspect of this embodiment, $R^{16}$ is $N(R^{20})(R^{21})$ wherein $R^{20}$ is $OR^{17a}$. In another aspect of this embodiment, $R^{16}$ is $OR^{17a}$. In another aspect of this embodiment, $R^{16}$ is $NH_2$ and each $R^{25}$ is H. In another aspect of this embodiment, $R^{16}$ is $OR^{17a}$ and $F^x$ is >C—$NR^{26}R^{27}$. In another aspect of this embodiment, $R^{16}$ is $NH_2$ and each $R^{25}$ is H. In another aspect of this embodiment, $R^{16}$ is $OR^{17a}$ and $F^x$ is >C—$NR^{26}R^{27}$. In another aspect of this embodiment, $R^{16}$ is OH and $F^x$ is >C—$NR^{26}R^{27}$ wherein each $R^{26}$ and $R^{27}$ is H. In another aspect of this embodiment, each $W^1$ and $W^2$ is independently $Y^2$—$R^x$ wherein each $Y^2$ is independently —O— or —N(R)— and $R^x$ is not H. In another aspect of this embodiment, each $W^1$ and $W^2$ is independently $Y^2$—$R^x$ wherein each $Y^2$ is —O— and $R^x$ is not H. In another aspect of this embodiment, each $W^1$ and $W^2$ is independently $Y^2$—$R^x$ wherein each $Y^2$ is independently —N(R)— and $R^x$ is not H.

In another preferred embodiment of Formula II, $B^2$ is

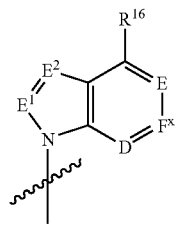

wherein each $E^1$, E, and D is >N, each $E^2$ and $F^x$ is independently >C—$R^{25}$, each $R^{10}$ is H, $L^1$ is O, and each $R^a$ is H. In one aspect of this embodiment, $R^{3b}$ is $CH_2R^9$ wherein $R^9$ is not H. In another aspect of this embodiment, $R^{3b}$ is alkenyl or substituted alkenyl. In another aspect of this embodiment, $R^{3b}$ is alkynyl or substituted alkynyl. In another aspect of this embodiment, each $W^1$ and $W^2$ is independently $Y^2$—$R^x$ wherein each $Y^2$ is independently —O— or —N(R)— and $R^x$ is not H. In another aspect of this embodiment, each $W^1$ and $W^2$ is independently $Y^2$—$R^x$ wherein each $Y^2$ is —O— and $R^x$ is not H. In another aspect of this embodiment, each $W^1$ and $W^2$ is independently $Y^2$—$R^x$ wherein each $Y^2$ is independently —N(R)— and $R^x$ is not H.

In another preferred embodiment of Formula II, B² is

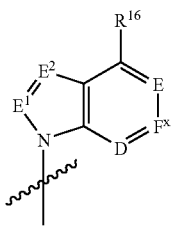

wherein each E and D is >N, each E¹ and F$^x$ is independently >C—R²⁵, E² is >C—R³⁰, each R¹⁰ is H, L¹ is O, and each R$^a$ is H. In one aspect of this embodiment, R$^{3b}$ is CH₂R⁹ wherein R⁹ is not H. In another aspect of this embodiment, R$^{3b}$ is alkenyl or substituted alkenyl. In another aspect of this embodiment, R$^{3b}$ is alkynyl or substituted alkynyl. In another aspect of this embodiment, R¹⁶ is N(R²⁰)(R²¹). In another aspect of this embodiment, R¹⁶ is N(R²⁰)(R²¹) wherein R²⁰ is OR$^{17a}$. In another aspect of this embodiment, R¹⁶ is OR$^{17a}$. In another aspect of this embodiment, R¹⁶ is NH₂ and each R²⁵ is H. In another aspect of this embodiment, R¹⁶ is OR$^{17a}$ and F$^x$ is >C—NR²⁶R²⁷. In another aspect of this embodiment, R¹⁶ is NH₂ and each R²⁵ is H. In another aspect of this embodiment, R¹⁶ is OR$^{17a}$ and F$^x$ is >C—NR²⁶R²⁷. In another aspect of this embodiment, R¹⁶ is OH and F$^x$ is >C—NR²⁶R²⁷ wherein each R²⁶ and R²⁷ is H. In another aspect of this embodiment, R³⁰ is ethynyl, 2-trimethylsilyl-ethynyl, 2-(2-pyridyl)ethynyl, 2-(4-pyridyl)ethynyl, 2-(4-methoxy)ethynyl, 2-(aminocarbonyl)ethynyl, 3,3-diethoxypropyn-1-yl, 2-(dimethylaminocarbonyl)ethynyl, 2-(N-amino(aminocarbonyl)ethynyl, 2-carboxyethynyl, 2-ethoxycarbonylethynyl, 2-methoxycarbonylethynyl, 2-phenylethynyl, 2-(4-fluorophenyl)ethynyl, 2-(4-methylphenyl)ethynyl, vinyl, 2-methoxyvinyl, formyl, —CH═N—NH₂, —CH═NOH, 1,1-diisopropoxymethyl, or —B(OH)₂. In another aspect of this embodiment, each W¹ and W² is independently Y²—R$^x$ wherein each Y² is independently —O— or —N(R)— and R$^x$ is not H. In another aspect of this embodiment, each W¹ and W² is independently Y²—R$^x$ wherein each Y² is —O— and R$^x$ is not H. In another aspect of this embodiment, each W¹ and W² is independently Y²—R$^x$ wherein each Y² is independently —N(R)— and R$^x$ is not H.

In another preferred embodiment of Formula II, B² is

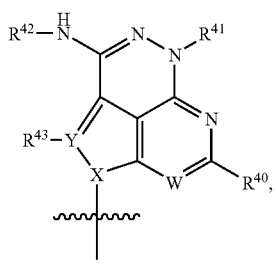

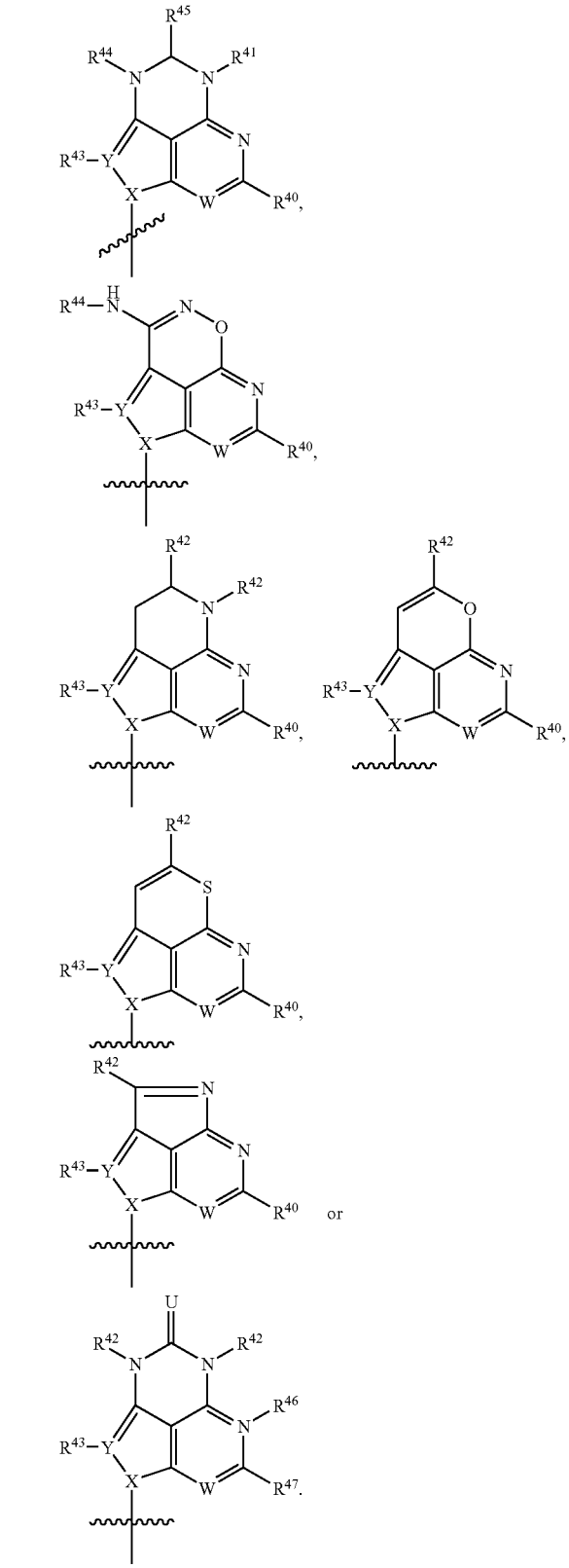

In one aspect of this embodiment, each R¹⁰ is H, L¹ is O, and each R$^a$ is H. In another aspect of this embodiment, R$^{3b}$ is CH$_2$R$^9$ wherein R$^9$ is not H. In another aspect of this embodiment, R$^{3b}$ is alkenyl or substituted alkenyl. In another aspect of this embodiment, R$^{3b}$ is alkynyl or substituted alkynyl. In another aspect of this embodiment, each W$^1$ and W$^2$ is independently Y$^2$—R$^x$ wherein each Y$^2$ is independently —O— or —N(R)— and R$^x$ is not H. In another aspect of this embodiment, each W$^1$ and W$^2$ is independently Y$^2$—R$^x$ wherein each Y$^2$ is —O— and R$^x$ is not H. In another aspect of this embodiment, each W$^1$ and W$^2$ is independently Y$^2$—R$^x$ wherein each Y$^2$ is independently —N(R)— and R$^x$ is not H.

In another preferred embodiment of Formula II, B$^2$ is

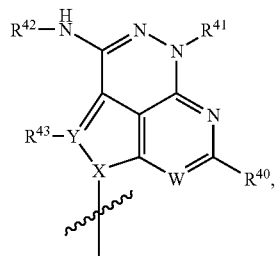

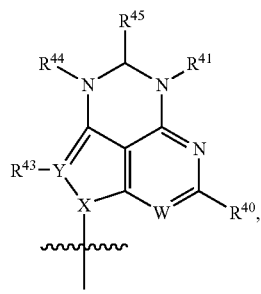

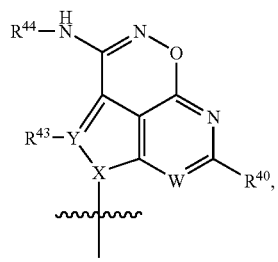

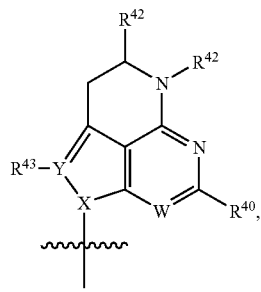

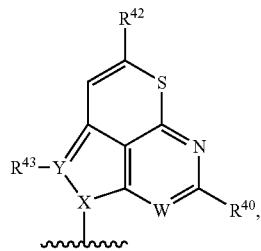

-continued

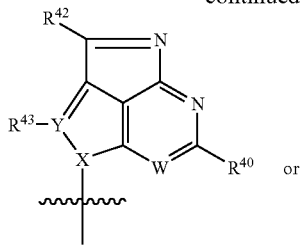

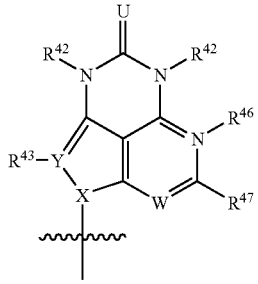

wherein each R$^{10}$ is H, L$^1$ is O, and each R$^a$ is H. In another aspect of this embodiment, R$^{3b}$ is CH$_2$R$^9$ wherein R$^9$ is not H. In another aspect of this embodiment, R$^{3b}$ is alkenyl or substituted alkenyl. In another aspect of this embodiment, R$^{3b}$ is alkynyl or substituted alkynyl. In another aspect of this embodiment, each W$^1$ and W$^2$ is independently Y$^2$—R$^x$ wherein each Y$^2$ is independently —O— or —N(R)— and R$^x$ is not H. In another aspect of this embodiment, each W$^1$ and W$^2$ is independently Y$^2$—R$^x$ wherein each Y$^2$ is —O— and R$^x$ is not H. In another aspect of this embodiment, each W$^1$ and W$^2$ is independently Y$^2$—R$^x$ wherein each Y$^2$ is independently —N(R)— and R$^x$ is not H.

In another preferred embodiment of Formula II, B$^2$ is

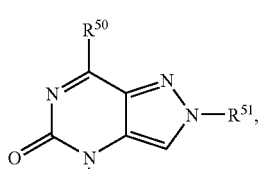 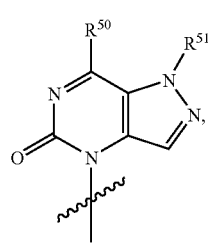

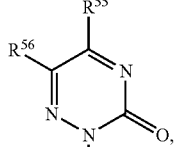

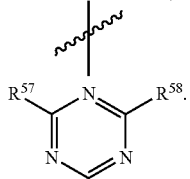 or

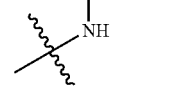

In one aspect of this embodiment, each $R^{10}$ is H, $L^1$ is O, and each $R^a$ is H. In another aspect of this embodiment, $R^{3b}$ is $CH_2R^9$ wherein $R^9$ is not H. In another aspect of this embodiment, $R^{3b}$ is alkenyl or substituted alkenyl. In another aspect of this embodiment, $R^{3b}$ is alkynyl or substituted alkynyl.

In another preferred embodiment of Formula II, $B^2$ is

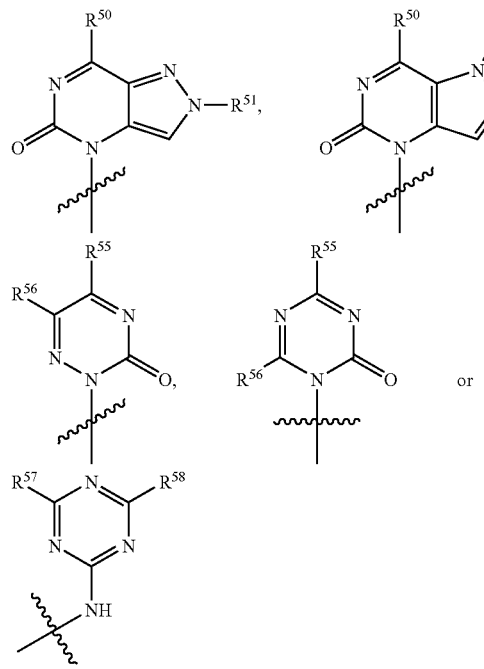

wherein each $R^{10}$ is H, $L^1$ is O, and each $R^a$ is H. In another aspect of this embodiment, $R^{3b}$ is $CH_2R^9$ wherein $R^9$ is not H. In another aspect of this embodiment, $R^{3b}$ is alkenyl or substituted alkenyl. In another aspect of this embodiment, $R^{3b}$ is alkynyl or substituted alkynyl. In another aspect of this embodiment, each $W^1$ and $W^2$ is independently $Y^2$—$R^x$ wherein each $Y^2$ is independently —O— or —N(R)— and $R^x$ is not H. In another aspect of this embodiment, each $W^1$ and $W^2$ is independently $Y^2$—$R^x$ wherein each $Y^2$ is —O— and $R^x$ is not H. In another aspect of this embodiment, each $W^1$ and $W^2$ is independently $Y^2$—$R^x$ wherein each $Y^2$ is independently —N(R)— and $R^x$ is not H.

In another preferred embodiment of Formula II, $B^2$ is

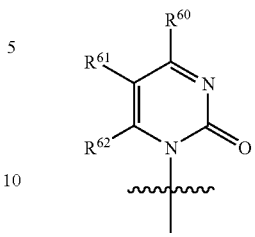

wherein each $R^{10}$ is H, $L^1$ is O, and each $R^a$ is H. In another aspect of this embodiment, $R^{3b}$ is $CH_2R^9$ wherein $R^9$ is not H. In another aspect of this embodiment, $R^{3b}$ is alkenyl or substituted alkenyl. In another aspect of this embodiment, $R^{3b}$ is alkynyl or substituted alkynyl. In another aspect of this embodiment, $R^{60}$ is $NR^{6b}R^{6c}$. In another aspect of this embodiment, $R^{60}$ is $NR^{6b}R^{6c}$ and $R^{62}$ is H. In another aspect of this embodiment, $R^{60}$ is $OR^{6b}$. In another aspect of this embodiment, $R^{60}$ is $OR^{6b}$ and $R^{62}$ is H. In another aspect of this embodiment, each $R^{61}$ and $R^{62}$ is H and $R^{60}$ is $NH_2$. In another aspect of this embodiment, each $R^{61}$ and $R^{62}$ is H and $R^{60}$ is OH. In another aspect of this embodiment, $R^{60}$ is not $NR^{6b}R^{6c}$ or $OR^{6b}$. In another aspect of this embodiment, each $W^1$ and $W^2$ is independently $Y^2$—$R^x$ wherein each $Y^2$ is independently —O— or —N(R)— and $R^x$ is not H. In another aspect of this embodiment, each $W^1$ and $W^2$ is independently $Y^2$—$R^x$ wherein each $Y^2$ is —O— and $R^x$ is not H. In another aspect of this embodiment, each $W^1$ and $W^2$ is independently $Y^2$—$R^x$ wherein each $Y^2$ is independently —N(R)— and $R^x$ is not H.

In another preferred embodiment of Formula II, $B^2$ is

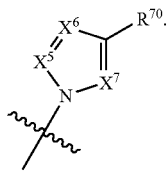

In one aspect of this embodiment, each $R^{10}$ is H, $L^1$ is O, and each $R^a$ is H. In another aspect of this embodiment, $R^{3b}$ is $CH_2R^9$ wherein $R^9$ is not H. In another aspect of this embodiment, $R^{3b}$ is alkenyl or substituted alkenyl. In another aspect of this embodiment, $R^{3b}$ is alkynyl or substituted alkynyl.

In another preferred embodiment of Formula II, $B^2$ is

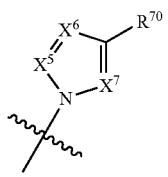

wherein each $R^{10}$ is H, $L^1$ is O, and each $R^a$ is H. In another aspect of this embodiment, $R^{3b}$ is $CH_2R^9$ wherein $R^9$ is not H. In another aspect of this embodiment, $R^{3b}$ is alkenyl or substituted alkenyl. In another aspect of this embodiment, $R^{3b}$ is alkynyl or substituted alkynyl. In another aspect of this embodiment, $X^5$ is CH and each $X^6$ and $X^7$ is N. In another aspect of this embodiment, $X^5$ is CH, each $X^6$ and $X^7$ is N, and $R^{70}$ is —C(O)$NR^{7b}R^{7c}$. In another aspect of this embodiment, each $W^1$ and $W^2$ is independently $Y^2$—$R^x$ wherein each $Y^2$ is independently —O— or —N(R)— and $R^x$ is not H. In another aspect of this embodiment, each $W^1$ and $W^2$ is independently $Y^2$—$R^x$ wherein each $Y^2$ is —O— and $R^x$ is not H. In another aspect of this embodiment, each $W^1$ and $W^2$ is independently $Y^2$—$R^x$ wherein each $Y^2$ is independently —N(R)— and $R^x$ is not H.

In another preferred embodiment of Formula II, $B^2$ is

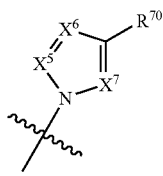

wherein $X^5$ is CH, each $X^6$ and $X^7$ is N, $R^{70}$ is —C(O)$NR^{7b}R^{7c}$, each $R^{10}$ is H, $L^1$ is O, and each $R^a$ is H. In another aspect of this embodiment, $R^{3b}$ is $CH_2R^9$ wherein $R^9$ is not H. In another aspect of this embodiment, $R^{3b}$ is alkenyl or substituted alkenyl. In another aspect of this embodiment, $R^{3b}$ is alkynyl or substituted alkynyl. In another aspect of this embodiment, each $R^{7b}$ and $R^{7c}$ is H. In another aspect of this embodiment, each $W^1$ and $W^2$ is independently $Y^2$—$R^x$ wherein each $Y^2$ is independently —O— or —N(R)— and $R^x$ is not H. In another aspect of this embodiment, each $W^1$ and $W^2$ is independently $Y^2$—$R^x$ wherein each $Y^2$ is —O— and $R^x$ is not H. In another aspect of this embodiment, each $W^1$ and $W^2$ is independently $Y^2$—$R^x$ wherein each $Y^2$ is independently —N(R)— and $R^x$ is not H.

In another preferred embodiment of Formula II, $B^2$ is

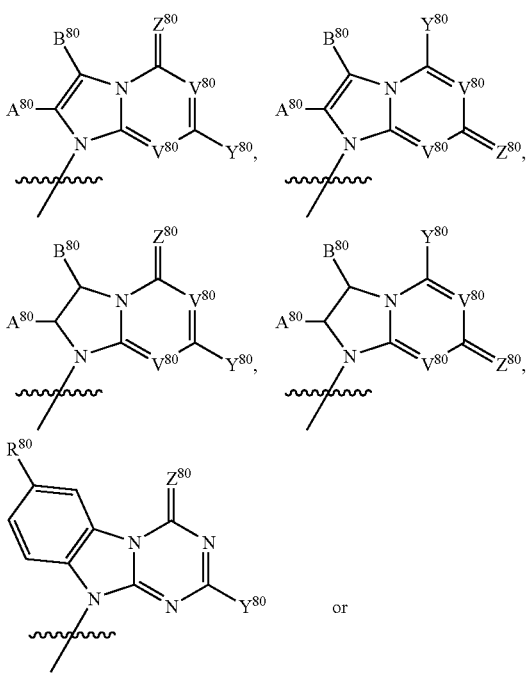

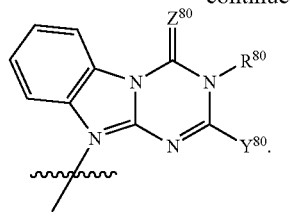

In one aspect of this embodiment, each $R^{10}$ is H, $L^1$ is O, and each $R^a$ is H. In another aspect of this embodiment, $R^{3b}$ is $CH_2R^9$ wherein $R^9$ is not H. In another aspect of this embodiment, $R^{3b}$ is alkenyl or substituted alkenyl. In another aspect of this embodiment, $R^{3b}$ is alkynyl or substituted alkynyl.

In another preferred embodiment of Formula II, $B^2$ is

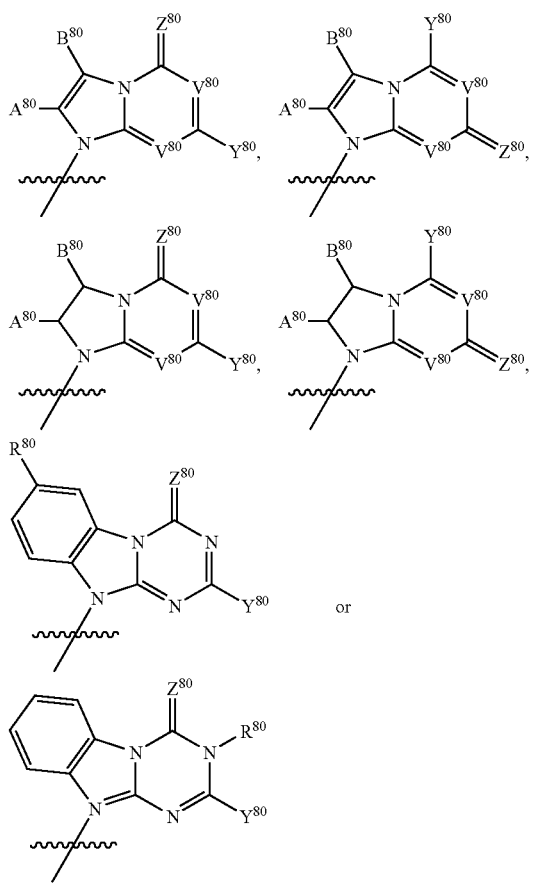

wherein each $R^{10}$ is H, $L^1$ is O, and each $R^a$ is H. In another aspect of this embodiment, $R^{3b}$ is $CH_2R^9$ wherein $R^9$ is not H. In another aspect of this embodiment, $R^{3b}$ is alkenyl or substituted alkenyl. In another aspect of this embodiment, $R^{3b}$ is alkynyl or substituted alkynyl. In another aspect of this embodiment, each $W^1$ and $W^2$ is independently $Y^2$—$R^x$ wherein each $Y^2$ is independently —O— or —N(R)— and $R^x$ is not H. In another aspect of this embodiment, each $W^1$ and $W^2$ is independently $Y^2$—$R^x$ wherein each $Y^2$ is —O— and $R^x$ is not H. In another aspect of this embodiment, each $W^1$ and $W^2$ is independently $Y^2$—$R^x$ wherein each $Y^2$ is independently —N(R)— and $R^x$ is not H.

In another preferred embodiment of Formula II, $B^2$ is

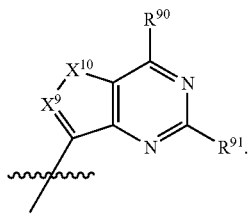

In one aspect of this embodiment, each $R^{10}$ is H, $L^1$ is O, and each $R^a$ is H. In another aspect of this embodiment, $R^{3b}$ is $CH_2R^9$ wherein $R^9$ is not H. In another aspect of this embodiment, $R^{3b}$ is alkenyl or substituted alkenyl. In another aspect of this embodiment, $R^{3b}$ is alkynyl or substituted alkynyl.

In another preferred embodiment of Formula II, $B^2$ is

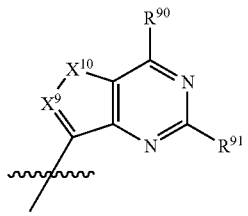

wherein each $R^{10}$ is H, $L^1$ is O, and each $R^a$ is H. In another aspect of this embodiment, $R^{3b}$ is $CH_2R^9$ wherein $R^9$ is not H. In another aspect of this embodiment, $R^{3b}$ is alkenyl or substituted alkenyl. In another aspect of this embodiment, $R^{3b}$ is alkynyl or substituted alkynyl. In another aspect of this embodiment, $X^9$ is $CR^{90a}$. In another aspect of this embodiment, $X^{10}$ is O, S, or $NR^{91a}$. In another aspect of this embodiment, $X^9$ is CH and $X^{10}$ is O, S, or $NR^{91a}$. In another aspect of this embodiment, each $W^1$ and $W^2$ is independently $Y^2$—$R^x$ wherein each $Y^2$ is independently —O— or —N(R)— and $R^x$ is not H. In another aspect of this embodiment, each $W^1$ and $W^2$ is independently $Y^2$—$R^x$ wherein each $Y^2$ is —O— and $R^x$ is not H. In another aspect of this embodiment, each $W^1$ and $W^2$ is independently $Y^2$—$R^x$ wherein each $Y^2$ is independently —N(R)— and $R^x$ is not H.

In another preferred embodiment of Formula II, $B^2$ is

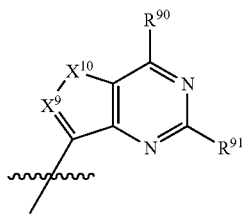

wherein $X^9$ is CH, $X^{10}$ is O, S, or $NR^{91a}$, each $R^{10}$ is H, $L^1$ is O, and each $R^a$ is H. In another aspect of this embodiment, $R^{3b}$ is $CH_2R^9$ wherein $R^9$ is not H. In another aspect of this embodiment, $R^{3b}$ is alkenyl or substituted alkenyl. In another aspect of this embodiment, $R^{3b}$ is alkynyl or substituted alkynyl. In another aspect of this embodiment, $X^{10}$ is O. In another aspect of this embodiment, $X^{10}$ is S. In another aspect of this embodiment, $X^{10}$ is $NR^{91a}$. In another aspect of this embodiment, each $W^1$ and $W^2$ is independently $Y^2$—$R^x$ wherein each $Y^2$ is independently —O— or —N(R)— and $R^x$ is not H. In another aspect of this embodiment, each $W^1$ and $W^2$ is independently $Y^2$—$R^x$ wherein each $Y^2$ is —O— and $R^x$ is not H. In another aspect of this embodiment, each $W^1$ and $W^2$ is independently $Y^2$—$R^x$ wherein each $Y^2$ is independently —N(R)— and $R^x$ is not H.

In another preferred embodiment of Formula II, $B^2$ is

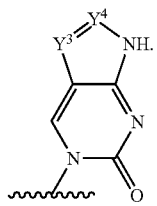

In one aspect of this embodiment, each $R^{10}$ is H, $L^1$ is O, and each $R^a$ is H. In another aspect of this embodiment, $R^{3b}$ is $CH_2R^9$ wherein $R^9$ is not H. In another aspect of this embodiment, $R^{3b}$ is alkenyl or substituted alkenyl. In another aspect of this embodiment, $R^{3b}$ is alkynyl or substituted alkynyl. In another aspect of this embodiment, each $W^1$ and $W^2$ is independently $Y^2$—$R^x$ wherein each $Y^2$ is independently —O— or —N(R)— and $R^x$ is not H. In another aspect of this embodiment, each $W^1$ and $W^2$ is independently $Y^2$—$R^x$ wherein each $Y^2$ is —O— and $R^x$ is not H. In another aspect of this embodiment, each $W^1$ and $W^2$ is independently $Y^2$—$R^x$ wherein each $Y^2$ is independently —N(R)— and $R^x$ is not H.

In another preferred embodiment of Formula II, $B^2$ is

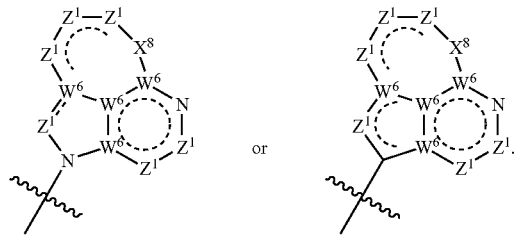

In one aspect of this embodiment, each $R^{10}$ is H, $L^1$ is O, and each $R^a$ is H. In another aspect of this embodiment, $R^{3b}$ is $CH_2R^9$ wherein $R^9$ is not H. In another aspect of this embodiment, $R^{3b}$ is alkenyl or substituted alkenyl. In another aspect of this embodiment, $R^{3b}$ is alkynyl or substituted alkynyl.

In another preferred embodiment of Formula II, $B^2$ is

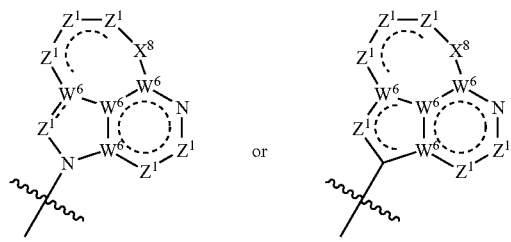

wherein each $R^{10}$ is H, $L^1$ is O, and each $R^a$ is H. In another aspect of this embodiment, $R^{3b}$ is $CH_2R^9$ wherein $R^9$ is not H. In another aspect of this embodiment, $R^{3b}$ is alkenyl or substituted alkenyl. In another aspect of this embodiment, $R^{3b}$ is alkynyl or substituted alkynyl. In another aspect of this embodiment, each $W^1$ and $W^2$ is independently $Y^2$—$R^x$ wherein each $Y^2$ is independently —O— or —N(R)— and $R^x$ is not H. In another aspect of this embodiment, each $W^1$ and $W^2$ is independently $Y^2$—$R^x$ wherein each $Y^2$ is —O— and $R^x$ is not H. In another aspect of this embodiment, each $W^1$ and $W^2$ is independently $Y^2$—$R^x$ wherein each $Y^2$ is independently —N(R)— and $R^x$ is not H. In another aspect of this embodiment, a specific value for $B^2$ is

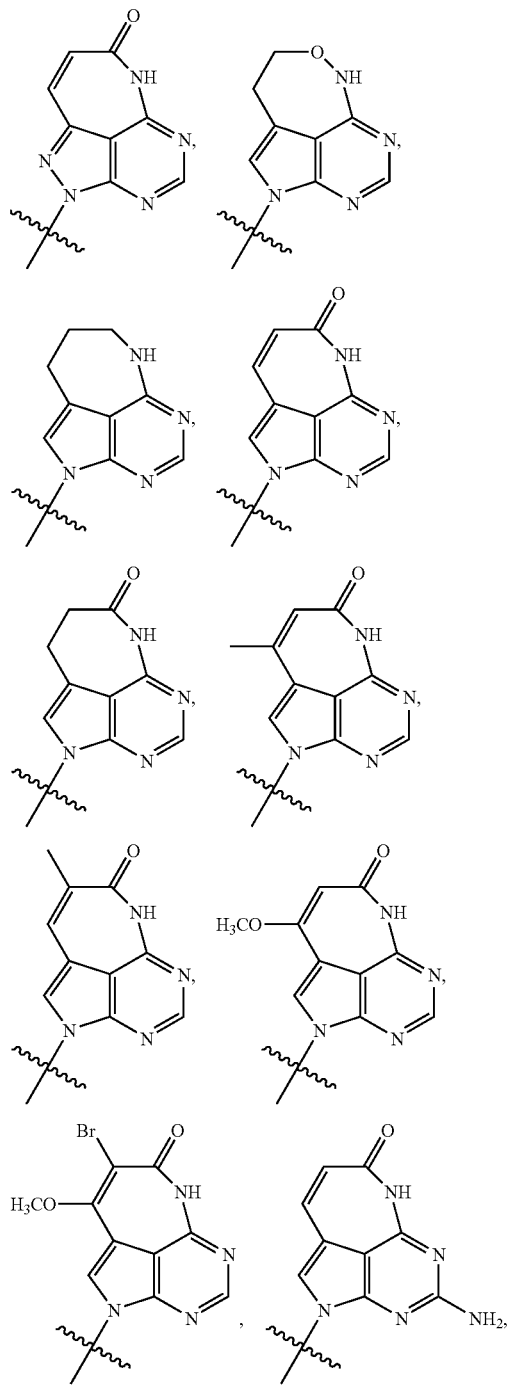

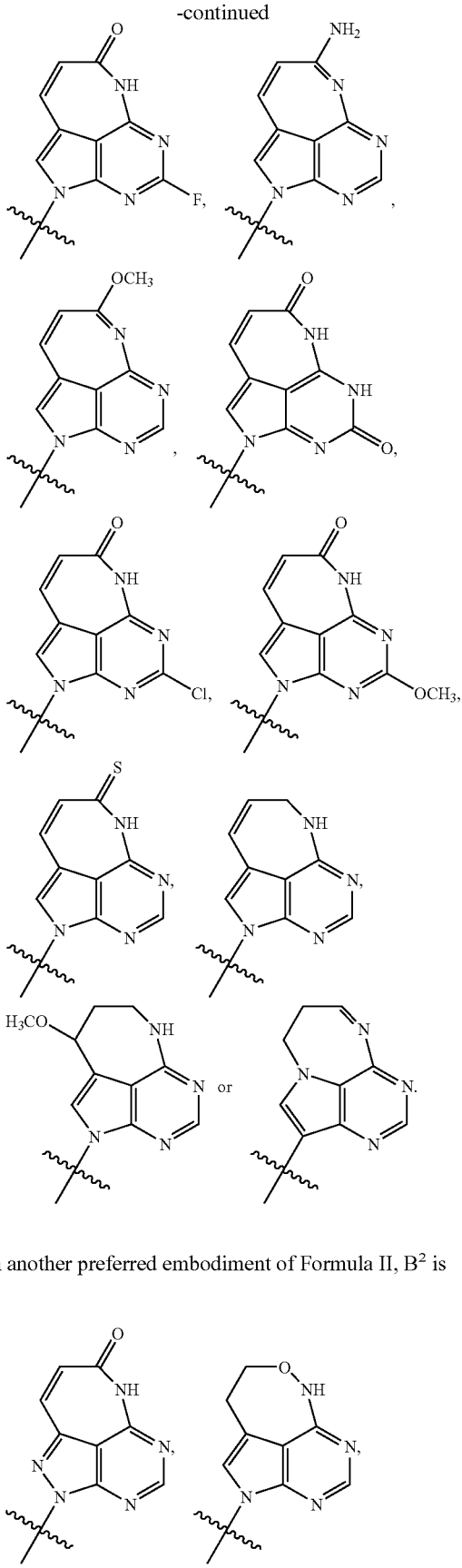

In another preferred embodiment of Formula II, $B^2$ is

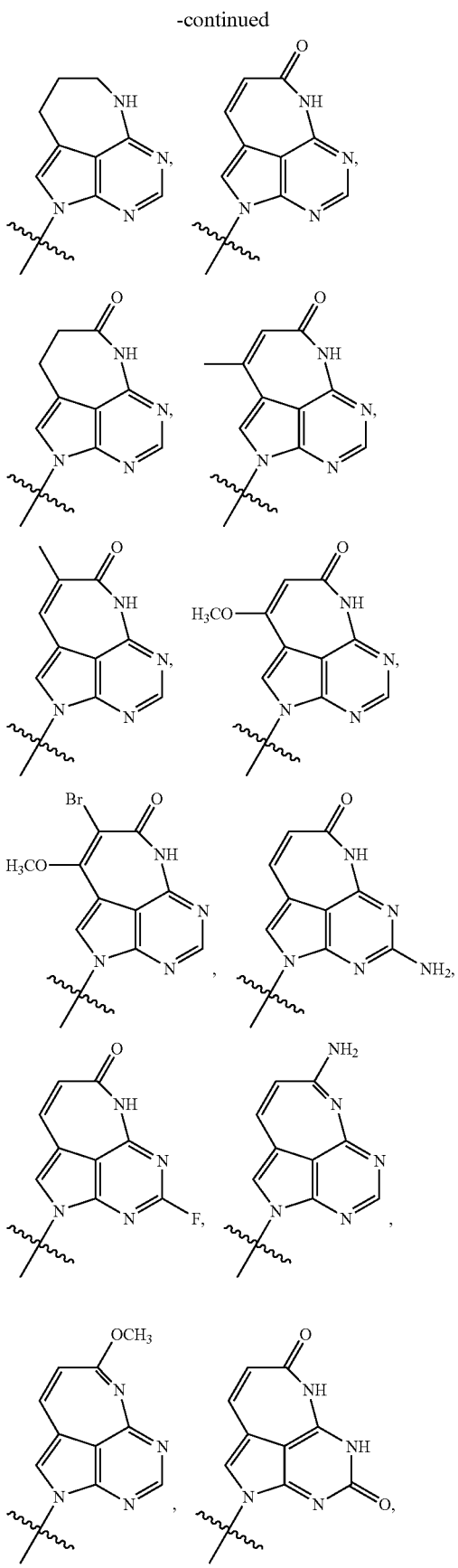

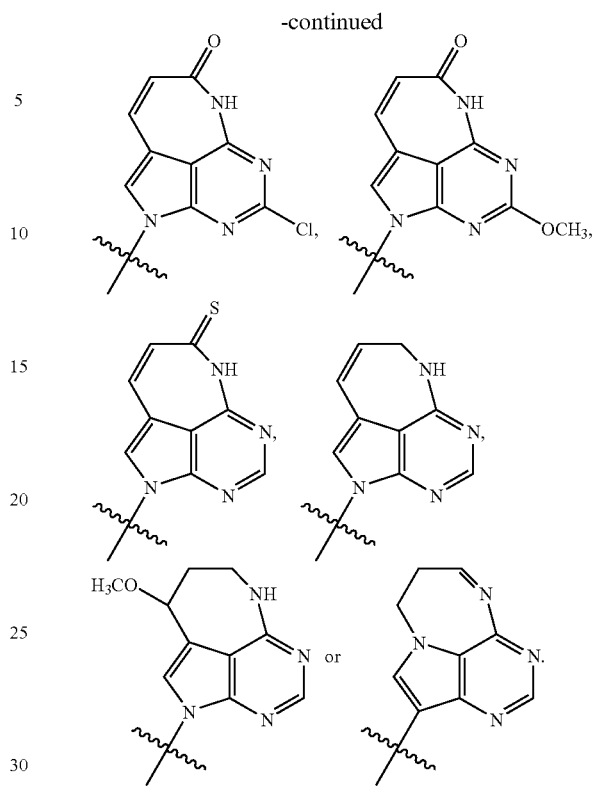

wherein each $R^{10}$ is H, $L^1$ is O, and each $R^a$ is H. In another aspect of this embodiment, $R^{3b}$ is $CH_2R^9$ wherein $R^9$ is not H. In another aspect of this embodiment, $R^{3b}$ is alkenyl or substituted alkenyl. In another aspect of this embodiment, $R^{3b}$ is alkynyl or substituted alkynyl. In another aspect of this embodiment, each $W^1$ and $W^2$ is independently $Y^2$—$R^x$ wherein each $Y^2$ is independently —O— or —N(R)— and $R^x$ is not H. In another aspect of this embodiment, each $W^1$ and $W^2$ is independently $Y^2$—$R^x$ wherein each $Y^2$ is —O— and $R^x$ is not H. In another aspect of this embodiment, each $W^1$ and $W^2$ is independently $Y^2$—$R^x$ wherein each $Y^2$ is independently —N(R)— and $R^x$ is not H.

In one embodiment, compounds of this invention are of Formula III:

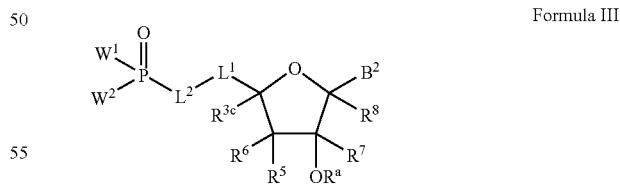

Formula III wherein all variables are defined as above for Formula III. In one aspect of this embodiment, $R^a$ is H. In another aspect of this embodiment, each $R^{10}$ is H and $L^1$ is O. In another aspect of this embodiment, $R^{3c}$ is $CH_2R^9$ wherein $R^9$ is not H, OH, or F. In another aspect of this embodiment, $R^{3c}$ is alkenyl or substituted alkenyl. In another aspect of this embodiment, $R^{3c}$ is alkynyl or substituted alkynyl. In another aspect of this embodiment, each $R^5$ and $R^6$ is H. In another aspect of this embodiment, $R^5$ and $R^6$, taken together, are =$CR^cR^d$.

In a preferred embodiment of Formula III, $B^2$ is

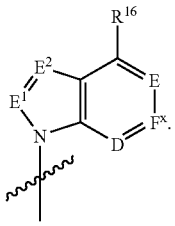

In one aspect of this embodiment, each $R^{10}$ is H, $L^1$ is O, and each $R^a$ is H. In another aspect of this embodiment, $R^{3c}$ is $CH_2R^9$ wherein $R^9$ is not H, OH, or F. In another aspect of this embodiment, $R^{3c}$ is alkenyl or substituted alkenyl. In another aspect of this embodiment, $R^{3c}$ is alkynyl or substituted alkynyl. In another aspect of this embodiment, each $R^5$ and $R^6$ is H. In another aspect of this embodiment, $R^5$ and $R^6$, taken together, are $=CR^cR^d$.

In another preferred embodiment of Formula III, $B^2$ is

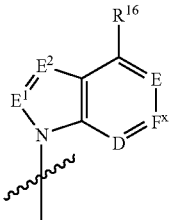

wherein each $R^{10}$ is H, $L^1$ is O, and each $R^a$ is H. In another aspect of this embodiment, $R^{3c}$ is $CH_2R^9$ wherein $R^9$ is not H, OH, or F. In another aspect of this embodiment, $R^{3c}$ is alkenyl or substituted alkenyl. In another aspect of this embodiment, $R^{3c}$ is alkynyl or substituted alkynyl. In another aspect of this embodiment, each $R^5$ and $R^6$ is H. In another aspect of this embodiment, $R^5$ and $R^6$, taken together, are $=CR^cR^d$. In another aspect of this embodiment, each $E^2$, E, and D is >N. In another aspect of this embodiment, each $E^2$, E, and D is >N and $F^x$ is >C—$R^{25}$. In another aspect of this embodiment, each $E^2$, E, and D is >N and each $E^1$ and $F^x$ is independently >C—$R^{25}$. In another aspect of this embodiment, each $E^1$, $E^2$, E, and D is >N and F is >C—$R^{25}$. In another aspect of this embodiment, each $E^1$, E, and D is >N and each $E^2$ and $F^x$ is independently >C—$R^{25}$. In another aspect of this embodiment, each E and D is >N; each $E^1$ and $F^x$ is independently >C—$R^{25}$; and $E^2$ is >C—$R^{30}$.

In another preferred embodiment of Formula III, $B^2$ is

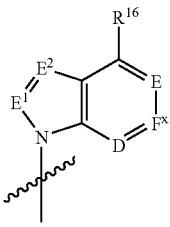

wherein each $E^2$, E, and D is >N, each $R^{10}$ is H, $L^1$ is O, and each $R^a$ is H. In another aspect of this embodiment, $R^{3c}$ is $CH_2R^9$ wherein $R^9$ is not H, OH, or F. In another aspect of this embodiment, $R^{3c}$ is alkenyl or substituted alkenyl. In another aspect of this embodiment, $R^{3c}$ is alkynyl or substituted alkynyl. In another aspect of this embodiment, each $R^5$ and $R^6$ is H. In another aspect of this embodiment, $R^5$ and $R^6$, taken together, are $=CR^cR^d$. In another aspect of this invention, $F^x$ is >C—$R^{25}$. In another aspect of this invention $E^1$ is >N. In another aspect of this invention, $E^1$ is >C—$R^{25}$.

In another preferred embodiment of Formula III, $B^2$ is

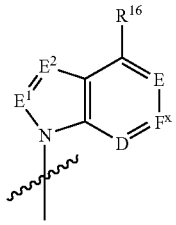

wherein each $E^2$, E, and D is >N, $F^x$ is >C—$R^{25}$, each $R^{10}$ is H, $L^1$ is O, and each $R^a$ is H. In another aspect of this embodiment, $R^{3c}$ is $CH_2R^9$ wherein $R^9$ is not H, OH, or F. In another aspect of this embodiment, $R^{3c}$ is alkenyl or substituted alkenyl. In another aspect of this embodiment, $R^{3c}$ is alkynyl or substituted alkynyl. In another aspect of this embodiment, each $R^5$ and $R^6$ is H. In another aspect of this embodiment, $R^5$ and $R^6$, taken together, are $=CR^cR^d$. In another aspect of this embodiment, $E^1$ is >N. In another aspect of this embodiment, $E^1$ is >C—$R^{25}$.

In another preferred embodiment of Formula III, $B^2$ is

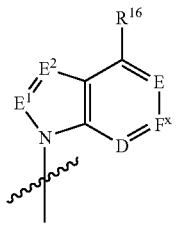

wherein each $E^2$, E, and D is >N, each $E^1$ and $F^x$ is independently >C—$R^{25}$, each $R^{10}$ is H, $L^1$ is O, and each $R^a$ is H. In another aspect of this embodiment, $R^{3c}$ is $CH_2R^9$ wherein $R^9$ is not H, OH, or F. In another aspect of this embodiment, $R^{3c}$ is alkenyl or substituted alkenyl. In another aspect of this embodiment, $R^{3c}$ is alkynyl or substituted alkynyl. In another aspect of this embodiment, each $R^5$ and $R^6$ is H. In another aspect of this embodiment, $R^5$ and $R^6$, taken together, are $=CR^cR^d$. In another aspect of this embodiment, each $R^{25}$ is H. In another aspect of this embodiment, $R^{16}$ is $N(R^{20})(R^{21})$. In another aspect of this embodiment, $R^{16}$ is $N(R^{20})(R^{21})$ wherein $R^{20}$ is $OR^{17a}$. In another aspect of this embodiment, $R^{16}$ is $OR^{17a}$. In another aspect of this embodiment, $R^{16}$ is $NH_2$ and each $R^{25}$ is H. In another aspect of this embodiment, $R^{16}$ is $OR^{17a}$ and $F^x$ is >C—$NR^{26}R^{27}$. In another aspect of this embodiment, $R^{16}$ is OH, $E^1$ is >C—$R^{25}$ wherein $R^{25}$ is H, and $F^x$ is >C—$NR^{26}R^{27}$ wherein each $R^{26}$ and $R^{27}$ is H. In another aspect of this embodiment, each $W^1$ and $W^2$ is independently $Y^2$—$R^x$ wherein each $Y^2$ is independently —O— or —N(R)— and $R^x$ is not H. In another aspect of this embodiment, each $W^1$ and $W^2$ is independently $Y^2$—$R^x$ wherein each $Y^2$ is —O— and $R^x$ is not H. In another aspect of this embodiment, each $W^1$ and $W^2$ is independently $Y^2$—$R^x$ wherein each $Y^2$ is independently —N(R)— and $R^x$ is not H.

In another preferred embodiment of Formula III, $B^2$ is

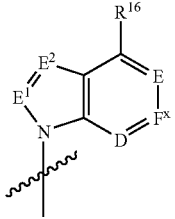

wherein each $E^1$, $E^2$, E, and D is >N, $F^x$ is >C—$R^{25}$, each $R^{10}$ is H, $L^1$ is O, and each $R^a$ is H. In another aspect of this embodiment, $R^{3c}$ is $CH_2R^9$ wherein $R^9$ is not H, OH, or F. In another aspect of this embodiment, $R^{3c}$ is alkenyl or substituted alkenyl. In another aspect of this embodiment, $R^{3c}$ is alkynyl or substituted alkynyl. In another aspect of this embodiment, each $R^5$ and $R^6$ is H. In another aspect of this embodiment, $R^5$ and $R^6$, taken together, are =$CR^cR^d$. In another aspect of this embodiment, $R^{16}$ is $N(R^{20})(R^{21})$. In another aspect of this embodiment, $R^{16}$ is $N(R^{20})(R^{21})$ wherein $R^{20}$ is $OR^{17a}$. In another aspect of this embodiment, $R^{16}$ is $OR^{17a}$. In another aspect of this embodiment, $R^{16}$ is $NH_2$ and each $R^{25}$ is H. In another aspect of this embodiment, $R^{16}$ is $OR^{17a}$ and $F^x$ is >C—$NR^{26}R^{27}$. In another aspect of this embodiment, $R^{16}$ is $NH_2$ and each $R^{25}$ is H. In another aspect of this embodiment, $R^{16}$ is $OR^{17a}$ and $F^x$ is >C—$NR^{26}R^{27}$. In another aspect of this embodiment, $R^{16}$ is OH and $F^x$ is >C—$NR^{26}R^{27}$ wherein each $R^{26}$ and $R^{27}$ is H. In another aspect of this embodiment, each $W^1$ and $W^2$ is independently $Y^2$—$R^x$ wherein each $Y^2$ is independently —O— or —N(R)— and $R^x$ is not H. In another aspect of this embodiment, each $W^1$ and $W^2$ is independently $Y^2$—$R^x$ wherein each $Y^2$ is —O— and $R^x$ is not H. In another aspect of this embodiment, each $W^1$ and $W^2$ is independently $Y^2$—$R^x$ wherein each $Y^2$ is independently —N(R)— and $R^x$ is not H.

In another preferred embodiment of Formula III, $B^2$ is

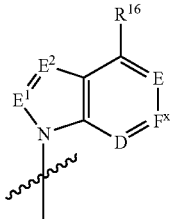

wherein each $E^1$, E, and D is >N, each $E^2$ and $F^x$ is independently >C—$R^{25}$, each $R^{10}$ is H, $L^1$ is O, and each $R^a$ is H. In another aspect of this embodiment, $R^{3c}$ is $CH_2R^9$ wherein $R^9$ is not H, OH, or F. In another aspect of this embodiment, $R^{3c}$ is alkenyl or substituted alkenyl. In another aspect of this embodiment, $R^{3c}$ is alkynyl or substituted alkynyl. In another aspect of this embodiment, each $R^5$ and $R^6$ is H. In another aspect of this embodiment, $R^5$ and $R^6$, taken together, are =$CR^cR^d$. In another aspect of this embodiment, each $W^1$ and $W^2$ is independently $Y^2$—$R^x$ wherein each $Y^2$ is independently —O— or —N(R)— and $R^x$ is not H. In another aspect of this embodiment, each $W^1$ and $W^2$ is independently $Y^2$—$R^x$ wherein each $Y^2$ is —O— and $R^x$ is not H. In another aspect of this embodiment, each $W^1$ and $W^2$ is independently $Y^2$—$R^x$ wherein each $Y^2$ is independently —N(R)— and $R^x$ is not H.

In another preferred embodiment of Formula III, $B^2$ is

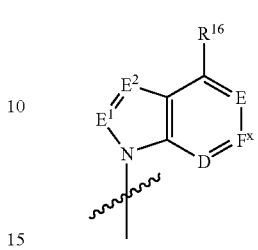

wherein each E and D is >N, each $E^1$ and $F^x$ is independently >C—$R^{25}$, $E^2$ is >C—$R^{30}$, each $R^{10}$ is H, $L^1$ is O, and each $R^a$ is H. In another aspect of this embodiment, $R^{3c}$ is $CH_2R^9$ wherein $R^9$ is not H, OH, or F. In another aspect of this embodiment, $R^{3c}$ is alkenyl or substituted alkenyl. In another aspect of this embodiment, $R^{3c}$ is alkynyl or substituted alkynyl. In another aspect of this embodiment, each $R^5$ and $R^6$ is H. In another aspect of this embodiment, $R^5$ and $R^6$, taken together, are =$CR^cR^d$. In another aspect of this embodiment, $R^{16}$ is $N(R^{20})(R^{21})$. In another aspect of this embodiment, $R^{16}$ is $N(R^{20})(R^{21})$ wherein $R^{20}$ is $OR^{17a}$. In another aspect of this embodiment, $R^{16}$ is $OR^{17a}$. In another aspect of this embodiment, $R^{16}$ is $NH_2$ and each $R^{25}$ is H. In another aspect of this embodiment, $R^{16}$ is $OR^{17a}$ and $F^x$ is >C—$NR^{26}R^{27}$. In another aspect of this embodiment, $R^{16}$ is $NH_2$ and each $R^{25}$ is H. In another aspect of this embodiment, $R^{16}$ is $OR^{17a}$ and $F^x$ is >C—$NR^{26}R^{27}$. In another aspect of this embodiment, $R^{16}$ is OH and $F^x$ is >C—$NR^{26}R^{27}$ wherein each $R^{26}$ and $R^{27}$ is H. In another aspect of this embodiment, $R^{30}$ is ethynyl, 2-trimethylsilylethynyl, 2-(2-pyridyl)ethynyl, 2-(4-pyridyl)ethynyl, 2-(4-methoxy)ethynyl, 2-(aminocarbonyl)ethynyl, 3,3-diethoxypropyn-1-yl, 2-(dimethylaminocarbonyl)ethynyl, 2-(N-amino(aminocarbonyl)ethynyl, 2-carboxyethynyl, 2-ethoxycarbonylethynyl, 2-methoxycarbonylethynyl, 2-phenylethynyl, 2-(4-fluorophenyl)ethynyl, 2-(4-methylphenyl)ethynyl, vinyl, 2-methoxyvinyl, formyl, —CH=N—$NH_2$, —CH=NOH, 1,1-diisopropoxymethyl, or —B(OH)$_2$. In another aspect of this embodiment, each $W^1$ and $W^2$ is independently $Y^2$—$R^x$ wherein each $Y^2$ is independently —O— or —N(R)— and $R^x$ is not H. In another aspect of this embodiment, each $W^1$ and $W^2$ is independently $Y^2$—$R^x$ wherein each $Y^2$ is —O— and $R^x$ is not H. In another aspect of this embodiment, each $W^1$ and $W^2$ is independently $Y^2$—$R^x$ wherein each $Y^2$ is independently —N(R)— and $R^x$ is not H.

In another preferred embodiment of Formula III, $B^2$ is

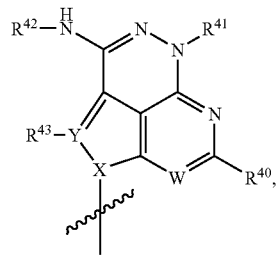

-continued

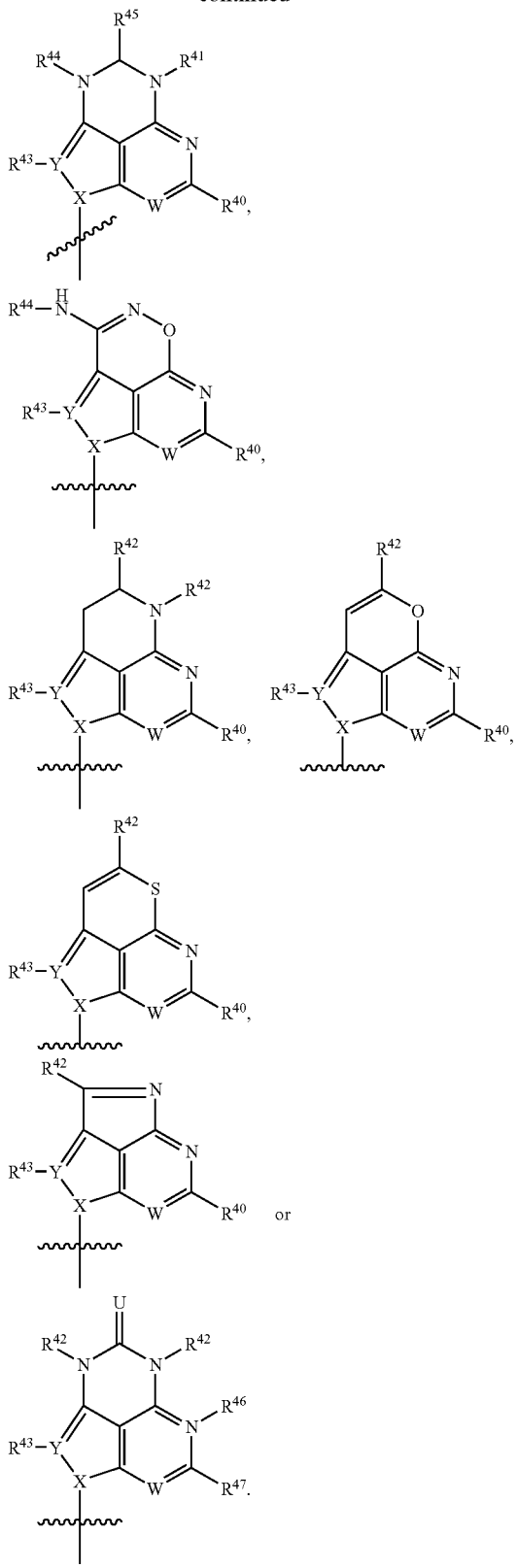

In one aspect of this embodiment, each $R^{10}$ is H, $L^1$ is O, and each $R^a$ is H. In another aspect of this embodiment, $R^{3c}$ is $CH_2R^9$ wherein $R^9$ is not H, OH, or F. In another aspect of this embodiment, $R^{3c}$ is alkenyl or substituted alkenyl. In another aspect of this embodiment, $R^{3c}$ is alkynyl or substituted alkynyl. In another aspect of this embodiment, each $R^5$ and $R^6$ is H. In another aspect of this embodiment, $R^5$ and $R^6$, taken together, are $=CR^cR^d$.

In another preferred embodiment of Formula III, $B^2$ is

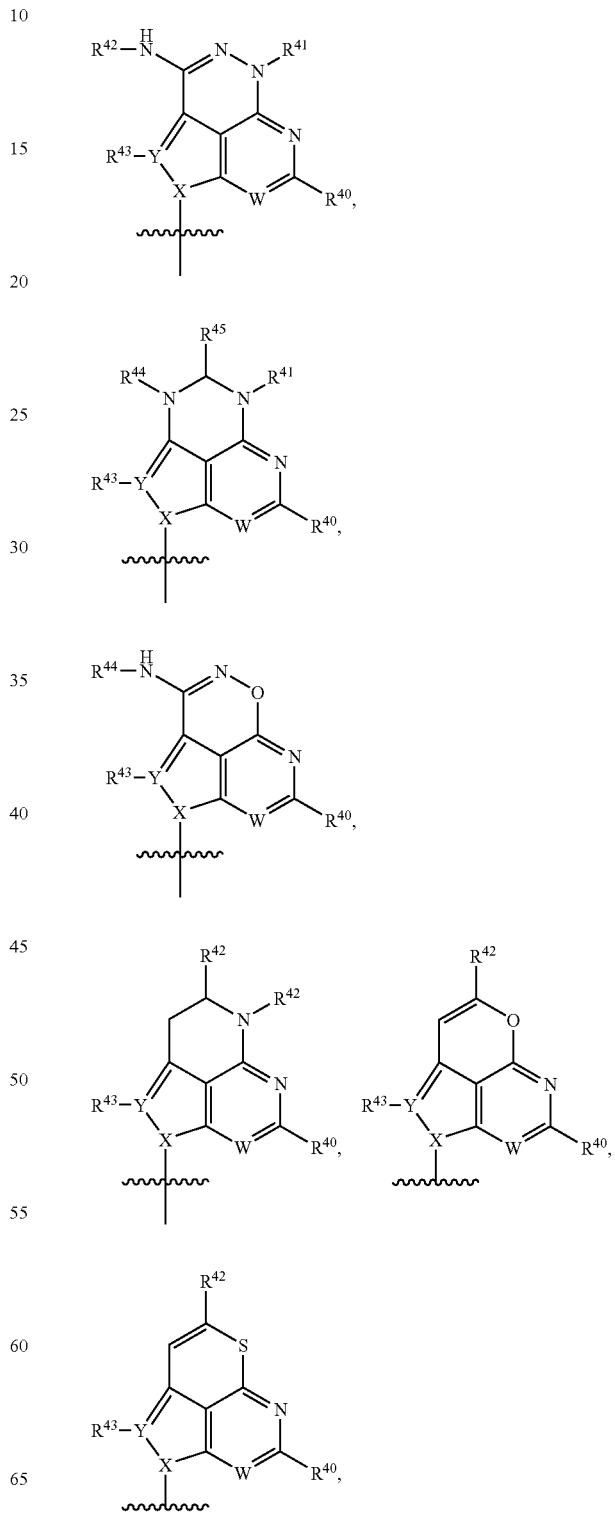

-continued

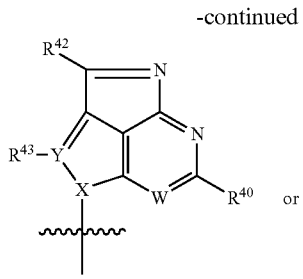

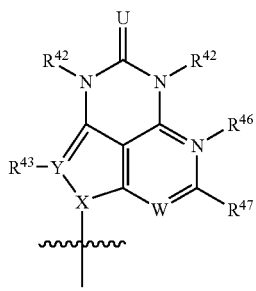

wherein each $R^{10}$ is H, $L^1$ is O, and each $R^a$ is H. In another aspect of this embodiment, $R^{3c}$ is CH$_2$R$^9$ wherein $R^9$ is not H, OH, or F. In another aspect of this embodiment, $R^{3c}$ is alkenyl or substituted alkenyl. In another aspect of this embodiment, $R^{3c}$ is alkynyl or substituted alkynyl. In another aspect of this embodiment, each $R^5$ and $R^6$ is H. In another aspect of this embodiment, $R^5$ and $R^6$, taken together, are =CR$^c$R$^d$. In another aspect of this embodiment, each $W^1$ and $W^2$ is independently $Y^2$—$R^x$ wherein each $Y^2$ is independently —O— or —N(R)— and $R^x$ is not H. In another aspect of this embodiment, each $W^1$ and $W^2$ is independently $Y^2$—$R^x$ wherein each $Y^2$ is —O— and $R^x$ is not H. In another aspect of this embodiment, each $W^1$ and $W^2$ is independently $Y^2$—$R^x$ wherein each $Y^2$ is independently —N(R)— and $R^x$ is not H.

In another preferred embodiment of Formula III, $B^2$ is

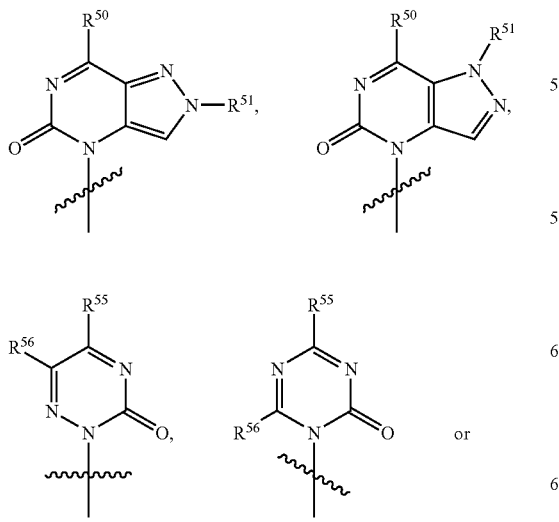

-continued

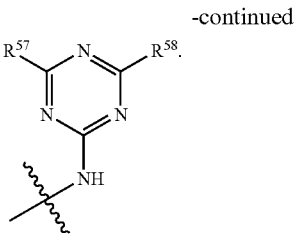

In one aspect of this embodiment, each $R^{10}$ is H, $L^1$ is O, and each $R^a$ is H. In another aspect of this embodiment, $R^{3c}$ is CH$_2$R$^9$ wherein $R^9$ is not H, OH, or F. In another aspect of this embodiment, $R^{3c}$ is alkenyl or substituted alkenyl. In another aspect of this embodiment, $R^{3c}$ is alkynyl or substituted alkynyl. In another aspect of this embodiment, each $R^5$ and $R^6$ is H. In another aspect of this embodiment, $R^5$ and $R^6$, taken together, are =CR$^c$R$^d$.

In another preferred embodiment of Formula III, $B^2$ is

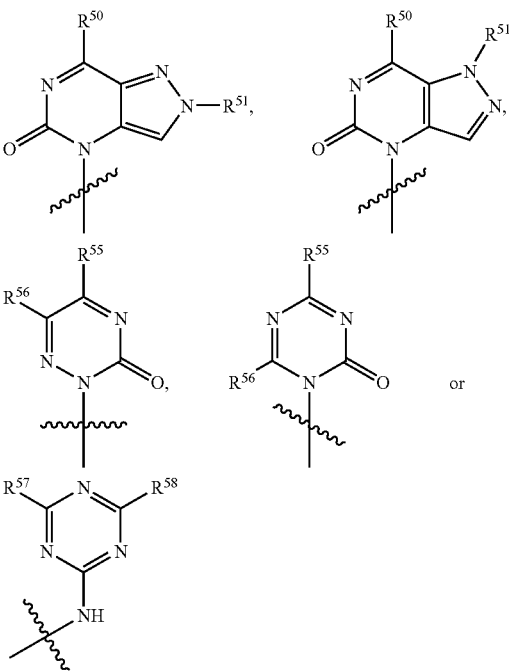

wherein $R^{10}$ is H, $L^1$ is O, and each $R^a$ is H. In another aspect of this embodiment, $R^{3c}$ is CH$_2$R$^9$ wherein $R^9$ is not H, OH, or F. In another aspect of this embodiment, $R^{3c}$ is alkenyl or substituted alkenyl. In another aspect of this embodiment, $R^{3c}$ is alkynyl or substituted alkynyl. In another aspect of this embodiment, each $R^5$ and $R^6$ is H. In another aspect of this embodiment, $R^5$ and $R^6$, taken together, are =CR$^c$R$^d$. In another aspect of this embodiment, each $W^1$ and $W^2$ is independently $Y^2$—$R^x$ wherein each $Y^2$ is independently —O— or —N(R)— and $R^x$ is not H. In another aspect of this embodiment, each $W^1$ and $W^2$ is independently $Y^2$—$R^x$ wherein each $Y^2$ is —O— and $R^x$ is not H. In another aspect of this embodiment, each $W^1$ and $W^2$ is independently $Y^2$—$R^x$ wherein each $Y^2$ is independently —N(R)— and $R^x$ is not H.

In another preferred embodiment of Formula III, $B^2$ is

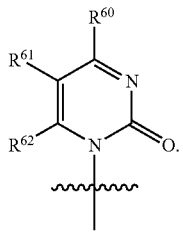

In one aspect of this embodiment, each $R^{10}$ is H, $L^1$ is O, and each $R^a$ is H. In another aspect of this embodiment, $R^{3c}$ is $CH_2R^9$ wherein $R^9$ is not H, OH, or F. In another aspect of this embodiment, $R^{3c}$ is alkenyl or substituted alkenyl. In another aspect of this embodiment, $R^{3c}$ is alkynyl or substituted alkynyl. In another aspect of this embodiment, each $R^5$ and $R^6$ is H. In another aspect of this embodiment, $R^5$ and $R^6$, taken together, are $=CR^cR^d$.

In another preferred embodiment of Formula III, $B^2$ is

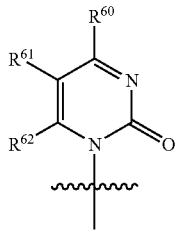

wherein each $R^{10}$ is H, $L^1$ is O, and each $R^a$ is H. In another aspect of this embodiment, $R^{3c}$ is $CH_2R^9$ wherein $R^9$ is not H, OH, or F. In another aspect of this embodiment, $R^{3c}$ is alkenyl or substituted alkenyl. In another aspect of this embodiment, $R^{3c}$ is alkynyl or substituted alkynyl. In another aspect of this embodiment, each $R^5$ and $R^6$ is H. In another aspect of this embodiment, $R^5$ and $R^6$, taken together, are $=CR^cR^d$. In another aspect of this embodiment, $R^{60}$ is $NR^{6b}R^{6c}$. In another aspect of this embodiment, $R^{60}$ is $NR^{6b}R^{6c}$ and $R^{62}$ is H. In another aspect of this embodiment, $R^{60}$ is $OR^{6b}$. In another aspect of this embodiment, $R^{60}$ is $OR^{6b}$ and $R^{62}$ is H. In another aspect of this embodiment, $R^{60}$ is OH and each $R^{61}$ and $R^{62}$ is H. In another aspect of this embodiment, $R^{60}$ is $NH_2$ and each $R^{61}$ and $R^{62}$ is H. In another aspect of this embodiment, $R^{60}$ is not $NR^{6b}R^{6c}$ or $OR^{6b}$. In another aspect of this embodiment, each $W^1$ and $W^2$ is independently $Y^2-R^x$ wherein each $Y^2$ is independently $-O-$ or $-N(R)-$ and $R^x$ is not H. In another aspect of this embodiment, each $W^1$ and $W^2$ is independently $Y^2-R^x$ wherein each $Y^2$ is $-O-$ and $R^x$ is not H. In another aspect of this embodiment, each $W^1$ and $W^2$ is independently $Y^2-R^x$ wherein each $Y^2$ is independently $-N(R)-$ and $R^x$ is not H.

In another preferred embodiment of Formula III, $B^2$ is

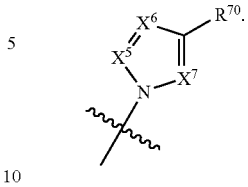

In one aspect of this embodiment, each $R^{10}$ is H, $L^1$ is O, and each $R^a$ is H. In another aspect of this embodiment, $R^{3c}$ is $CH_2R^9$ wherein $R^9$ is not H, OH, or F. In another aspect of this embodiment, $R^{3c}$ is alkenyl or substituted alkenyl. In another aspect of this embodiment, $R^{3c}$ is alkynyl or substituted alkynyl. In another aspect of this embodiment, each $R^5$ and $R^6$ is H. In another aspect of this embodiment, $R^5$ and $R^6$, taken together, are $=CR^cR^d$.

In another preferred embodiment of Formula III, $B^2$ is

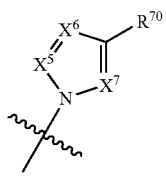

wherein each $R^{10}$ is H, $L^1$ is O, and each $R^a$ is H. In another aspect of this embodiment, $R^{3c}$ is $CH_2R^9$ wherein $R^9$ is not H, OH, or F. In another aspect of this embodiment, $R^{3c}$ is alkenyl or substituted alkenyl. In another aspect of this embodiment, $R^{3c}$ is alkynyl or substituted alkynyl. In another aspect of this embodiment, each $R^5$ and $R^6$ is H. In another aspect of this embodiment, $R^5$ and $R^6$, taken together, are $=CR^cR^d$. In another aspect of this embodiment, $X^5$ is CH and each $X^6$ and $X^7$ is N. In another aspect of this embodiment, $X^5$ is CH, each $X^6$ and $X^7$ is N, and $R^{70}$ is $-C(O)NR^{7b}R^{7c}$. In another aspect of this embodiment, each $W^1$ and $W^2$ is independently $Y^2-R^x$ wherein each $Y^2$ is independently $-O-$ or $-N(R)-$ and $R^x$ is not H. In another aspect of this embodiment, each $W^1$ and $W^2$ is independently $Y^2-R^x$ wherein each $Y^2$ is $-O-$ and $R^x$ is not H. In another aspect of this embodiment, each $W^1$ and $W^2$ is independently $Y^2-R^x$ wherein each $Y^2$ is independently $-N(R)-$ and $R^x$ is not H.

In another preferred embodiment of Formula III, $B^2$ is

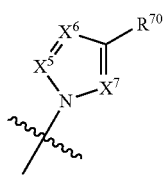

wherein $X^5$ is CH, each $X^6$ and $X^7$ is N, $R^{70}$ is $-C(O)NR^{7b}R^{7c}$, each $R^{10}$ is H, $L^1$ is O, and each $R^a$ is H. In another aspect of this embodiment, $R^{3c}$ is $CH_2R^9$ wherein $R^9$ is not H, OH, or F. In another aspect of this embodiment, $R^{3c}$ is alkenyl or substituted alkenyl. In another aspect of this embodiment, $R^{3c}$ is alkynyl or substituted alkynyl. In another aspect of this embodiment, each $R^5$ and $R^6$ is H. In another aspect of this embodiment, $R^5$ and $R^6$, taken together, are $=CR^cR^d$. In another aspect of this embodiment, each $W^1$ and $W^2$ is independently $Y^2$—$R^x$ wherein each $Y^2$ is independently —O— or —N(R)— and $R^x$ is not H. In another aspect of this embodiment, each $W^1$ and $W^2$ is independently $Y^2$—$R^x$ wherein each $Y^2$ is —O— and $R^x$ is not H. In another aspect of this embodiment, each $W^1$ and $W^2$ is independently $Y^2$—$R^x$ wherein each $Y^2$ is independently —N(R)— and $R^x$ is not H.

In another preferred embodiment of Formula III, $B^2$ is

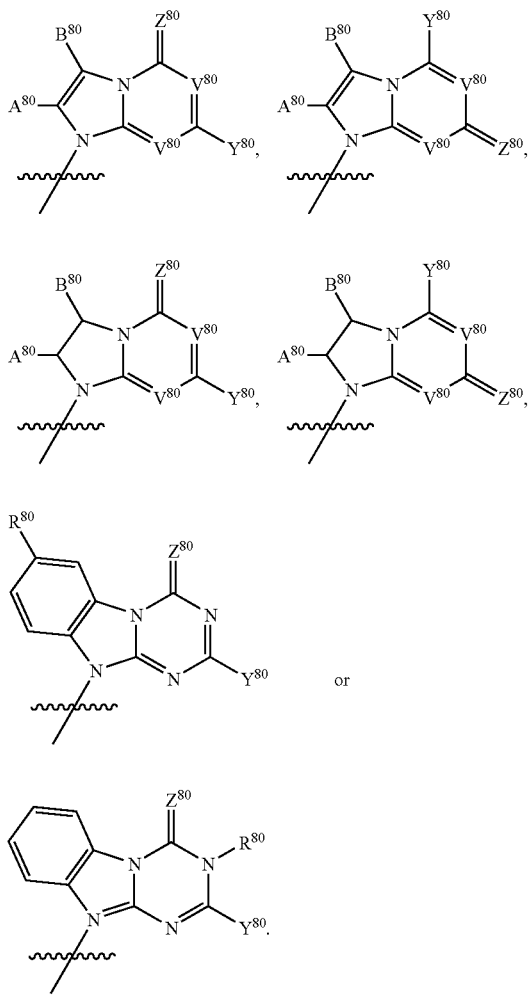

or

In one aspect of this embodiment, each $R^{10}$ is H, $L^1$ is O, and each $R^a$ is H. In another aspect of this embodiment, $R^{3c}$ is $CH_2R^9$ wherein $R^9$ is not H, OH, or F. In another aspect of this embodiment, $R^{3c}$ is alkenyl or substituted alkenyl. In another aspect of this embodiment, $R^{3c}$ is alkynyl or substituted alkynyl. In another aspect of this embodiment, each $R^5$ and $R^6$ is H. In another aspect of this embodiment, $R^5$ and $R^6$, taken together, are =$CR^cR^d$. In another aspect of this embodiment, each $W^1$ and $W^2$ is independently $Y^2$—$R^x$ wherein each $Y^2$ is independently —O— or —N(R)— and $R^x$ is not H. In another aspect of this embodiment, each $W^1$ and $W^2$ is independently $Y^2$—$R^x$ wherein each $Y^2$ is —O— and $R^x$ is not H. In another aspect of this embodiment, each $W^1$ and $W^2$ is independently $Y^2$—$R^x$ wherein each $Y^2$ is independently —N(R)— and $R^x$ is not H.

In another preferred embodiment of Formula III, $B^2$ is

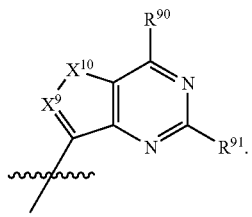

In one aspect of this embodiment, each $R^{10}$ is H, $L^1$ is O, and each $R^a$ is H. In another aspect of this embodiment, $R^{3c}$ is $CH_2R^9$ wherein $R^9$ is not H, OH, or F. In another aspect of this embodiment, $R^{3c}$ is alkenyl or substituted alkenyl. In another aspect of this embodiment, $R^{3c}$ is alkynyl or substituted alkynyl. In another aspect of this embodiment, each $R^5$ and $R^6$ is H. In another aspect of this embodiment, $R^5$ and $R^6$, taken together, are =$CR^cR^d$.

In another preferred embodiment of Formula III, $B^2$ is

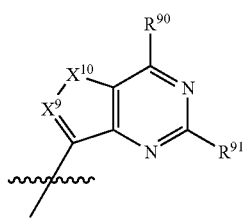

wherein each $R^{10}$ is H, $L^1$ is O, and each $R^a$ is H. In another aspect of this embodiment, $R^{3c}$ is $CH_2R^9$ wherein $R^9$ is not H, OH, or F. In another aspect of this embodiment, $R^{3c}$ is alkenyl or substituted alkenyl. In another aspect of this embodiment, $R^{3c}$ is alkynyl or substituted alkynyl. In another aspect of this embodiment, each $R^5$ and $R^6$ is H. In another aspect of this embodiment, $R^5$ and $R^6$, taken together, are =$CR^cR^d$. In another aspect of this embodiment, $X^9$ is $CR^{90a}$. In another aspect of this embodiment, $X^{10}$ is O, S, or $NR^{91a}$. In another aspect of this embodiment, $X^9$ is CH and $X^{10}$ is O, S, or $NR^{91a}$. In another aspect of this embodiment, each $W^1$ and $W^2$ is independently $Y^2$—$R^x$ wherein each $Y^2$ is independently —O— or —N(R)— and $R^x$ is not H. In another aspect of this embodiment, each $W^1$ and $W^2$ is independently $Y^2$—$R^x$ wherein each $Y^2$ is —O— and $R^x$ is not H. In another aspect of this embodiment, each $W^1$ and $W^2$ is independently $Y^2$—$R^x$ wherein each $Y^2$ is independently —N(R)— and $R^x$ is not H.

In another preferred embodiment of Formula III, $B^2$ is

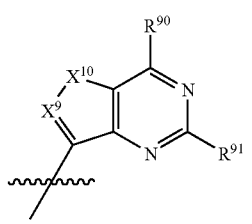

wherein $X^9$ is CH, $X^{10}$ is O, S, or $NR^{91a}$, each $R^{10}$ is H, $L^1$ is O, and each $R^a$ is H. In another aspect of this embodiment, $R^{3b}$ is $CH_2R^9$ wherein $R^9$ is not H. In another aspect of this embodiment, $R^{3c}$ is $CH_2R^9$ wherein $R^9$ is not H, OH, or F. In another aspect of this embodiment, $R^{3c}$ is alkenyl or substituted alkenyl. In another aspect of this embodiment, $R^{3c}$ is alkynyl or substituted alkynyl. In another aspect of this embodiment, each $R^5$ and $R^6$ is H. In another aspect of this embodiment, $R^5$ and $R^6$, taken together, are $=CR^cR^d$. In another aspect of this embodiment, $X^{10}$ is O. In another aspect of this embodiment, $X^{10}$ is S. In another aspect of this embodiment, $X^{10}$ is $NR^{91a}$. In another aspect of this embodiment, each $W^1$ and $W^2$ is independently $Y^2$—$R^x$ wherein each $Y^2$ is independently —O— or —N(R)— and $R^x$ is not H. In another aspect of this embodiment, each $W^1$ and $W^2$ is independently $Y^2$—$R^x$ wherein each $Y^2$ is —O— and $R^x$ is not H. In another aspect of this embodiment, each $W^1$ and $W^2$ is independently $Y^2$—$R^x$ wherein each $Y^2$ is independently —N(R)— and $R^x$ is not H.

In another preferred embodiment of Formula III, $B^2$ is

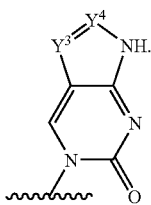

In one aspect of this embodiment, each $R^{10}$ is H, $L^1$ is O, and each $R^a$ is H. In another aspect of this embodiment, $R^{3c}$ is $CH_2R^9$ wherein $R^9$ is not H, OH, or F. In another aspect of this embodiment, $R^{3c}$ is alkenyl or substituted alkenyl. In another aspect of this embodiment, $R^{3c}$ is alkynyl or substituted alkynyl. In another aspect of this embodiment, each $R^5$ and $R^6$ is H. In another aspect of this embodiment, $R^5$ and $R^6$, taken together, are $=CR^cR^d$. In another aspect of this embodiment, each $W^1$ and $W^2$ is independently $Y^2$—$R^x$ wherein each $Y^2$ is independently —O— or —N(R)— and $R^x$ is not H. In another aspect of this embodiment, each $W^1$ and $W^2$ is independently $Y^2$—$R^x$ wherein each $Y^2$ is —O— and $R^x$ is not H. In another aspect of this embodiment, each $W^1$ and $W^2$ is independently $Y^2$—$R^x$ wherein each $Y^2$ is independently —N(R)— and $R^x$ is not H.

In another preferred embodiment of Formula III, $B^2$ is

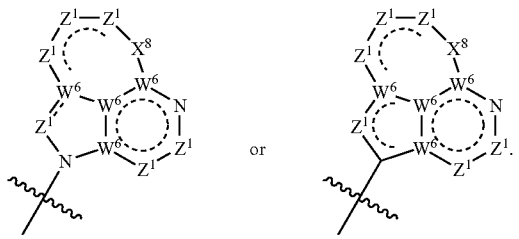

In one aspect of this embodiment, each $R^{10}$ is H, $L^1$ is O, and each $R^a$ is H. In another aspect of this embodiment, $R^{3c}$ is $CH_2R^9$ wherein $R^9$ is not H, OH, or F. In another aspect of this embodiment, $R^{3c}$ is alkenyl or substituted alkenyl. In another aspect of this embodiment, $R^{3c}$ is alkynyl or substituted alkynyl. In another aspect of this embodiment, each $R^5$ and $R^6$ is H. In another aspect of this embodiment, $R^5$ and $R^6$, taken together, are $=CR^cR^d$.

In another preferred embodiment of Formula III, $B^2$ is

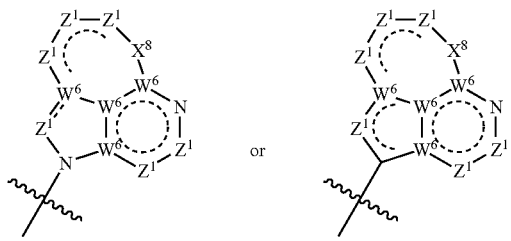

wherein each $R^{10}$ is H, $L^1$ is O, and each $R^a$ is H. In another aspect of this embodiment, $R^{3c}$ is $CH_2R^9$ wherein $R^9$ is not H, OH, or F. In another aspect of this embodiment, $R^{3c}$ is alkenyl or substituted alkenyl. In another aspect of this embodiment, $R^{3c}$ is alkynyl or substituted alkynyl. In another aspect of this embodiment, each $R^5$ and $R^6$ is H. In another aspect of this embodiment, $R^5$ and $R^6$, taken together, are $=CR^cR^d$. In another aspect of this embodiment, each $W^1$ and $W^2$ is independently $Y^2$—$R^x$ wherein each $Y^2$ is independently —O— or —N(R)— and $R^x$ is not H. In another aspect of this embodiment, each $W^1$ and $W^2$ is independently $Y^2$—$R^x$ wherein each $Y^2$ is —O— and $R^x$ is not H. In another aspect of this embodiment, each $W^1$ and $W^2$ is independently $Y^2$—$R^x$ wherein each $Y^2$ is independently —N(R)— and $R^x$ is not H. In another aspect of this embodiment, a specific value for $B^2$ is

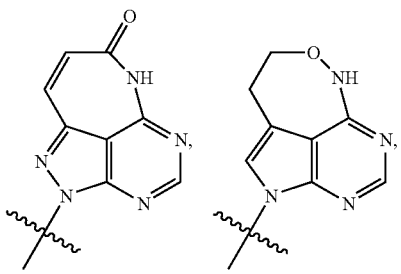

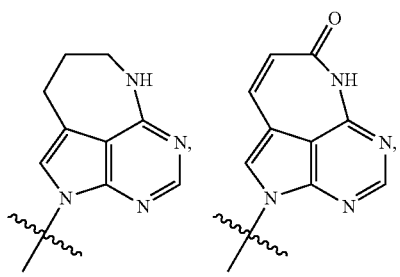

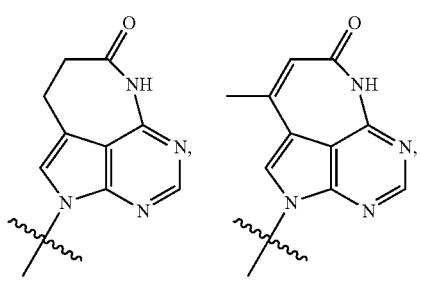

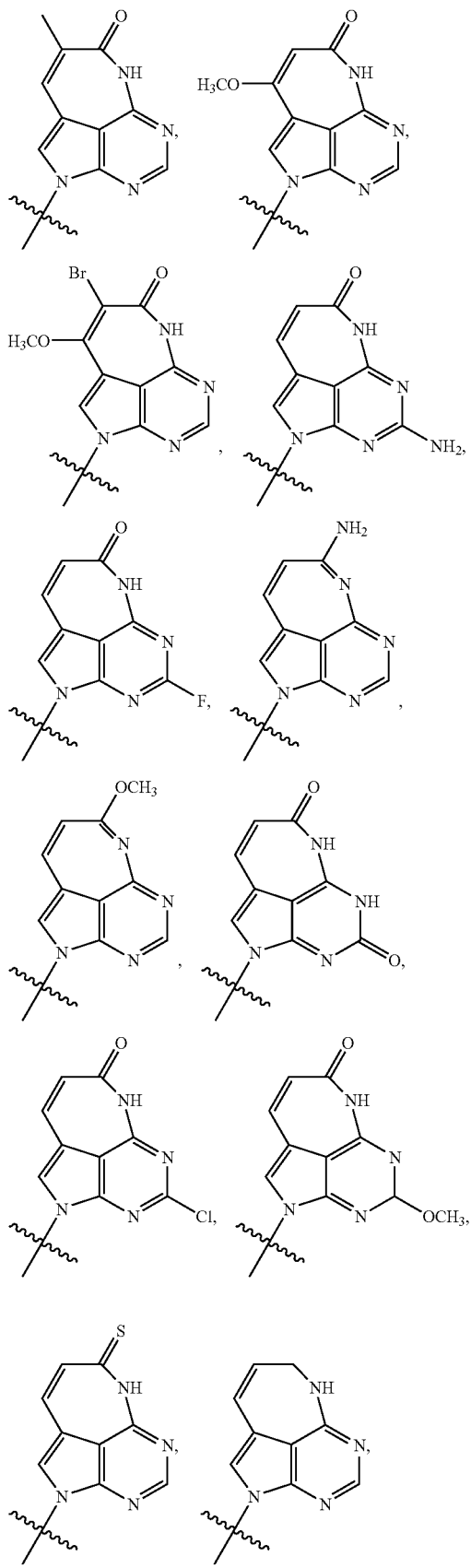
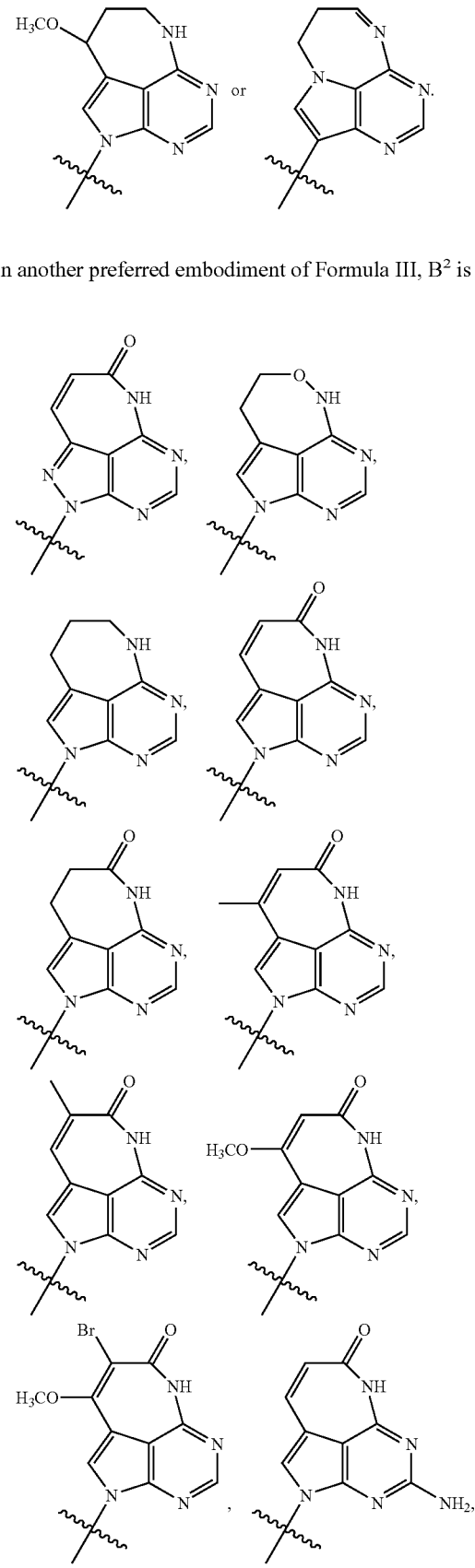
In another preferred embodiment of Formula III, $B^2$ is -continued

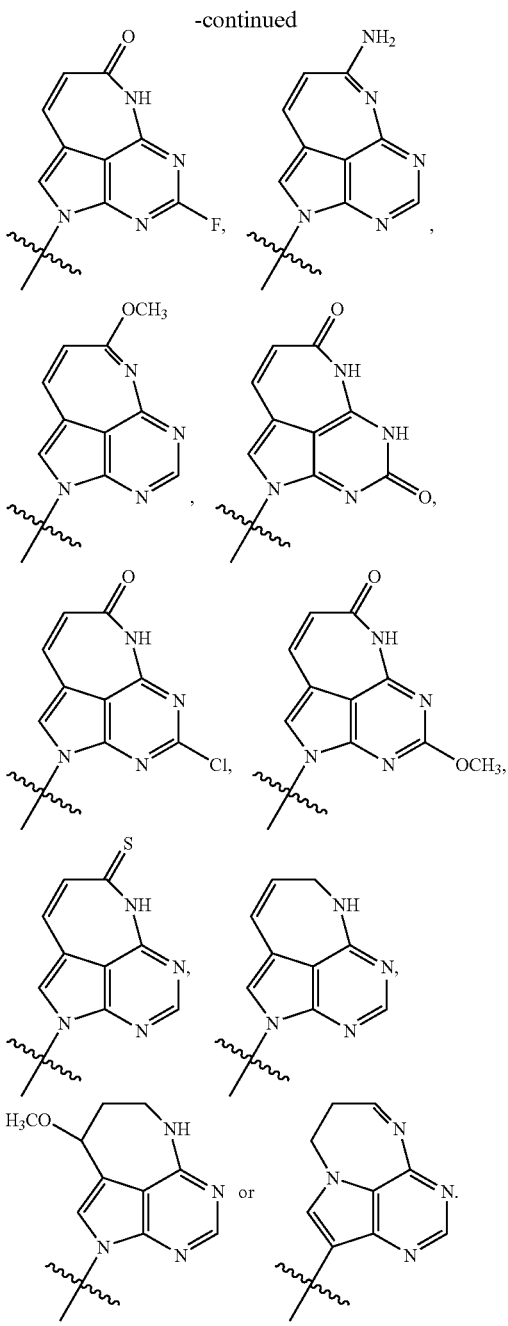

wherein each $R^{10}$ is H, $L^1$ is O, and each $R^a$ is H. In another aspect of this embodiment, $R^{3c}$ is $CH_2R^9$ wherein $R^9$ is not H, OH, or F. In another aspect of this embodiment, $R^{3c}$ is alkenyl or substituted alkenyl. In another aspect of this embodiment, $R^{3c}$ is alkynyl or substituted alkynyl. In another aspect of this embodiment, each $R^5$ and $R^6$ is H. In another aspect of this embodiment, $R^5$ and $R^6$, taken together, are $=CR^cR^d$. In another aspect of this embodiment, each $W^1$ and $W^2$ is independently $Y^2$—$R^x$ wherein each $Y^2$ is independently —O— or —N(R)— and $R^x$ is not H. In another aspect of this embodiment, each $W^1$ and $W^2$ is independently $Y^2$—$R^x$ wherein each $Y^2$ is —O— and $R^x$ is not H. In another aspect of this embodiment, each $W^1$ and $W^2$ is independently $Y^2$—$R^x$ wherein each $Y^2$ is independently —N(R)— and $R^x$ is not H.

In one embodiment, compounds of this invention are of Formula IV:

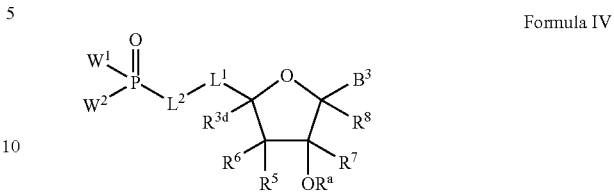

Formula IV wherein all variables are defined as above for Formula IV. In one aspect of this embodiment, $R^a$ is H. In another aspect of this embodiment, each $R^{10}$ is H and $L^1$ is O. In another aspect of this embodiment, $R^{3d}$ is H. In another aspect of this embodiment, $R^{3d}$ is $CH_2R^9$. In another aspect of this embodiment, $R^{3d}$ is alkenyl or substituted alkenyl. In another aspect of this embodiment, $R^{3d}$ is alkynyl or substituted alkynyl. In another aspect of this embodiment, each $R^5$ and $R^6$ is H. In another aspect of this embodiment, $R^5$ and $R^6$, taken together, are $=CR^cR^d$. In another aspect of this embodiment, $R^a$ is H, each $R^{10}$ is H and $L^1$ is O. In another aspect of this embodiment, $R^a$ is H, each $R^{10}$ is H, $L^1$ is O and $R^{3d}$ is H. In another aspect of this embodiment, $R^a$ is H, each $R^{10}$ is H, $L^1$ is O and $R^{3d}$ is $CH_2R^9$. In another aspect of this embodiment, $R^a$ is H, each $R^{10}$ is H, $L^1$ is O and $R^{3d}$ is alkenyl or substituted alkenyl. In another aspect of this embodiment, $R^a$ is H, each $R^{10}$ is H, $L^1$ is O and $R^{3d}$ is alkynyl or substituted alkynyl.

In a preferred embodiment of Formula IV, $B^3$ is

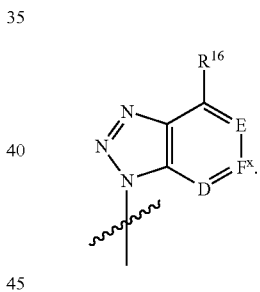

In one aspect of this embodiment, $R^a$ is H. In another aspect of this embodiment, each $R^{10}$ is H and $L^1$ is O. In another aspect of this embodiment, $R^{3d}$ is H. In another aspect of this embodiment, $R^{3d}$ is $CH_2R^9$. In another aspect of this embodiment, $R^{3d}$ is alkenyl or substituted alkenyl. In another aspect of this embodiment, $R^{3d}$ is alkynyl or substituted alkynyl. In another aspect of this embodiment, each $R^5$ and $R^6$ is H. In another aspect of this embodiment, $R^5$ and $R^6$, taken together, are $=CR^cR^d$. In another aspect of this embodiment, $R^a$ is H, each $R^{10}$ is H and $L^1$ is O. In another aspect of this embodiment, $R^a$ is H, each $R^{10}$ is H, $L^1$ is O and $R^{3d}$ is H. In another aspect of this embodiment, $R^a$ is H, each $R^{10}$ is H, $L^1$ is O and $R^{3d}$ is $CH_2R^9$. In another aspect of this embodiment, $R^a$ is H, each $R^{10}$ is H, $L^1$ is O and $R^{3d}$ is alkenyl or substituted alkenyl. In another aspect of this embodiment, $R^a$ is H, each $R^{10}$ is H, $L^1$ is O and $R^{3d}$ is alkynyl or substituted alkynyl. In another aspect of this embodiment, each E and D is >N. In another aspect of this embodiment, each E and D is >N and $F^x$ is >C—$R^{25}$.

In another preferred embodiment of Formula IV, B³ is

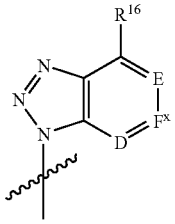

wherein R^a is H, each R¹⁰ is H and L¹ is O. In another aspect of this embodiment, R^{3d} is H. In another aspect of this embodiment, R^{3d} is CH₂R⁹. In another aspect of this embodiment, R^{3d} is alkenyl or substituted alkenyl. In another aspect of this embodiment, R^{3d} is alkynyl or substituted alkynyl. In another aspect of this embodiment, each R⁵ and R⁶ is H. In another aspect of this embodiment, R⁵ and R⁶, taken together, are =CR^cR^d. In another aspect of this embodiment, each E and D is >N. In another aspect of this embodiment, each E and D is >N and F^x is >C—R²⁵.

In another preferred embodiment of Formula IV, B³ is

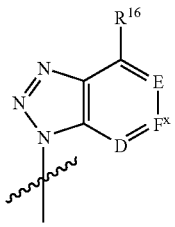

wherein R^a is H, each R¹⁰ is H, L¹ is O and each E and D is >N. In another aspect of this embodiment, R^{3d} is H. In another aspect of this embodiment, R^{3d} is CH₂R⁹. In another aspect of this embodiment, R^{3d} is alkenyl or substituted alkenyl. In another aspect of this embodiment, R^{3d} is alkynyl or substituted alkynyl. In another aspect of this embodiment, each R⁵ and R⁶ is H. In another aspect of this embodiment, R⁵ and R⁶, taken together, are =CR^cR^d. In another aspect of this embodiment, F^x is >C—R²⁵. In another aspect of this embodiment, R¹⁶ is N(R²⁰)(R²¹). In another aspect of this embodiment, R¹⁶ is OR^{17a}. In another aspect of this embodiment, R¹⁶ is N(R²⁰)(R²¹) and F^x is >C—H. In another aspect of this embodiment, R¹⁶ is OR^{17a} and F^x is >C—NR²⁶R²⁷.

In another preferred embodiment of Formula IV, B³ is

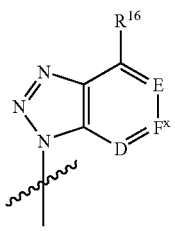

wherein R^a is H, each R¹⁰ is H, L¹ is O, each E and D is >N and F^x is >C—R²⁵. In another aspect of this embodiment, R^{3d} is H. In another aspect of this embodiment, R^{3d} is CH₂R⁹. In another aspect of this embodiment, R^{3d} is alkenyl or substituted alkenyl. In another aspect of this embodiment, R^{3d} is alkynyl or substituted alkynyl. In another aspect of this embodiment, each R⁵ and R⁶ is H. In another aspect of this embodiment, R⁵ and R⁶, taken together, are =CR^cR^d. In another aspect of this embodiment, R¹⁶ is N(R²⁰)(R²¹). In another aspect of this embodiment, R¹⁶ is OR^{17a}. In another aspect of this embodiment, R¹⁶ is N(R²⁰)(R²¹) and R²⁵ is H. In another aspect of this embodiment, R¹⁶ is OR^{17a} and R²⁵ is NR²⁶R²⁷. In another aspect of this embodiment, R¹⁶ is OH and R²⁵ is NH₂. In another aspect of this embodiment, R¹⁶ is NH₂ and R²⁵ is H. In another aspect of this embodiment, each W¹ and W² is independently Y²—R^x wherein each Y² is independently —O— or —N(R)— and R^x is not H. In another aspect of this embodiment, each W¹ and W² is independently Y²—R^x wherein each Y² is —O— and R^x is not H. In another aspect of this embodiment, each W¹ and W² is independently Y²—R^x wherein each Y² is independently —N(R)— and R^x is not H.

In another preferred embodiment of Formula IV, B³ is

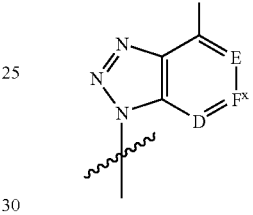

wherein R^a is H, each R¹⁰ is H, L¹ is O, each E and D is >N, F^x is >C—R²⁵ and each R⁵ and R⁶ is H. In another aspect of this embodiment, R^{3d} is H. In another aspect of this embodiment, R^{3d} is CH₂R⁹. In another aspect of this embodiment, R^{3d} is alkenyl or substituted alkenyl. In another aspect of this embodiment, R^{3d} is alkynyl or substituted alkynyl. In another aspect of this embodiment, R¹⁶ is N(R²⁰)(R²¹). In another aspect of this embodiment, R¹⁶ is OR^{17a}. In another aspect of this embodiment, R¹⁶ is N(R²⁰)(R²¹) and R²⁵ is H. In another aspect of this embodiment, R¹⁶ is OR^{17a} and R²⁵ is NR²⁶R²⁷. In another aspect of this embodiment, R¹⁶ is OH and R²⁵ is NH₂. In another aspect of this embodiment, R¹⁶ is NH₂ and R²⁵ is H. In another aspect of this embodiment, each W¹ and W² is independently Y²—R^x wherein each Y² is independently —O— or —N(R)— and R^x is not H. In another aspect of this embodiment, each W¹ and W² is independently Y²—R^x wherein each Y² is —O— and R^x is not H. In another aspect of this embodiment, each W¹ and W² is independently Y²—R^x wherein each Y² is independently —N(R)— and R^x is not H.

In another preferred embodiment of Formula IV, B³ is

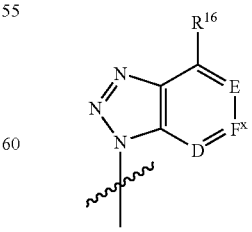

wherein R^a is H, each R¹⁰ is H, L¹ is O, each E and D is >N, F^x is >C—R²⁵ and R⁵ and R⁶, taken together, are =CR^cR^d. In another aspect of this embodiment, $R^{3d}$ is H. In another aspect of this embodiment, $R^{3d}$ is $CH_2R^9$. In another aspect of this embodiment, $R^{3d}$ is alkenyl or substituted alkenyl. In another aspect of this embodiment, $R^{3d}$ is alkynyl or substituted alkynyl. In another aspect of this embodiment, $R^{16}$ is $N(R^{20})(R^{21})$. In another aspect of this embodiment, $R^{16}$ is $OR^{17a}$. In another aspect of this embodiment, $R^{16}$ is $N(R^{20})(R^{21})$ and $R^{25}$ is H. In another aspect of this embodiment, $R^{16}$ is $OR^{17a}$ and $R^{25}$ is $NR^{26}R^{27}$. In another aspect of this embodiment, $R^{16}$ is OH and $R^{25}$ is $NH_2$. In another aspect of this embodiment, $R^{16}$ is $NH_2$ and $R^{25}$ is H. In another aspect of this embodiment, each $W^1$ and $W^2$ is independently $Y^2-R^x$ wherein each $Y^2$ is independently —O— or —N(R)— and $R^x$ is not H. In another aspect of this embodiment, each $W^1$ and $W^2$ is independently $Y^2-R^x$ wherein each $Y^2$ is —O— and $R^x$ is not H. In another aspect of this embodiment, each $W^1$ and $W^2$ is independently $Y^2-R^x$ wherein each $Y^2$ is independently —N(R)— and $R^x$ is not H.

In another preferred embodiment of Formula IV, $B^3$ is

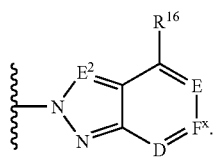

In one aspect of this embodiment, $R^a$ is H. In another aspect of this embodiment, each $R^{10}$ is H and $L^1$ is O. In another aspect of this embodiment, $R^{3d}$ is H. In another aspect of this embodiment, $R^{3d}$ is $CH_2R^9$. In another aspect of this embodiment, $R^{3d}$ is alkenyl or substituted alkenyl. In another aspect of this embodiment, $R^{3d}$ is alkynyl or substituted alkynyl. In another aspect of this embodiment, each $R^5$ and $R^6$ is H. In another aspect of this embodiment, $R^5$ and $R^6$, taken together, are $=CR^cR^d$. In another aspect of this embodiment, $R^a$ is H, each $R^{10}$ is H and $L^1$ is O. In another aspect of this embodiment, $R^a$ is H, each $R^{10}$ is H, $L^1$ is O and $R^{3d}$ is H. In another aspect of this embodiment, $R^a$ is H, each $R^{10}$ is H, $L^1$ is O and $R^{3d}$ is $CH_2R^9$. In another aspect of this embodiment, $R^a$ is H, each $R^{10}$ is H, $L^1$ is O and $R^{3d}$ is alkenyl or substituted alkenyl. In another aspect of this embodiment, $R^a$ is H, each $R^{10}$ is H, $L^1$ is O and $R^{3d}$ is alkynyl or substituted alkynyl. In another aspect of this embodiment, each E and D is >N. In another aspect of this embodiment, each E and D is >N and $F^x$ is >C—$R^{25}$. In another aspect of this embodiment, $E^2$ is >N. In another aspect of this embodiment, $E^2$ is >C—$R^{25}$. In another aspect of this embodiment, $E^2$ is >C—$R^{30}$.

In another preferred embodiment of Formula IV, $B^3$ is

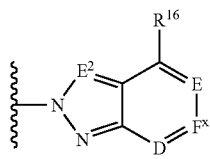

wherein $R^a$ is H, each $R^{10}$ is H and $L^1$ is O. In another aspect of this embodiment, $R^{3d}$ is H. In another aspect of this embodiment, $R^{3d}$ is $CH_2R^9$. In another aspect of this embodiment, $R^{3d}$ is alkenyl or substituted alkenyl. In another aspect of this embodiment, $R^{3d}$ is alkynyl or substituted alkynyl. In another aspect of this embodiment, each $R^5$ and $R^6$ is H. In another aspect of this embodiment, $R^5$ and $R^6$, taken together, are $=CR^cR^d$. In another aspect of this embodiment, $R^a$ is H, each $R^{10}$ is H and $L^1$ is O. In another aspect of this embodiment, $R^a$ is H, each $R^{10}$ is H, $L^1$ is O and $R^{3d}$ is H. In another aspect of this embodiment, $R^a$ is H, each $R^{10}$ is H, $L^1$ is O and $R^{3d}$ is $CH_2R^9$. In another aspect of this embodiment, $R^a$ is H, each $R^{10}$ is H, $L^1$ is O and $R^{3d}$ is alkenyl or substituted alkenyl. In another aspect of this embodiment, $R^a$ is H, each $R^{10}$ is H, $L^1$ is O and $R^{3d}$ is alkynyl or substituted alkynyl. In another aspect of this embodiment, each E and D is >N. In another aspect of this embodiment, each E and D is >N and $F^x$ is >C—$R^{25}$. In another aspect of this embodiment, $E^2$ is >N. In another aspect of this embodiment, $E^2$ is >C—$R^{25}$. In another aspect of this embodiment, $E^2$ is >C—$R^{30}$. In another aspect of this embodiment, each $W^1$ and $W^2$ is independently $Y^2-R^x$ wherein each $Y^2$ is independently —O— or —N(R)— and $R^x$ is not H. In another aspect of this embodiment, each $W^1$ and $W^2$ is independently $Y^2-R^x$ wherein each $Y^2$ is —O— and $R^x$ is not H. In another aspect of this embodiment, each $W^1$ and $W^2$ is independently $Y^2-R^x$ wherein each $Y^2$ is independently —N(R)— and $R^x$ is not H.

In another preferred embodiment of Formula IV, $B^3$ is

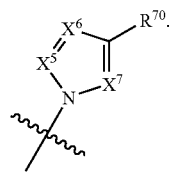

In one aspect of this embodiment, $R^a$ is H, each $R^{10}$ is H and $L^1$ is O. In another aspect of this embodiment, $R^{3d}$ is H. In another aspect of this embodiment, $R^{3d}$ is $CH_2R^9$. In another aspect of this embodiment, $R^{3d}$ is alkenyl or substituted alkenyl. In another aspect of this embodiment, $R^{3d}$ is alkynyl or substituted alkynyl. In another aspect of this embodiment, each $R^5$ and $R^6$ is H. In another aspect of this embodiment, $R^5$ and $R^6$, taken together, are $=CR^cR^d$. In another aspect of this embodiment, $R^a$ is H, each $R^{10}$ is H, $L^1$ is O and $R^{3d}$ is H. In another aspect of this embodiment, $R^a$ is H, each $R^{10}$ is H, $L^1$ is O and $R^{3d}$ is $CH_2R^9$. In another aspect of this embodiment, $R^a$ is H, each $R^{10}$ is H, $L^1$ is O and $R^{3d}$ is alkenyl or substituted alkenyl. In another aspect of this embodiment, $R^a$ is H, each $R^{10}$ is H, $L^1$ is O and $R^{3d}$ is alkynyl or substituted alkynyl.

In another preferred embodiment of Formula IV, $B^3$ is

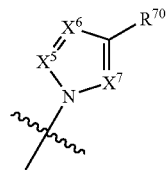

wherein $R^a$ is H, each $R^{10}$ is H and $L^1$ is O. In another aspect of this embodiment, $R^{3d}$ is H, and each $R^5$ and $R^6$ is H. In another aspect of this embodiment, $R^{3d}$ is H, and $R^5$ and $R^6$, taken together, are $=CR^cR^d$. In another aspect of this embodiment, $R^{3d}$ is $CH_2R^9$, and each $R^5$ and $R^6$ is H. In another aspect of this embodiment, $R^{3d}$ is $CH_2R^9$, and $R^5$ and $R^6$, taken together, are $=CR^cR^d$. In another aspect of this embodiment, $R^{3d}$ is alkenyl or substituted alkenyl, and each $R^5$ and $R^6$ is H. In another aspect of this embodiment, $R^{3d}$ is alkenyl or substituted alkenyl, and $R^5$ and $R^6$, taken together, are $=CR^cR^d$. In another aspect of this embodiment, $R^{3d}$ is alkynyl or substituted alkynyl, and each $R^5$ and $R^6$ is H. In another aspect of this embodiment, $R^{3d}$ is alkynyl or substituted alkynyl, and $R^5$ and $R^6$, taken together, are $=CR^cR^d$. In another aspect of this embodiment, $X^5$ is CH and each $X^6$ and $X^7$ is N. In another aspect of this embodiment, $X^5$ is CH, each $X^6$ and $X^7$ is N, and $R^{70}$ is $-C(O)NR^{7b}R^{7c}$. In another aspect of this embodiment, each $W^1$ and $W^2$ is independently $Y^2-R^x$ wherein each $Y^2$ is independently $-O-$ or $-N(R)-$ and $R^x$ is not H. In another aspect of this embodiment, each $W^1$ and $W^2$ is independently $Y^2-R^x$ wherein each $Y^2$ is $-O-$ and $R^x$ is not H. In another aspect of this embodiment, each $W^1$ and $W^2$ is independently $Y^2-R^x$ wherein each $Y^2$ is independently $-N(R)-$ and $R^x$ is not H.

In another preferred embodiment of Formula IV, $B^3$ is

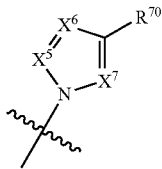

wherein $X^5$ is CH, each $X^6$ and $X^7$ is N, $R^a$ is H, each $R^{10}$ is H and $L^1$ is O. In another aspect of this embodiment, $R^{3d}$ is H, and each $R^5$ and $R^6$ is H. In another aspect of this embodiment, $R^{3d}$ is H, and $R^5$ and $R^6$, taken together, are $=CR^cR^d$. In another aspect of this embodiment, $R^{3d}$ is $CH_2R^9$, and each $R^5$ and $R^6$ is H. In another aspect of this embodiment, $R^{3d}$ is $CH_2R^9$, and $R^5$ and $R^6$, taken together, are $=CR^cR^d$. In another aspect of this embodiment, $R^{3d}$ is alkenyl or substituted alkenyl, and each $R^5$ and $R^6$ is H. In another aspect of this embodiment, $R^{3d}$ is alkenyl or substituted alkenyl, and $R^5$ and $R^6$, taken together, are $=CR^cR^d$. In another aspect of this embodiment, $R^{3d}$ is alkynyl or substituted alkynyl, and each $R^5$ and $R^6$ is H. In another aspect of this embodiment, $R^{3d}$ is alkynyl or substituted alkynyl, and $R^5$ and $R^6$, taken together, are $=CR^cR^d$. In another aspect of this embodiment, $R^{70}$ is $-C(O)NR^{7b}R^{7c}$.

In another preferred embodiment of Formula IV, $B^3$ is

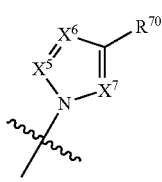

wherein $R^{70}$ is $-C(O)NH_2$, $X^5$ is CH, each $X^6$ and $X^7$ is N, $R^a$ is H, each $R^{10}$ is H and $L^1$ is O. In another aspect of this embodiment, $R^{3d}$ is H, and each $R^5$ and $R^6$ is H. In another aspect of this embodiment, $R^{3d}$ is H, and $R^5$ and $R^6$, taken together, are $=CR^cR^d$. In another aspect of this embodiment, $R^{3d}$ is $CH_2R^9$, and each $R^5$ and $R^6$ is H. In another aspect of this embodiment, $R^{3d}$ is $CH_2R^9$, and $R^5$ and $R^6$, taken together, are $=CR^cR^d$. In another aspect of this embodiment, $R^{3d}$ is alkenyl or substituted alkenyl, and each $R^5$ and $R^6$ is H. In another aspect of this embodiment, $R^{3d}$ is alkenyl or substituted alkenyl, and $R^5$ and $R^6$, taken together, are $=CR^cR^d$. In another aspect of this embodiment, $R^{3d}$ is alkynyl or substituted alkynyl, and each $R^5$ and $R^6$ is H. In another aspect of this embodiment, $R^{3d}$ is alkynyl or substituted alkynyl, and $R^5$ and $R^6$, taken together, are $=CR^cR^d$. In another aspect of this embodiment, each $W^1$ and $W^2$ is independently $Y^2-R^x$ wherein each $Y^2$ is independently $-O-$ or $-N(R)-$ and $R^x$ is not H. In another aspect of this embodiment, each $W^1$ and $W^2$ is independently $Y^2-R^x$ wherein each $Y^2$ is $-O-$ and $R^x$ is not H. In another aspect of this embodiment, each $W^1$ and $W^2$ is independently $Y^2-R^x$ wherein each $Y^2$ is independently $-N(R)-$ and $R^x$ is not H.

The compounds of the Formulas I, II, III and IV bear a phosphonate group,

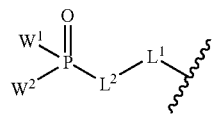

which may be a prodrug moiety wherein $W^1$ and $W^2$ are each independently a group of the formula:

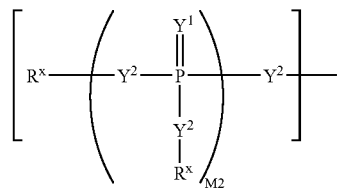

wherein:
each $Y^2$ is independently a bond, O, $CR_2$, NR, $^+N(O)(R)$, N(OR), $^+N(O)(OR)$, N—$NR_2$, S, S—S, S(O), or $S(O)_2$;
M2 is 0, 1 or 2;
each $R^y$ is independently H, F, Cl, Br, I, OH, R, $-C(=Y^1)$R, $-C(=Y^1)$OR, $-C(=Y^1)N(R)_2$, $-N(R)_2$, $-^+N(R)_3$, $-SR$, $-S(O)R$, $-S(O)_2R$, $-S(O)(OR)$, $-S(O)_2(OR)$, $-OC(=Y^1)R$, $-OC(=Y^1)OR$, $-OC(=Y^1)(N(R)_2)$, $-SC(=Y^1)R$, $-SC(=Y^1)OR$, $-SC(=Y^1)(N(R)_2)$, $-N(R)C(=Y^1)R$, $-N(R)C(=Y^1)OR$, or $-N(R)C(=Y^1)N(R)_2$, amino ($-NH_2$), ammonium ($-NH_3^+$), alkylamino, dialkylamino, trialkylammonium, $C_1$-$C_8$ alkyl, $C_1$-$C_8$ alkylhalide, carboxylate, sulfate, sulfamate, sulfonate, $C_1$-$C_8$ alkylsulfonate, $C_1$-$C_8$ alkylamino, $C_1$-$C_8$ alkylhydroxyl, $C_1$-$C_8$ alkylthiol, alkylsulfone ($-SO_2R$), sulfonamide ($-SO_2NR_2$), alkylsulfoxide ($-SOR$), ester ($-C(=O)OR$), amido ($-C(=O)NR_2$), nitrile ($-CN$), azido ($-N_3$), nitro ($-NO_2$), $C_1$-$C_8$ alkoxy ($-OR$), $C_1$-$C_8$ alkyl, $C_1$-$C_8$ substituted alkyl, $C_2$-$C_8$ alkenyl, $C_2$-$C_8$ substituted alkenyl, $C_2$-$C_8$ alkynyl, $C_2$-$C_8$ substituted alkynyl, a protecting group or $W^3$; or when taken together, two $R^y$ on the same carbon atom form a carbocyclic ring of 3 to 7 carbon atoms;
each $R^x$ is independently $R^y$, a protecting group, or the formula:

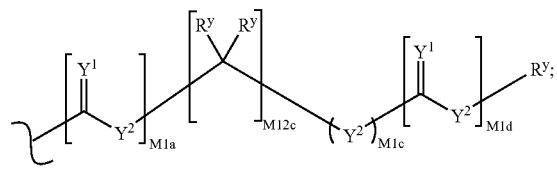

wherein:
M1a, M1c, and M1d are independently 0 or 1;
M12c is 0, 1, 2, 3, 4, 5, 6, 7, 8, 9, 10, 11 or 12; or when taken together, two $R^x$ are optionally substituted $C_2$-$C_4$ alkylene thereby forming a phosphorous-containing heterocycle;

each R is H, halogen, $C_1$-$C_8$ alkyl, $C_1$-$C_8$ substituted alkyl, $C_2$-$C_8$ alkenyl, $C_2$-$C_8$ substituted alkenyl, $C_2$-$C_8$ alkynyl, $C_2$-$C_8$ substituted alkynyl, $C_6$-$C_{20}$ aryl, $C_6$-$C_{20}$ substituted aryl, $C_2$-$C_{20}$ heterocycle, $C_2$-$C_{20}$ substituted heterocycle, or a protecting group;

$W^3$ is $W^4$ or $W^5$; $W^4$ is R, $—C(Y^1)R^y$, $—C(Y^1)W^5$, $—SO_2R^y$, or $—SO_2W^5$; and $W^5$ is a carbocycle or a heterocycle wherein $W^5$ is independently substituted with 0 to 3 $R^y$ groups.

$W^5$ carbocycles and $W^5$ heterocycles may be independently substituted with 0 to 3 $R^y$ groups. $W^5$ may be a saturated, unsaturated or aromatic ring comprising a mono- or bicyclic carbocycle or heterocycle. $W^5$ may have 3 to 10 ring atoms, e.g., 3 to 7 ring atoms. The $W^5$ rings are saturated when containing 3 ring atoms, saturated or mono-unsaturated when containing 4 ring atoms, saturated, or mono- or di-unsaturated when containing 5 ring atoms, and saturated, mono- or di-unsaturated, or aromatic when containing 6 ring atoms.

A $W^5$ heterocycle may be a monocycle having 3 to 7 ring members (2 to 6 carbon atoms and 1 to 3 heteroatoms selected from N, O, P, and S) or a bicycle having 7 to 10 ring members (4 to 9 carbon atoms and 1 to 3 heteroatoms selected from N, O, P, and S). $W^5$ heterocyclic monocycles may have 3 to 6 ring atoms (2 to 5 carbon atoms and 1 to 2 heteroatoms selected from N, O, and S); or 5 or 6 ring atoms (3 to 5 carbon atoms and 1 to 2 heteroatoms selected from N and S). $W^5$ heterocyclic bicycles have 7 to 10 ring atoms (6 to 9 carbon atoms and 1 to 2 heteroatoms selected from N, O, and S) arranged as a bicyclo [4,5], [5,5], [5,6], or [6,6] system; or 9 to 10 ring atoms (8 to 9 carbon atoms and 1 to 2 hetero atoms selected from N and S) arranged as a bicyclo [5,6] or [6,6] system. The $W^5$ heterocycle may be bonded to $Y^2$ through a carbon, nitrogen, sulfur or other atom by a stable covalent bond.

$W^5$ heterocycles include for example, pyridyl, dihydropyridyl isomers, piperidine, pyridazinyl, pyrimidinyl, pyrazinyl, s-triazinyl, oxazolyl, imidazolyl, thiazolyl, isoxazolyl, pyrazolyl, isothiazolyl, furanyl, thiofuranyl, thienyl, and pyrrolyl. $W^5$ also includes, but is not limited to, examples such as:

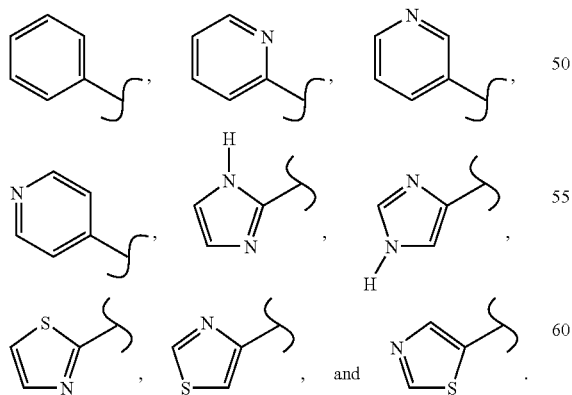

$W^5$ carbocycles and heterocycles may be independently substituted with 0 to 3 R groups, as defined above. For example, substituted $W^5$ carbocycles include:

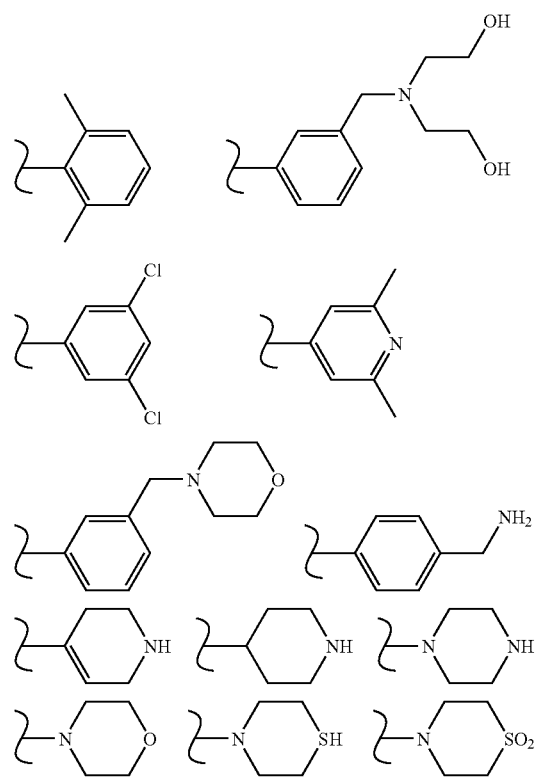

Examples of substituted phenyl carbocycles include:

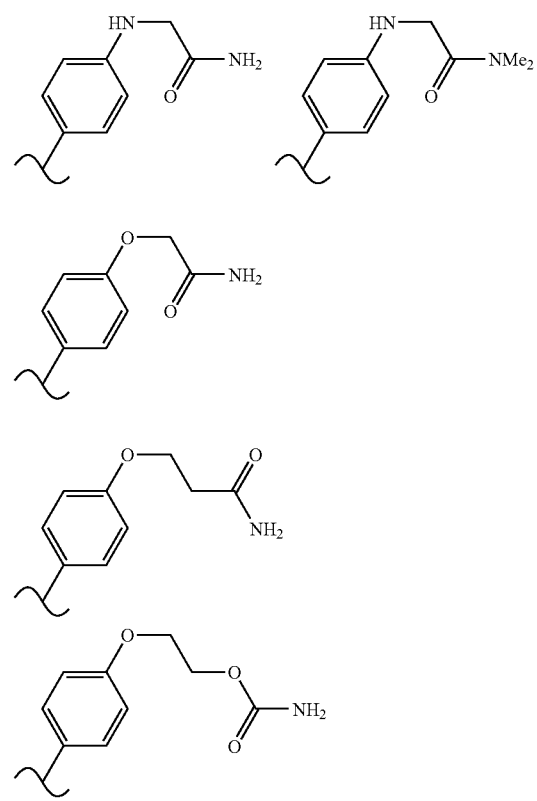

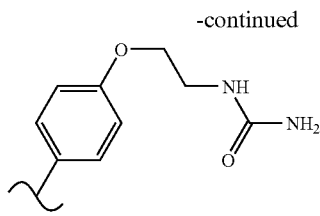

Embodiments of

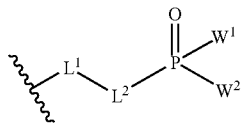

of Formula I, II, III or IV compounds include substructures such as:

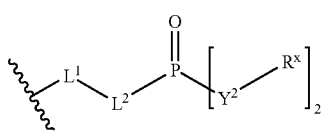

wherein $Y^2$ is —O— or —N(R)—.

Another embodiment of

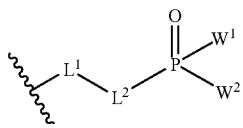

of Formula I, II, III or IV includes the substructures:

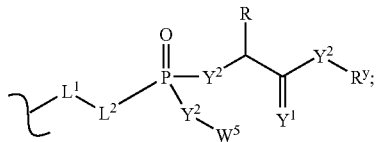

wherein $Y^2$ is O, N(R) or S.

Another embodiment of

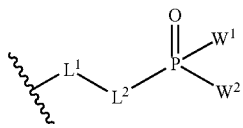

of Formula I, II, III or IV compounds include the substructures:

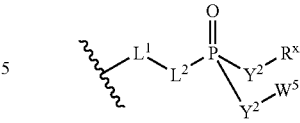

wherein $W^5$ is a carbocycle such as phenyl or substituted phenyl. Such a substructure includes:

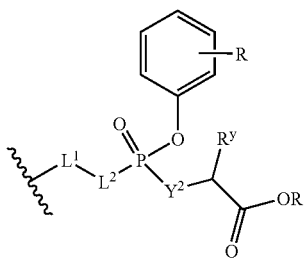

wherein $Y^2$ is O or N(R) and the phenyl carbocycle is substituted with 0 to 3 $R^y$ groups.

An embodiment of

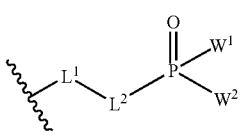

of Formula I, II, III or IV includes phenyl phosphonamidate amino acids, e.g. alanate esters and phenyl phosphonate-lactate esters:

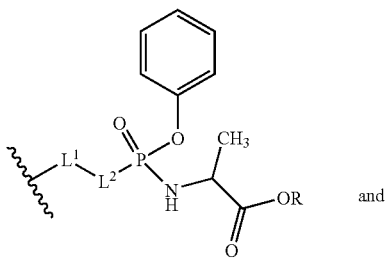 and

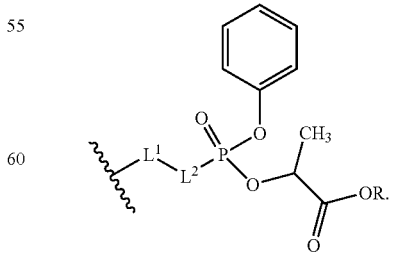

The chiral carbon of the amino acid and lactate moieties may be either the R or S configuration or the racemic mixture.

Another embodiment of

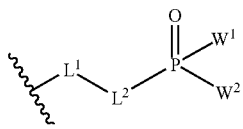

of Formula I, Formula II, Formula III, or Formula IV is

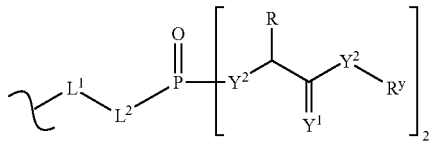

wherein $Y^1$ is O or S and each $Y^2$ is —O— or —N(R)—. In a preferred embodiment, $W^1$ and $W^2$ are independently nitrogen-linked naturally occurring amino acids or their enantiomers. In another preferred embodiment, $W^1$ and $W^2$ are independently naturally occurring 2-hydroxy carboxylic acids or their enantiomers that are linked through the 2-hydroxy group.

Another embodiment of

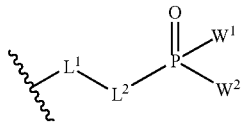

of Formula I, Formula II, Formula III, or Formula IV is

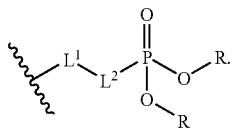

In one preferred embodiment each R is independently $C_1$-$C_8$ alkyl. In another preferred embodiment each R is independently $C_6$-$C_{20}$ aryl or $C_6$-$C_{20}$ substituted aryl.

Embodiments of $R^x$ include esters, carbamates, carbonates, thioesters, amides, thioamides, and urea groups:

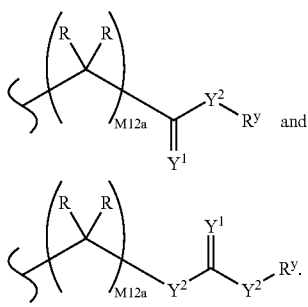

Cellular Accumulation

One aspect of the invention is HCV polymerase inhibitor compounds capable of accumulating in human PBMC (peripheral blood monocyte cells).

Optionally, the compounds of the invention demonstrate improved intracellular half-life of the compounds or intracellular metabolites of the compounds in human PBMC when compared to analogs of the compounds not having the phosphonate or phosphonate prodrug. Typically, the half-life is improved by at least about 50%, more typically at least in the range 50-100%, still more typically at least about 100%, more typically yet greater than about 100%.

In one embodiment, the intracellular half-life of a metabolite of the compound in human PBMC is improved when compared to an analog of the compound not having the phosphonate or phosphonate prodrug. In such embodiments, the metabolite is typically generated intracellularly, more typically, it is generated within human PBMC. Still more typically, the metabolite is a product of the cleavage of a phosphonate prodrug within human PBMCs. More typically yet, the phosphonate prodrug is cleaved to form a metabolite having at least one negative charge at physiological pH. Most typically, the phosphonate prodrug is enzymatically cleaved within human PBMC to form a phosphonate having at least one active hydrogen atom of the form P—OH.

Recursive Substituents

Selected substituents within the compounds of the invention are present to a recursive degree. In this context, "recursive substituent" means that a substituent may recite another instance of itself. Because of the recursive nature of such substituents, theoretically, a large number of compounds may be present in any given embodiment. For example, $R^x$ contains a $R^y$ substituent. $R^y$ can be R. One of ordinary skill in the art of medicinal chemistry understands that the total number of such substituents is reasonably limited by the desired properties of the compound intended. Such properties include, by of example and not limitation, physical properties such as molecular weight, solubility or log P, application properties such as activity against the intended target, and practical properties such as ease of synthesis.

By way of example and not limitation, $W^3$ and $R^y$ are recursive substituents in certain embodiments. Typically, each of these may independently occur 20, 19, 18, 17, 16, 15, 14, 13, 12, 11, 10, 9, 8, 7, 6, 5, 4, 3, 2, 1, or 0, times in a given embodiment. More typically, each of these may independently occur 12 or fewer times in a given embodiment. More typically yet, $W^3$ will occur 0 to 8 times, $R^y$ will occur 0 to 6 times in a given embodiment. Even more typically, $W^3$ will occur 0 to 6 times, $R^y$ will occur 0 to 4 times and $R^3$ will occur 0 to 8 times in a given embodiment.

Recursive substituents are an intended aspect of the invention. One of ordinary skill in the art of medicinal chemistry understands the versatility of such substituents. To the degree that recursive substituents are present in an embodiment of the invention, the total number will be determined as set forth above.

Protecting Groups

In the context of the present invention, embodiments of protecting groups include prodrug moieties and chemical protecting groups.

Protecting groups are available, commonly known and used, and are optionally used to prevent side reactions with the protected group during synthetic procedures, i.e. routes or methods to prepare the compounds of the invention. For the most part the decision as to which groups to protect, when to do so, and the nature of the chemical protecting group "PRT"

will be dependent upon the chemistry of the reaction to be protected against (e.g., acidic, basic, oxidative, reductive or other conditions) and the intended direction of the synthesis. The PRT groups do not need to be, and generally are not, the same if the compound is substituted with multiple PRT. In general, PRT will be used to protect functional groups such as carboxyl, hydroxyl or amino groups and to thus prevent side reactions or to otherwise facilitate the synthetic efficiency. The order of deprotection to yield free, deprotected groups is dependent upon the intended direction of the synthesis and the reaction conditions to be encountered, and may occur in any order as determined by the artisan.

Various functional groups of the compounds of the invention may be protection. For example, protecting groups for —OH groups (whether hydroxyl, carboxylic acid, phosphonic acid, or other functions) are embodiments of "ether- or ester-forming groups". Ether- or ester-forming groups are capable of functioning as chemical protecting groups in the synthetic schemes set forth herein. However, some hydroxyl and thio protecting groups are neither ether-nor ester-forming groups, as will be understood by those skilled in the art, and are included with amides, discussed below.

A very large number of hydroxyl protecting groups and amide-forming groups and corresponding chemical cleavage reactions are described in "Protective Groups in Organic Chemistry", Theodora W. Greene (John Wiley & Sons, Inc., New York, 1991, ISBN 0-471-62301-6) ("Greene"). See also Kocienski, Philip J.; "Protecting Groups" (Georg Thieme Verlag Stuttgart, New York, 1994), which is incorporated by reference in its entirety herein. In particular Chapter 1, Protecting Groups An Overview, pages 1-20, Chapter 2, Hydroxyl Protecting Groups, pages 21-94, Chapter 3, Diol Protecting Groups, pages 95-117, Chapter 4, Carboxyl Protecting Groups, pages 118-154, Chapter 5, Carbonyl Protecting Groups, pages 155-184. For protecting groups for carboxylic acid, phosphonic acid, phosphonate, sulfonic acid and other protecting groups for acids see Greene as set forth below. Such groups include by way of example and not limitation, esters, amides, hydrazides, and the like.

Ether- and Ester-Forming Protecting Groups

Ester-forming groups include: (1) phosphonate ester-forming groups, such as phosphonamidate esters, phosphorothioate esters, phosphonate esters, and phosphon-bis-amidates; (2) carboxyl ester-forming groups, and (3) sulphur ester-forming groups, such as sulphonate, sulfate, and sulfinate.

The phosphonate moieties of the compounds of the invention may or may not be prodrug moieties, i.e. they may or may not be susceptible to hydrolytic or enzymatic cleavage or modification. Certain phosphonate moieties are stable under most or nearly all metabolic conditions. For example, a dialkylphosphonate, where the alkyl groups are two or more carbons, may have appreciable stability in vivo due to a slow rate of hydrolysis.

Within the context of phosphonate prodrug moieties, a large number of structurally-diverse prodrugs have been described for phosphonic acids (Freeman and Ross in *Progress in Medicinal Chemistry* 34:112-147 (1997) and are included within the scope of the present invention. An exemplary embodiment of a phosphonate ester-forming group is the phenyl carbocycle in a substructure having the formula:

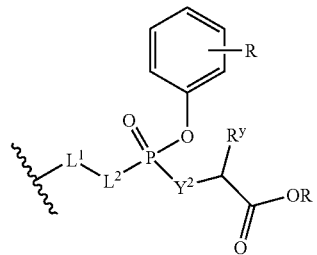

wherein the phenyl carbocycle is substituted with 0 to 3 R groups. Also, in this embodiment, where $Y^2$ is O, a lactate ester is formed. Alternatively, where $Y^2$ is NR, N—OR or N—N(R)$_2$, then phosphonamidate esters result. R substituents include H and $C_1$-$C_{12}$ alkyl.

In its ester-forming role, a protecting group typically is bound to any acidic group such as, by way of example and not limitation, a —CO$_2$H or —C(S)OH group, thereby resulting in —CO$_2$R$^x$ where R$^x$ is defined herein. Also, R$^x$ for example includes the enumerated ester groups of WO 95/07920.

Examples of protecting groups include (a)-(j):

(a) $C_3$-$C_{12}$ heterocycle (described above) or aryl. These aromatic groups optionally are polycyclic or monocyclic. Examples include phenyl, spiryl, 2- and 3-pyrrolyl, 2- and 3-thienyl, 2- and 4-imidazolyl, 2-, 4- and 5-oxazolyl, 3- and 4-isoxazolyl, 2-, 4- and 5-thiazolyl, 3-, 4- and 5-isothiazolyl, 3- and 4-pyrazolyl, 1-, 2-, 3- and 4-pyridinyl, and 1-, 2-, 4- and 5-pyrimidinyl.

(b) $C_3$-$C_{12}$ heterocycle or aryl substituted with halo, R$^1$, R$^1$—O—$C_1$-$C_{12}$ alkylene, $C_1$-$C_{12}$ alkoxy, CN, NO$_2$, OH, carboxy, carboxyester, thiol, thioester, $C_1$-$C_{12}$ haloalkyl (1-6 halogen atoms), $C_2$-$C_{12}$ alkenyl or $C_2$-$C_{12}$ alkynyl. Such groups include, but are not limited to, 2-, 3- and 4-alkoxyphenyl ($C_1$-$C_{12}$ alkyl); 2-, 3- and 4-methoxyphenyl; 2-, 3- and 4-ethoxyphenyl; 2,3-, 2,4-, 2,5-, 2,6-, 3,4- and 3,5-diethoxyphenyl; 2- and 3-carboethoxy-4-hydroxyphenyl; 2- and 3-ethoxy-4-hydroxyphenyl; 2- and 3-ethoxy-5-hydroxyphenyl; 2- and 3-ethoxy-6-hydroxyphenyl; 2-, 3- and 4-O-acetylphenyl; 2-, 3- and 4-dimethylaminophenyl; 2-, 3- and 4-methylmercaptophenyl; 2-, 3- and 4-halophenyl (including 2-, 3- and 4-fluorophenyl and 2-, 3- and 4-chlorophenyl); 2,3-, 2,4-, 2,5-, 2,6-, 3,4- and 3,5-dimethylphenyl; 2,3-, 2,4-, 2,5-, 2,6-, 3,4- and 3,5-biscarboxyethylphenyl; 2,3-, 2,4-, 2,5-, 2,6-, 3,4- and 3,5-dimethoxyphenyl; 2,3-, 2,4-, 2,5-, 2,6-, 3,4- and 3,5-dihalophenyl (including 2,4-difluorophenyl and 3,5-difluorophenyl); 2-, 3- and 4-haloalkylphenyl (1 to 5 halogen atoms, $C_1$-$C_{12}$ alkyl including 4-trifluoromethylphenyl); 2-, 3- and 4-cyanophenyl; 2-, 3- and 4-nitrophenyl; 2-, 3- and 4-haloalkylbenzyl (1 to 5 halogen atoms, $C_1$-$C_{12}$ alkyl including 4-trifluoromethylbenzyl and 2-, 3- and 4-trichloromethylphenyl and 2-, 3- and 4-trichloromethylphenyl); 4-N-methylpiperidinyl; 3-N-methylpiperidinyl; 1-ethylpiperazinyl; benzyl; alkylsalicylphenyl ($C_1$-$C_4$ alkyl, including 2-, 3- and 4-ethylsalicylphenyl); 2-, 3- and 4-acetylphenyl; 1,8-dihydroxynaphthyl (—$C_{10}H_6$—OH) and aryloxy ethyl [$C_6$-$C_9$ aryl (including phenoxy ethyl)], 2,2'-dihydroxybiphenyl; 2-, 3- and 4-N,N-dialkylaminophenol; —$C_6H_4CH_2$—N(CH$_3$)$_2$; trimethoxybenzyl; triethoxybenzyl; and 2-alkyl pyridinyl ($C_{1-4}$ alkyl).

(c)

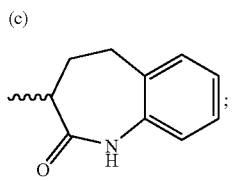

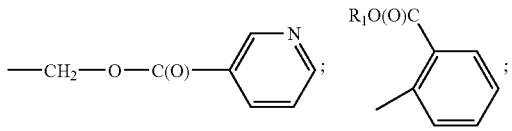

$C_4$-$C_8$ esters of 2-carboxyphenyl; and $C_1$-$C_4$ alkylene-$C_3$-$C_6$ aryl (including benzyl, —$CH_2$-pyrrolyl, —$CH_2$-thienyl, —$CH_2$-imidazolyl, —$CH_2$-oxazolyl, —$CH_2$-isoxazolyl, —$CH_2$-thiazolyl, —$CH_2$-isothiazolyl, —$CH_2$-pyrazolyl, —$CH_2$-pyridinyl and —$CH_2$-pyrimidinyl) substituted in the aryl moiety by 3 to 5 halogen atoms or 1 to 2 atoms or groups selected from halogen, $C_1$-$C_{12}$ alkoxy (including methoxy and ethoxy), cyano, nitro, OH, $C_1$-$C_{12}$ haloalkyl (1 to 6 halogen atoms; including —$CH_2CCl_3$), $C_1$-$C_{12}$ alkyl (including methyl and ethyl), $C_2$-$C_{12}$ alkenyl or $C_2$-$C_{12}$ alkynyl.

(d) Alkoxy ethyl [$C_1$-$C_6$ alkyl including —$CH_2$—$CH_2$—O—$CH_3$ (methoxy ethyl)], alkyl substituted by any of the groups set forth above for aryl, in particular OH or by 1 to 3 halo atoms (including —$CH_3$, —$CH(CH_3)_2$, —$C(CH_3)_3$, —$CH_2CH_3$, —$(CH_2)_2CH_3$, —$(CH_2)_3CH_3$, —$(CH_2)_4CH_3$, —$(CH_2)_5CH_3$, $CH_2CH_2F$, —$CH_2CH_2Cl$, —$CH_2CF_3$, and —$CH_2CCl_3$),

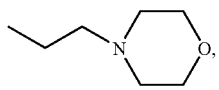

—N-2-propylmorpholino, 2,3-dihydro-6-hydroxyindene, sesamol, catechol monoester, —$CH_2$—C(O)—N($R^1$)$_2$, —$CH_2$—S(O)($R^1$), —$CH_2$—S(O)$_2$($R^1$), —$CH_2$—CH(OC(O)$CH_2R^1$)—$CH_2$(OC(O)$CH_2R^1$), cholesteryl, enolpyruvate (HOOC—C(=$CH_2$)—) or glycerol.

(e) A 5 or 6 carbon monosaccharide, disaccharide or oligosaccharide (3 to 9 monosaccharide residues).

(f) Triglycerides such as α-D-β-diglycerides (wherein the fatty acids composing glyceride lipids generally are naturally-occurring saturated or unsaturated $C_{6-26}$, $C_{6-18}$ or $C_{6-10}$ fatty acids such as linoleic, lauric, myristic, palmitic, stearic, oleic, palmitoleic, linolenic and the like fatty acids) linked to acyl of the parental compounds herein through a glyceryl oxygen of the triglyceride;

(g) Phospholipids linked to the carboxyl group through the phosphate of the phospholipid.

(h) Phthalidyl (shown in FIG. 1 of Clayton et al., *Antimicrob. Agents Chemo.* (1974) 5 (6):670-671.

(i) Cyclic carbonates such as (5-$R_d$-2-oxo-1,3-dioxolen-4-yl)methyl esters (Sakamoto et al., *Chem. Pharm. Bull.* (1984) 32 (6) 2241-2248) where $R_d$ is $R_1$, $R_4$ or aryl.

(j)

The hydroxyl groups of the compounds of this invention optionally are substituted with one of groups III, IV or V disclosed in WO 94/21604, or with isopropyl.

As further embodiments, Table A lists examples of protecting group ester moieties that for example can be bonded via oxygen to —C(O)O— and —P(O)(O—)$_2$ groups. Several amidates also are shown, which are bound directly to —C(O)— or —P(O)$_2$. Esters of structures 1-5, 8-10 and 16, 17, 19-22 are synthesized by reacting the compound herein having a free hydroxyl with the corresponding halide (chloride or acyl chloride and the like) and N,N-dicyclohexyl-N-morpholine carboxamidine (or another base such as DBU, triethylamine, $CsCO_3$, N,N-dimethylaniline and the like) in DMF (or other solvent such as acetonitrile or N-methylpyrrolidone). When the compound to be protected is a phosphonate, the esters of structures 5-7, 11, 12, 21, and 23-26 are synthesized by reaction of the alcohol or alkoxide salt (or the corresponding amines in the case of compounds such as 13, 14 and 15) with the monochlorophosphonate or dichlorophosphonate (or another activated phosphonate).

TABLE A

| | |
|---|---|
| 1. | —$CH_2$—C(O)—N($R_1$)$_2$* |
| 2. | —$CH_2$—S(O)($R_1$) |
| 3. | —$CH_2$—S(O)$_2$($R_1$) |
| 4. | —$CH_2$—O—C(O)—$CH_2$—$C_6H_5$ |
| 5. | 3-cholesteryl |
| 6. | 3-pyridyl |
| 7. | N-ethylmorpholino |
| 8. | —$CH_2$—O—C(O)—$C_6H_5$ |
| 9. | —$CH_2$—O—C(O)—$CH_2CH_3$ |
| 10. | —$CH_2$—O—C(O)—C($CH_3$)$_3$ |
| 11. | —$CH_2$—$CCl_3$ |
| 12. | —$C_6H_5$ |
| 13. | —NH—$CH_2$—C(O)O—$CH_2CH_3$ |
| 14. | —N($CH_3$)—$CH_2$—C(O)O—$CH_2CH_3$ |
| 15. | —NH$R_1$ |
| 16. | —$CH_2$—O—C(O)—$C_{10}H_{15}$ |
| 17. | —$CH_2$—O—C(O)—CH($CH_3$)$_2$ |
| 18. | —$CH_2$—C#H(OC(O)$CH_2R_1$)—$CH_2$—(OC(O)$CH_2R_1$)* |
| 19. | 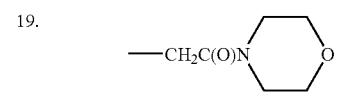 |
| 20. | 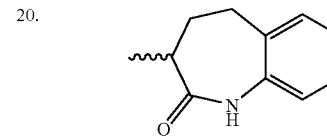 |
| 21. | 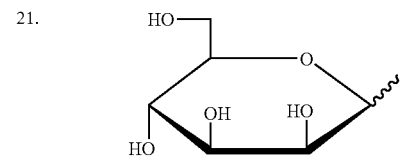 |

TABLE A-continued

| | |
|---|---|
| 22. | 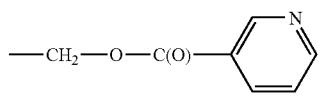 —CH₂—O—C(O)— (pyridyl) |
| 23. | 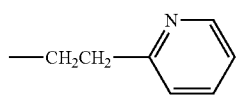 —CH₂CH₂— (pyridyl) |
| 24. | 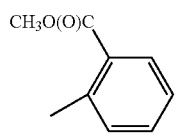 CH₃O(O)C— |
| 25. | 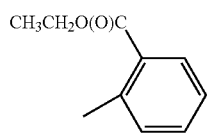 CH₃CH₂O(O)C— |
| 26. | 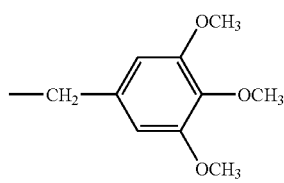 —CH₂— (trimethoxyphenyl, OCH₃) |

\# - chiral center is (R), (S) or racemate.

Other esters that are suitable for use herein are described in EP 632048.

Protecting groups also includes "double ester" forming profunctionalities such as —CH$_2$OC(O)OCH$_3$,

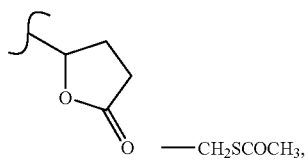 —CH$_2$SCOCH$_3$,

—CH$_2$OCON(CH$_3$)$_2$, or alkyl- or aryl-acyloxyalkyl groups of the structure —CH(R$^1$ or W$^5$)O((CO)R$^{37}$) or —CH(R$^1$ or W$^5$)((CO)OR$^{38}$) (linked to oxygen of the acidic group) wherein R$^{37}$ and R$^{38}$ are alkyl, aryl, or alkylaryl groups (see U.S. Pat. No. 4,968,788). Frequently R$^{37}$ and R$^{38}$ are bulky groups such as branched alkyl, ortho-substituted aryl, meta-substituted aryl, or combinations thereof, including normal, secondary, iso- and tertiary alkyls of 1-6 carbon atoms. An example is the pivaloyloxymethyl group. These are of particular use with prodrugs for oral administration. Examples of such useful protecting groups are alkylacyloxymethyl esters and their derivatives, including —CH(CH$_2$CH$_2$OCH$_3$)OC(O)C(CH$_3$)$_3$,

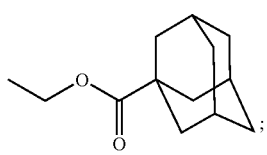

—CH$_2$OC(O)C$_{10}$H$_{15}$, —CH$_2$OC(O)C(CH$_3$)$_3$, —CH(CH$_2$OCH$_3$)OC(O)C(CH$_3$)$_3$, —CH(CH(CH$_3$)$_2$)OC(O)C(CH$_3$)$_3$, —CH$_2$OC(O)CH$_2$CH(CH$_3$)$_2$, —CH$_2$OC(O)C$_6$H$_{11}$, —CH$_2$OC(O)C$_6$H$_5$, —CH$_2$OC(O)C$_{10}$H$_{15}$, —CH$_2$OC(O)CH$_2$CH$_3$, —CH$_2$OC(O)CH(CH$_3$)$_2$, —CH$_2$OC(O)C(CH$_3$)$_3$ and —CH$_2$OC(O)CH$_2$C$_6$H$_5$.

For prodrug purposes, the ester typically chosen is one heretofore used for antibiotic drugs, in particular the cyclic carbonates, double esters, or the phthalidyl, aryl or alkyl esters.

In some embodiments the protected acidic group is an ester of the acidic group and is the residue of a hydroxyl-containing functionality. In other embodiments, an amino compound is used to protect the acid functionality. The residues of suitable hydroxyl or amino-containing functionalities are set forth above or are found in WO 95/07920. Of particular interest are the residues of amino acids, amino acid esters, polypeptides, or aryl alcohols. Typical amino acid, polypeptide and carboxyl-esterified amino acid residues are described on pages 11-18 and related text of WO 95/07920 as groups L$^1$ or L$^2$. WO 95/07920 expressly teaches the amidates of phosphonic acids, but it will be understood that such amidates are formed with any of the acid groups set forth herein and the amino acid residues set forth in WO 95/07920.

Typical esters for protecting acidic functionalities are also described in WO 95/07920, again understanding that the same esters can be formed with the acidic groups herein as with the phosphonate of the '920 publication. Typical ester groups are defined at least on WO 95/07920 pages 89-93 (under R$^{31}$ or R$^{35}$), the table on page 105, and pages 21-23 (as R). Of particular interest are esters of unsubstituted aryl such as phenyl or arylalkyl such benzyl, or hydroxy-, halo-, alkoxy-, carboxy- and/or alkylestercarboxy-substituted aryl or alkylaryl, especially phenyl, ortho-ethoxyphenyl, or C$_1$-C$_4$ alkylestercarboxyphenyl (salicylate C$_1$-C$_{12}$ alkylesters).

The protected acidic groups, particularly when using the esters or amides of WO 95/07920, are useful as prodrugs for oral administration. However, it is not essential that the acidic group be protected in order for the compounds of this invention to be effectively administered by the oral route. When the compounds of the invention having protected groups, in particular amino acid amidates or substituted and unsubstituted aryl esters are administered systemically or orally they are capable of hydrolytic cleavage in vivo to yield the free acid.

A plurality of the acidic hydroxyls may be protected. If more than one acidic hydroxyl is protected then the same or a different protecting group is employed, e.g., the esters may be different or the same, or a mixed amidate and ester may be used.

Typical acid hydroxy protecting groups described in Greene (pages 14-118) include substituted methyl and alkyl ethers, substituted benzyl ethers, silyl ethers, esters including sulfonic acid esters, and carbonates. For example:

Ethers (methyl, t-butyl, allyl);

Substituted Methyl Ethers (Methoxymethyl, Methylthiomethyl, t-Butylthiomethyl, (Phenyldimethylsilyl)methoxymethyl, Benzyloxymethyl, p-Methoxybenzyloxymethyl, (4-Methoxyphenoxy)methyl, Guaiacolmethyl, t-Butoxymethyl, 4-Pentenyloxymethyl, Siloxymethyl, 2-Methoxyethoxymethyl, 2,2,2-Trichloroethoxymethyl, Bis(2-chloroethoxy)methyl, 2-(Trimethylsilyl)ethoxymethyl, Tetrahydropyranyl, 3-Bromotetrahydropyranyl, Tetrahydrothiopyranyl, 1-Methoxycyclohexyl, 4-Methoxytetrahydropyranyl, 4-Methoxytetrahydrothiopyranyl, 4-Methoxytetrahydrothiopyranyl S,S-Dioxido, 1-[(2-Chloro-4-methyl)phenyl]-4-methoxypiperidin-4-yl, 1,4-Dioxan-2-yl, Tetrahydrofuranyl, Tetrahydrothiofuranyl, 2,3,3a,4,5,6,7,7a-Octahydro-7,8,8-trimethyl-4,7-methanobenzofuran-2-yl));

Substituted Ethyl Ethers (1-Ethoxyethyl, 1-(2-Chloroethoxy)ethyl, 1-Methyl-1-methoxyethyl, 1-Methyl-1-benzyloxyethyl, 1-Methyl-1-benzyloxy-2-fluoroethyl, 2,2,2-Trichloroethyl, 2-Trimethylsilylethyl, 2-(Phenylselenyl)ethyl, p-Chlorophenyl, p-Methoxyphenyl, 2,4-Dinitrophenyl, Benzyl);

Substituted Benzyl Ethers (p-Methoxybenzyl, 3,4-Dimethoxybenzyl, o-Nitrobenzyl, p-Nitrobenzyl, p-Halobenzyl, 2,6-Dichlorobenzyl, p-Cyanobenzyl, p-Phenylbenzyl, 2- and 4-Picolyl, 3-Methyl-2-picolyl N-Oxido, Diphenylmethyl, p,p'-Dinitrobenzhydryl, 5-Dibenzosuberyl, Triphenylmethyl, α-Naphthyldiphenylmethyl, p-methoxyphenyldiphenylmethyl, Di(p-methoxyphenyl)phenylmethyl, Tri(p-methoxyphenyl)methyl, 4-(4'-Bromophenacyloxy)phenyldiphenylmethyl, 4,4',4"-Tris(4,5-dichlorophthalimidophenyl)methyl, 4,4',4"-Tris(levulinoyloxyphenyl)methyl, 4,4',4"-Tris(benzoyloxyphenyl)methyl, 3-(Imidazol-1-ylmethyl) bis(4',4"-dimethoxyphenyl)methyl, 1,1-Bis(4-methoxyphenyl)-1'-pyrenylmethyl, 9-Anthryl, 9-(9-Phenyl)xanthenyl, 9-(9-Phenyl-10-oxo)anthryl, 1,3-Benzodithiolan-2-yl, Benzisothiazolyl S,S-Dioxido);

Silyl Ethers (Trimethylsilyl, Triethylsilyl, Triisopropylsilyl, Dimethylisopropylsilyl, Diethylisopropylsilyl, Dimethylthexylsilyl, t-Butyldimethylsilyl, t-Butyldiphenylsilyl, Tribenzylsilyl, Tri-p-xylylsilyl, Triphenylsilyl, Diphenylmethylsilyl, t-Butylmethoxyphenylsilyl);

Esters (Formate, Benzoylformate, Acetate, Choroacetate, Dichloroacetate, Trichloroacetate, Trifluoroacetate, Methoxyacetate, Triphenylmethoxyacetate, Phenoxyacetate, p-Chlorophenoxyacetate, p-poly-Phenylacetate, 3-Phenylpropionate, 4-Oxopentanoate (Levulinate), 4,4-(Ethylenedithio)pentanoate, Pivaloate, Adamantoate, Crotonate, 4-Methoxycrotonate, Benzoate, p-Phenylbenzoate, 2,4,6-Trimethylbenzoate (Mesitoate));

Carbonates (Methyl, 9-Fluorenylmethyl, Ethyl, 2,2,2-Trichloroethyl, 2-(Trimethylsilyl)ethyl, 2-(Phenylsulfonyl)ethyl, 2-(Triphenylphosphonio)ethyl, Isobutyl, Vinyl, Allyl, p-Nitrophenyl, Benzyl, p-Methoxybenzyl, 3,4-Dimethoxybenzyl, o-Nitrobenzyl, p-Nitrobenzyl, S-Benzyl Thiocarbonate, 4-Ethoxy-1-naphthyl, Methyl Dithiocarbonate);

Groups With Assisted Cleavage (2-Iodobenzoate, 4-Azidobutyrate, 4-Nitro-4-methylpentanoate, o-(Dibromomethyl)benzoate, 2-Formylbenzenesulfonate, 2-(Methylthiomethoxy)ethyl Carbonate, 4-(Methylthiomethoxy)butyrate, 2-(Methylthiomethoxymethyl)benzoate); Miscellaneous Esters (2,6-Dichloro-4-methylphenoxyacetate, 2,6-Dichloro-4-(1,1,3,3 tetramethylbutyl)phenoxyacetate, 2,4-Bis(1,1-dimethylpropyl)phenoxyacetate, Chlorodiphenylacetate, Isobutyrate, Monosuccinate, (E)-2-Methyl-2-butenoate (Tigloate), o-(Methoxycarbonyl)benzoate, p-poly-Benzoate, α-Naphthoate, Nitrate, Alkyl N,N,N',N'-Tetramethylphosphorodiamidate, N-Phenylcarbamate, Borate, Dimethylphosphinothioyl, 2,4-Dinitrophenylsulfenate); and Sulfonates (Sulfate, Methanesulfonate (Mesylate), Benzylsulfonate, Tosylate).

Typical 1,2-diol protecting groups (thus, generally where two OH groups are taken together with the protecting functionality) are described in Greene at pages 118-142 and include Cyclic Acetals and Ketals (Methylene, Ethylidene, 1-t-Butylethylidene, 1-Phenylethylidene, (4-Methoxyphenyl)ethylidene, 2,2,2-Trichloroethylidene, Acetonide (Isopropylidene), Cyclopentylidene, Cyclohexylidene, Cycloheptylidene, Benzylidene, p-Methoxybenzylidene, 2,4-Dimethoxybenzylidene, 3,4-Dimethoxybenzylidene, 2-Nitrobenzylidene); Cyclic Ortho Esters (Methoxymethylene, Ethoxymethylene, Dimethoxymethylene, 1-Methoxyethylidene, 1-Ethoxyethylidine, 1,2-Dimethoxyethylidene, α-Methoxybenzylidene, 1-(N,N-Dimethylamino)ethylidene Derivative, α-(N,N-Dimethylamino)benzylidene Derivative, 2-Oxacyclopentylidene); Silyl Derivatives (Di-t-butylsilylene Group, 1,3-(1,1,3,3-Tetraisopropyldisiloxanylidene), and Tetra-t-butoxydisiloxane-1,3-diylidene), Cyclic Carbonates, Cyclic Boronates, Ethyl Boronate and Phenyl Boronate.

More typically, 1,2-diol protecting groups include those shown in Table B, still more typically, epoxides, acetonides, cyclic ketals and aryl acetals.

TABLE B

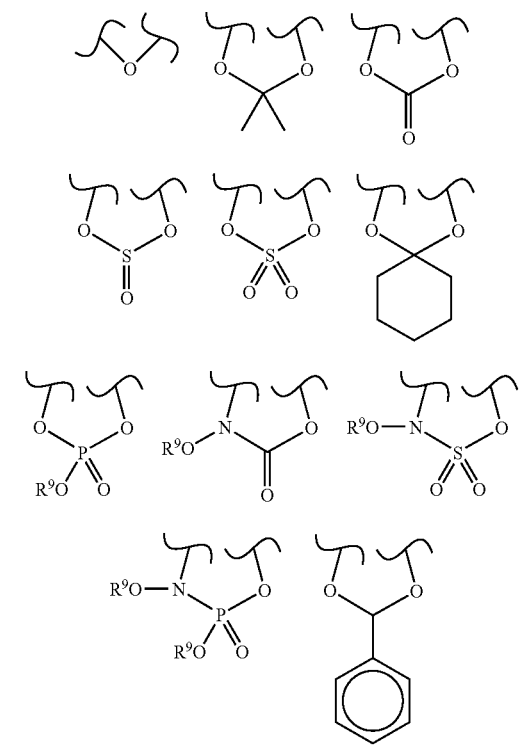

wherein $R^9$ in Table B is $C_1$-$C_6$ alkyl.

Amino Protecting Groups

Another set of protecting groups include any of the typical amino protecting groups described by Greene at pages 315-385. They include:

Carbamates: (methyl and ethyl, 9-fluorenylmethyl, 9(2-sulfo)fluorenylmethyl, 9-(2,7-dibromo)fluorenylmethyl, 2,7-di-t-butyl-[9-(10,10-dioxo-10,10,10-tetrahydrothioxanthyl)]methyl, 4-methoxyphenacyl);

Substituted Ethyl: (2,2,2-trichloroethyl, 2-trimethylsilylethyl, 2-phenylethyl, 1-(1-adamantyl)-1-methylethyl, 1,1-dimethyl-2-haloethyl, 1,1-dimethyl-2,2-dibromoethyl, 1,1-dimethyl-2,2,2-trichloroethyl, 1-methyl-1-(4-biphenylyl)ethyl, 1-(3,5-di-t-butylphenyl)-1-methylethyl, 2-(2'- and 4'-pyridyl)ethyl, 2-(N,N-dicyclohexylcarboxamido)ethyl, t-butyl, 1-adamantyl, vinyl, allyl, 1-isopropylallyl, cinnamyl, 4-nitrocinnamyl, 8-quinolyl, N-hydroxypiperidinyl, alkyldithio, benzyl, p-methoxybenzyl, p-nitrobenzyl, p-bromobenzyl, p-chlorobenzyl, 2,4-dichlorobenzyl, 4-methylsulfinylbenzyl, 9-anthrylmethyl, diphenylmethyl);

Groups With Assisted Cleavage: (2-methylthioethyl, 2-methylsulfonylethyl, 2-(p-toluenesulfonyl)ethyl, [2-(1,3-dithianyl)]methyl, 4-methylthiophenyl, 2,4-dimethylthiophenyl, 2-phosphonioethyl, 2-triphenylphosphonioisopropyl, 1,1-dimethyl-2-cyanoethyl, m-chloro-p-acyloxybenzyl, p-(dihydroxyboryl)benzyl, 5-benzisoxazolylmethyl, 2-(trifluoromethyl)-6-chromonylmethyl);

Groups Capable of Photolytic Cleavage: (m-nitrophenyl, 3,5-dimethoxybenzyl, o-nitrobenzyl, 3,4-dimethoxy-6-nitrobenzyl, phenyl(o-nitrophenyl)methyl); Urea-Type Derivatives (phenothiazinyl-(10)-carbonyl, N'-p-toluenesulfonylaminocarbonyl, N'-phenylaminothiocarbonyl);

Miscellaneous Carbamates: (t-amyl, S-benzyl thiocarbamate, p-cyanobenzyl, cyclobutyl, cyclohexyl, cyclopentyl, cyclopropylmethyl, p-decyloxybenzyl, diisopropylmethyl, 2,2-dimethoxycarbonylvinyl, o-(N,N-dimethylcarboxamido)benzyl, 1,1-dimethyl-3-(N,N-dimethylcarboxamido)propyl, 1,1-dimethylpropynyl, di(2-pyridyl)methyl, 2-furanylmethyl, 2-Iodoethyl, Isobornyl, Isobutyl, Isonicotinyl, p-(p'-Methoxyphenylazo)benzyl, 1-methylcyclobutyl, 1-methylcyclohexyl, 1-methyl-1-cyclopropylmethyl, 1-methyl-1-(3,5-dimethoxyphenyl)ethyl, 1-methyl-1-(p-phenylazophenyl)ethyl, 1-methyl-1-phenylethyl, 1-methyl-1-(4-pyridyl)ethyl, phenyl, p-(phenylazo)benzyl, 2,4,6-tri-t-butylphenyl, 4-(trimethylammonium)benzyl, 2,4,6-trimethylbenzyl);

Amides: (N-formyl, N-acetyl, N-choroacetyl, N-trichoroacetyl, N-trifluoroacetyl, N-phenylacetyl, N-3-phenylpropionyl, N-picolinoyl, N-3-pyridylcarboxamide, N-benzoylphenylalanyl, N-benzoyl, N-p-phenylbenzoyl);

Amides With Assisted Cleavage: (N-o-nitrophenylacetyl, N-o-nitrophenoxyacetyl, N-acetoacetyl, (N'-dithiobenzyloxycarbonylamino)acetyl, N-3-(p-hydroxyphenyl)propionyl, N-3-(o-nitrophenyl)propionyl, N-2-methyl-2-(o-nitrophenoxy)propionyl, N-2-methyl-2-(o-phenylazophenoxy)propionyl, N-4-chlorobutyryl, N-3-methyl-3-nitrobutyryl, N-o-nitrocinnamoyl, N-acetylmethionine, N-o-nitrobenzoyl, N-o-(benzoyloxymethyl)benzoyl, 4,5-diphenyl-3-oxazolin-2-one);

Cyclic Imide Derivatives: (N-phthalimide, N-dithiasuccinoyl, N-2,3-diphenylmaleoyl, N-2,5-dimethylpyrrolyl, N-1,1,4,4-tetramethyldisilylazacyclopentane adduct, 5-substituted 1,3-dimethyl-1,3,5-triazacyclohexan-2-one, 5-substituted 1,3-dibenzyl-1,3-5-triazacyclohexan-2-one, 1-substituted 3,5-dinitro-4-pyridonyl);

N-Alkyl and N-Aryl Amines: (N-methyl, N-allyl, N-[2-(trimethylsilyl)ethoxy]methyl, N-3-acetoxypropyl, N-(1-isopropyl-4-nitro-2-oxo-3-pyrrolin-3-yl), Quaternary Ammonium Salts, N-benzyl, N-di(4-methoxyphenyl)methyl, N-5-dibenzosuberyl, N-triphenylmethyl, N-(4-methoxyphenyl)diphenylmethyl, N-9-phenylfluorenyl, N-2,7-dichloro-9-fluorenylmethylene, N-ferrocenylmethyl, N-2-picolylamine N'-oxide);

Imine Derivatives: (N-1,1-dimethylthiomethylene, N-benzylidene, N-p-methoxybenzylidene, N-diphenylmethylene, N-[(2-pyridyl)mesityl]methylene, N,(N',N'-dimethylaminomethylene, N,N'-isopropylidene, N-p-nitrobenzylidene, N-salicylidene, N-5-chlorosalicylidene, N-(5-chloro-2-hydroxyphenyl)phenylmethylene, N-cyclohexylidene);

Enamine Derivatives: (N-(5,5-dimethyl-3-oxo-1-cyclohexenyl));

N-Metal Derivatives (N-borane derivatives, N-diphenylborinic acid derivatives, N-[phenyl(pentacarbonylchromium- or -tungsten)]carbenzyl, N-copper or N-zinc chelate);

N—N Derivatives: (N-nitro, N-nitroso, N-oxide);

N—P Derivatives: (N-diphenylphosphinyl, N-dimethylthiophosphinyl, N-diphenylthiophosphinyl, N-dialkyl phosphoryl, N-dibenzyl phosphoryl, N-diphenyl phosphoryl);

N—Si Derivatives, N—S Derivatives, and N-Sulfenyl Derivatives: (N-benzenesulfenyl, N-o-nitrobenzenesulfenyl, N-2,4-dinitrobenzenesulfenyl, N-pentachlorobenzenesulfenyl, N-2-nitro-4-methoxybenzenesulfenyl, N-triphenylmethylsulfenyl, N-3-nitropyridinesulfenyl); and N-sulfonyl Derivatives (N-p-toluenesulfonyl, N-benzenesulfonyl, N-2,3,6-trimethyl-4-methoxybenzenesulfonyl, N-2,4,6-trimethoxybenzenesulfonyl, N-2,6-dimethyl-4-methoxybenzenesulfonyl, N-pentamethylbenzenesulfonyl, N-2,3,5,6-tetramethyl-4-methoxybenzenesulfonyl, N-4-methoxybenzenesulfonyl, N-2,4,6-trimethylbenzenesulfonyl, N-2,6-dimethoxy-4-methylbenzenesulfonyl, N-2,2,5,7,8-pentamethylchroman-6-sulfonyl, N-methanesulfonyl, N-β-trimethylsilyethanesulfonyl, N-9-anthracenesulfonyl, N-4-(4',8'-dimethoxynaphthylmethyl)benzenesulfonyl, N-benzylsulfonyl, N-trifluoromethylsulfonyl, N-phenacylsulfonyl).

Protected amino groups include carbamates, amides and amidines, e.g. —NHC(O)OR$^1$, —NHC(O)R$^1$ or —N=CR$^1$N(R$^1$)$_2$. Another protecting group, also useful as a prodrug for amino or —NH(R$^5$), is:

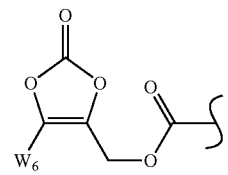

See for example Alexander, J. et al (1996) *J. Med. Chem.* 39:480-486.

Amino Acid and Polypeptide Protecting Group and Conjugates

An amino acid or polypeptide protecting group of a compound of the invention has the structure $R^{15a}$NHCH($R^{16a}$)C(O)—, where $R^{15a}$ is H, an amino acid or polypeptide residue, or $R^{15a}$, and $R^{16a}$ is defined below.

$R^{16a}$ is lower alkyl or lower alkyl ($C_1$-$C_6$) substituted with amino, carboxyl, amide, carboxyl ester, hydroxyl, $C_6$-$C_7$ aryl, guanidinyl, imidazolyl, indolyl, sulfhydryl, sulfoxide, and/or alkylphosphate. $R^{16a}$ also is taken together with the amino acid α-N to form a proline residue ($R^{16}$=—$CH_2$)$_3$—). However, $R^{16}$ is generally the side group of a naturally-occurring amino acid such as H, —$CH_3$, —CH($CH_3$)$_2$, —$CH_2$—CH (CH₃)₂, —CHCH₃—CH₂—CH₃, —CH₂—C₆H₅, —CH₂CH₂—S—CH₃, —CH₂OH, —CH(OH)—CH₃, —CH₂—SH, —CH₂—C₆H₄OH, —CH₂—CO—NH₂, —CH₂—CH₂—CO—NH₂, —CH₂—COOH, —CH₂—CH₂—COOH, —(CH₂)₄—NH₂ and —(CH₂)₃—NH—C (NH₂)—NH₂. $R^{16a}$ also includes 1-guanidinoprop-3-yl, benzyl, 4-hydroxybenzyl, imidazol-4-yl, indol-3-yl, methoxyphenyl and ethoxyphenyl.

Another set of protecting groups include the residue of an amino-containing compound, in particular an amino acid, a polypeptide, a protecting group, —NHSO₂R, NHC(O)R, —N(R)₂, NH₂ or —NH(R)(H), whereby for example a carboxylic acid is reacted, i.e. coupled, with the amine to form an amide, as in C(O)NR². A phosphonic acid may be reacted with the amine to form a phosphonamidate, as in —P(O)(OR)(NR²).

Amino acids have the structure $R^{17c}C(O)CH(R^{16a})NH—$, where $R^{17c}$ is —OH, —OR, an amino acid or a polypeptide residue. Amino acids are low molecular weight compounds, on the order of less than about 1000 MW and which contain at least one amino or imino group and at least one carboxyl group. Generally the amino acids will be found in nature, i.e., can be detected in biological material such as bacteria or other microbes, plants, animals or man. Suitable amino acids typically are alpha amino acids, i.e. compounds characterized by one amino or imino nitrogen atom separated from the carbon atom of one carboxyl group by a single substituted or unsubstituted alpha carbon atom. Of particular interest are hydrophobic residues such as mono- or di-alkyl or aryl amino acids, cycloalkylamino acids and the like. These residues contribute to cell permeability by increasing the partition coefficient of the parental drug. Typically, the residue does not contain a sulfhydryl or guanidino substituent.

Naturally-occurring amino acid residues are those residues found naturally in plants, animals or microbes, especially proteins thereof. Polypeptides most typically will be substantially composed of such naturally-occurring amino acid residues. These amino acids are glycine, alanine, valine, leucine, isoleucine, serine, threonine, cysteine, methionine, glutamic acid, aspartic acid, lysine, hydroxylysine, arginine, histidine, phenylalanine, tyrosine, tryptophan, proline, asparagine, glutamine and hydroxyproline. Additionally, unnatural amino acids, for example, valanine, phenylglycine and homoarginine are also included. Commonly encountered amino acids that are not gene-encoded may also be used in the present invention. All of the amino acids used in the present invention may be either the D- or L-optical isomer. In addition, other peptidomimetics are also useful in the present invention. For a general review, see Spatola, A. F., in *Chemistry and Biochemistry of Amino Acids, Peptides and Proteins*, B. Weinstein, eds., Marcel Dekker, New York, p. 267 (1983).

When protecting groups are single amino acid residues or polypeptides they optionally are substituted with substituents. These conjugates are generally produced by forming an amide bond between a carboxyl group of the amino acid (or C-terminal amino acid of a polypeptide for example). Generally, only one of any site in the scaffold drug-like compound is amidated with an amino acid as described herein, although it is within the scope of this invention to introduce amino acids at more than one permitted site. Usually, a carboxyl group of R³ is amidated with an amino acid. In general, the α-amino or α-carboxyl group of the amino acid or the terminal amino or carboxyl group of a polypeptide are bonded to the scaffold, parental functionalities. Carboxyl or amino groups in the amino acid side chains generally may be used to form the amide bonds with the parental compound or these groups may need to be protected during synthesis of the conjugates as described further below.

With respect to the carboxyl-containing side chains of amino acids or polypeptides it will be understood that the carboxyl group optionally will be blocked, e.g. esterified or amidated with R.

Such ester or amide bonds with side chain amino or carboxyl groups, like the esters or amides with the parental molecule, optionally are hydrolyzable in vivo or in vitro under acidic (pH<3) or basic (pH>10) conditions. Alternatively, they are substantially stable in the gastrointestinal tract of humans but are hydrolyzed enzymatically in blood or in intracellular environments. The esters or amino acid or polypeptide amidates also are useful as intermediates for the preparation of the parental molecule containing free amino or carboxyl groups. The free acid or base of the parental compound, for example, is readily formed from the esters or amino acid or polypeptide conjugates of this invention by conventional hydrolysis procedures.

When an amino acid residue contains one or more chiral centers, any of the D, L, meso, threo or erythro (as appropriate) racemates, scalemates or mixtures thereof may be used. In general, if the intermediates are to be hydrolyzed non-enzymatically (as would be the case where the amides are used as chemical intermediates for the free acids or free amines), D isomers are useful. On the other hand, L isomers are more versatile since they can be susceptible to both non-enzymatic and enzymatic hydrolysis, and are more efficiently transported by amino acid or dipeptidyl transport systems in the gastrointestinal tract.

Examples of suitable amino acids whose residues are represented by $R^x$ or $R^y$ include the following:

Glycine;

Aminopolycarboxylic acids, e.g., aspartic acid, β-hydroxyaspartic acid, glutamic acid, β-hydroxyglutamic acid, β-methylaspartic acid, β-methylglutamic acid, β,β-dimethylaspartic acid, γ-hydroxyglutamic acid, β,γ-dihydroxyglutamic acid, β-phenylglutamic acid, γ-methyleneglutamic acid, 3-aminoadipic acid, 2-aminopimelic acid, 2-aminosuberic acid and 2-aminosebacic acid;

Amino acid amides such as glutamine and asparagine;

Polyamino- or polybasic-monocarboxylic acids such as arginine, lysine, β-aminoalanine, γ-aminobutyrine, ornithine, citruline, homoarginine, homocitrulline, hydroxylysine, allohydroxylsine and diaminobutyric acid;

Other basic amino acid residues such as histidine;

Diaminodicarboxylic acids such as α,α'-diaminosuccinic acid, α,α'-diaminoglutaric acid, α,α'-diaminoadipic acid, α,α'-diaminopimelic acid, α,α'-diamino-β-hydroxypimelic acid, α,α'-diaminosuberic acid, α,α'-diaminoazelaic acid, and α,α'-diaminosebacic acid;

Imino acids such as proline, hydroxyproline, allohydroxyproline, γ-methylproline, pipecolic acid, 5-hydroxypipecolic acid, and azetidine-2-carboxylic acid;

A mono- or di-alkyl (typically $C_1$-$C_8$ branched or normal) amino acid such as alanine, valine, leucine, allylglycine, butyrine, norvaline, norleucine, heptyline, α-methylserine, α-amino-α-methyl-γ-hydroxyvaleric acid, α-amino-α-methyl-δ-hydroxyvaleric acid, α-amino-α-methyl-ε-hydroxycaproic acid, isovaline, α-methylglutamic acid, α-aminoisobutyric acid, α-aminodiethylacetic acid, α-aminodiisopropylacetic acid, α-aminodi-n-propylacetic acid, α-aminodiisobutylacetic acid, α-aminodi-n-butylacetic acid, α-aminoethylisopropylacetic acid, α-amino-n-propylacetic acid, α-aminodiisoamyacetic acid, α-methylaspartic acid, α-methylglutamic acid, 1-aminocyclopropane-1-carboxylic acid, isoleucine, alloisoleucine, tert-leucine, β-methyltryptophan and α-amino-β-ethyl-β-phenylpropionic acid;
β-phenylserinyl;

Aliphatic α-amino-β-hydroxy acids such as serine, β-hydroxyleucine, β-hydroxynorleucine, β-hydroxynorvaline, and α-amino-β-hydroxystearic acid;

α-Amino, α-, γ-, δ- or ε-hydroxy acids such as homoserine, δ-hydroxynorvaline, γ-hydroxynorvaline and ε-hydroxynorleucine residues; canavine and canaline; γ-hydroxyornithine;

2-hexosaminic acids such as D-glucosaminic acid or D-galactosaminic acid;

α-Amino-β-thiols such as penicillamine, β-thiolnorvaline or β-thiolbutyrine;

Other sulfur containing amino acid residues including cysteine; homocystine, β-phenylmethionine, methionine, S-allyl-L-cysteine sulfoxide, 2-thiolhistidine, cystathionine, and thiol ethers of cysteine or homocysteine;

Phenylalanine, tryptophan and ring-substituted α-amino acids such as the phenyl- or cyclohexylamino acids α-aminophenylacetic acid, α-aminocyclohexylacetic acid and α-amino-β-cyclohexylpropionic acid; phenylalanine analogues and derivatives comprising aryl, lower alkyl, hydroxy, guanidino, oxyalkylether, nitro, sulfur or halo-substituted phenyl (e.g., tyrosine, methyltyrosine and o-chloro-, p-chloro-, 3,4-dichloro, o-, m- or p-methyl-, 2,4,6-trimethyl-, 2-ethoxy-5-nitro-, 2-hydroxy-5-nitro- and p-nitro-phenylalanine); furyl-, thienyl-, pyridyl-, pyrimidinyl-, purinyl- or naphthyl-alanines; and tryptophan analogues and derivatives including kynurenine, 3-hydroxykynurenine, 2-hydroxytryptophan and 4-carboxytryptophan;

α-Amino substituted amino acids including sarcosine (N-methylglycine), N-benzylglycine, N-methylalanine, N-benzylalanine, N-methylphenylalanine, N-benzylphenylalanine, N-methylvaline and N-benzylvaline; and α-Hydroxy and substituted α-hydroxy amino acids including serine, threonine, allothreonine, phosphoserine and phosphothreonine.

Polypeptides are polymers of amino acids in which a carboxyl group of one amino acid monomer is bonded to an amino or imino group of the next amino acid monomer by an amide bond. Polypeptides include dipeptides, low molecular weight polypeptides (about 1500-5000 MW) and proteins. Proteins optionally contain 3, 5, 10, 50, 75, 100 or more residues, and suitably are substantially sequence-homologous with human, animal, plant or microbial proteins. They include enzymes (e.g., hydrogen peroxidase) as well as immunogens such as KLH, or antibodies or proteins of any type against which one wishes to raise an immune response. The nature and identity of the polypeptide may vary widely.

The polypeptide amidates are useful as immunogens in raising antibodies against either the polypeptide (if it is not immunogenic in the animal to which it is administered) or against the epitopes on the remainder of the compound of this invention.

Antibodies capable of binding to the parental non-peptidyl compound are used to separate the parental compound from mixtures, for example in diagnosis or manufacturing of the parental compound. The conjugates of parental compound and polypeptide generally are more immunogenic than the polypeptides in closely homologous animals, and therefore make the polypeptide more immunogenic for facilitating raising antibodies against it. Accordingly, the polypeptide or protein may be immunogenic in an animal typically used to raise antibodies, e.g., rabbit, mouse, horse, or rat. The polypeptide optionally contains a peptidolytic enzyme cleavage site at the peptide bond between the first and second residues adjacent to the acidic heteroatom. Such cleavage sites are flanked by enzymatic recognition structures, e.g. a particular sequence of residues recognized by a peptidolytic enzyme.

Peptidolytic enzymes for cleaving the polypeptide conjugates of this invention are well known, and in particular include carboxypeptidases, which digest polypeptides by removing C-terminal residues, and are specific in many instances for particular C-terminal sequences. Such enzymes and their substrate requirements in general are well known. For example, a dipeptide (having a given pair of residues and a free carboxyl terminus) is covalently bonded through its α-amino group to the phosphorus or carbon atoms of the compounds herein. In certain embodiments, a phosphonate group substituted with an amino acid or peptide will be cleaved by the appropriate peptidolytic enzyme, leaving the carboxyl of the proximal amino acid residue to autocatalytically cleave the phosphonoamidate bond.

Suitable dipeptidyl groups (designated by their single letter code) are AA, AR, AN, AD, AC, AE, AQ, AG, AH, AI, AL, AK, AM, AF, AP, AS, AT, AW, AY, AV, RA, RR, RN, RD, RC, RE, RQ, RG, RH, RI, RL, RK, RM, RF, RP, RS, RT, RW, RY, RV, NA, NR, NN, ND, NC, NE, NQ, NG, NH, NI, NL, NK, NM, NF, NP, NS, NT, NR, NY, NV, DA, DR, DN, DD, DC, DE, DQ, DG, DH, DI, DL, DK, DM, DF, DP, DS, DT, DW, DY, DV, CA, CR, CN, CD, CC, CE, CQ, CG, CH, CI, CL, CK, CM, CF, CP, CS, CT, CW, CY, CV, EA, ER, EN, ED, EC, EE, EQ, EG, EH, EI, EL, EK, EM, EF, EP, ES, ET, EW, EY, EV, QA, QR, QN, QD, QC, QE, QQ, QG, QH, QI, QL, QK, QM, QF, QP, QS, QT, QW, QY, QV, GA, GR, GN, GD, GC, GE, GQ, GG, GH, GI, GL, GK, GM, GF, GP, GS, GT, GW, GY, GV, HA, HR, HN, HD, HC, HE, HQ, HG, HH, HI, HL, HK, HM, HF, HP, HS, HT, HW, HY, HV, IA, IR, IN, ID, IC, IE, IQ, IG, IH, II, IL, IK, IM, IF, IP, IS, IT, IW, IY, IV, LA, LR, LN, LD, LC, LE, LQ, LG, LH, LI, LL, LK, LM, LF, LP, LS, LT, LW, LY, LV, KA, KR, KN, KD, KC, KE, KQ, KG, KH, KI, KL, KK, KM, KF, KP, KS, KT, KW, KY, KV, MA, MR, MN, MD, MC, ME, MQ, MG, MH, MI, ML, MK, MM, MF, MP, MS, MT, MW, MY, MV, FA, FR, FN, FD, FC, FE, FQ, FG, FH, FI, FL, FK, FM, FF, FP, FS, FT, FW, FY, FV, PA, PR, PN, PD, PC, PE, PQ, PG, PH, PI, PL, PK, PM, PF, PP, PS, PT, PW, PY, PV, SA, SR, SN, SD, SC, SE, SQ SG, SH, SI, SL, SK, SM, SF, SP, SS, ST, SW, SY, SV, TA, TR, TN, TD, TC, TE, TQ, TG, TH, TI, TL, TK, TM, TF, TP, TS, TT, TW, TY, TV, WA, WR, WN, WD, WC, WE, WQ, WG, WH, WI, WL, WK, WM, WF, WP, WS, WT, WW, WY, WV, YA, YR, YN, YD, YC, YE, YQ, YG, YH, YI, YL, YK, YM, YF, YP, YS, YT, YW, YY, YV, VA, VR, VN, VD, VC, VE, VQ, VG, VH, VI, VL, VK, VM, VF, VP, VS, VT, VW, VY and VV.

Tripeptide residues are also useful as protecting groups. When a phosphonate is to be protected, the sequence —$X^{40}$-pro-$^{50}$- (where $X^{40}$ is any amino acid residue and $X^{50}$ is an amino acid residue, a carboxyl ester of proline, or hydrogen) will be cleaved by luminal carboxypeptidase to yield $X^{40}$ with a free carboxyl, which in turn is expected to autocatalytically cleave the phosphonoamidate bond. The carboxy group of $X^{50}$ optionally is esterified with benzyl.

Dipeptide or tripeptide species can be selected on the basis of known transport properties and/or susceptibility to peptidases that can affect transport to intestinal mucosal or other cell types. Dipeptides and tripeptides lacking an α-amino group are transport substrates for the peptide transporter found in brush border membrane of intestinal mucosal cells (Bai, J. P. F., (1992) Pharm Res. 9:969-978. Transport competent peptides can thus be used to enhance bioavailability of the amidate compounds. Di- or tripeptides having one or more amino acids in the D configuration may be compatible with peptide transport. Amino acids in the D configuration can be used to reduce the susceptibility of a di- or tripeptide to hydrolysis by proteases common to the brush border such as aminopeptidase N. In addition, di- or tripeptides alternatively are selected on the basis of their relative resistance to hydrolysis by proteases found in the lumen of the intestine. For example, tripeptides or polypeptides lacking asp and/or glu are poor substrates for aminopeptidase A, di- or tripeptides lacking amino acid residues on the N-terminal side of hydrophobic amino acids (leu, tyr, phe, val, trp) are poor substrates for endopeptidase, and peptides lacking a pro residue at the penultimate position at a free carboxyl terminus are poor substrates for carboxypeptidase P. Similar considerations can also be applied to the selection of peptides that are either relatively resistant or relatively susceptible to hydrolysis by cytosolic, renal, hepatic, serum or other peptidases. Such poorly cleaved polypeptide amidates are immunogens or are useful for bonding to proteins in order to prepare immunogens.

Intracellular Targeting

The phosphonate group of Formula I-IV compounds may cleave in vivo in stages after they have reached the desired site of action, i.e. inside a cell. One mechanism of action inside a cell may entail a first cleavage, e.g. by esterase, to provide a negatively-charged "locked-in" intermediate. Cleavage of a terminal ester grouping in Formula I-IV compounds thus affords an unstable intermediate which releases a negatively charged "locked in" intermediate.

After passage inside a cell, intracellular enzymatic cleavage or modification of the phosphonate prodrug compound may result in an intracellular accumulation or retention of the cleaved or modified compound by a "trapping" mechanism. The cleaved or modified compound, i.e. active metabolite, may then be "locked-in" the cell, i.e. accumulate in the cell by a significant change in charge, polarity, or other physical property change which decreases the rate at which the cleaved or modified compound can exit the cell, relative to the rate at which it entered as the phosphonate prodrug. Other mechanisms by which a therapeutic effect is achieved may be operative as well. Enzymes which are capable of an enzymatic activation mechanism with the phosphonate prodrug compounds of the invention include, but are not limited to, amidases, esterases, microbial enzymes, phospholipases, cholinesterases, and phosphatases.

It is known that the drug is activated in vivo by phosphorylation. Such activation may occur in the present system by enzymatic conversion of the "locked-in" intermediate with phosphokinase to the active phosphonate diphosphate and/or by phosphorylation of the drug itself after its release from the "locked-in" intermediate as described above. In either case, the original nucleoside-type drug will be converted, via the derivatives of this invention, to the active phosphorylated species.

From the foregoing, it will be apparent that many structurally different known approved and experimental HCV polymerase inhibitor drugs can be derivatized in accord with the present invention. Numerous such drugs are specifically mentioned herein. However, it should be understood that the discussion of drug families and their specific members for derivatization according to this invention is not intended to be exhaustive, but merely illustrative.

As another example, when the selected drug contains multiple reactive hydroxyl functions, a mixture of intermediates and final products may again be obtained. In the unusual case in which all hydroxy groups are approximately equally reactive, there is not expected to be a single, predominant product, as each mono-substituted product will be obtained in approximate by equal amounts, while a lesser amount of multiply-substituted product will also result. Generally speaking, however, one of the hydroxyl groups will be more susceptible to substitution than the other(s), e.g. a primary hydroxyl will be more reactive than a secondary hydroxyl, an unhindered hydroxyl will be more reactive than a hindered one. Consequently, the major product will be a mono-substituted one in which the most reactive hydroxyl has been derivatized while other mono-substituted and multiply-substituted products may be obtained as minor products.

Stereoisomers

The compounds of the invention, exemplified by Formula I, II, III or IV may have chiral centers, e.g. chiral carbon or phosphorus atoms. The compounds of the invention thus include racemic mixtures of all stereoisomers, including enantiomers, diastereomers, and atropisomers. In addition, the compounds of the invention include enriched or resolved optical isomers at any or all asymmetric, chiral atoms. In other words, the chiral centers apparent from the depictions are provided as the chiral isomers or racemic mixtures. Both racemic and diastereomeric mixtures, as well as the individual optical isomers isolated or synthesized, substantially free of their enantiomeric or diastereomeric partners, are all within the scope of the invention. The racemic mixtures are separated into their individual, substantially optically pure isomers through well-known techniques such as, for example, the separation of diastereomeric salts formed with optically active adjuncts, e.g., acids or bases followed by conversion back to the optically active substances. In most instances, the desired optical isomer is synthesized by means of stereospecific reactions, beginning with the appropriate stereoisomer of the desired starting material.

The compounds of the invention can also exist as tautomeric isomers in certain cases. Although only one delocalized resonance structure may be depicted, all such forms are contemplated within the scope of the invention. For example, ene-amine tautomers can exist for purine, pyrimidine, imidazole, guanidine, amidine, and tetrazole systems and all their possible tautomeric forms are within the scope of the invention.

Metabolites of the Compounds of the Invention

Also falling within the scope of this invention are the in vivo metabolic products of the compounds described herein, to the extent such products are novel and unobvious over the prior art. Such products may result for example from the oxidation, reduction, hydrolysis, amidation, esterification and the like of the administered compound, primarily due to enzymatic processes. Accordingly, the invention includes novel and unobvious compounds produced by a process comprising contacting a compound of this invention with a mammal for a period of time sufficient to yield a metabolic product thereof. Such products typically are identified by preparing a radiolabelled (e.g. $^{14}C$ or $^{3}H$) compound of the invention, administering it parenterally in a detectable dose (e.g. greater than about 0.5 mg/kg) to an animal such as rat, mouse, guinea pig, monkey, or to man, allowing sufficient time for metabolism to occur (typically about 30 seconds to 30 hours) and isolating its conversion products from the urine, blood or other biological samples. These products are easily isolated since they are labeled (others are isolated by the use of antibodies capable of binding epitopes surviving in the metabolite). The metabolite structures are determined in conventional fashion, e.g. by MS or NMR analysis. In general, analysis of metabolites is done in the same way as conventional drug metabolism studies well-known to those skilled in the art. The conversion products, so long as they are not otherwise found in vivo, are useful in diagnostic assays for therapeutic dosing of the compounds of the invention even if they possess no HCV polymerase inhibitory activity of their own.

Recipes and methods for determining stability of compounds in surrogate gastrointestinal secretions are known. Compounds are defined herein as stable in the gastrointestinal tract where less than about 50 mole percent of the protected groups are deprotected in surrogate intestinal or gastric juice upon incubation for 1 hour at 37° C. Simply because the compounds are stable to the gastrointestinal tract does not mean that they cannot be hydrolyzed in vivo. The phosphonate prodrugs of the invention typically will be stable in the digestive system but may be substantially hydrolyzed to the parental drug in the digestive lumen, liver or other metabolic organ, or within cells in general.

Exemplary Methods of Making the Compounds of the Invention.

The invention provides many methods of making the compositions of the invention. The compositions are prepared by any of the applicable techniques of organic synthesis. Many such techniques are well known in the art, such as those elaborated in "Compendium of Organic Synthetic Methods" (John Wiley & Sons, New York), Vol. 1, Ian T. Harrison and Shuyen Harrison, 1971; Vol. 2, Ian T. Harrison and Shuyen Harrison, 1974; Vol. 3, Louis S. Hegedus and Leroy Wade, 1977; Vol. 4, Leroy G. Wade, jr., 1980; Vol. 5, Leroy G. Wade, Jr., 1984; and Vol. 6, Michael B. Smith; as well as March, J., "Advanced Organic Chemistry, Third Edition", (John Wiley & Sons, New York, 1985), "Comprehensive Organic Synthesis. Selectivity, Strategy & Efficiency in Modern Organic Chemistry. In 9 Volumes", Barry M. Trost, Editor-in-Chief (Pergamon Press, New York, 1993 printing).

Dialkyl phosphonates may be prepared according to the methods of: Quast et al (1974) *Synthesis* 490; Stowell et al (1990) *Tetrahedron Lett.* 3261; U.S. Pat. No. 5,663,159.

In general, synthesis of phosphonate esters is achieved by coupling a nucleophile amine or alcohol with the corresponding activated phosphonate electrophilic precursor. For example, chlorophosphonate addition on to 5'-hydroxy of nucleoside is a well known method for preparation of nucleoside phosphate monoesters. The activated precursor can be prepared by several well known methods. Chlorophosphonates useful for synthesis of the prodrugs are prepared from the substituted-1,3-propanediol (Wissner, et al. (1992) *J. Med. Chem.* 35:1650). Chlorophosphonates are made by oxidation of the corresponding chlorophospholanes (Anderson, et al, (1984) *J. Org. Chem.* 49:1304) which are obtained by reaction of the substituted diol with phosphorus trichloride. Alternatively, the chlorophosphonate agent is made by treating substituted-1,3-diols with phosphorusoxychloride (Patois, et al, (1990) *J. Chem. Soc. Perkin Trans. I*, 1577). Chlorophosphonate species may also be generated in situ from corresponding cyclic phosphites (Silverburg, et al., (1996) *Tetrahedron Lett.*, 37:771-774), which in turn can be either made from chlorophospholane or phosphoramidate intermediate. Phosphoroflouridate intermediate prepared either from pyrophosphate or phosphoric acid may also act as precursor in preparation of cyclic prodrugs (Watanabe et al., (1988) *Tetrahedron Lett.*, 29:5763-66). Caution: fluorophosphonate compounds may be highly toxic!

Phosphonate prodrugs of the present invention may also be prepared from the precursor free acid by Mitsunobu reactions (Mitsunobu, (1981) *Synthesis*, 1; Campbell, (1992) *J. Org. Chem.*, 52:6331), and other acid coupling reagents including, but not limited to, carbodiimides (Alexander, et al, (1994) *Collect. Czech. Chem. Commun.* 59:1853; Casara, et al, (1992) *Bioorg. Med. Chem. Lett.*, 2:145; Ohashi, et al, (1988) *Tetrahedron Lett.*, 29:1189), and benzotriazolyloxytris-(dimethylamino)phosphonium salts (Campagne, et al, (1993) *Tetrahedron Lett.*, 34:6743).

Aryl halides undergo $Ni^{+2}$ catalyzed reaction with phosphite derivatives to give aryl phosphonate containing compounds (Balthazar, et al (1980) *J. Org. Chem.* 45:5425). Phosphonates may also be prepared from the chlorophosphonate in the presence of a palladium catalyst using aromatic triflates (Petrakis, et al, (1987) *J. Am. Chem. Soc.* 109:2831; Lu, et al, (1987) *Synthesis*, 726). In another method, aryl phosphonate esters are prepared from aryl phosphates under anionic rearrangement conditions (Melvin (1981) *Tetrahedron Lett.* 22:3375; Casteel, et al, (1991) *Synthesis*, 691). N-Alkoxy aryl salts with alkali metal derivatives of cyclic alkyl phosphonate provide general synthesis for heteroaryl-2-phosphonate linkers (Redmore (1970) *J. Org. Chem.* 35:4114). These above mentioned methods can also be extended to compounds where the $W^5$ group is a heterocycle. Cyclic-1,3-propanyl prodrugs of phosphonates are also synthesized from phosphonic diacids and substituted propane-1,3-diols using a coupling reagent such as 1,3-dicyclohexylcarbodiimide (DCC) in presence of a base (e.g., pyridine). Other carbodiimide based coupling agents like 1,3-disopropylcarbodiimide or water soluble reagent, 1-(3-dimethylaminopropyl)-3-ethylcarbodiimide hydrochloride (EDCI) can also be utilized for the synthesis of cyclic phosphonate prodrugs.

The carbamoyl group may be formed by reaction of a hydroxy group according to the methods known in the art, including the teachings of Ellis, US 2002/0103378 A1 and Hajima, U.S. Pat. No. 6,018,049.

SCHEMES AND EXAMPLES

A number of exemplary methods for the preparation of the compositions of the invention are provided below. These methods are intended to illustrate the nature of such preparations are not intended to limit the scope of applicable methods.

General aspects of these exemplary methods are described below and in the Examples. Each of the products of the following processes is optionally separated, isolated, and/or purified prior to its use in subsequent processes.

Generally, the reaction conditions such as temperature, reaction time, solvents, work-up procedures, and the like, will be those common in the art for the particular reaction to be performed. The cited reference material, together with material cited therein, contains detailed descriptions of such conditions. Typically the temperatures will be −100° C. to 200° C., solvents will be aprotic or protic, and reaction times will be 10 seconds to 10 days. Work-up typically consists of quenching any unreacted reagents followed by partition between a water/organic layer system (extraction) and separating the layer containing the product.

Oxidation and reduction reactions are typically carried out at temperatures near room temperature (about 20° C.), although for metal hydride reductions frequently the temperature is reduced to 0° C. to −100° C., solvents are typically aprotic for reductions and may be either protic or aprotic for oxidations. Reaction times are adjusted to achieve desired conversions.

Condensation reactions are typically carried out at temperatures near room temperature, although for non-equilibrating, kinetically controlled condensations reduced temperatures (0° C. to −100° C.) are also common. Solvents can be either protic (common in equilibrating reactions) or aprotic (common in kinetically controlled reactions).

Standard synthetic techniques such as azeotropic removal of reaction by-products and use of anhydrous reaction conditions (e.g. inert gas environments) are common in the art and will be applied when applicable.

The terms "treated", "treating", "treatment", and the like, mean contacting, mixing, reacting, allowing to react, bringing into contact, and other terms common in the art for indicating that one or more chemical entities is treated in such a manner as to convert it to one or more other chemical entities. This means that "treating compound one with compound two" is synonymous with "allowing compound one to react with compound two", "contacting compound one with compound two", "reacting compound one with compound two", and other expressions common in the art of organic synthesis for reasonably indicating that compound one was "treated", "reacted", "allowed to react", etc., with compound two.

"Treating" indicates the reasonable and usual manner in which organic chemicals are allowed to react. Normal concentrations (0.01M to 10M, typically 0.1M to 1M), temperatures (−100° C. to 250° C., typically −78° C. to 150° C., more typically −78° C. to 100° C., still more typically 0° C. to 100° C.), reaction vessels (typically glass, plastic, metal), solvents, pressures, atmospheres (typically air for oxygen and water insensitive reactions or nitrogen or argon for oxygen or water sensitive), etc., are intended unless otherwise indicated. The knowledge of similar reactions known in the art of organic synthesis are used in selecting the conditions and apparatus for "treating" in a given process. In particular, one of ordinary skill in the art of organic synthesis selects conditions and apparatus reasonably expected to successfully carry out the chemical reactions of the described processes based on the knowledge in the art.

Modifications of each of the exemplary schemes above and in the examples (hereafter "exemplary schemes") leads to various analogs of the specific exemplary materials produce. The above cited citations describing suitable methods of organic synthesis are applicable to such modifications.

In each of the exemplary schemes it may be advantageous to separate reaction products from one another and/or from starting materials. The desired products of each step or series of steps is separated and/or purified (hereinafter separated) to the desired degree of homogeneity by the techniques common in the art. Typically such separations involve multiphase extraction, crystallization from a solvent or solvent mixture, distillation, sublimation, or chromatography. Chromatography can involve any number of methods including, for example: reverse-phase and normal phase; size exclusion; ion exchange; high, medium, and low pressure liquid chromatography methods and apparatus; small scale analytical; simulated moving bed (SMB) and preparative thin or thick layer chromatography, as well as techniques of small scale thin layer and flash chromatography.

Another class of separation methods involves treatment of a mixture with a reagent selected to bind to or render otherwise separable a desired product, unreacted starting material, reaction by product, or the like. Such reagents include adsorbents or absorbents such as activated carbon, molecular sieves, ion exchange media, or the like. Alternatively, the reagents can be acids in the case of a basic material, bases in the case of an acidic material, binding reagents such as antibodies, binding proteins, selective chelators such as crown ethers, liquid/liquid ion extraction reagents (LIX), or the like.

Selection of appropriate methods of separation depends on the nature of the materials involved. For example, boiling point, and molecular weight in distillation and sublimation, presence or absence of polar functional groups in chromatography, stability of materials in acidic and basic media in multiphase extraction, and the like. One skilled in the art will apply techniques most likely to achieve the desired separation.

A single stereoisomer, e.g. an enantiomer, substantially free of its stereoisomer may be obtained by resolution of the racemic mixture using a method such as formation of diastereomers using optically active resolving agents ("Stereochemistry of Carbon Compounds," (1962) by E. L. Eliel, McGraw Hill; Lochmuller, C. H., (1975) *J. Chromatogr.*, 113:(3) 283-302). Racemic mixtures of chiral compounds of the invention can be separated and isolated by any suitable method, including: (1) formation of ionic, diastereomeric salts with chiral compounds and separation by fractional crystallization or other methods, (2) formation of diastereomeric compounds with chiral derivatizing reagents, separation of the diastereomers, and conversion to the pure stereoisomers, and (3) separation of the substantially pure or enriched stereoisomers directly under chiral conditions.

Under method (1), diastereomeric salts can be formed by reaction of enantiomerically pure chiral bases such as brucine, quinine, ephedrine, strychnine, α-methyl-β-phenylethylamine (amphetamine), and the like with asymmetric compounds bearing acidic functionality, such as carboxylic acid and sulfonic acid. The diastereomeric salts may be induced to separate by fractional crystallization or ionic chromatography. For separation of the optical isomers of amino compounds, addition of chiral carboxylic or sulfonic acids, such as camphorsulfonic acid, tartaric acid, mandelic acid, or lactic acid can result in formation of the diastereomeric salts.

Alternatively, by method (2), the substrate to be resolved is reacted with one enantiomer of a chiral compound to form a diastereomeric pair (Eliel, E. and Wilen, S. (1994) *Stereochemistry of Organic Compounds*, John Wiley & Sons, Inc., p. 322). Diastereomeric compounds can be formed by reacting asymmetric compounds with enantiomerically pure chiral derivatizing reagents, such as menthyl derivatives, followed by separation of the diastereomers and hydrolysis to yield the free, enantiomerically enriched xanthene. A method of determining optical purity involves making chiral esters, such as a menthyl ester, e.g. (−) menthyl chloroformate in the presence of base, or Mosher ester, α-methoxy-α-(trifluoromethyl)phenyl acetate (Jacob III. (1982) *J. Org. Chem.* 47:4165), of the racemic mixture, and analyzing the NMR spectrum for the presence of the two atropisomeric diastereomers. Stable diastereomers of atropisomeric compounds can be separated and isolated by normal- and reverse-phase chromatography following methods for separation of atropisomeric naphthyl-isoquinolines (Hoye, T., WO 96/15111). By method (3), a racemic mixture of two enantiomers can be separated by chromatography using a chiral stationary phase (*Chiral Liquid Chromatography* (1989) W. J. Lough, Ed. Chapman and Hall, New York; Okamoto, (1990) *J. of Chromatogr.* 513:375-378). Enriched or purified enantiomers can be distinguished by methods used to distinguish other chiral molecules with asymmetric carbon atoms, such as optical rotation and circular dichroism.

All literature and patent citations above are hereby expressly incorporated by reference at the locations of their citation. Specifically cited sections or pages of the above cited works are incorporated by reference with specificity. The invention has been described in detail sufficient to allow one of ordinary skill in the art to make and use the subject matter of the following Embodiments. It is apparent that certain modifications of the methods and compositions of the following Embodiments can be made within the scope and spirit of the invention.

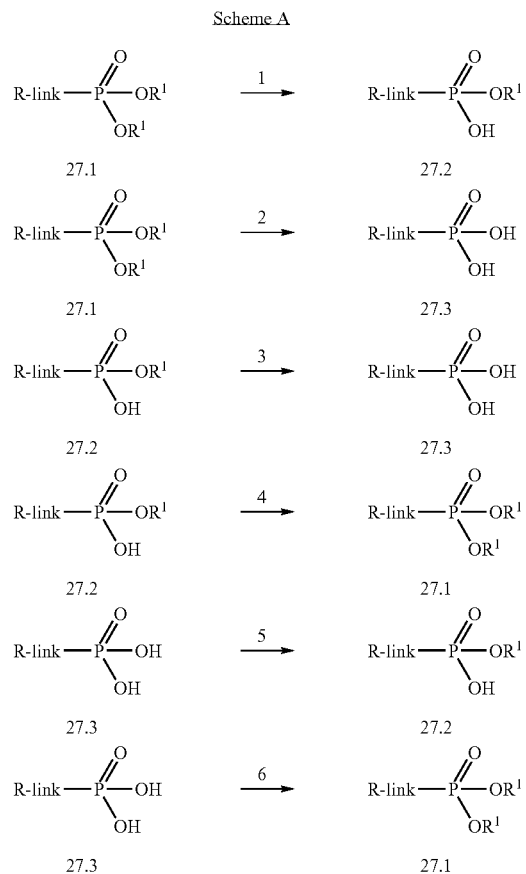

Scheme A

Scheme A shows the general interconversions of certain phosphonate compounds: acids —P(O)(OH)$_2$; mono-esters —P(O)(OR$_1$)(OH); and diesters —P(O)(OR$_1$)$_2$ in which the R$^1$ groups are independently selected, and defined herein before, and the phosphorus is attached through a carbon moiety (link, i.e. linker), which is attached to the rest of the molecule, e.g. drug or drug intermediate (R). The R$^1$ groups attached to the phosphonate esters in Scheme 1 may be changed using established chemical transformations. The interconversions may be carried out in the precursor compounds or the final products using the methods described below. The methods employed for a given phosphonate transformation depend on the nature of the substituent R$^1$. The preparation and hydrolysis of phosphonate esters is described in *Organic Phosphorus Compounds*, G. M. Kosolapoff, L. Maeir, eds, Wiley, 1976, p. 9ff.

The conversion of a phosphonate diester 27.1 into the corresponding phosphonate monoester 27.2 (Scheme A, Reaction 1) can be accomplished by a number of methods. For example, the ester 27.1 in which R$^1$ is an arylalkyl group such as benzyl, can be converted into the monoester compound 27.2 by reaction with a tertiary organic base such as diazabicyclooctane (DABCO) or quinuclidine, as described in *J. Org. Chem.*, 1995, 60:2946. The reaction is performed in an inert hydrocarbon solvent such as toluene or xylene, at about 110° C. The conversion of the diester 27.1 in which R$^1$ is an aryl group such as phenyl, or an alkenyl group such as allyl, into the monoester 27.2 can be effected by treatment of the ester 27.1 with a base such as aqueous sodium hydroxide in acetonitrile or lithium hydroxide in aqueous tetrahydrofuran. Phosphonate diesters 27.2 in which one of the groups R$^1$ is arylalkyl, such as benzyl, and the other is alkyl, can be converted into the monoesters 27.2 in which R$^1$ is alkyl, by hydrogenation, for example using a palladium on carbon catalyst. Phosphonate diesters in which both of the groups R$^1$ are alkenyl, such as allyl, can be converted into the monoester 27.2 in which R$^1$ is alkenyl, by treatment with chloro tris (triphenylphosphine)rhodium (Wilkinson's catalyst) in aqueous ethanol at reflux, optionally in the presence of diazabicyclooctane, for example by using the procedure described in *J. Org. Chem.*, 38:3224 1973 for the cleavage of allyl carboxylates.

The conversion of a phosphonate diester 27.1 or a phosphonate monoester 27.2 into the corresponding phosphonic acid 27.3 (Scheme A, Reactions 2 and 3) can effected by reaction of the diester or the monoester with trimethylsilyl bromide, as described in *J. Chem. Soc., Chem. Comm.*, 739, 1979. The reaction is conducted in an inert solvent such as, for example, dichloromethane, optionally in the presence of a silylating agent such as bis(trimethylsilyl)trifluoroacetamide, at ambient temperature. A phosphonate monoester 27.2 in which R$^1$ is arylalkyl such as benzyl, can be converted into the corresponding phosphonic acid 27.3 by hydrogenation over a palladium catalyst, or by treatment with hydrogen chloride in an ethereal solvent such as dioxane. A phosphonate monoester 27.2 in which R$^1$ is alkenyl such as, for example, allyl, can be converted into the phosphonic acid 27.3 by reaction with Wilkinson's catalyst in an aqueous organic solvent, for example in 15% aqueous acetonitrile, or in aqueous ethanol, for example using the procedure described in *Helv. Chim. Acta.*, 68:618, 1985. Palladium catalyzed hydrogenolysis of phosphonate esters 27.1 in which R$^1$ is benzyl is described in *J. Org. Chem.*, 24:434, 1959. Platinum-catalyzed hydrogenolysis of phosphonate esters 27.1 in which R$^1$ is phenyl is described in *J. Amer. Chem. Soc.*, 78:2336, 1956.

The conversion of a phosphonate monoester 27.2 into a phosphonate diester 27.1 (Scheme A, Reaction 4) in which the newly introduced R$^1$ group is alkyl, arylalkyl, or haloalkyl such as chloroethyl, can be effected by a number of reactions in which the substrate 27.2 is reacted with a hydroxy compound R$^1$OH, in the presence of a coupling agent. Suitable coupling agents are those employed for the preparation of carboxylate esters, and include a carbodiimide such as dicyclohexylcarbodiimide, in which case the reaction is preferably conducted in a basic organic solvent such as pyridine, or (benzotriazol-1-yloxy)tripyrrolidinophosphonium hexafluorophosphate (PYBOP, Sigma), in which case the reaction is performed in a polar solvent such as dimethylformamide, in the presence of a tertiary organic base such as diisopropylethylamine, or Aldrithiol-2 (Aldrich) in which case the reaction is conducted in a basic solvent such as pyridine, in the presence of a triaryl phosphine such as triphenylphosphine. Alternatively, the conversion of the phosphonate monoester 27.1 to the diester 27.1 can be effected by the use of the Mitsunobu reaction. The substrate is reacted with the hydroxy compound R$^1$OH, in the presence of diethyl azodicarboxylate and a triarylphosphine such as triphenyl phosphine. Alternatively, the phosphonate monoester 27.2 can be transformed into the phosphonate diester 27.1, in which the introduced R$^1$ group is alkenyl or arylalkyl, by reaction of the monoester with the halide R$^1$Br, in which R$^1$ is as alkenyl or arylalkyl. The alkylation reaction is conducted in a polar organic solvent such as dimethylformamide or acetonitrile, in the presence of a base such as cesium carbonate. Alternatively, the phosphonate monoester can be transformed into the phosphonate diester in a two step procedure. In the first step, the phosphonate monoester 27.2 is transformed into the chloro analog —P(O)(OR$^1$)Cl by reaction with thionyl chloride or oxalyl chloride and the like, as described in Organic Phosphorus Compounds, G. M. Kosolapoff, L. Maeir, eds, Wiley, 1976, p. 17, and the thus-obtained product —P(O)(OR$^1$)Cl is then reacted with the hydroxy compound R$^1$OH, in the presence of a base such as triethylamine, to afford the phosphonate diester 27.1.

A phosphonic acid —P(O)(OH)$_2$ can be transformed into a phosphonate monoester —P(O)(OR$^1$)(OH) (Scheme A, Reaction 5) by means of the methods described above of for the preparation of the phosphonate diester —P(O)(OR$^1$)$_2$ 27.1, except that only one molar proportion of the component R$^1$OH or R$^1$Br is employed.

A phosphonic acid —P(O)(OH)$_2$ 27.3 can be transformed into a phosphonate diester —P(O)(OR$^1$)$_2$ 27.1 (Scheme A, Reaction 6) by a coupling reaction with the hydroxy compound R$^1$OH, in the presence of a coupling agent such as Aldrithiol-2 (Aldrich) and triphenylphosphine. The reaction is conducted in a basic solvent such as pyridine. Alternatively, phosphonic acids 27.3 can be transformed into phosphonic esters 27.1 in which R$^1$ is aryl, such as phenyl, by means of a coupling reaction employing, for example, phenol and dicyclohexylcarbodiimide in pyridine at about 70° C. Alternatively, phosphonic acids 27.3 can be transformed into phosphonic esters 27.1 in which R$^1$ is alkenyl, by means of an alkylation reaction. The phosphonic acid is reacted with the alkenyl bromide R$^1$Br in a polar organic solvent such as acetonitrile solution at reflux temperature, in the presence of a base such as cesium carbonate, to afford the phosphonic ester 27.1.

Phosphonate prodrugs of the present invention may also be prepared from the precursor free acid by Mitsunobu reactions (Mitsunobu, (1981) *Synthesis*, 1; Campbell, (1992) *J. Org. Chem.*, 52:6331), and other acid coupling reagents including, but not limited to, carbodiimides (Alexander, et al, (1994) *Collect. Czech. Chem. Commun.* 59:1853; Casara, et al, (1992) *Bioorg. Med. Chem. Lett.*, 2:145; Ohashi, et al, (1988) *Tetrahedron Lett.*, 29:1189), and benzotriazolyloxytris-(dimethylamino)phosphonium salts (Campagne, et al, (1993) *Tetrahedron Lett.*, 34:6743).

Preparation of Carboalkoxy-Substituted Phosphonate Bisamidates, Monoamidates, Diesters and Monoesters.

A number of methods are available for the conversion of phosphonic acids into amidates and esters. In one group of methods, the phosphonic acid is either converted into an isolated activated intermediate such as a phosphoryl chloride, or the phosphonic acid is activated in situ for reaction with an amine or a hydroxy compound.

The conversion of phosphonic acids into phosphoryl chlorides is accomplished by reaction with thionyl chloride, for example as described in J. Gen. Chem. USSR, 1983, 53, 480, Zh. Obschei Khim., 1958, 28, 1063, or J. Org. Chem., 1994, 59, 6144, or by reaction with oxalyl chloride, as described in J. Am. Chem. Soc., 1994, 116, 3251, or J. Org. Chem., 1994, 59, 6144, or by reaction with phosphorus pentachloride, as described in J. Org. Chem., 2001, 66, 329, or in J. Med. Chem., 1995, 38, 1372. The resultant phosphoryl chlorides are then reacted with amines or hydroxy compounds in the presence of a base to afford the amidate or ester products.

Phosphonic acids are converted into activated imidazolyl derivatives by reaction with carbonyl diimidazole, as described in J. Chem. Soc., Chem. Comm., 1991, 312, or Nucleosides Nucleotides 2000, 19, 1885. Activated sulfonyloxy derivatives are obtained by the reaction of phosphonic acids with trichloromethylsulfonyl chloride, as described in J. Med. Chem. 1995, 38, 4958, or with triisopropylbenzenesulfonyl chloride, as described in Tet. Lett., 1996, 7857, or Bioorg. Med. Chem. Lett., 1998, 8, 663. The activated sulfonyloxy derivatives are then reacted with amines or hydroxy compounds to afford amidates or esters.

Alternatively, the phosphonic acid and the amine or hydroxy reactant are combined in the presence of a diimide coupling agent. The preparation of phosphonic amidates and esters by means of coupling reactions in the presence of dicyclohexyl carbodiimide is described, for example, in J. Chem. Soc., Chem. Comm., 1991, 312, or J. Med. Chem., 1980, 23, 1299 or Coll. Czech. Chem. Comm., 1987, 52, 2792. The use of ethyl dimethylaminopropyl carbodiimide for activation and coupling of phosphonic acids is described in Tet. Lett., 2001, 42, 8841, or Nucleosides Nucleotides, 2000, 19, 1885.

A number of additional coupling reagents have been described for the preparation of amidates and esters from phosphonic acids. The agents include Aldrithiol-2, and PYBOP and BOP, as described in J. Org. Chem., 1995, 60, 5214, and J. Med. Chem., 1997, 40, 3842, mesitylene-2-sulfonyl-3-nitro-1,2,4-triazole (MSNT), as described in J. Med. Chem., 1996, 39, 4958, diphenylphosphoryl azide, as described in J. Org. Chem., 1984, 49, 1158, 1-(2,4,6-triisopropylbenzenesulfonyl-3-nitro-1,2,4-triazole (TPSNT) as described in Bioorg. Med. Chem. Lett., 1998, 8, 1013, bromotris(dimethylamino)phosphonium hexafluorophosphate (BroP), as described in Tet. Lett., 1996, 37, 3997, 2-chloro-5,5-dimethyl-2-oxo-1,3,2-dioxaphosphinane, as described in Nucleosides Nucleotides 1995, 14, 871, and diphenyl chlorophosphate, as described in J. Med. Chem., 1988, 31, 1305.

Phosphonic acids are converted into amidates and esters by means of the Mitsonobu reaction, in which the phosphonic acid and the amine or hydroxy reactant are combined in the presence of a triaryl phosphine and a dialkyl azodicarboxylate. The procedure is described in Org. Lett., 2001, 3, 643, or J. Med. Chem., 1997, 40, 3842.

Phosphonic esters are also obtained by the reaction between phosphonic acids and halo compounds, in the presence of a suitable base. The method is described, for example, in Anal. Chem., 1987, 59, 1056, or J. Chem. Soc. Perkin Trans., I, 1993, 19, 2303, or J. Med. Chem., 1995, 38, 1372, or Tet. Lett., 2002, 43, 1161.

Schemes 1-4 illustrate the conversion of phosphonate esters and phosphonic acids into carboalkoxy-substituted phosphorobisamidates (Scheme 1), phosphoroamidates (Scheme 2), phosphonate monoesters (Scheme 3) and phosphonate diesters, (Scheme 4).

Scheme 1 illustrates various methods for the conversion of phosphonate diesters 1.1 into phosphorobisamidates 1.5. The diester 1.1, prepared as described previously, is hydrolyzed, either to the monoester 1.2 or to the phosphonic acid 1.6. The methods employed for these transformations are described above. The monoester 1.2 is converted into the monoamidate 1.3 by reaction with an aminoester 1.9, in which the group R$^2$ is H or alkyl, the group R$^4$ is an alkylene moiety such as, for example, CHCH$_3$, CHPr$^i$, CH(CH$_2$Ph), CH$_2$CH(CH$_3$) and the like, or a group present in natural or modified aminoacids, and the group R$^5$ is alkyl. The reactants are combined in the presence of a coupling agent such as a carbodiimide, for example dicyclohexyl carbodiimide, as described in J. Am. Chem. Soc., 1957, 79, 3575, optionally in the presence of an activating agent such as hydroxybenztriazole, to yield the amidate product 1.3. The amidate-forming reaction is also effected in the presence of coupling agents such as BOP, as described in J. Org. Chem., 1995, 60, 5214, Aldrithiol, PYBOP and similar coupling agents used for the preparation of amides and esters. Alternatively, the reactants 1.2 and 1.9 are transformed into the monoamidate 1.3 by means of a Mitsonobu reaction. The preparation of amidates by means of the Mitsonobu reaction is described in J. Med. Chem., 1995, 38, 2742. Equimolar amounts of the reactants are combined in an inert solvent such as tetrahydrofuran in the presence of a triaryl phosphine and a dialkyl azodicarboxylate. The thus-obtained monoamidate ester 1.3 is then transformed into amidate phosphonic acid 1.4. The conditions used for the hydrolysis reaction depend on the nature of the $R^1$ group, as described previously. The phosphonic acid amidate 1.4 is then reacted with an aminoester 1.9, as described above, to yield the bisamidate product 1.5, in which the amino substituents are the same or different.

An example of this procedure is shown in Scheme 1, Example 1. In this procedure, a dibenzyl phosphonate 1.14 is reacted with diazabicyclooctane (DABCO) in toluene at reflux, as described in J. Org. Chem., 1995, 60, 2946, to afford the monobenzyl phosphonate 1.15. The product is then reacted with equimolar amounts of ethyl alaninate 1.16 and dicyclohexyl carbodiimide in pyridine, to yield the amidate product 1.17. The benzyl group is then removed, for example by hydrogenolysis over a palladium catalyst, to give the monoacid product 1.18. This compound is then reacted in a Mitsonobu reaction with ethyl leucinate 1.19, triphenyl phosphine and diethylazodicarboxylate, as described in J. Med. Chem., 1995, 38, 2742, to produce the bisamidate product 1.20.

Using the above procedures, but employing, in place of ethyl leucinate 1.19 or ethyl alaninate 1.16, different aminoesters 1.9, the corresponding products 1.5 are obtained.

Alternatively, the phosphonic acid 1.6 is converted into the bisamidate 1.5 by use of the coupling reactions described above. The reaction is performed in one step, in which case the nitrogen-related substituents present in the product 1.5 are the same, or in two steps, in which case the nitrogen-related substituents can be different.

An example of the method is shown in Scheme 1, Example 2. In this procedure, a phosphonic acid 1.6 is reacted in pyridine solution with excess ethyl phenylalaninate 1.21 and dicyclohexylcarbodiimide, for example as described in J. Chem. Soc., Chem. Comm., 1991, 1063, to give the bisamidate product 1.22.

Using the above procedures, but employing, in place of ethyl phenylalaninate, different aminoesters 1.9, the corresponding products 1.5 are obtained.

As a further alternative, the phosphonic acid 1.6 is converted into the mono or bis-activated derivative 1.7, in which Lv is a leaving group such as chloro, imidazolyl, triisopropylbenzenesulfonyloxy etc. The conversion of phosphonic acids into chlorides 1.7 (Lv=Cl) is effected by reaction with thionyl chloride or oxalyl chloride and the like, as described in Organic Phosphorus Compounds, G. M. Kosolapoff, L. Maeir, eds, Wiley, 1976, p. 17. The conversion of phosphonic acids into monoimidazolides 1.7 (Lv=imidazolyl) is described in J. Med. Chem., 2002, 45, 1284 and in J. Chem. Soc. Chem. Comm., 1991, 312. Alternatively, the phosphonic acid is activated by reaction with triisopropylbenzenesulfonyl chloride, as described in Nucleosides and Nucleotides, 2000, 10, 1885. The activated product is then reacted with the aminoester 1.9, in the presence of a base, to give the bisamidate 1.5. The reaction is performed in one step, in which case the nitrogen substituents present in the product 1.5 are the same, or in two steps, via the intermediate 1.11, in which case the nitrogen substituents can be different.

Examples of these methods are shown in Scheme 1, Examples 3 and 5. In the procedure illustrated in Scheme 1, Example 3, a phosphonic acid 1.6 is reacted with ten molar equivalents of thionyl chloride, as described in Zh. Obschei Khim., 1958, 28, 1063, to give the dichloro compound 1.23. The product is then reacted at reflux temperature in a polar aprotic solvent such as acetonitrile, and in the presence of a base such as triethylamine, with butyl serinate 1.24 to afford the bisamidate product 1.25.

Using the above procedures, but employing, in place of butyl serinate 1.24, different aminoesters 1.9, the corresponding products 1.5 are obtained.

In the procedure illustrated in Scheme 1, Example 5, the phosphonic acid 1.6 is reacted, as described in J. Chem. Soc. Chem. Comm., 1991, 312, with carbonyl diimidazole to give the imidazolide 1.32. The product is then reacted in acetonitrile solution at ambient temperature, with one molar equivalent of ethyl alaninate 1.33 to yield the monodisplacement product 1.34. The latter compound is then reacted with carbonyl diimidazole to produce the activated intermediate 1.35, and the product is then reacted, under the same conditions, with ethyl N-methylalaninate 1.33a to give the bisamidate product 1.36.

Using the above procedures, but employing, in place of ethyl alaninate 1.33 or ethyl N-methylalaninate 1.33a, different aminoesters 1.9, the corresponding products 1.5 are obtained.

The intermediate monoamidate 1.3 is also prepared from the monoester 1.2 by first converting the monoester into the activated derivative 1.8 in which Lv is a leaving group such as halo, imidazolyl etc, using the procedures described above. The product 1.8 is then reacted with an aminoester 1.9 in the presence of a base such as pyridine, to give an intermediate monoamidate product 1.3. The latter compound is then converted, by removal of the $R^1$ group and coupling of the product with the aminoester 1.9, as described above, into the bisamidate 1.5.

An example of this procedure, in which the phosphonic acid is activated by conversion to the chloro derivative 1.26, is shown in Scheme 1, Example 4. In this procedure, the phosphonic monobenzyl ester 1.15 is reacted, in dichloromethane, with thionyl chloride, as described in Tet. Let., 1994, 35, 4097, to afford the phosphoryl chloride 1.26. The product is then reacted in acetonitrile solution at ambient temperature with one molar equivalent of ethyl 3-amino-2-methylpropionate 1.27 to yield the monoamidate product 1.28. The latter compound is hydrogenated in ethyl acetate over a 5% palladium on carbon catalyst to produce the monoacid product 1.29. The product is subjected to a Mitsonobu coupling procedure, with equimolar amounts of butyl alaninate 1.30, triphenyl phosphine, diethylazodicarboxylate and triethylamine in tetrahydrofuran, to give the bisamidate product 1.31.

Using the above procedures, but employing, in place of ethyl 3-amino-2-methylpropionate 1.27 or butyl alaninate 1.30, different aminoesters 1.9, the corresponding products 1.5 are obtained.

The activated phosphonic acid derivative 1.7 is also converted into the bisamidate 1.5 via the diamino compound 1.10. The conversion of activated phosphonic acid derivatives such as phosphoryl chlorides into the corresponding amino analogs 1.10, by reaction with ammonia, is described in Organic Phosphorus Compounds, G. M. Kosolapoff, L. Maeir, eds, Wiley, 1976. The diamino compound 1.10 is then reacted at elevated temperature with a haloester 1.12, in a polar organic solvent such as dimethylformamide, in the presence of a base such as dimethylaminopyridine or potassium carbonate, to yield the bisamidate 1.5.

An example of this procedure is shown in Scheme 1, Example 6. In this method, a dichlorophosphonate 1.23 is reacted with ammonia to afford the diamide 1.37. The reaction is performed in aqueous, aqueous alcoholic or alcoholic solution, at reflux temperature. The resulting diamino compound is then reacted with two molar equivalents of ethyl 2-bromo-3-methylbutyrate 1.38, in a polar organic solvent such as N-methylpyrrolidinone at ca. 150° C., in the presence of a base such as potassium carbonate, and optionally in the presence of a catalytic amount of potassium iodide, to afford the bisamidate product 1.39.

Using the above procedures, but employing, in place of ethyl 2-bromo-3-methylbutyrate 1.38, different haloesters 1.12 the corresponding products 1.5 are obtained.

The procedures shown in Scheme 1 are also applicable to the preparation of bisamidates in which the aminoester moiety incorporates different functional groups. Scheme 1, Example 7 illustrates the preparation of bisamidates derived from tyrosine. In this procedure, the monoimidazolide 1.32 is reacted with propyl tyrosinate 1.40, as described in Example 5, to yield the monoamidate 1.41. The product is reacted with carbonyl diimidazole to give the imidazolide 1.42, and this material is reacted with a further molar equivalent of propyl tyrosinate to produce the bisamidate product 1.43.

Using the above procedures, but employing, in place of propyl tyrosinate 1.40, different aminoesters 1.9, the corresponding products 1.5 are obtained. The aminoesters employed in the two stages of the above procedure can be the same or different, so that bisamidates with the same or different amino substituents are prepared.

Scheme 2 illustrates methods for the preparation of phosphonate monoamidates.

In one procedure, a phosphonate monoester 1.1 is converted, as described in Scheme 1, into the activated derivative 1.8. This compound is then reacted, as described above, with an aminoester 1.9, in the presence of a base, to afford the monoamidate product 2.1. The procedure is illustrated in Scheme 2, Example 1. In this method, a monophenyl phosphonate 2.7 is reacted with, for example, thionyl chloride, as described in J. Gen. Chem. USSR., 1983, 32, 367, to give the chloro product 2.8. The product is then reacted, as described in Scheme 1, with ethyl alaninate 2.9, to yield the amidate 2.10.

Using the above procedures, but employing, in place of ethyl alaninate 2.9, different aminoesters 1.9, the corresponding products 2.1 are obtained.

Alternatively, the phosphonate monoester 1.1 is coupled, as described in Scheme 1, with an aminoester 1.9 to produce the amidate 2.1. If necessary, the $R^1$ substituent is then altered, by initial cleavage to afford the phosphonic acid 2.2. The procedures for this transformation depend on the nature of the $R^1$ group, and are described above. The phosphonic acid is then transformed into the ester amidate product 2.3, by reaction with the hydroxy compound $R^3OH$, in which the group $R^3$ is aryl, heteroaryl, alkyl, cycloalkyl, haloalkyl etc, using the same coupling procedures (carbodiimide, Aldrithiol-2, PYBOP, Mitsonobu reaction etc) described in Scheme 1 for the coupling of amines and phosphonic acids.

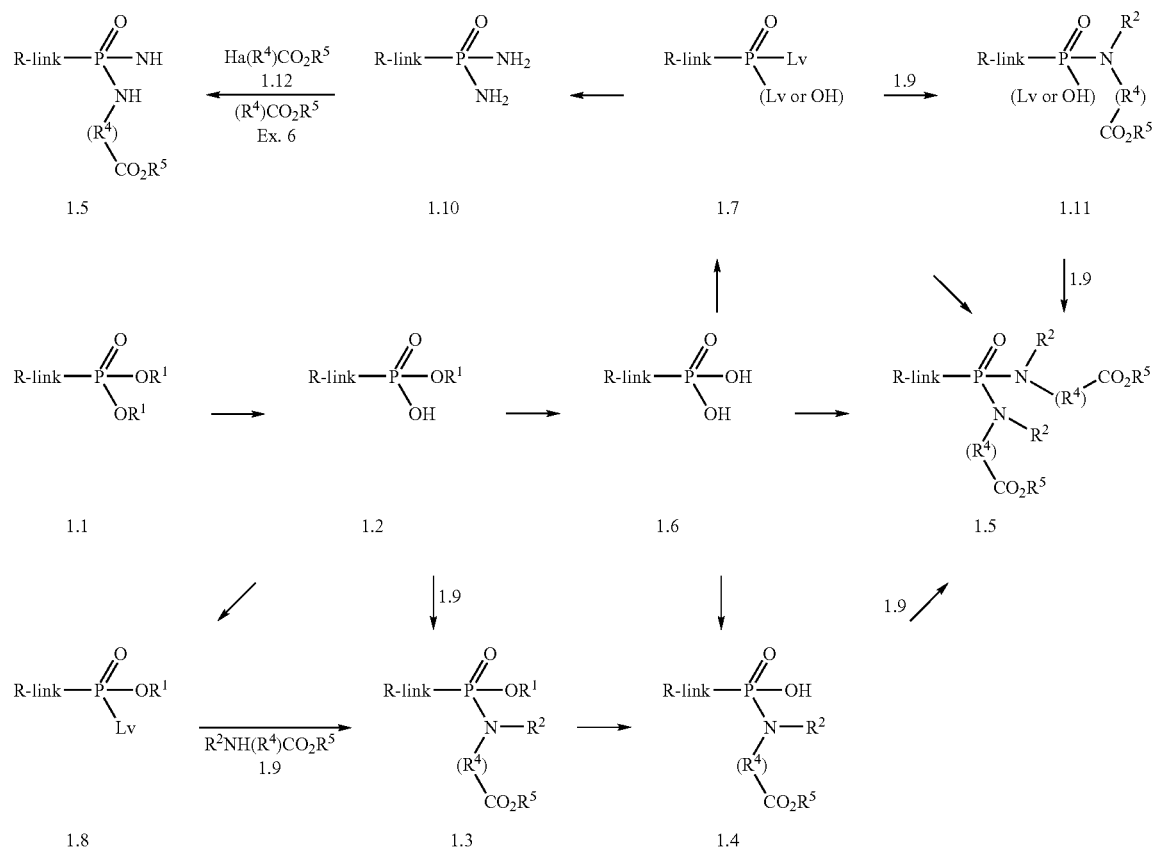

Scheme 1

-continued
Scheme 1 Example 1
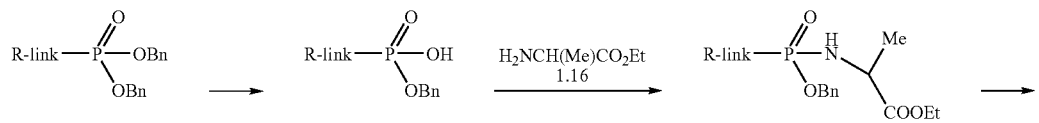
Scheme 1 Example 2
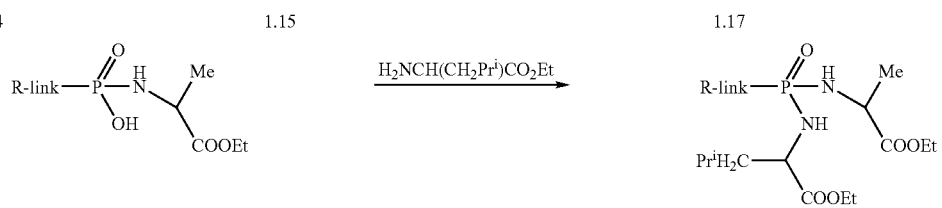
Scheme 1 Example 3
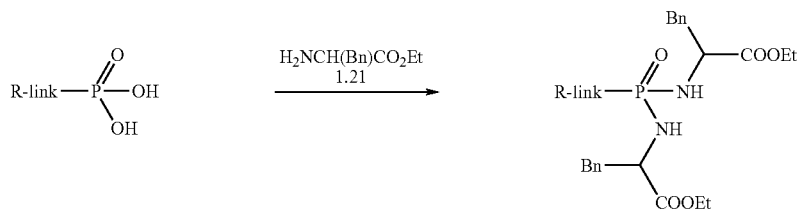
Scheme 1 Example 4
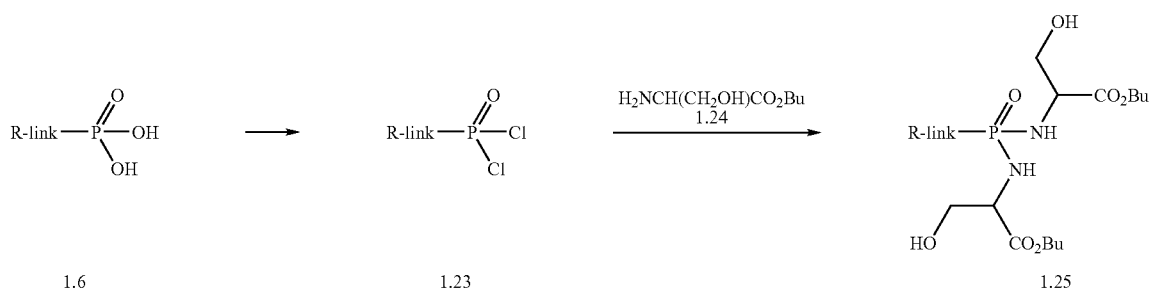
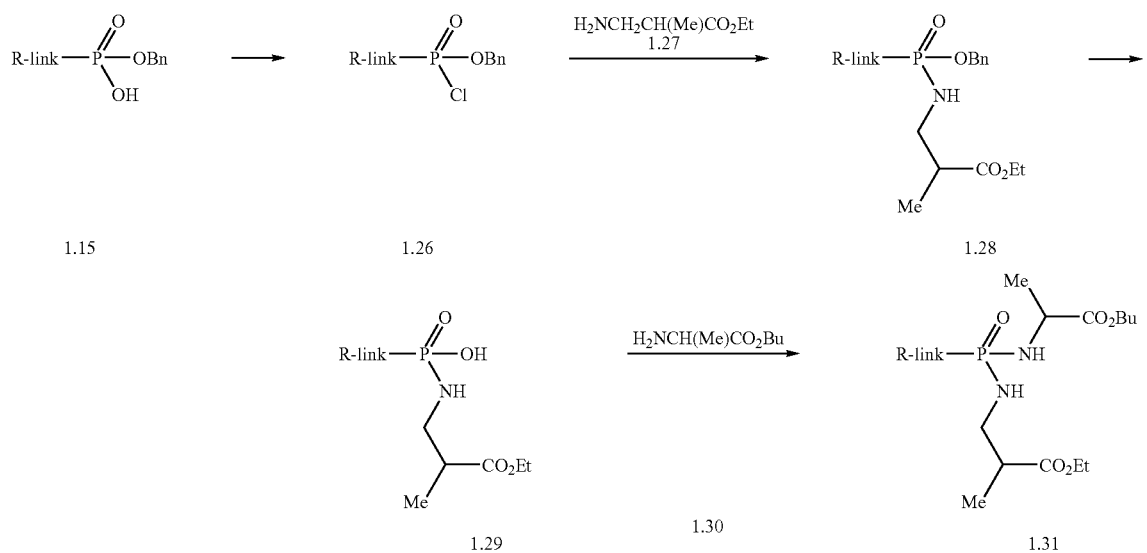

-continued
Scheme 1 Example 5
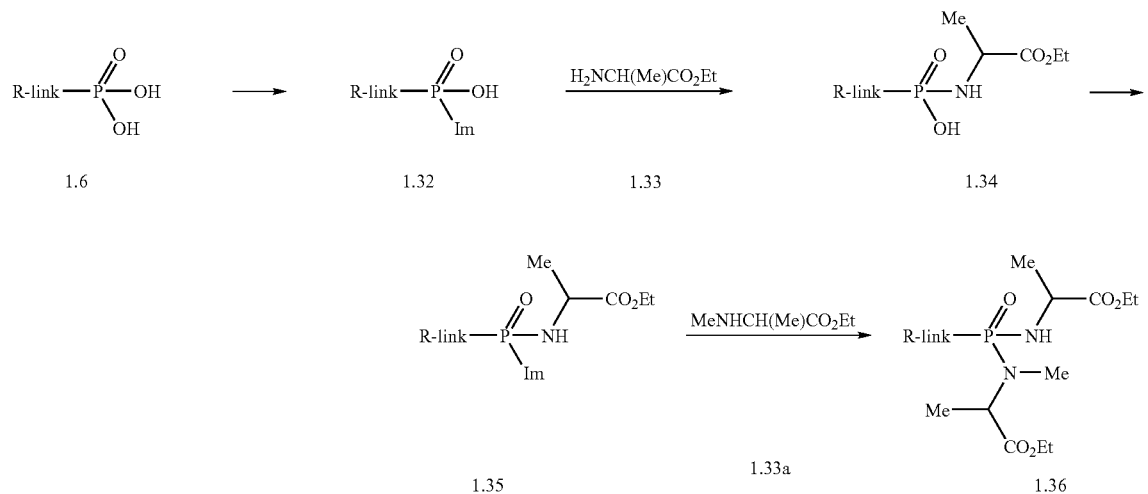
Scheme 1 Example 6
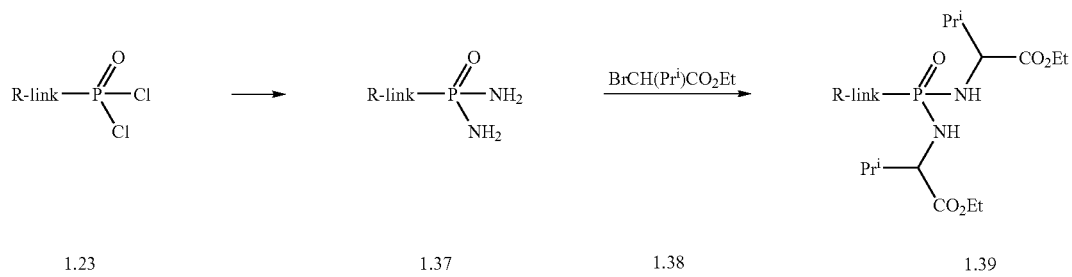
Scheme 1 Example 7
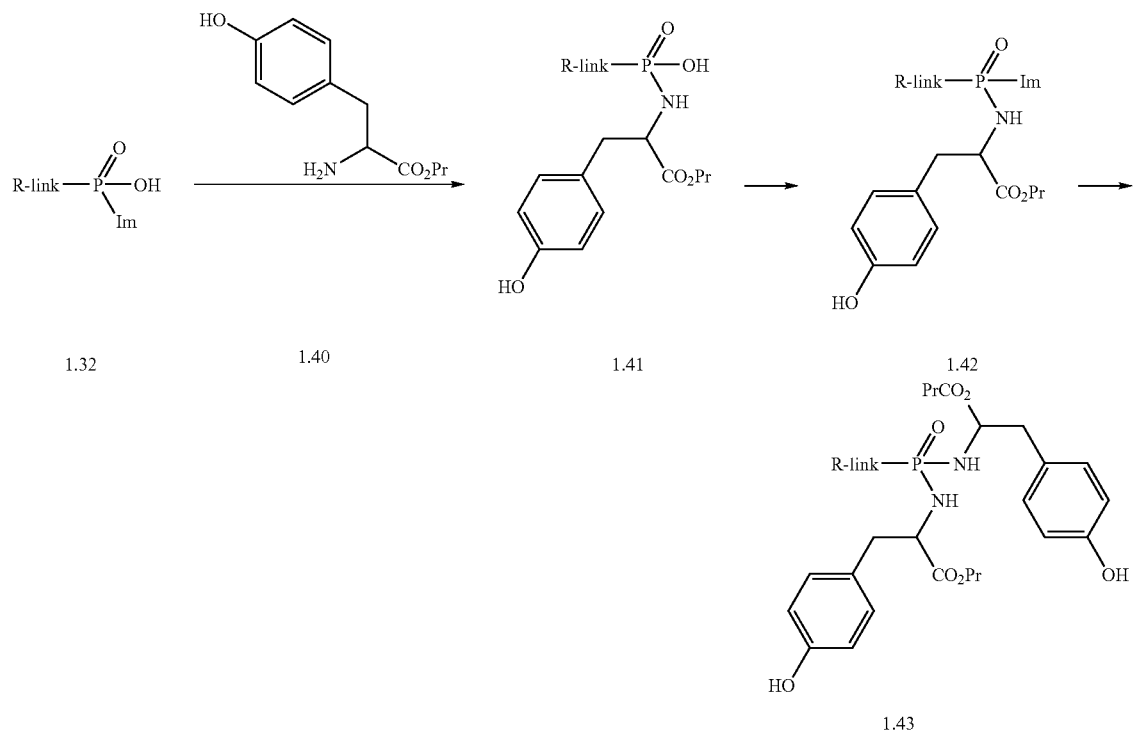

Examples of this method are shown in Scheme 2, Examples and 2 and 3. In the sequence shown in Example 2, a monobenzyl phosphonate 2.11 is transformed by reaction with ethyl alaninate, using one of the methods described above, into the monoamidate 2.12. The benzyl group is then removed by catalytic hydrogenation in ethyl acetate solution over a 5% palladium on carbon catalyst, to afford the phosphonic acid amidate 2.13. The product is then reacted in dichloromethane solution at ambient temperature with equimolar amounts of 1-(dimethylaminopropyl)-3-ethylcarbodiimide and trifluoroethanol 2.14, for example as described in Tet. Lett., 2001, 42, 8841, to yield the amidate ester 2.15.

In the sequence shown in Scheme 2, Example 3, the monoamidate 2.13 is coupled, in tetrahydrofuran solution at ambient temperature, with equimolar amounts of dicyclohexyl carbodiimide and 4-hydroxy-N-methylpiperidine 2.16, to produce the amidate ester product 2.17.

Using the above procedures, but employing, in place of the ethyl alaninate product 2.12 different monoacids 2.2, and in place of trifluoroethanol 2.14 or 4-hydroxy-N-methylpiperidine 2.16, different hydroxy compounds $R^3OH$, the corresponding products 2.3 are obtained.

Alternatively, the activated phosphonate ester 1.8 is reacted with ammonia to yield the amidate 2.4. The product is then reacted, as described in Scheme 1, with a haloester 2.5, in the presence of a base, to produce the amidate product 2.6. If appropriate, the nature of the $R^1$ group is changed, using the procedures described above, to give the product 2.3. The method is illustrated in Scheme 2, Example 4. In this sequence, the monophenyl phosphoryl chloride 2.18 is reacted, as described in Scheme 1, with ammonia, to yield the amino product 2.19. This material is then reacted in N-methylpyrrolidinone solution at 170° C. with butyl 2-bromo-3-phenylpropionate 2.20 and potassium carbonate, to afford the amidate product 2.21.

Using these procedures, but employing, in place of butyl 2-bromo-3-phenylpropionate 2.20, different haloesters 2.5, the corresponding products 2.6 are obtained.

The monoamidate products 2.3 are also prepared from the doubly activated phosphonate derivatives 1.7. In this procedure, examples of which are described in Synlett., 1998, 1, 73, the intermediate 1.7 is reacted with a limited amount of the aminoester 1.9 to give the mono-displacement product 1.11. The latter compound is then reacted with the hydroxy compound $R^3OH$ in a polar organic solvent such as dimethylformamide, in the presence of a base such as diisopropylethylamine, to yield the monoamidate ester 2.3.

The method is illustrated in Scheme 2, Example 5. In this method, the phosphoryl dichloride 2.22 is reacted in dichloromethane solution with one molar equivalent of ethyl N-methyl tyrosinate 2.23 and dimethylaminopyridine, to generate the monoamidate 2.24. The product is then reacted with phenol 2.25 in dimethylformamide containing potassium carbonate, to yield the ester amidate product 2.26.

Using these procedures, but employing, in place of ethyl N-methyl tyrosinate 2.23 or phenol 2.25, the aminoesters 1.9 and/or the hydroxy compounds $R^3OH$, the corresponding products 2.3 are obtained.

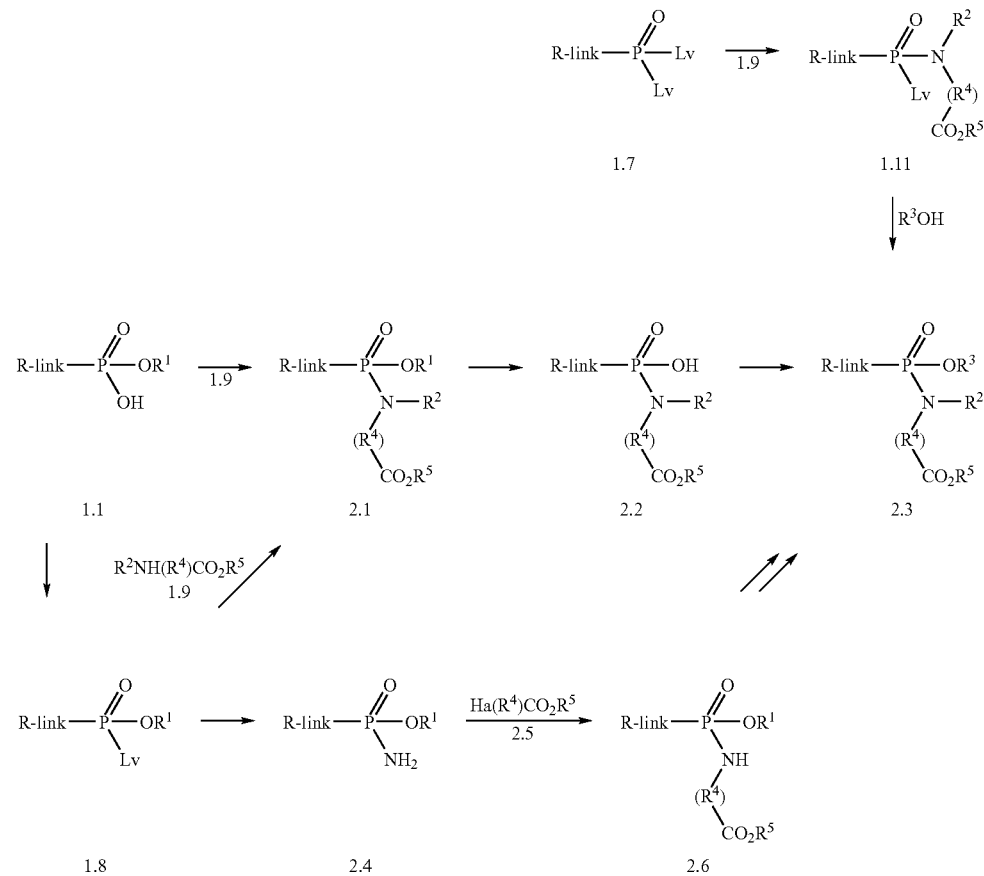

-continued
Scheme 2 Example 1

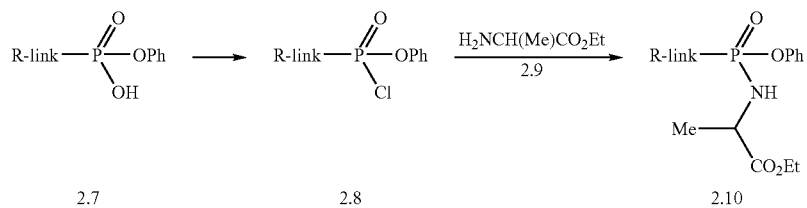

Scheme 2 Example 2

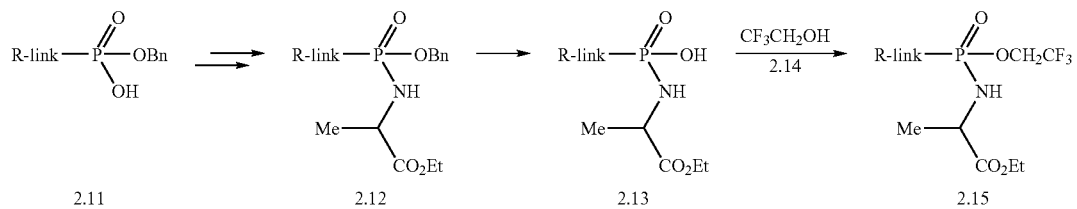

Scheme 2 Example 3

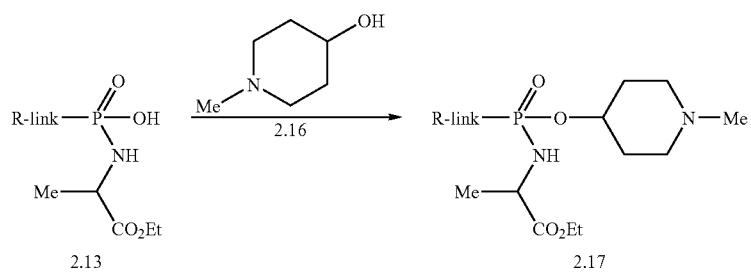

Scheme 2 Example 4

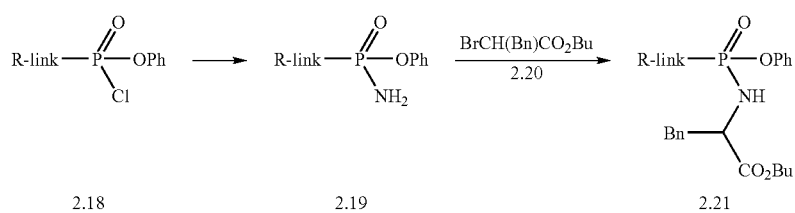

Scheme 2 Example 5

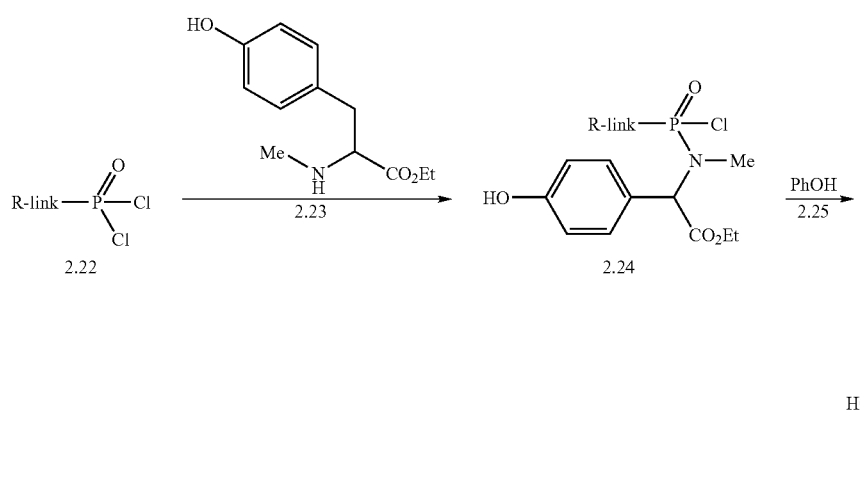

Scheme 3 illustrates methods for the preparation of carboalkoxy-substituted phosphonate diesters in which one of the ester groups incorporates a carboalkoxy substituent.

In one procedure, a phosphonate monoester 1.1, prepared as described above, is coupled, using one of the methods described above, with a hydroxyester 3.1, in which the groups $R^4$ and $R^5$ are as described in Scheme 1. For example, equimolar amounts of the reactants are coupled in the presence of a carbodiimide such as dicyclohexyl carbodiimide, as described in Aust. J. Chem., 1963, 609, optionally in the presence of dimethylaminopyridine, as described in Tet., 1999, 55, 12997. The reaction is conducted in an inert solvent at ambient temperature.

The procedure is illustrated in Scheme 3, Example 1. In this method, a monophenyl phosphonate 3.9 is coupled, in dichloromethane solution in the presence of dicyclohexyl carbodiimide, with ethyl 3-hydroxy-2-methylpropionate 3.10 to yield the phosphonate mixed diester 3.11.

Using this procedure, but employing, in place of ethyl 3-hydroxy-2-methylpropionate 3.10, different hydroxyesters 3.1, the corresponding products 3.2 are obtained.

The conversion of a phosphonate monoester 1.1 into a mixed diester 3.2 is also accomplished by means of a Mitsonobu coupling reaction with the hydroxyester 3.1, as described in Org. Lett., 2001, 643. In this method, the reactants 1.1 and 3.1 are combined in a polar solvent such as tetrahydrofuran, in the presence of a triarylphosphine and a dialkyl azodicarboxylate, to give the mixed diester 3.2. The $R^1$ substituent is varied by cleavage, using the methods described previously, to afford the monoacid product 3.3. The product is then coupled, for example using methods described above, with the hydroxy compound $R^3OH$, to give the diester product 3.4.

The procedure is illustrated in Scheme 3, Example 2. In this method, a monoallyl phosphonate 3.12 is coupled in tetrahydrofuran solution, in the presence of triphenylphosphine and diethylazodicarboxylate, with ethyl lactate 3.13 to give the mixed diester 3.14. The product is reacted with tris(triphenylphosphine) rhodium chloride (Wilkinson catalyst) in acetonitrile, as described previously, to remove the allyl group and produce the monoacid product 3.15. The latter compound is then coupled, in pyridine solution at ambient temperature, in the presence of dicyclohexyl carbodiimide, with one molar equivalent of 3-hydroxypyridine 3.16 to yield the mixed diester 3.17.

Using the above procedures, but employing, in place of the ethyl lactate 3.13 or 3-hydroxypyridine, a different hydroxyester 3.1 and/or a different hydroxy compound $R^3OH$, the corresponding products 3.4 are obtained.

The mixed diesters 3.2 are also obtained from the monoesters 1.1 via the intermediacy of the activated monoesters 3.5. In this procedure, the monoester 1.1 is converted into the activated compound 3.5 by reaction with, for example, phosphorus pentachloride, as described in J. Org. Chem., 2001, 66, 329, or with thionyl chloride or oxalyl chloride (Lv=Cl), or with triisopropylbenzenesulfonyl chloride in pyridine, as described in Nucleosides and Nucleotides, 2000, 19, 1885, or with carbonyl diimidazole, as described in J. Med. Chem., 2002, 45, 1284. The resultant activated monoester is then reacted with the hydroxyester 3.1, as described above, to yield the mixed diester 3.2.

The procedure is illustrated in Scheme 3, Example 3. In this sequence, a monophenyl phosphonate 3.9 is reacted, in acetonitrile solution at 70° C., with ten equivalents of thionyl chloride, so as to produce the phosphoryl chloride 3.19. The product is then reacted with ethyl 4-carbamoyl-2-hydroxybutyrate 3.20 in dichloromethane containing triethylamine, to give the mixed diester 3.21.

Using the above procedures, but employing, in place of ethyl 4-carbamoyl-2-hydroxybutyrate 3.20, different hydroxyesters 3.1, the corresponding products 3.2 are obtained.

The mixed phosphonate diesters are also obtained by an alternative route for incorporation of the $R^{30}$ group into intermediates 3.3 in which the hydroxyester moiety is already incorporated. In this procedure, the monoacid intermediate 3.3 is converted into the activated derivative 3.6 in which Lv is a leaving group such as chloro, imidazole, and the like, as previously described. The activated intermediate is then reacted with the hydroxy compound $R^3OH$, in the presence of a base, to yield the mixed diester product 3.4.

The method is illustrated in Scheme 3, Example 4. In this sequence, the phosphonate monoacid 3.22 is reacted with trichloromethanesulfonyl chloride in tetrahydrofuran containing collidine, as described in J. Med. Chem., 1995, 38, 4648, to produce the trichloromethanesulfonyloxy product 3.23. This compound is reacted with 3-(morpholinomethyl)phenol 3.24 in dichloromethane containing triethylamine, to yield the mixed diester product 3.25.

Using the above procedures, but employing, in place of with 3-(morpholinomethyl)phenol 3.24, different carbinols $R^3OH$, the corresponding products 3.4 are obtained.

The phosphonate esters 3.4 are also obtained by means of alkylation reactions performed on the monoesters 1.1. The reaction between the monoacid 1.1 and the haloester 3.7 is performed in a polar solvent in the presence of a base such as diisopropylethylamine, as described in Anal. Chem., 1987, 59, 1056, or triethylamine, as described in J. Med. Chem., 1995, 38, 1372, or in a non-polar solvent such as benzene, in the presence of 18-crown-6, as described in Syn. Comm., 1995, 25, 3565.

The method is illustrated in Scheme 3, Example 5. In this procedure, the monoacid 3.26 is reacted with ethyl 2-bromo-3-phenylpropionate 3.27 and diisopropylethylamine in dimethylformamide at 80° C. to afford the mixed diester product 3.28.

Using the above procedure, but employing, in place of ethyl 2-bromo-3-phenylpropionate 3.27, different haloesters 3.7, the corresponding products 3.4 are obtained.

Scheme 3

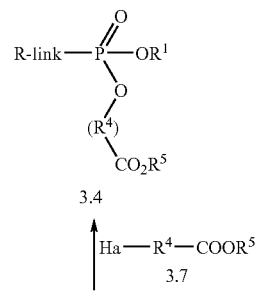

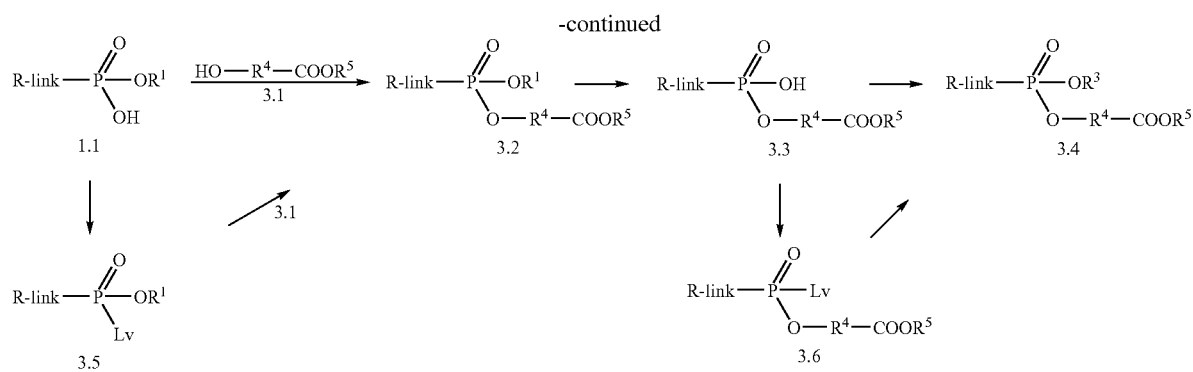
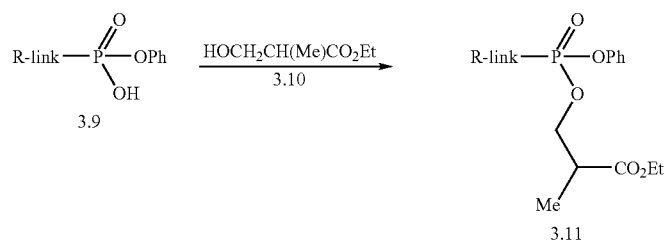
Scheme 3 Example 1
Scheme 3 Example 2
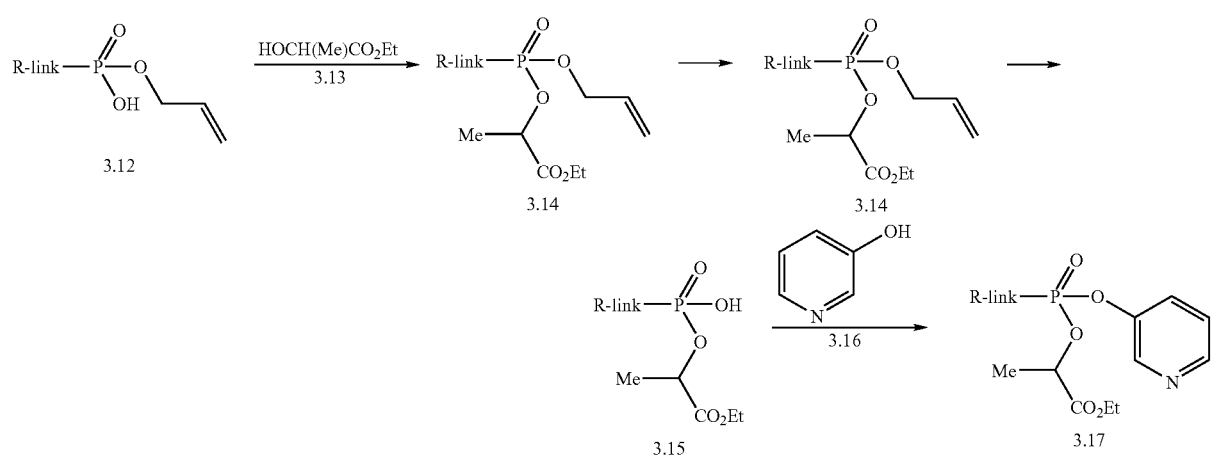
Scheme 3 Example 3
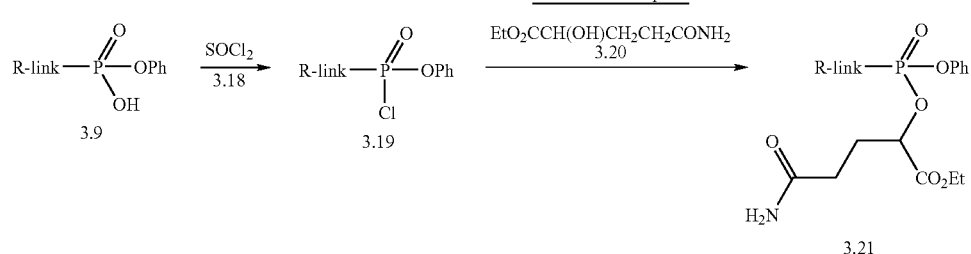
Scheme 3 Example 4
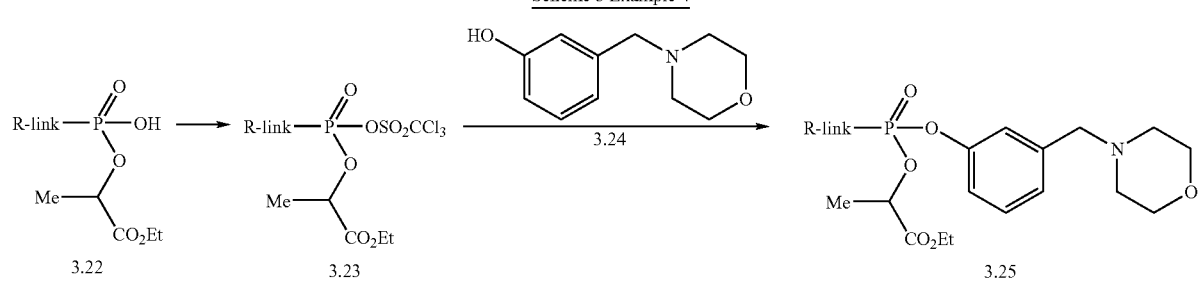

-continued
Scheme 3 Example 5

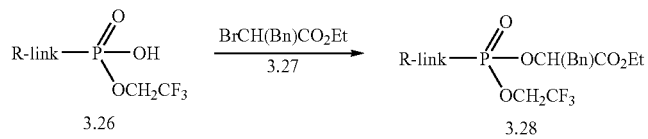

Scheme 4 illustrates methods for the preparation of phosphonate diesters in which both the ester substituents incorporate carboalkoxy groups.

The compounds are prepared directly or indirectly from the phosphonic acids 1.6. In one alternative, the phosphonic acid is coupled with the hydroxyester 4.2, using the conditions described previously in Schemes 1-3, such as coupling reactions using dicyclohexyl carbodiimide or similar reagents, or under the conditions of the Mitsonobu reaction, to afford the diester product 4.3 in which the ester substituents are identical.

This method is illustrated in Scheme 4, Example 1. In this procedure, the phosphonic acid 1.6 is reacted with three molar equivalents of butyl lactate 4.5 in the presence of Aldrithiol-2 and triphenyl phosphine in pyridine at ca. 70° C., to afford the diester 4.6.

Using the above procedure, but employing, in place of butyl lactate 4.5, different hydroxyesters 4.2, the corresponding products 4.3 are obtained.

Alternatively, the diesters 4.3 are obtained by alkylation of the phosphonic acid 1.6 with a haloester 4.1. The alkylation reaction is performed as described in Scheme 3 for the preparation of the esters 3.4.

This method is illustrated in Scheme 4, Example 2. In this procedure, the phosphonic acid 1.6 is reacted with excess ethyl 3-bromo-2-methylpropionate 4.7 and diisopropylethylamine in dimethylformamide at ca. 80° C., as described in Anal. Chem., 1987, 59, 1056, to produce the diester 4.8.

Using the above procedure, but employing, in place of ethyl 3-bromo-2-methylpropionate 4.7, different haloesters 4.1, the corresponding products 4.3 are obtained.

The diesters 4.3 are also obtained by displacement reactions of activated derivatives 1.7 of the phosphonic acid with the hydroxyesters 4.2. The displacement reaction is performed in a polar solvent in the presence of a suitable base, as described in Scheme 3. The displacement reaction is performed in the presence of an excess of the hydroxyester, to afford the diester product 4.3 in which the ester substituents are identical, or sequentially with limited amounts of different hydroxyesters, to prepare diesters 4.3 in which the ester substituents are different.

The methods are illustrated in Scheme 4, Examples 3 and 4. As shown in Example 3, the phosphoryl dichloride 2.22 is reacted with three molar equivalents of ethyl 3-hydroxy-2-(hydroxymethyl)propionate 4.9 in tetrahydrofuran containing potassium carbonate, to obtain the diester product 4.10.

Using the above procedure, but employing, in place of ethyl 3-hydroxy-2-(hydroxymethyl)propionate 4.9, different hydroxyesters 4.2, the corresponding products 4.3 are obtained.

Scheme 4, Example 4 depicts the displacement reaction between equimolar amounts of the phosphoryl dichloride 2.22 and ethyl 2-methyl-3-hydroxypropionate 4.11, to yield the monoester product 4.12. The reaction is conducted in acetonitrile at 70° C. in the presence of diisopropylethylamine. The product 4.12 is then reacted, under the same conditions, with one molar equivalent of ethyl lactate 4.13, to give the diester product 4.14. Using the above procedures, but employing, in place of ethyl 2-methyl-3-hydroxypropionate 4.11 and ethyl lactate 4.13, sequential reactions with different hydroxyesters 4.2, the corresponding products 4.3 are obtained.

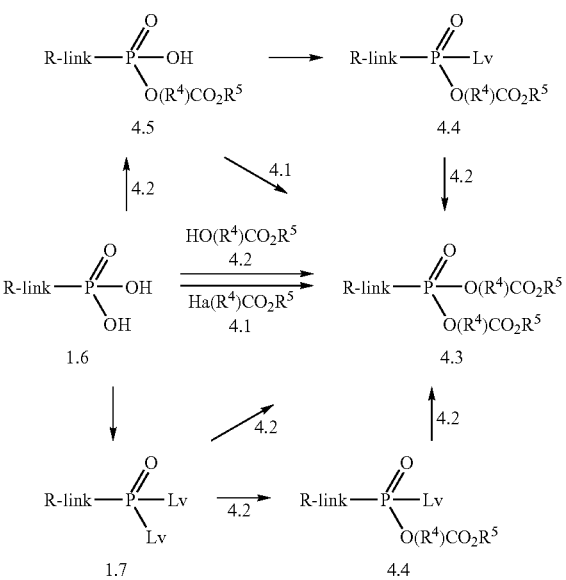

-continued
Scheme 3 Example 3
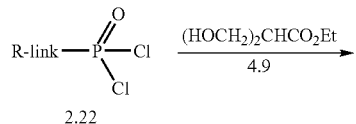
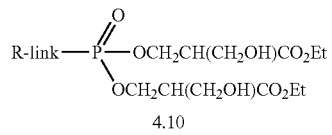
Scheme 4 Example 4
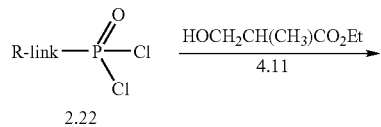
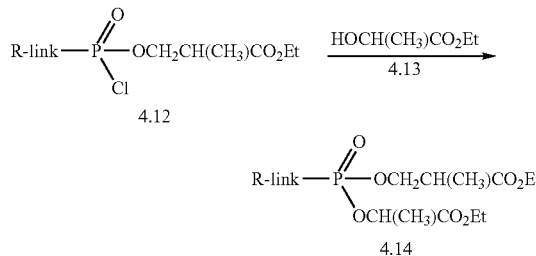
The compounds of Formula I-IV include all stereoisomers, and mixtures thereof. For example and not by way of limitation, the compounds of Formula I include at least the following stereoisomers:
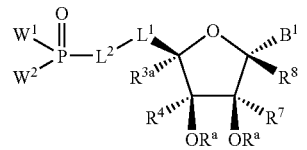
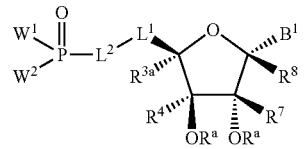
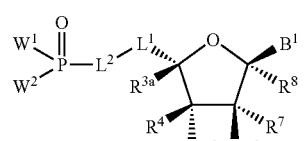
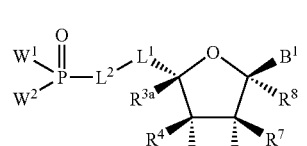
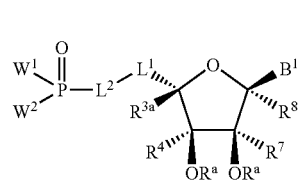
-continued
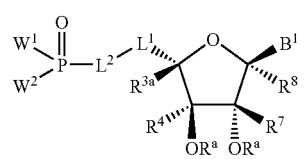
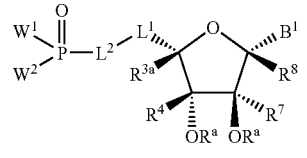
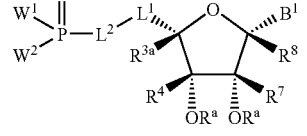
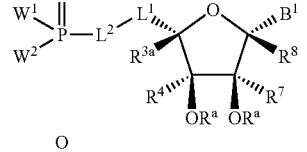
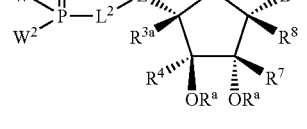

In another embodiment, the compounds of Formula I-IV are selected from the group consisting of
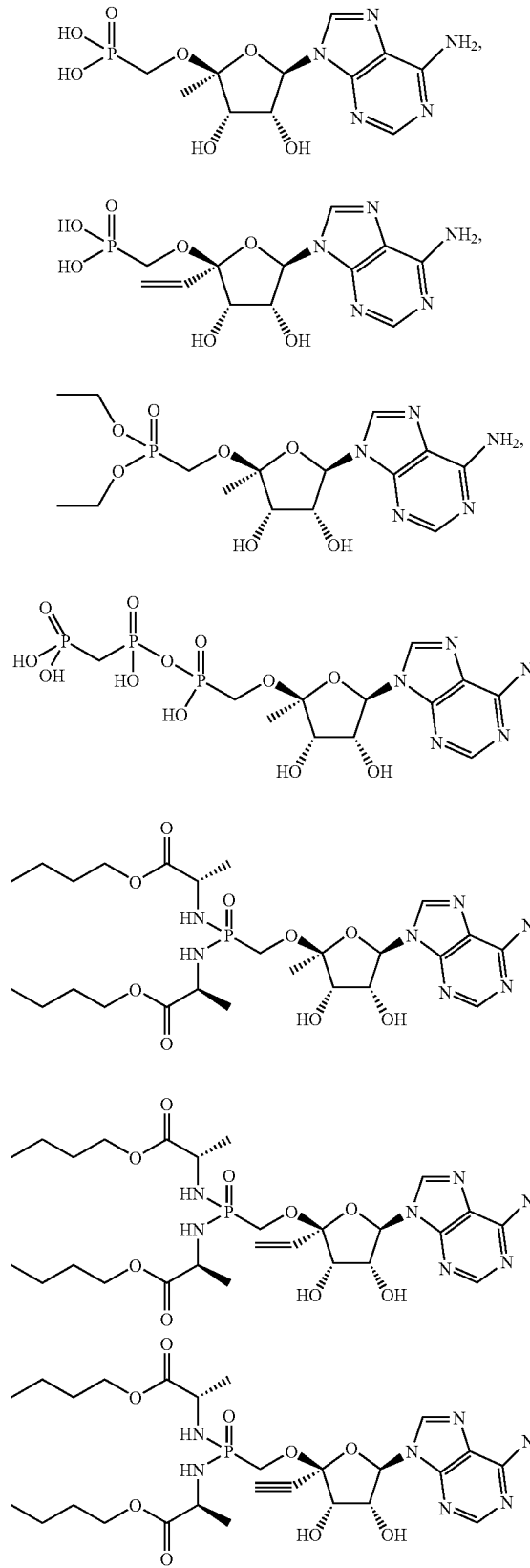
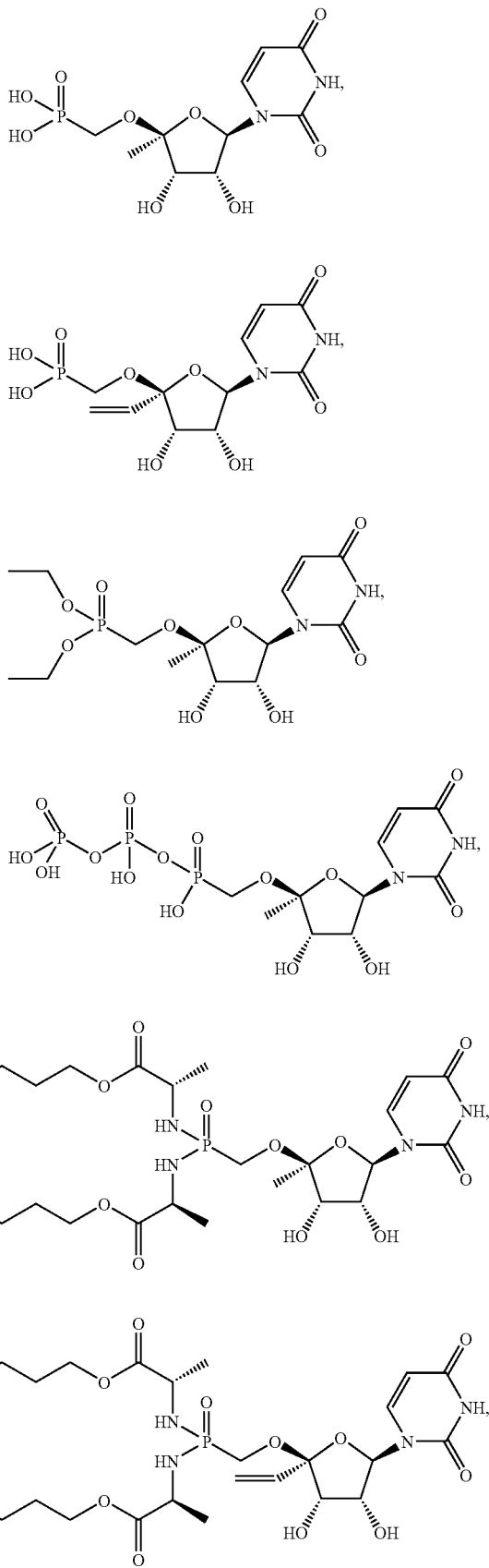

119 120
-continued -continued
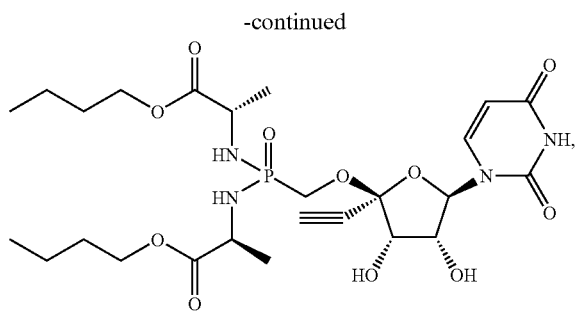
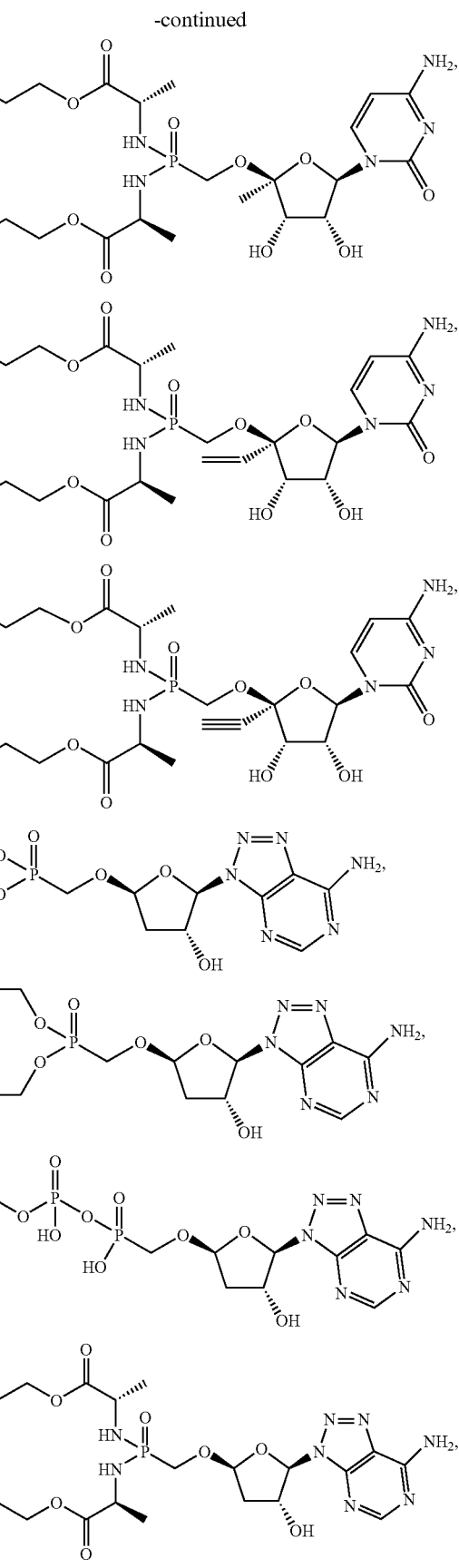

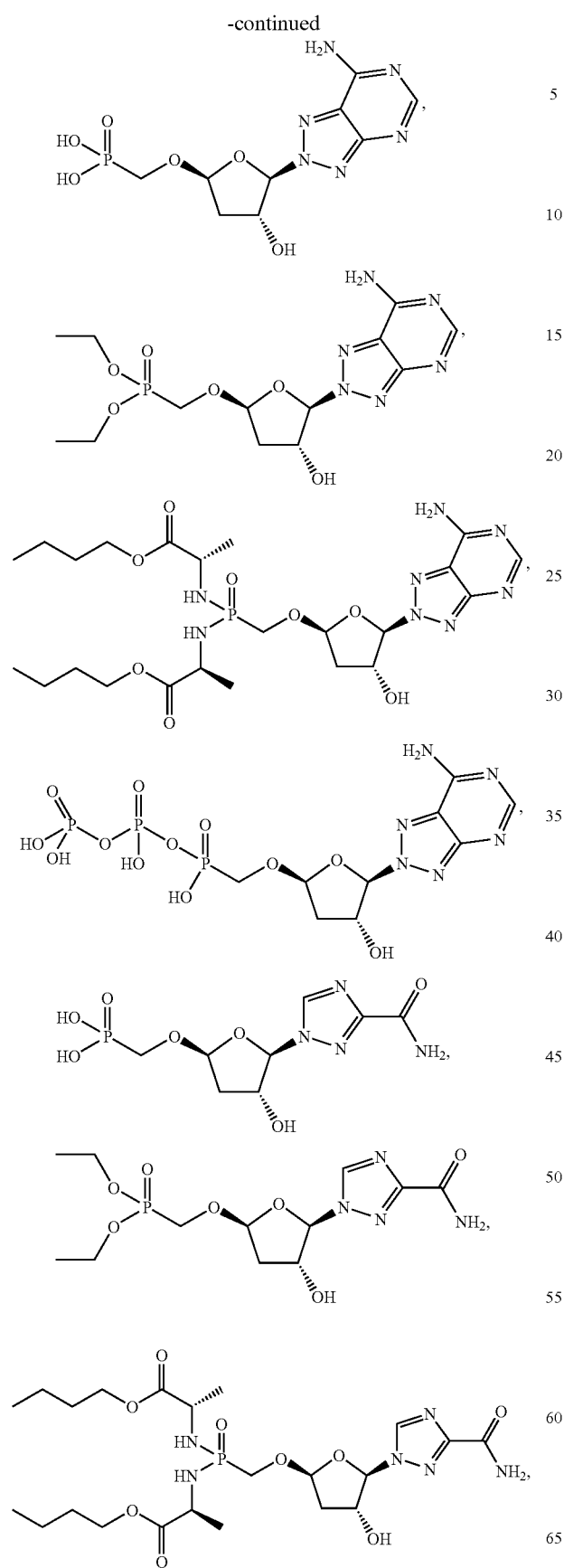
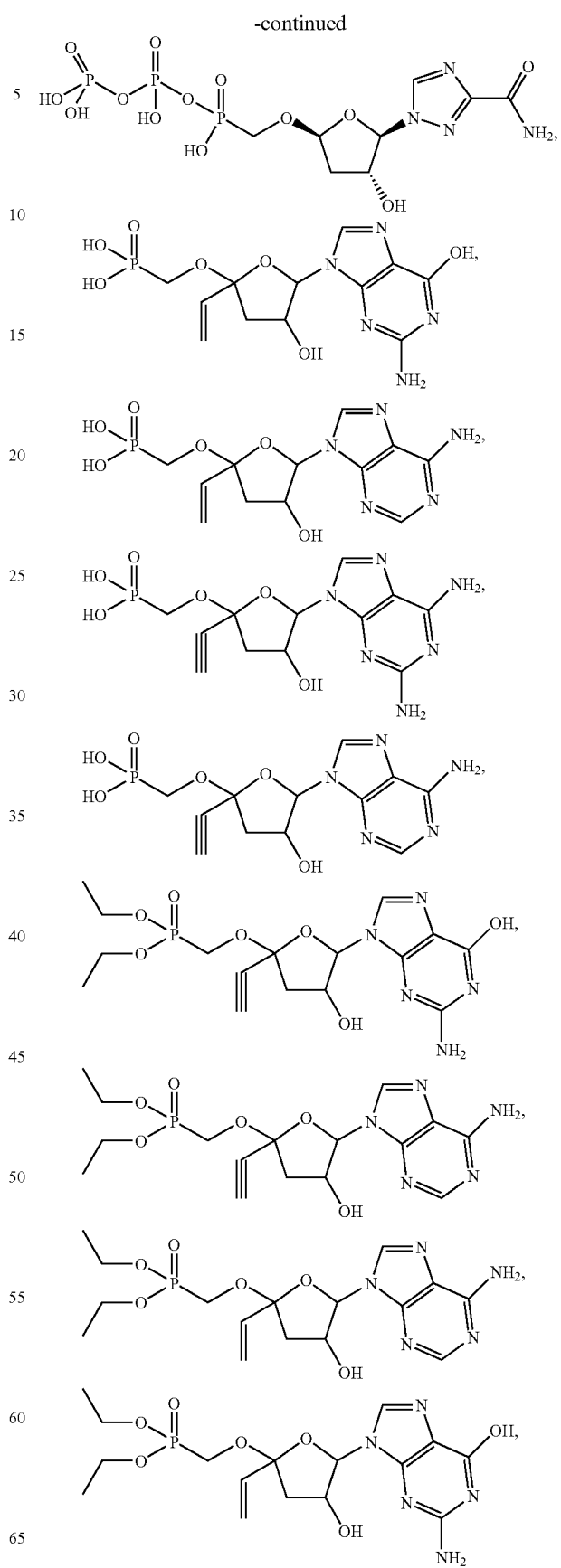

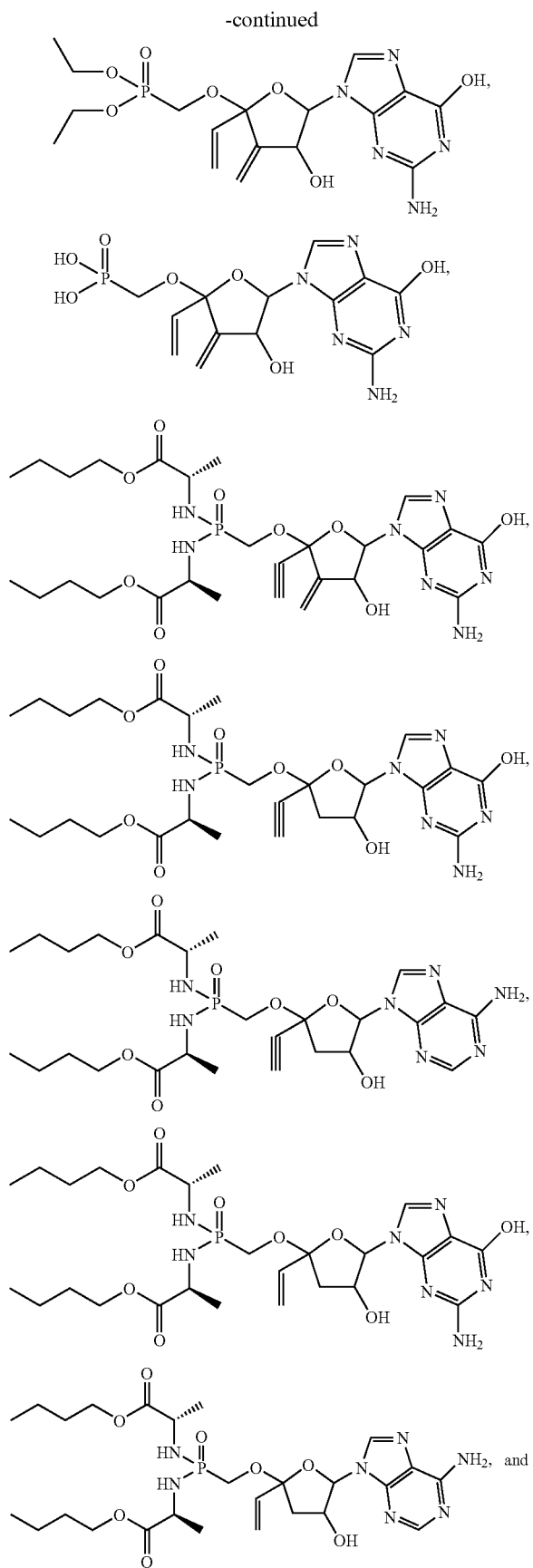

or pharmaceutically acceptable salts, solvates, and/or esters thereof.

In another embodiment of the compounds of Formula I-IV, -$L^1$-$L^2$-P(O)$W^1W^2$ is —O—C($R^{10}$)$_2$—P(O)$W^1W^2$, wherein each $R^{10}$ is independently H, alkoxy, alkyl, or halo. Non-limiting examples of suitable —O—C($R^{10}$)$_2$—P(O)$W^1W^2$ groups include —O—CH$_2$—P(O)$W^1W^2$, —CHCl—O—P(O)$W^1W^2$, —CCl$_2$—O—P(O)$W^1W^2$, —CH(CH$_3$)—O—P(O)$W^1W^2$, —C(CH$_3$)$_2$—O—P(O)$W^1W^2$, etc.

In another embodiment of the compounds of Formula I-IV, -$L^1$-$L^2$-P(O)$W^1W^2$ is —S—C($R^{10}$)$_2$—P(O)$W^1W^2$, wherein each $R^{10}$ is independently H, alkoxy, alkyl, or halo. Non-limiting examples of suitable —S—C($R^{10}$)$_2$—P(O)$W^1W^2$ groups include —S—CH$_2$—P(O)$W^1W^2$, —S—CHCl—P(O)$W^1W^2$, —S—CHF—P(O)$W^1W^2$, —S—CH(CH$_3$)—P(O)$W^1W^2$—S—CF$_2$—P(O)$W^1W^2$, etc.

In another embodiment of the compounds of Formula I-IV, -$L^1$-$L^2$-P(O)$W^1W^2$ is —N($R^{11}$)—C($R^{10}$)$_2$—P(O)$W^1W^2$, wherein each $R^{10}$ is independently H, alkoxy, alkyl, or halo and $R^{10}$ is H, alkyl, aryl, or substituted aryl. Non-limiting examples of suitable —N($R^{11}$)—C($R^{10}$)$_2$—P(O)$W^1W^2$ groups include —NH—CH$_2$—P(O)$W^1W^2$, —NH—CHCl—P(O)$W^1W^2$, —NH—CHF—P(O)$W^1W^2$, —NH—CH(CH$_3$)—P(O)$W^1W^2$, —NH—CF$_2$—P(O)$W^1W^2$, —N(CH$_3$)—CH$_2$—P(O)$W^1W^2$, —N(CH$_3$)—CHCl—P(O)$W^1W^2$, —N(CH$_3$)—CF$_2$—P(O)$W^1W^2$, —N(CH$_3$)—CH(CH$_3$)—P(O)$W^1W^2$, —N(CH$_3$)—CHF—P(O)$W^1W^2$, —N(phenyl)-CH$_2$—P(O)$W^1W^2$, —N(phenyl)-CHCl—P(O)$W^1W^2$, —N(phenyl)-CF$_2$—P(O)$W^1W^2$, —N(phenyl)-CH(CH$_3$)—P(O)$W^1W^2$, etc.

One skilled in the art will recognize that nucleobases can exist in tautomeric forms. For example, structures (a) and (b) can have equivalent tautomeric forms as shown below:

All possible tautomeric forms of the nucleobases of all of the embodiments are within the scope of the invention.
By way of example and not by limitation, nucleobases B¹, B², or B³ for Formula I-IV that are within the scope of the invention include:
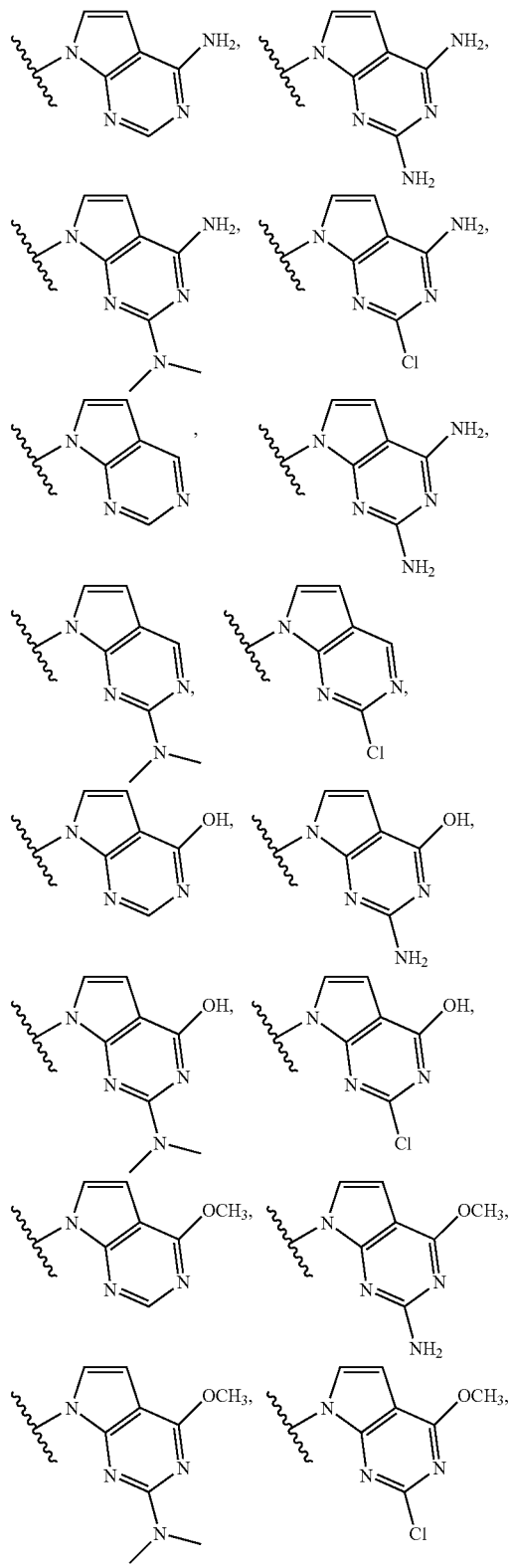
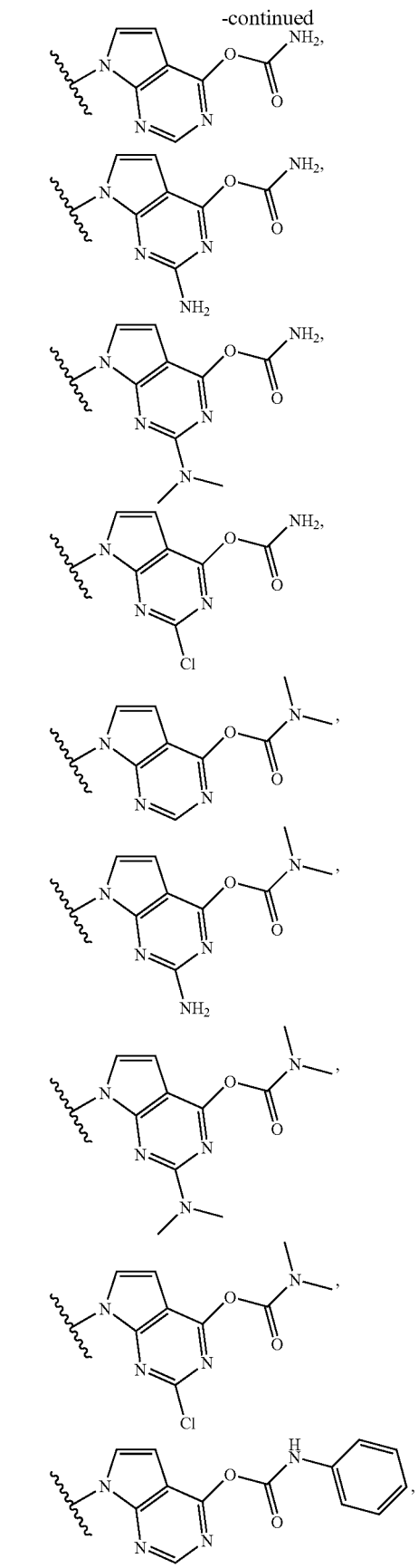

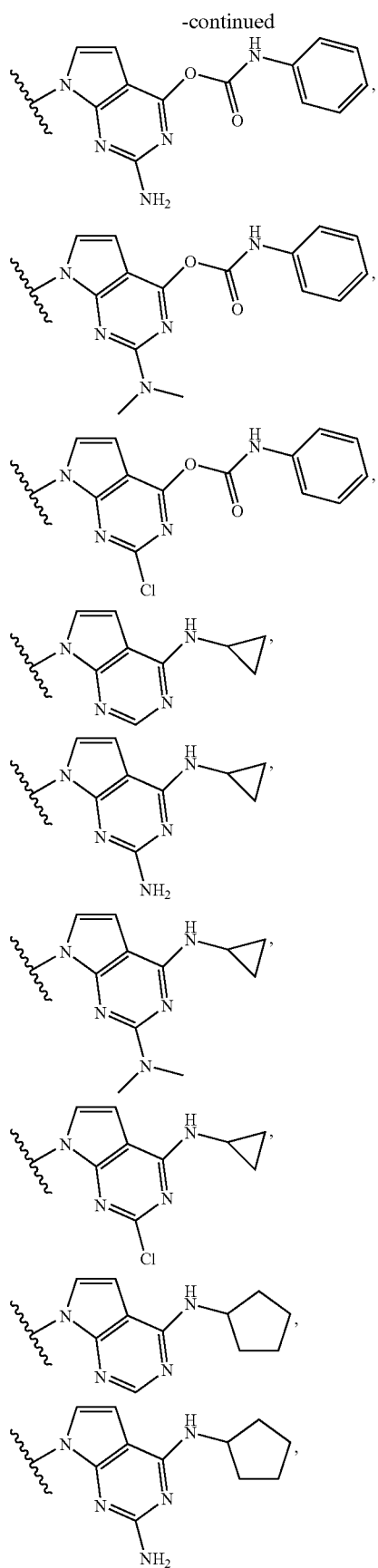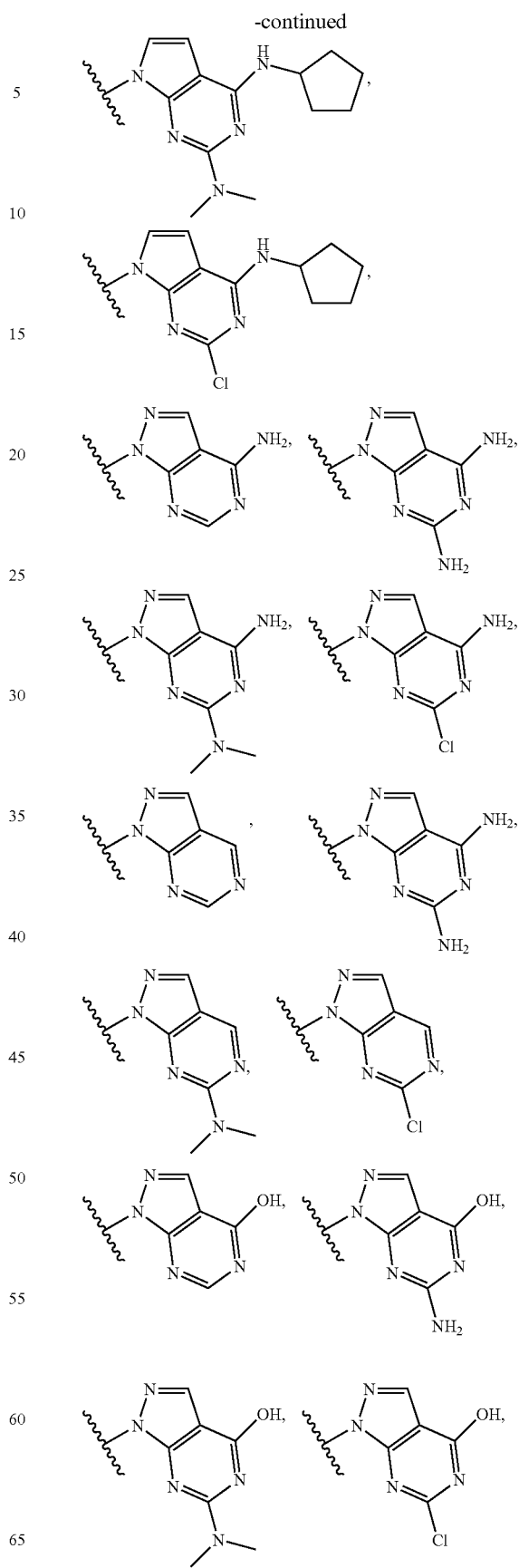

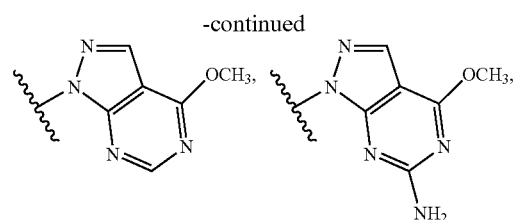
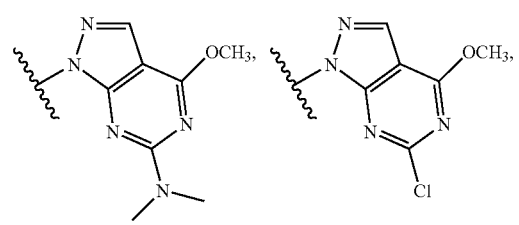
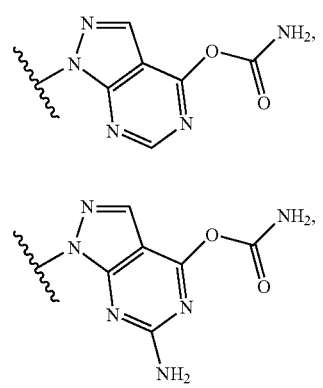
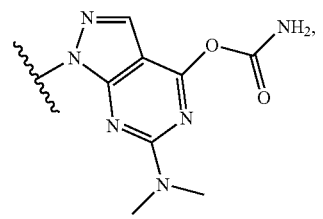
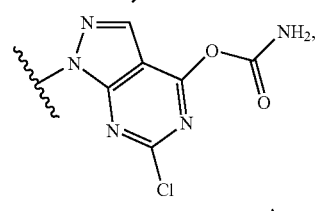
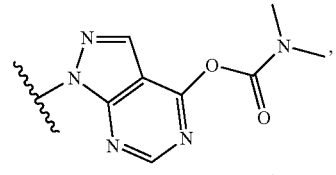
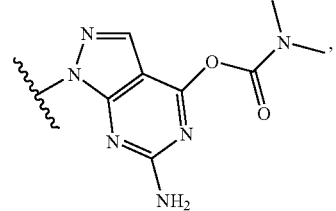
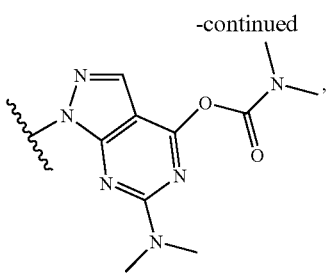
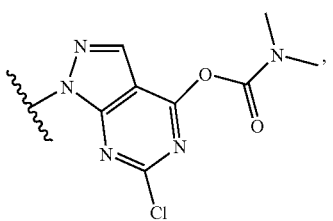
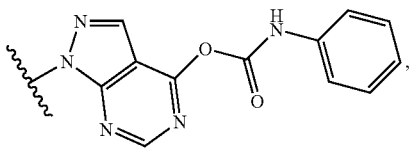
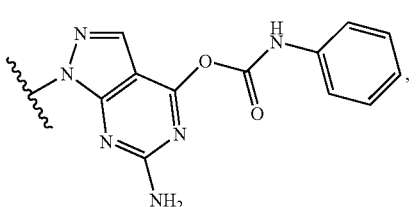
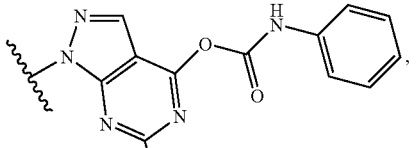
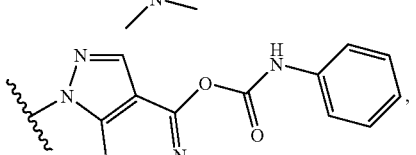
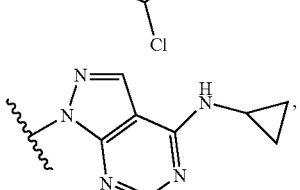
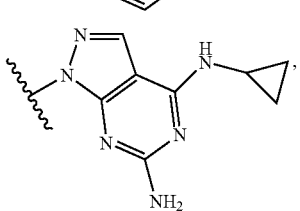

-continued
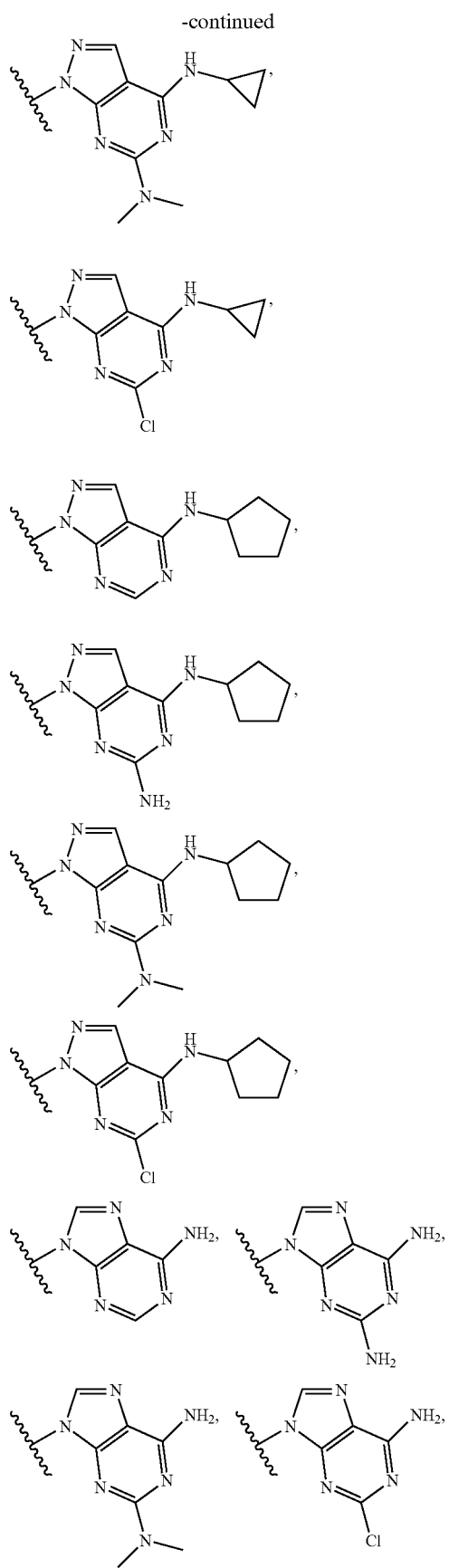
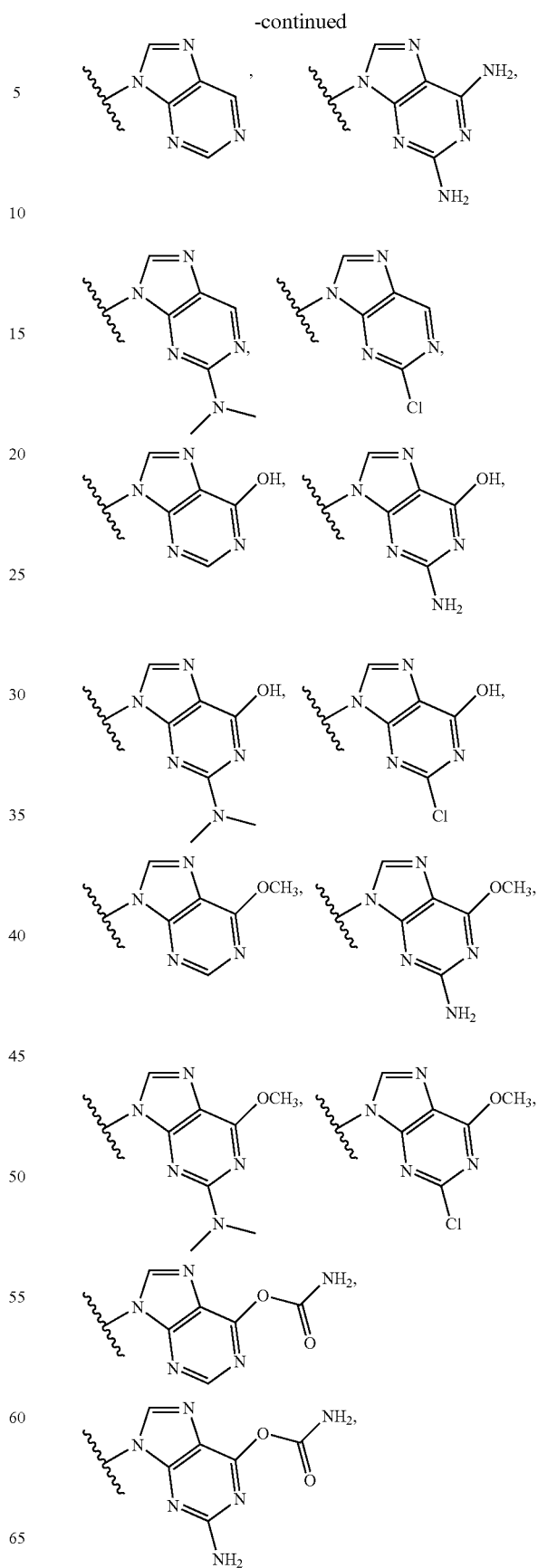

133
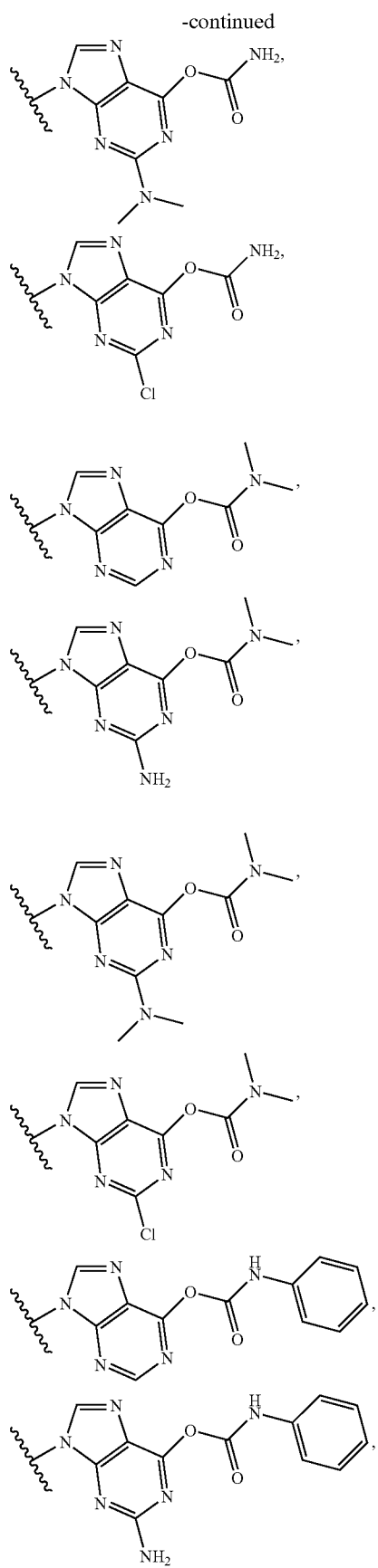
134
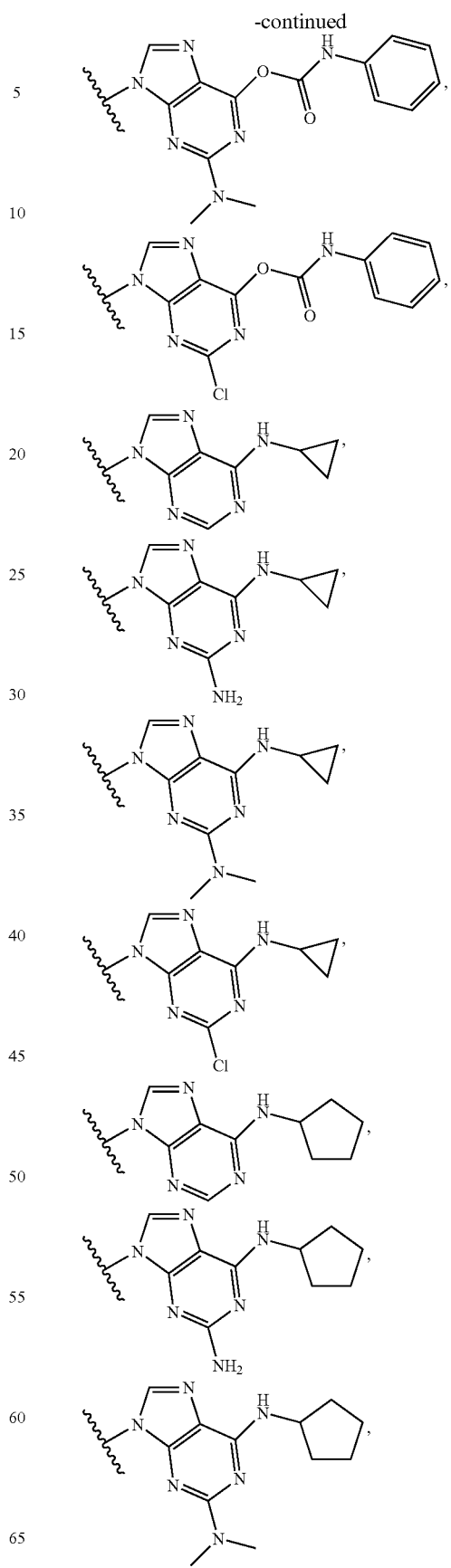

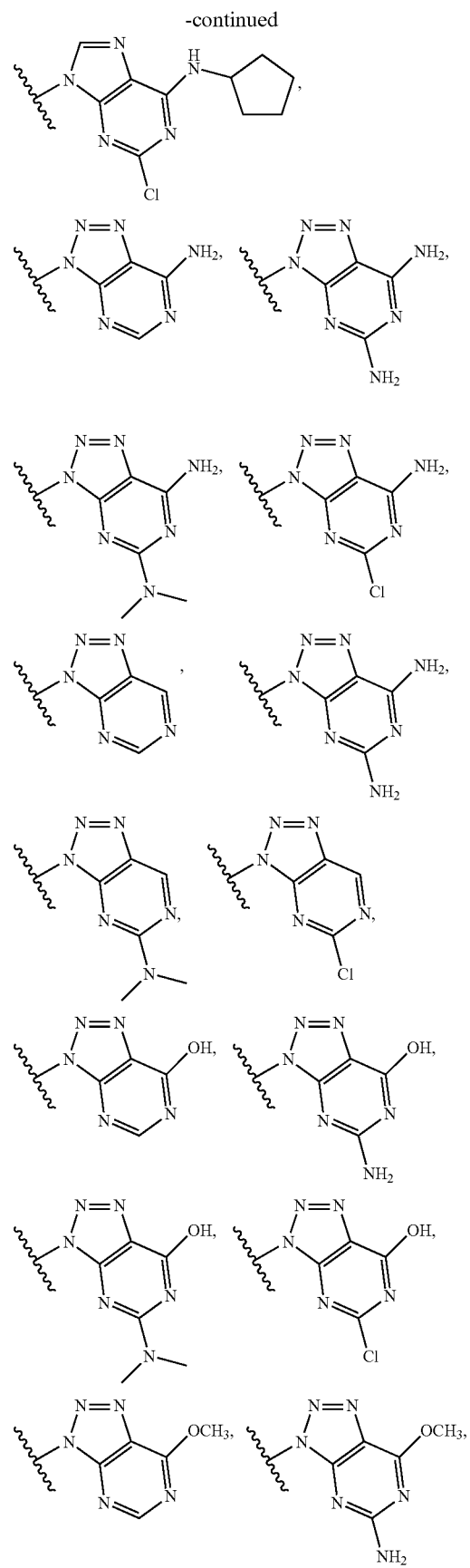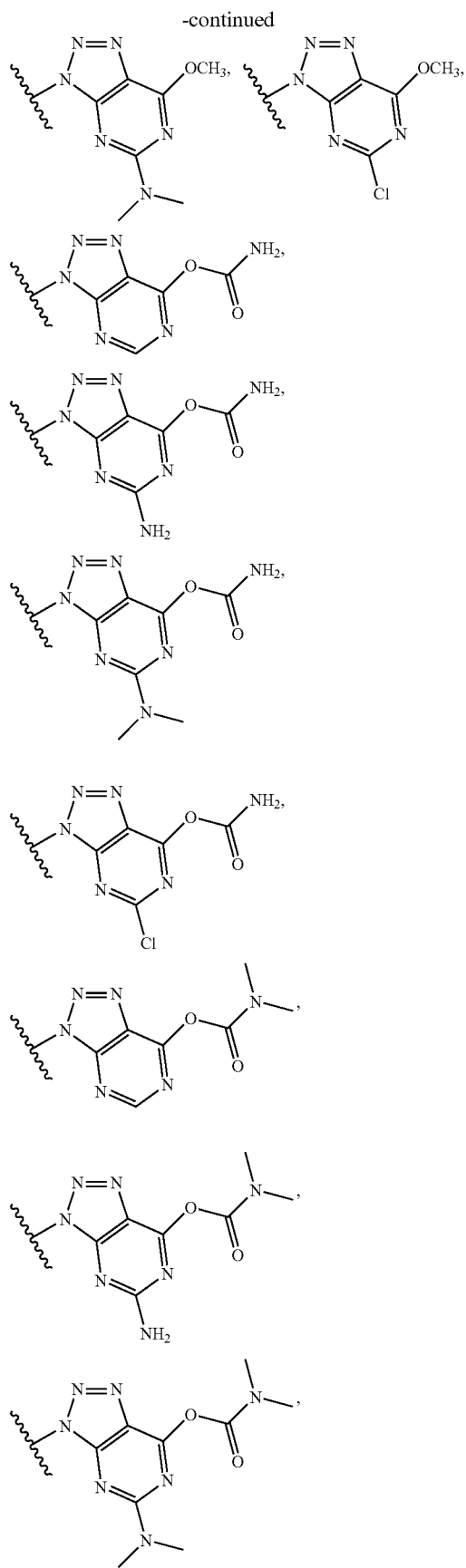

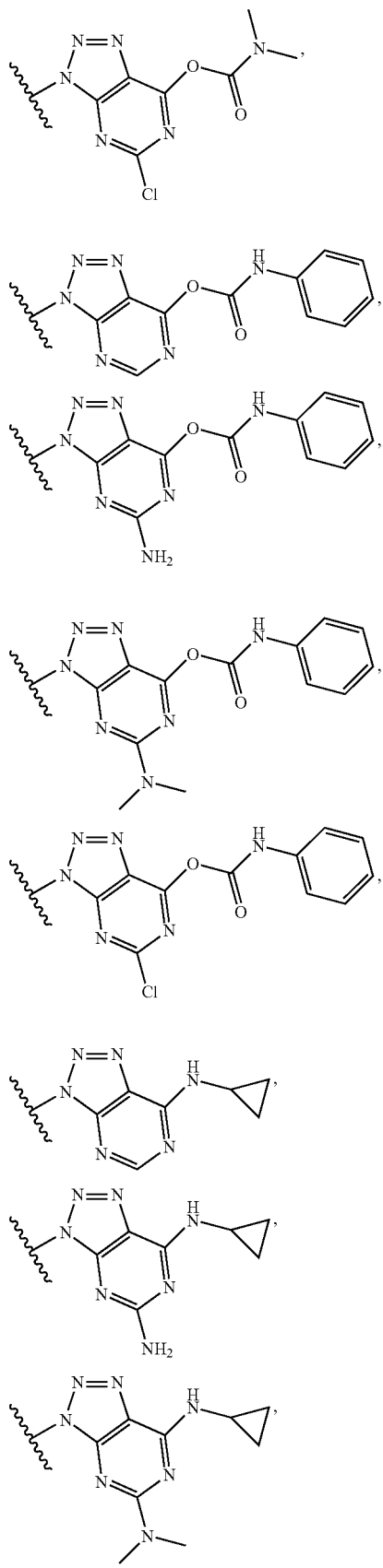
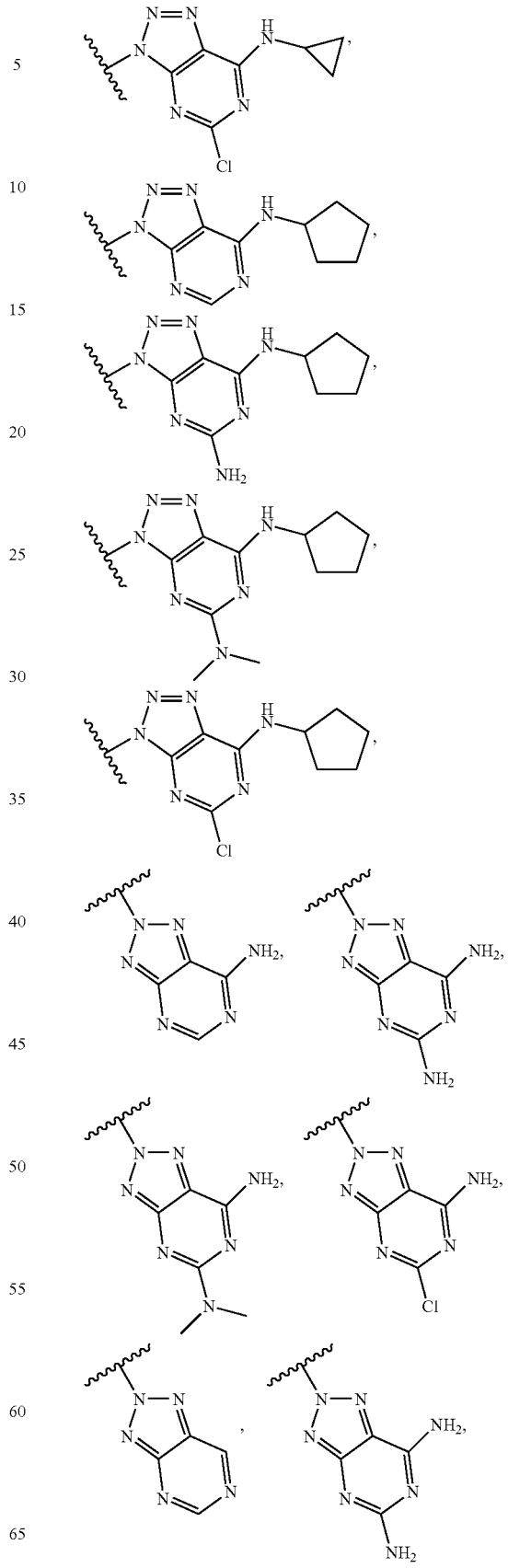

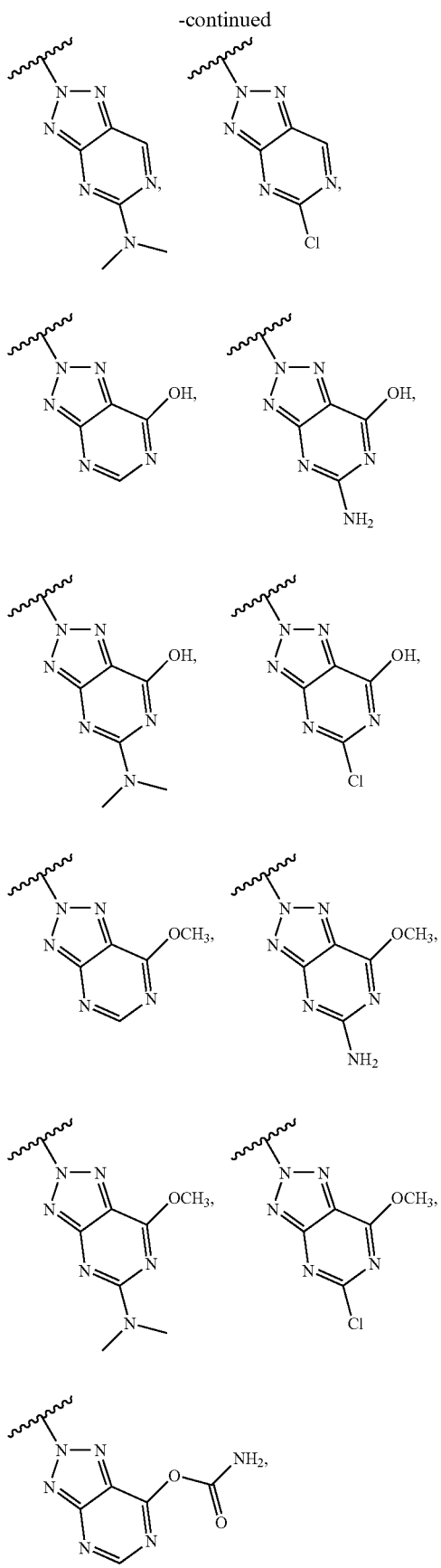

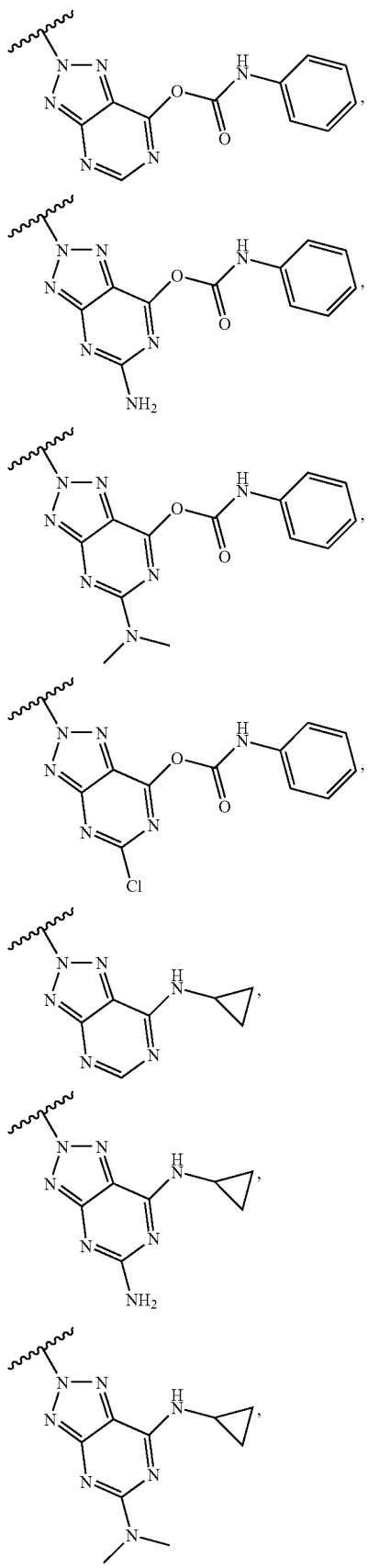

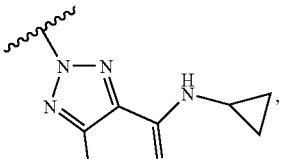

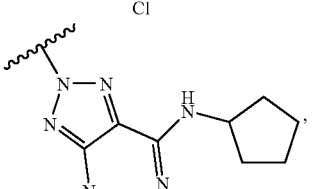

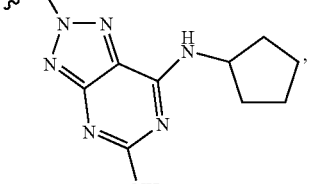

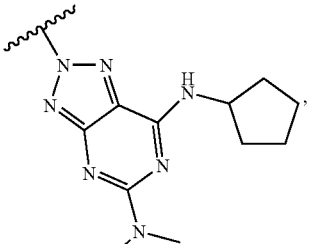

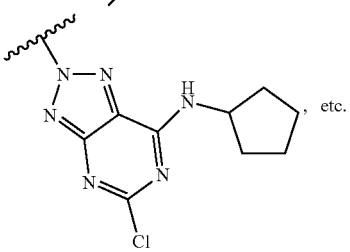

, etc.

In still another embodiment, the compounds of Formula I, Formula II, Formula III, or Formula IV are named below in tabular format (Table 6) as compounds of general Formula V:

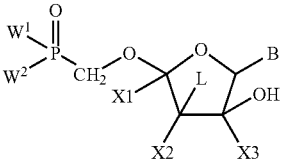

Formula V wherein X1, X2, X3, and L represent substituents attached to the tetrahydrofuranyl ring as defined in Tables 1-4, below; B is a purine defined in Table 5, below; and each $W^1$ and $W^2$ are as previously defined above.

The point of attachment of the core structure C is indicated in each of the structures of X1, X2, X3, L and B. Each structure in Tables 1-5 is represented by an alphanumeric "code". Each structure of a compound of Formula V can thus be designated in tabular form by combining the "code" representing each structural moiety using the following syntax: X1.X2.X3.L.B. Thus, for example, X1a.X2c.X3a.L1.B1 represents the following structure:

TABLE 1

X1 Structures

| Code | Structure |
|---|---|
| X1a | ethylenyl |
| X1b | alkenyl or substituted alkenyl |
| X1c | alkynyl or substituted alkynyl |
| X1d | ethynyl |

TABLE 2

X2 Structures

| Code | Structure |
|---|---|
| X2a | H |
| X2b | OH |
| X2c | halo |

TABLE 3

X3 Structures

| Code | Structure |
|---|---|
| X3a | H |
| X3b | —CH$_2$R$^9$ |
| X3c | alkenyl or substituted alkenyl |

TABLE 4

L Structures

| Code | Structure |
|---|---|
| L1 | H |
| L2 | alkenyl or substituted alkenyl |
| L3 | —CH$_2$R$^9$ |

TABLE 5

B Structures

| Code | Structure |
|---|---|
| B1 | 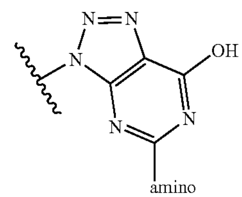 |
| B2 | 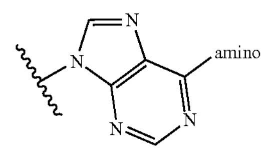 |
| B3 | 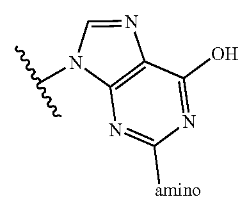 |
| B4 | 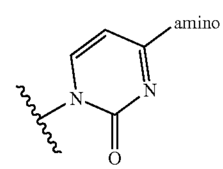 |

TABLE 6

List of Compounds of Formula V

X1a.X2a.X3a.L1.B1, X1a.X2a.X3a.L1.B2, X1a.X2a.X3a.L1.B3, X1a.X2a.X3a.L1.B4,
X1a.X2a.X3a.L2.B1, X1a.X2a.X3a.L2.B2, X1a.X2a.X3a.L2.B3, X1a.X2a.X3a.L2.B4,
X1a.X2a.X3a.L3.B1, X1a.X2a.X3a.L3.B2, X1a.X2a.X3a.L3.B3, X1a.X2a.X3a.L3.B4,
X1a.X2a.X3b.L1.B1, X1a.X2a.X3b.L1.B2, X1a.X2a.X3b.L1.B3, X1a.X2a.X3b.L1.B4,
X1a.X2a.X3b.L2.B1, X1a.X2a.X3b.L2.B2, X1a.X2a.X3b.L2.B3, X1a.X2a.X3b.L2.B4,
X1a.X2a.X3b.L3.B1, X1a.X2a.X3b.L3.B2, X1a.X2a.X3b.L3.B3, X1a.X2a.X3b.L3.B4,
X1a.X2a.X3c.L1.B1, X1a.X2a.X3c.L1.B2, X1a.X2a.X3c.L1.B3, X1a.X2a.X3c.L1.B4,
X1a.X2a.X3c.L2.B1, X1a.X2a.X3c.L2.B2, X1a.X2a.X3c.L2.B3, X1a.X2a.X3c.L2.B4,
X1a.X2a.X3c.L3.B1, X1a.X2a.X3c.L3.B2, X1a.X2a.X3c.L3.B3, X1a.X2a.X3c.L3.B4,
X1a.X2b.X3a.L1.B1, X1a.X2b.X3a.L1.B2, X1a.X2b.X3a.L1.B3, X1a.X2b.X3a.L1.B4,
X1a.X2b.X3a.L2.B1, X1a.X2b.X3a.L2.B2, X1a.X2b.X3a.L2.B3, X1a.X2b.X3a.L2.B4,
X1a.X2b.X3a.L3.B1, X1a.X2b.X3a.L3.B2, X1a.X2b.X3a.L3.B3, X1a.X2b.X3a.L3.B4,
X1a.X2b.X3b.L1.B1, X1a.X2b.X3b.L1.B2, X1a.X2b.X3b.L1.B3, X1a.X2b.X3b.L1.B4,
X1a.X2b.X3b.L2.B1, X1a.X2b.X3b.L2.B2, X1a.X2b.X3b.L2.B3, X1a.X2b.X3b.L2.B4,
X1a.X2b.X3b.L3.B1, X1a.X2b.X3b.L3.B2, X1a.X2b.X3b.L3.B3, X1a.X2b.X3b.L3.B4,
X1a.X2b.X3c.L1.B1, X1a.X2b.X3c.L1.B2, X1a.X2b.X3c.L1.B3, X1a.X2b.X3c.L1.B4,
X1a.X2b.X3c.L2.B1, X1a.X2b.X3c.L2.B2, X1a.X2b.X3c.L2.B3, X1a.X2b.X3c.L2.B4,

TABLE 6-continued

List of Compounds of Formula V

X1a.X2b.X3c.L3.B1, X1a.X2b.X3c.L3.B2, X1a.X2b.X3c.L3.B3, X1a.X2b.X3c.L3.B4,
X1a.X2c.X3a.L1.B1, X1a.X2c.X3a.L1.B2, X1a.X2c.X3a.L1.B3, X1a.X2c.X3a.L1.B4,
X1a.X2c.X3a.L2.B1, X1a.X2c.X3a.L2.B2, X1a.X2c.X3a.L2.B3, X1a.X2c.X3a.L2.B4,
X1a.X2c.X3a.L3.B1, X1a.X2c.X3a.L3.B2, X1a.X2c.X3a.L3.B3, X1a.X2c.X3a.L3.B4,
X1a.X2c.X3b.L1.B1, X1a.X2c.X3b.L1.B2, X1a.X2c.X3b.L1.B3, X1a.X2c.X3b.L1.B4,
X1a.X2c.X3b.L2.B1, X1a.X2c.X3b.L2.B2, X1a.X2c.X3b.L2.B3, X1a.X2c.X3b.L2.B4,
X1a.X2c.X3b.L3.B1, X1a.X2c.X3b.L3.B2, X1a.X2c.X3b.L3.B3, X1a.X2c.X3b.L3.B4,
X1a.X2c.X3c.L1.B1, X1a.X2c.X3c.L1.B2, X1a.X2c.X3c.L1.B3, X1a.X2c.X3c.L1.B4,
X1a.X2c.X3c.L2.B1, X1a.X2c.X3c.L2.B2, X1a.X2c.X3c.L2.B3, X1a.X2c.X3c.L2.B4,
X1a.X2c.X3c.L3.B1, X1a.X2c.X3c.L3.B2, X1a.X2c.X3c.L3.B3, X1a.X2c.X3c.L3.B4,
X1b.X2a.X3a.L1.B1, X1b.X2a.X3a.L1.B2, X1b.X2a.X3a.L1.B3, X1b.X2a.X3a.L1.B4,
X1b.X2a.X3a.L2.B1, X1b.X2a.X3a.L2.B2, X1b.X2a.X3a.L2.B3, X1b.X2a.X3a.L2.B4,
X1b.X2a.X3a.L3.B1, X1b.X2a.X3a.L3.B2, X1b.X2a.X3a.L3.B3, X1b.X2a.X3a.L3.B4,
X1b.X2a.X3b.L1.B1, X1b.X2a.X3b.L1.B2, X1b.X2a.X3b.L1.B3, X1b.X2a.X3b.L1.B4,
X1b.X2a.X3b.L2.B1, X1b.X2a.X3b.L2.B2, X1b.X2a.X3b.L2.B3, X1b.X2a.X3b.L2.B4,
X1b.X2a.X3b.L3.B1, X1b.X2a.X3b.L3.B2, X1b.X2a.X3b.L3.B3, X1b.X2a.X3b.L3.B4,
X1b.X2a.X3c.L1.B1, X1b.X2a.X3c.L1.B2, X1b.X2a.X3c.L1.B3, X1b.X2a.X3c.L1.B4,
X1b.X2a.X3c.L2.B1, X1b.X2a.X3c.L2.B2, X1b.X2a.X3c.L2.B3, X1b.X2a.X3c.L2.B4,
X1b.X2a.X3c.L3.B1, X1b.X2a.X3c.L3.B2, X1b.X2a.X3c.L3.B3, X1b.X2a.X3c.L3.B4,
X1b.X2b.X3a.L1.B1, X1b.X2b.X3a.L1.B2, X1b.X2b.X3a.L1.B3, X1b.X2b.X3a.L1.B4,
X1b.X2b.X3a.L2.B1, X1b.X2b.X3a.L2.B2, X1b.X2b.X3a.L2.B3, X1b.X2b.X3a.L2.B4,
X1b.X2b.X3a.L3.B1, X1b.X2b.X3a.L3.B2, X1b.X2b.X3a.L3.B3, X1b.X2b.X3a.L3.B4,
X1b.X2b.X3b.L1.B1, X1b.X2b.X3b.L1.B2, X1b.X2b.X3b.L1.B3, X1b.X2b.X3b.L1.B4,
X1b.X2b.X3b.L2.B1, X1b.X2b.X3b.L2.B2, X1b.X2b.X3b.L2.B3, X1b.X2b.X3b.L2.B4,
X1b.X2b.X3b.L3.B1, X1b.X2b.X3b.L3.B2, X1b.X2b.X3b.L3.B3, X1b.X2b.X3b.L3.B4,
X1b.X2b.X3c.L1.B1, X1b.X2b.X3c.L1.B2, X1b.X2b.X3c.L1.B3, X1b.X2b.X3c.L1.B4,
X1b.X2b.X3c.L2.B1, X1b.X2b.X3c.L2.B2, X1b.X2b.X3c.L2.B3, X1b.X2b.X3c.L2.B4,
X1b.X2b.X3c.L3.B1, X1b.X2b.X3c.L3.B2, X1b.X2b.X3c.L3.B3, X1b.X2b.X3c.L3.B4,
X1b.X2c.X3a.L1.B1, X1b.X2c.X3a.L1.B2, X1b.X2c.X3a.L1.B3, X1b.X2c.X3a.L1.B4,
X1b.X2c.X3a.L2.B1, X1b.X2c.X3a.L2.B2, X1b.X2c.X3a.L2.B3, X1b.X2c.X3a.L2.B4,
X1b.X2c.X3a.L3.B1, X1b.X2c.X3a.L3.B2, X1b.X2c.X3a.L3.B3, X1b.X2c.X3a.L3.B4,
X1b.X2c.X3b.L1.B1, X1b.X2c.X3b.L1.B2, X1b.X2c.X3b.L1.B3, X1b.X2c.X3b.L1.B4,
X1b.X2c.X3b.L2.B1, X1b.X2c.X3b.L2.B2, X1b.X2c.X3b.L2.B3, X1b.X2c.X3b.L2.B4,
X1b.X2c.X3b.L3.B1, X1b.X2c.X3b.L3.B2, X1b.X2c.X3b.L3.B3, X1b.X2c.X3b.L3.B4,
X1b.X2c.X3c.L1.B1, X1b.X2c.X3c.L1.B2, X1b.X2c.X3c.L1.B3, X1b.X2c.X3c.L1.B4,
X1b.X2c.X3c.L2.B1, X1b.X2c.X3c.L2.B2, X1b.X2c.X3c.L2.B3, X1b.X2c.X3c.L2.B4,
X1b.X2c.X3c.L3.B1, X1b.X2c.X3c.L3.B2, X1b.X2c.X3c.L3.B3, X1b.X2c.X3c.L3.B4,
X1c.X2a.X3a.L1.B1, X1c.X2a.X3a.L1.B2, X1c.X2a.X3a.L1.B3, X1c.X2a.X3a.L1.B4,
X1c.X2a.X3a.L2.B1, X1c.X2a.X3a.L2.B2, X1c.X2a.X3a.L2.B3, X1c.X2a.X3a.L2.B4,
X1c.X2a.X3a.L3.B1, X1c.X2a.X3a.L3.B2, X1c.X2a.X3a.L3.B3, X1c.X2a.X3a.L3.B4,
X1c.X2a.X3b.L1.B1, X1c.X2a.X3b.L1.B2, X1c.X2a.X3b.L1.B3, X1c.X2a.X3b.L1.B4,
X1c.X2a.X3b.L2.B1, X1c.X2a.X3b.L2.B2, X1c.X2a.X3b.L2.B3, X1c.X2a.X3b.L2.B4,
X1c.X2a.X3b.L3.B1, X1c.X2a.X3b.L3.B2, X1c.X2a.X3b.L3.B3, X1c.X2a.X3b.L3.B4,
X1c.X2a.X3c.L1.B1, X1c.X2a.X3c.L1.B2, X1c.X2a.X3c.L1.B3, X1c.X2a.X3c.L1.B4,
X1c.X2a.X3c.L2.B1, X1c.X2a.X3c.L2.B2, X1c.X2a.X3c.L2.B3, X1c.X2a.X3c.L2.B4,
X1c.X2a.X3c.L3.B1, X1c.X2a.X3c.L3.B2, X1c.X2a.X3c.L3.B3, X1c.X2a.X3c.L3.B4,
X1c.X2b.X3a.L1.B1, X1c.X2b.X3a.L1.B2, X1c.X2b.X3a.L1.B3, X1c.X2b.X3a.L1.B4,
X1c.X2b.X3a.L2.B1, X1c.X2b.X3a.L2.B2, X1c.X2b.X3a.L2.B3, X1c.X2b.X3a.L2.B4,
X1c.X2b.X3a.L3.B1, X1c.X2b.X3a.L3.B2, X1c.X2b.X3a.L3.B3, X1c.X2b.X3a.L3.B4,
X1c.X2b.X3b.L1.B1, X1c.X2b.X3b.L1.B2, X1c.X2b.X3b.L1.B3, X1c.X2b.X3b.L1.B4,
X1c.X2b.X3b.L2.B1, X1c.X2b.X3b.L2.B2, X1c.X2b.X3b.L2.B3, X1c.X2b.X3b.L2.B4,
X1c.X2b.X3b.L3.B1, X1c.X2b.X3b.L3.B2, X1c.X2b.X3b.L3.B3, X1c.X2b.X3b.L3.B4,
X1c.X2b.X3c.L1.B1, X1c.X2b.X3c.L1.B2, X1c.X2b.X3c.L1.B3, X1c.X2b.X3c.L1.B4,
X1c.X2b.X3c.L2.B1, X1c.X2b.X3c.L2.B2, X1c.X2b.X3c.L2.B3, X1c.X2b.X3c.L2.B4,
X1c.X2b.X3c.L3.B1, X1c.X2b.X3c.L3.B2, X1c.X2b.X3c.L3.B3, X1c.X2b.X3c.L3.B4,
X1c.X2c.X3a.L1.B1, X1c.X2c.X3a.L1.B2, X1c.X2c.X3a.L1.B3, X1c.X2c.X3a.L1.B4,
X1c.X2c.X3a.L2.B1, X1c.X2c.X3a.L2.B2, X1c.X2c.X3a.L2.B3, X1c.X2c.X3a.L2.B4,
X1c.X2c.X3a.L3.B1, X1c.X2c.X3a.L3.B2, X1c.X2c.X3a.L3.B3, X1c.X2c.X3a.L3.B4,
X1c.X2c.X3b.L1.B1, X1c.X2c.X3b.L1.B2, X1c.X2c.X3b.L1.B3, X1c.X2c.X3b.L1.B4,
X1c.X2c.X3b.L2.B1, X1c.X2c.X3b.L2.B2, X1c.X2c.X3b.L2.B3, X1c.X2c.X3b.L2.B4,
X1c.X2c.X3b.L3.B1, X1c.X2c.X3b.L3.B2, X1c.X2c.X3b.L3.B3, X1c.X2c.X3b.L3.B4,
X1c.X2c.X3c.L1.B1, X1c.X2c.X3c.L1.B2, X1c.X2c.X3c.L1.B3, X1c.X2c.X3c.L1.B4,
X1c.X2c.X3c.L2.B1, X1c.X2c.X3c.L2.B2, X1c.X2c.X3c.L2.B3, X1c.X2c.X3c.L2.B4,
X1c.X2c.X3c.L3.B1, X1c.X2c.X3c.L3.B2, X1c.X2c.X3c.L3.B3, X1c.X2c.X3c.L3.B4,

Phosphonate Embodiments of Compounds of Formula I-IV

By way of example and not limitation, the phosphonate embodiments of Formula I-IV may be represented by the general formula "MBF":

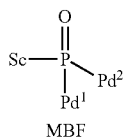

MBF

Each embodiment of MBF is depicted as a substituted nucleus (Sc). Sc is described in formulae A-G of Table 1.1 below, wherein Sc is a generic formula for a compound of Formula I, Formula II, Formula III, or Formula IV, and the point of attachment to —P(O)Pd$^1$Pd$^2$ is indicated with a wavy line.

TABLE 1.1

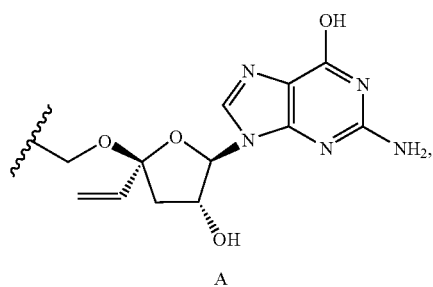

A

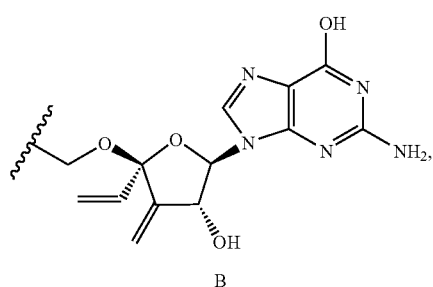

B

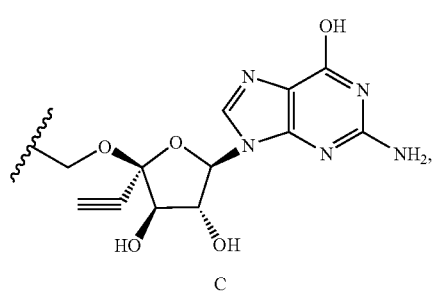

C

TABLE 1.1-continued

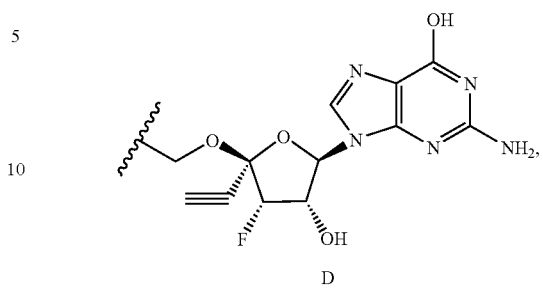

D

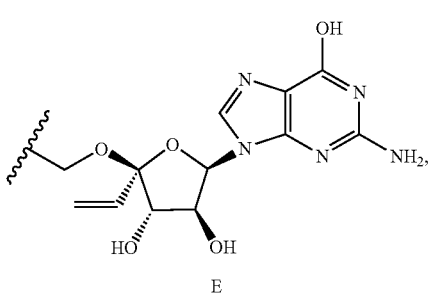

E

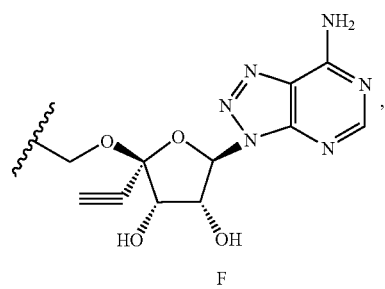

F

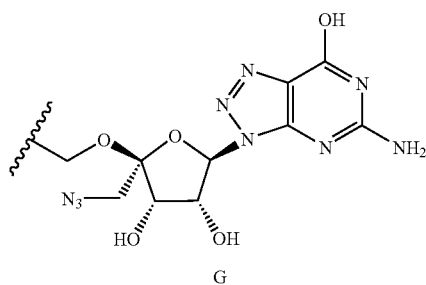

G

Pd$^1$ and Pd$^2$ are each independently selected from species in Tables 20.1 to 20.37. The variables used in Tables 20.1-20.37 (e.g., W$^3$, R$^1$, etc.) pertain only to Tables 20.1-20.37, unless otherwise indicated. Additional phosphonate groups are disclosed in U.S. patent publication No. 2004/100960, the entirety of which is incorporated herein by reference.

The variables used in Tables 20.1 to 20.37 have the following definitions:

R$^1$ is independently H or alkyl of 1 to 18 carbon atoms;

R$^2$ is independently H, R$^1$, R$^3$ or R$^4$ wherein each R$^4$ is independently substituted with 0 to 3 R$^3$ groups or taken together at a carbon atom, two R$^2$ groups form a ring of 3 to 8 carbons and the ring may be substituted with 0 to 3 R$^3$ groups;

R$^3$ is R$^{3a}$, R$^{3b}$, R$^{3c}$ or R$^{3d}$, provided that when R$^3$ is bound to a heteroatom, then R$^3$ is R$^{3c}$ or R$^{3d}$;

R$^{3a}$ is F, Cl, Br, I, —CN, N$_3$ or —NO$_2$;

R$^{3b}$ is Y$^1$;

$R^{3c}$ is —$R^x$, —$N(R^x)(R^x)$, —$SR^x$, —$S(O)R^x$, —$S(O)_2R^x$, —$S(O)(OR^x)$, —$S(O)_2(OR^x)$, —$OC(Y^1)R^x$, —$OC(Y^1)OR^x$, —$OC(Y^1)(N(R^x)(R^x))$, —$SC(Y^1)R^x$, —$SC(Y^1)OR^x$, —$SC(Y^1)(N(R^x)(R^x))$, —$N(R^x)C(Y^1)R^x$, —$N(R^x)C(Y^1)OR^x$, or —$N(R^x)C(Y^1)(N(R^x)(R^x))$;

$R^{3d}$ is —$C(Y^1)R^x$, —$C(Y^1)OR^x$ or —$C(Y^1)(N(R^x)(R^x))$;

$R^4$ is an alkyl of 1 to 18 carbon atoms, alkenyl of 2 to 18 carbon atoms, or alkynyl of 2 to 18 carbon atoms;

$R^5$ is $R^4$ wherein each $R^4$ is substituted with 0 to 3 $R^3$ groups;

$R^{5a}$ is independently alkylene of 1 to 18 carbon atoms, alkenylene of 2 to 18 carbon atoms, or alkynylene of 2-18 carbon atoms any one of which alkylene, alkenylene or alkynylene is substituted with 0-3 $R^3$ groups;

$W^3$ is $W^4$ or $W^5$;

$W^4$ is $R^5$, —$C(Y^1)R^5$, —$C(Y^1)W^5$, —$SO_2R^5$, or —$SO_2W^5$;

$W^5$ is carbocycle or heterocycle wherein $W^5$ is independently substituted with 0 to 3 $R^2$ groups;

TABLE 20.1

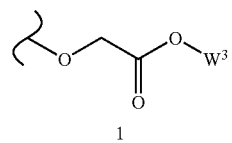

1

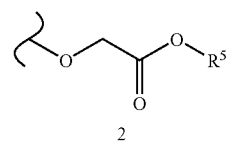

2

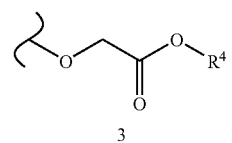

3

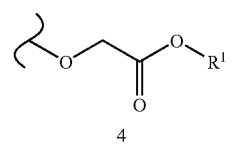

4

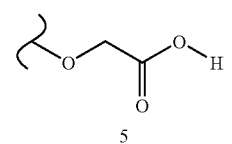

5

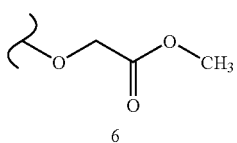

6

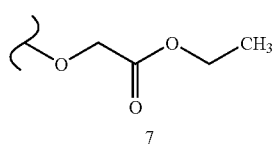

7

TABLE 20.1-continued

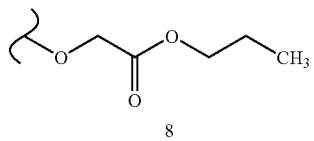

8

TABLE 20.2

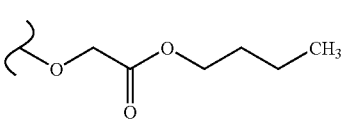

9

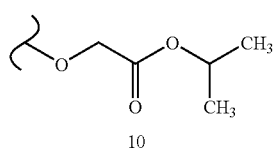

10

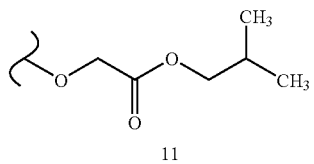

11

TABLE 20.3

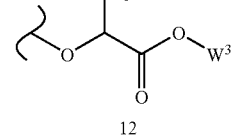

12

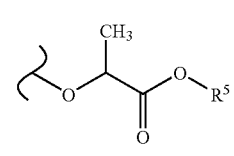

13

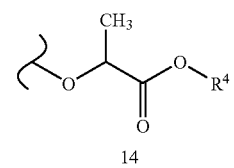

14

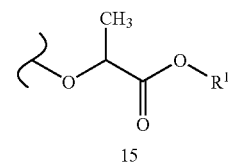

15

TABLE 20.3-continued
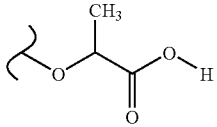
16
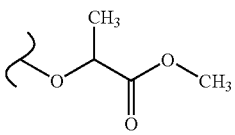
17
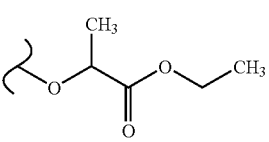
18
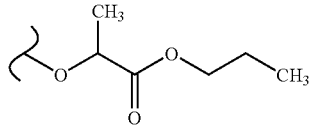
19
TABLE 20.4
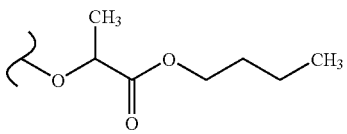
20
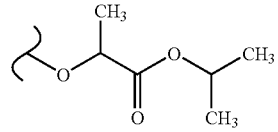
21
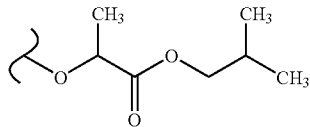
22
TABLE 20.5
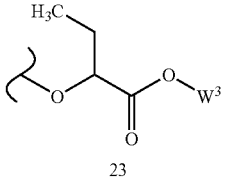
23
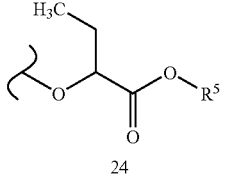
24
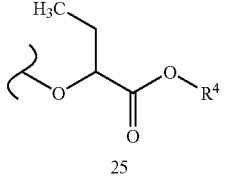
25
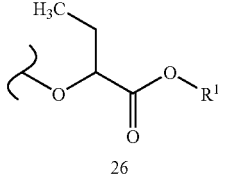
26
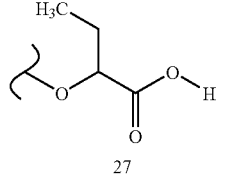
27
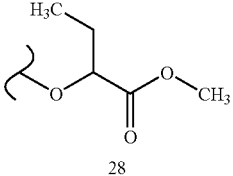
28
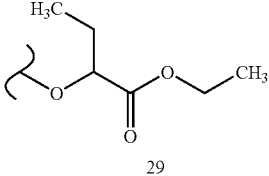
29
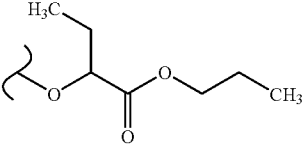
30

TABLE 20.6
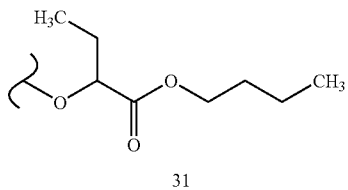
31
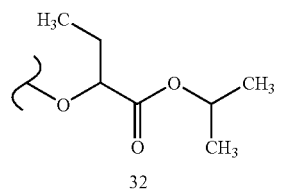
32
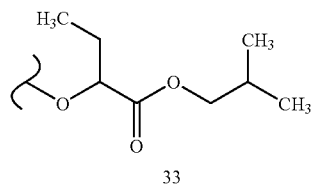
33
TABLE 20.7
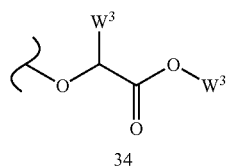
34
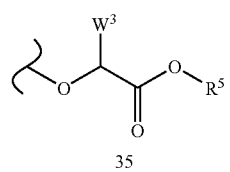
35
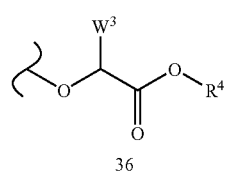
36
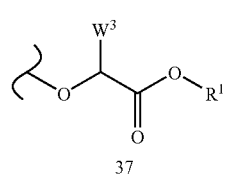
37
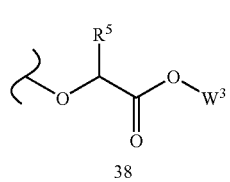
38
TABLE 20.7-continued
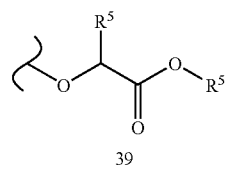
39
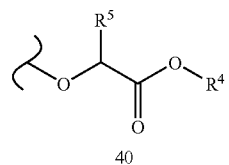
40
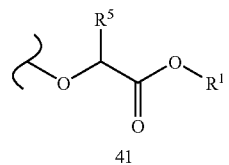
41
TABLE 20.8
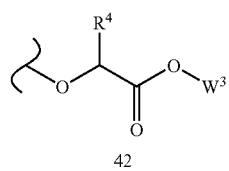
42
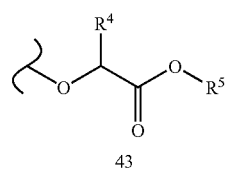
43
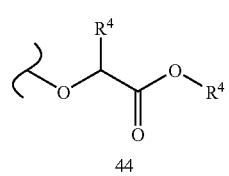
44
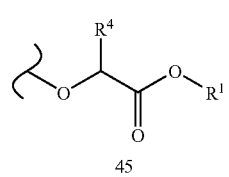
45
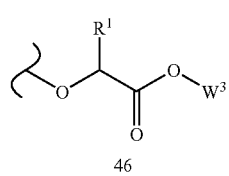
46

TABLE 20.8-continued
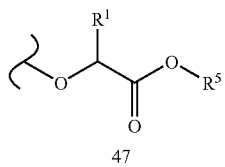
47
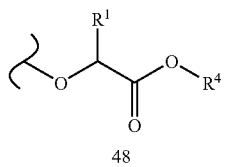
48
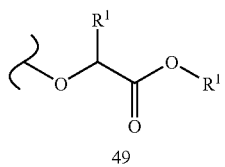
49
TABLE 20.9
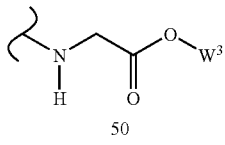
50
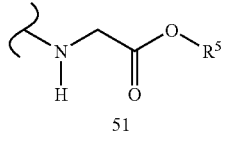
51
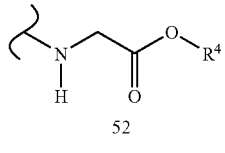
52
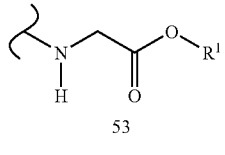
53
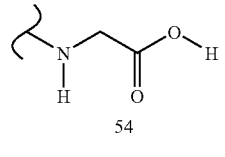
54
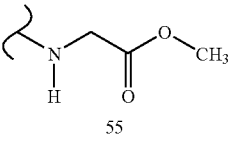
55
TABLE 20.9-continued
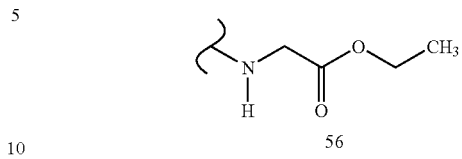
56
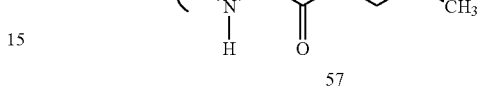
57
TABLE 20.10
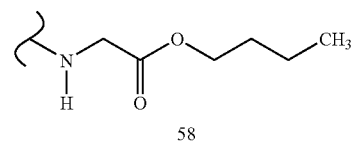
58
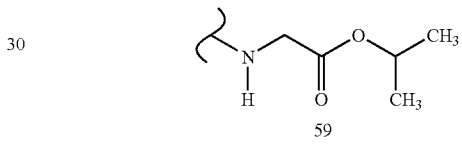
59
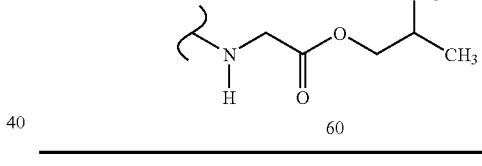
60
TABLE 20.11
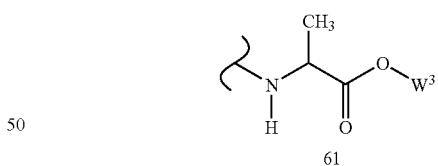
61
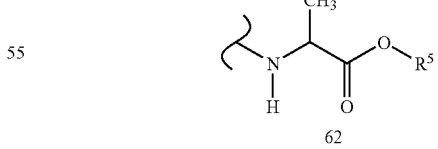
62
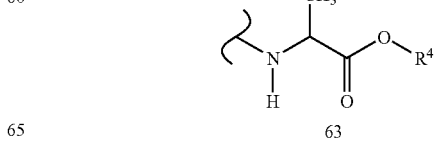
63

TABLE 20.11-continued
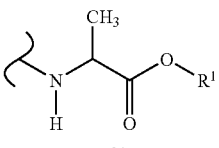
64
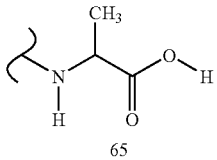
65
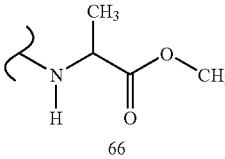
66
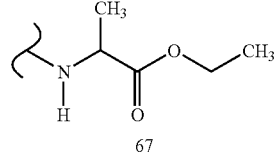
67
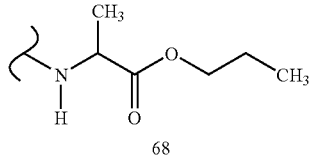
68
TABLE 20.12
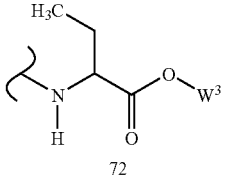
69
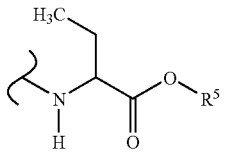
70
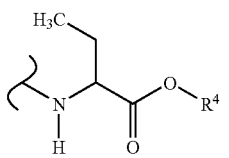
71
TABLE 20.13
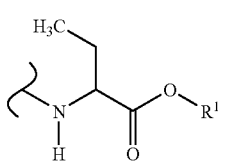
72
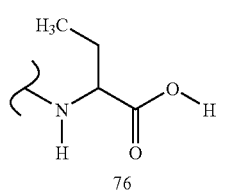
73
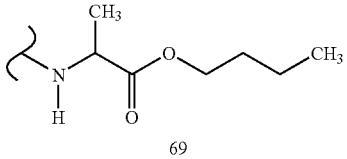
74
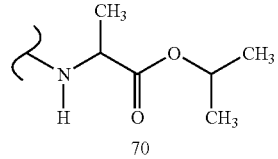
75
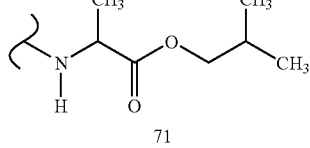
76
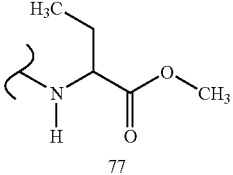
77
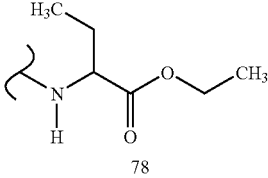
78
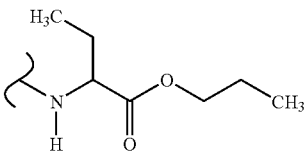
79

TABLE 20.14
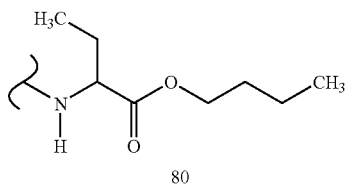
80
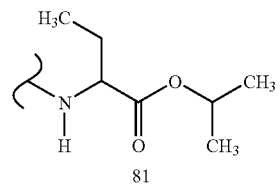
81
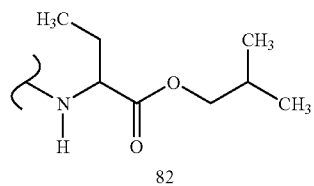
82
TABLE 20.15
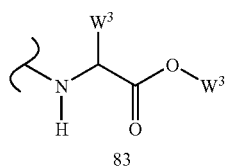
83
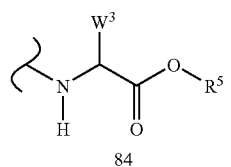
84
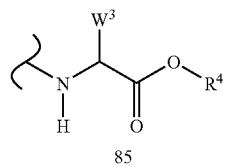
85
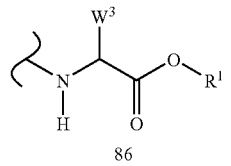
86
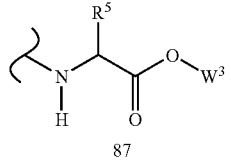
87
TABLE 20.15-continued
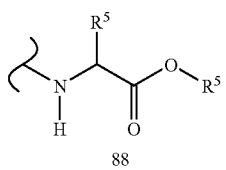
88
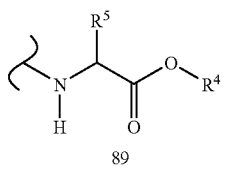
89
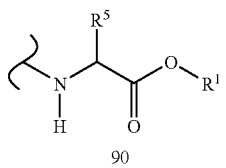
90
TABLE 20.16
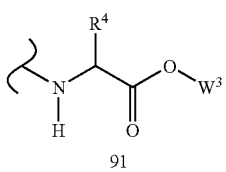
91
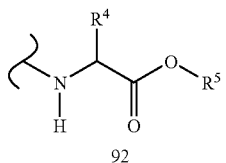
92
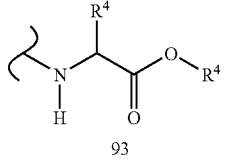
93
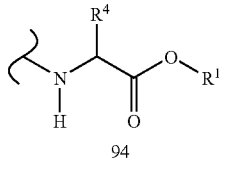
94
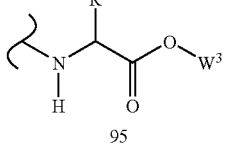
95

TABLE 20.16-continued
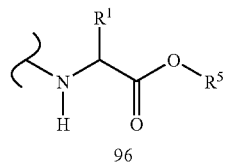
96
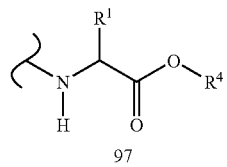
97
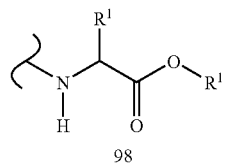
98
TABLE 20.17
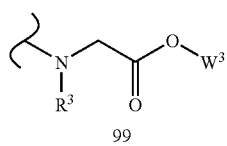
99
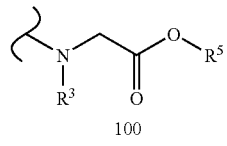
100
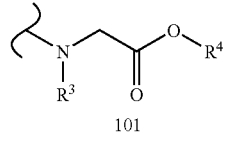
101
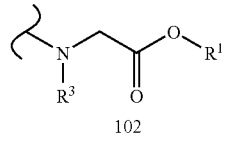
102
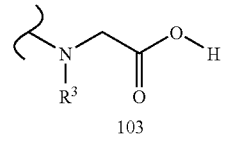
103
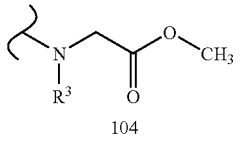
104
TABLE 20.17-continued
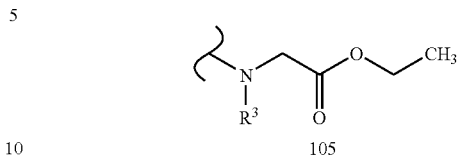
105
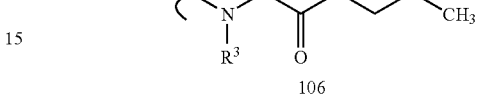
106
TABLE 20.18
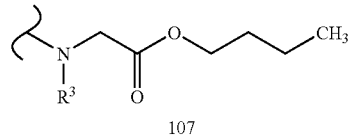
107
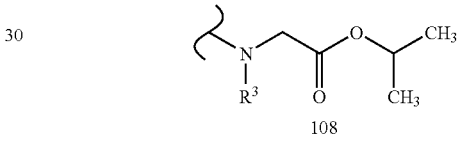
108
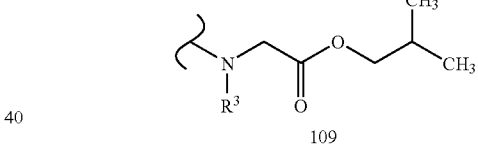
109
TABLE 20.19
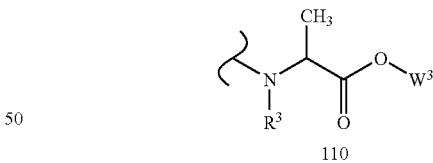
110
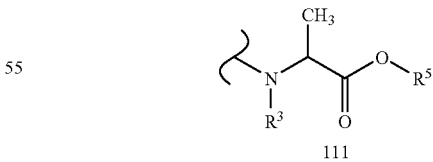
111
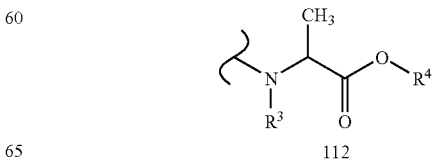
112

TABLE 20.19-continued
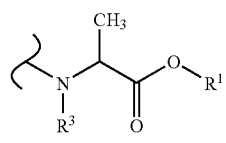
113
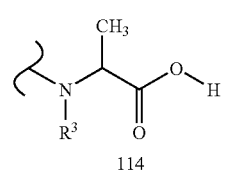
114
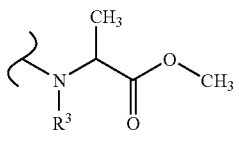
115
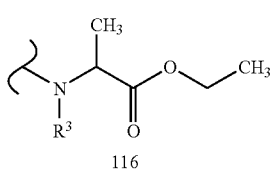
116
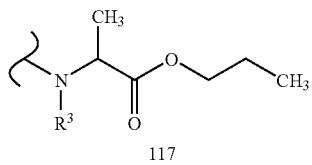
117
TABLE 20.20
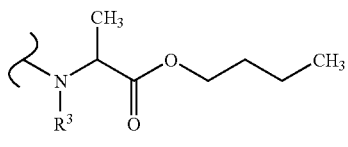
118
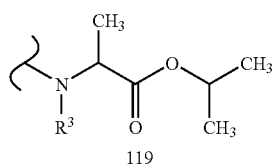
119
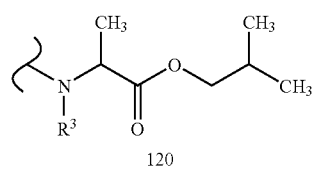
120
TABLE 20.21
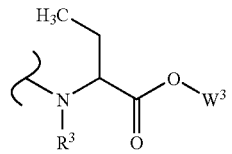
121
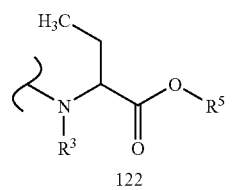
122
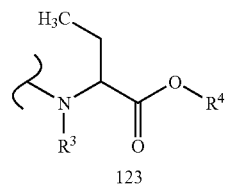
123
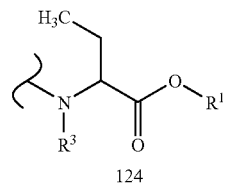
124
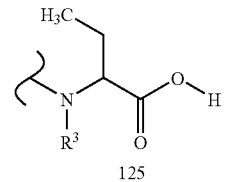
125
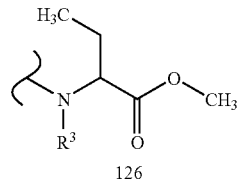
126
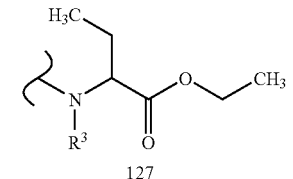
127
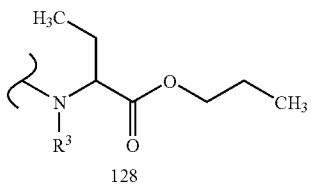
128

TABLE 20.22
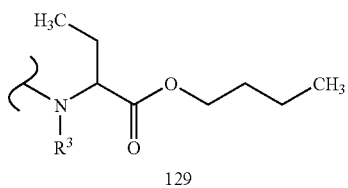
129
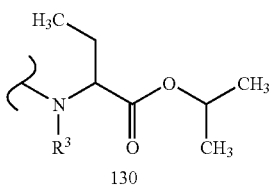
130
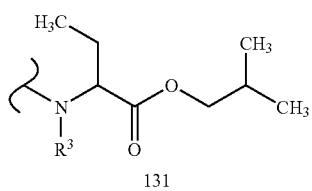
131
TABLE 20.23
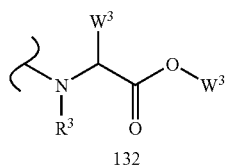
132
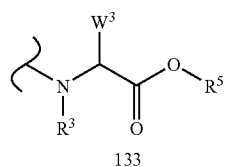
133
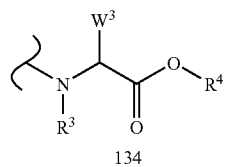
134
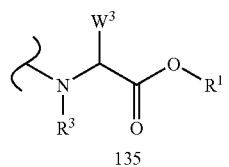
135
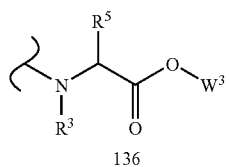
136
TABLE 20.23-continued
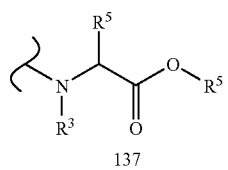
137
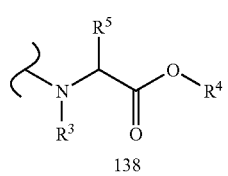
138
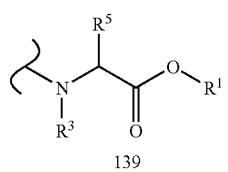
139
TABLE 20.24
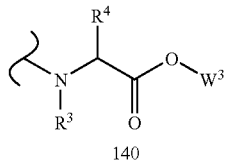
140
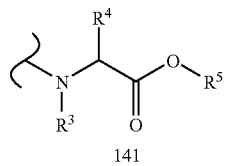
141
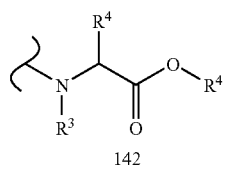
142
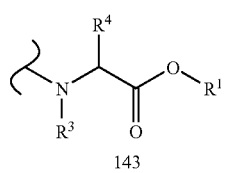
143
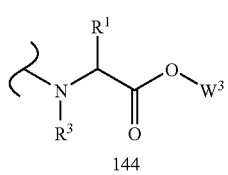
144

TABLE 20.24-continued
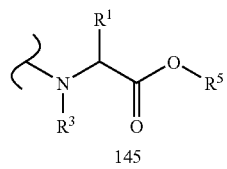
145
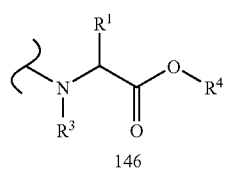
146
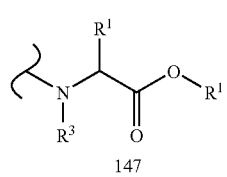
147
TABLE 20.25
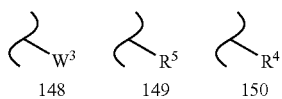
148   149   150
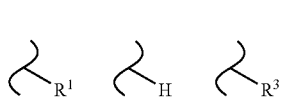
151   152   153
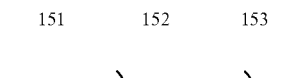
154   155   156
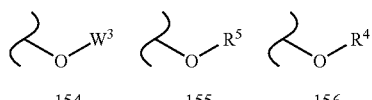
157   158   159
TABLE 20.26
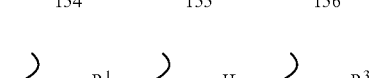
160   161   162
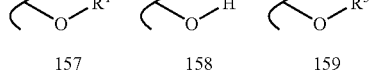
163   164   165
TABLE 20.26-continued
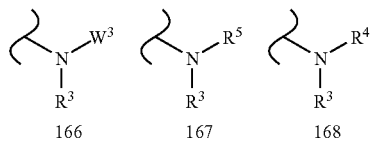
166   167   168
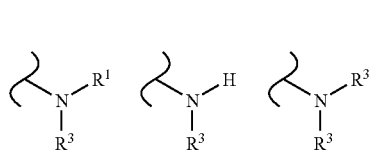
169   170   171
TABLE 20.27
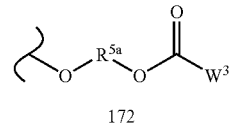
172
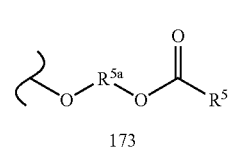
173
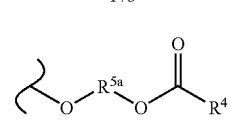
174
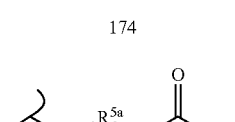
175
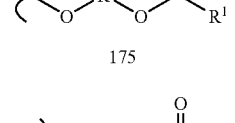
176
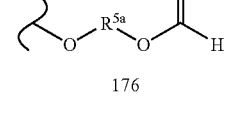
177
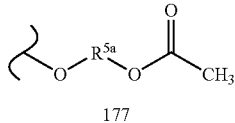
178
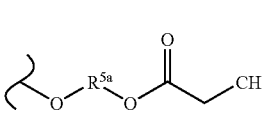
179

TABLE 20.28
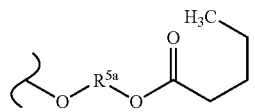
180
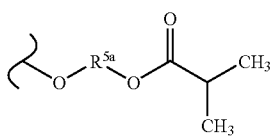
181
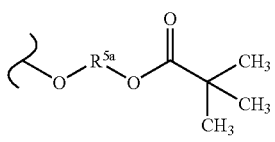
182
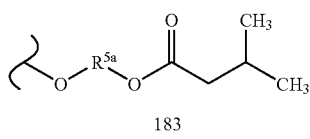
183
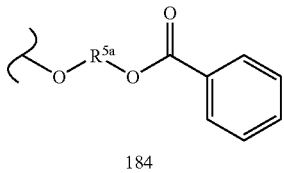
184
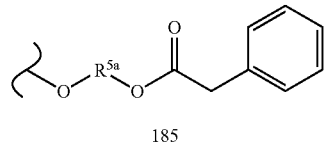
185
TABLE 20.29
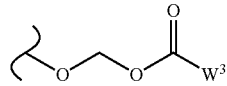
186
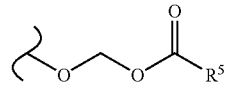
187
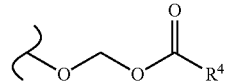
188
TABLE 20.29-continued
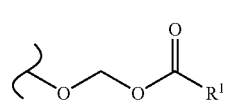
189
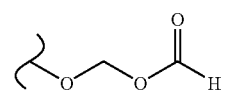
190
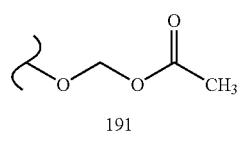
191
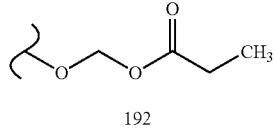
192
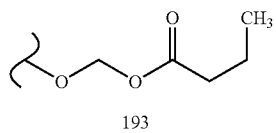
193
TABLE 20.30
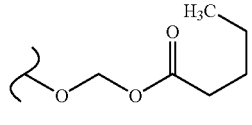
194
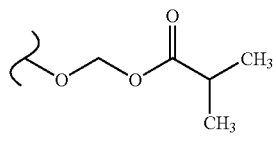
195
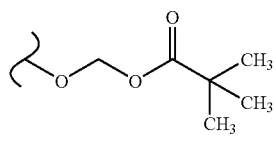
196
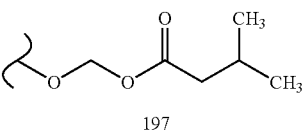
197

TABLE 20.30-continued
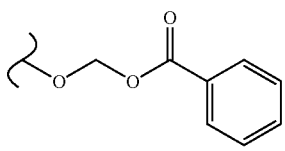
198
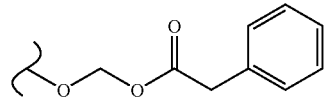
199
TABLE 20.31
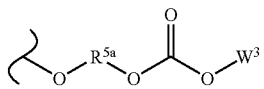
200
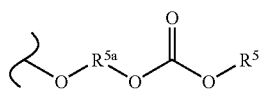
201
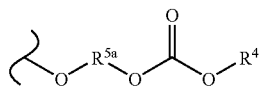
202
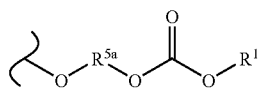
203
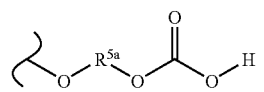
204
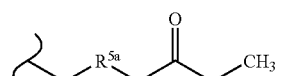
205
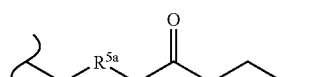
206
TABLE 20.31-continued
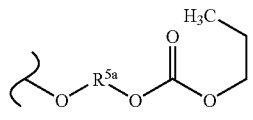
207
TABLE 20.32
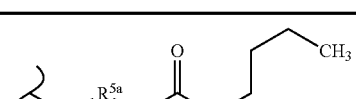
208
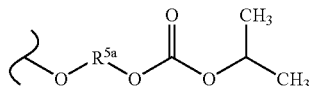
209
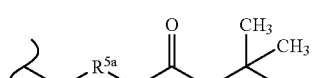
210
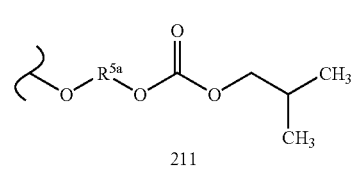
211
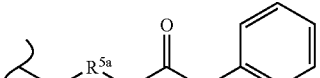
212
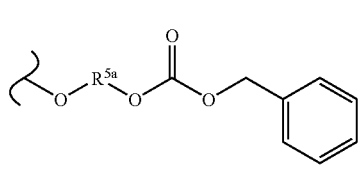
213
TABLE 20.33
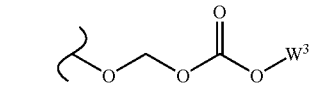
214
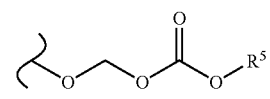
215

TABLE 20.33-continued
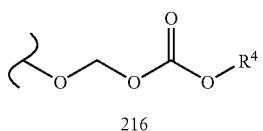
216
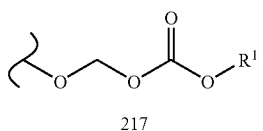
217
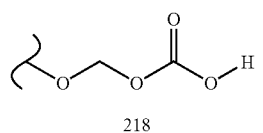
218
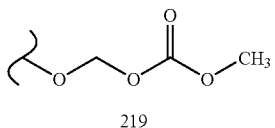
219
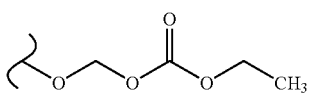
220
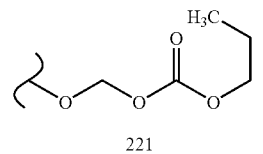
221
TABLE 20.34
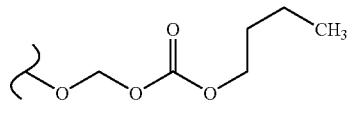
222
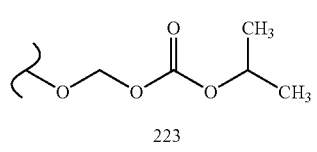
223
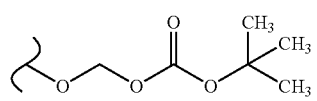
224
TABLE 20.34-continued
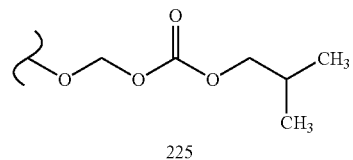
225
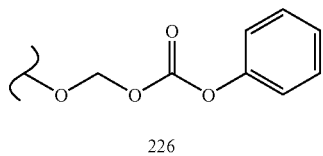
226
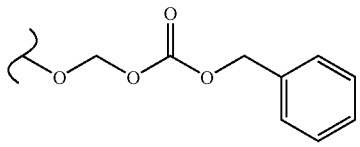
227
TABLE 20.35
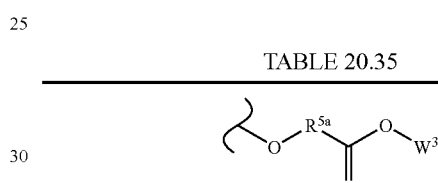
228
229
230
231
232
233

TABLE 20.35-continued
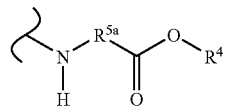
234
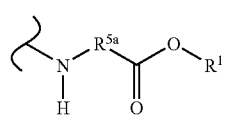
235
TABLE 20.36
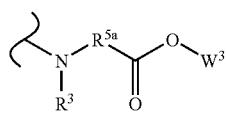
236
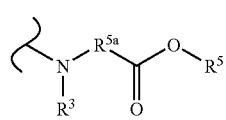
237
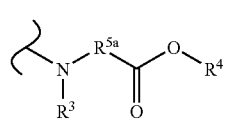
238
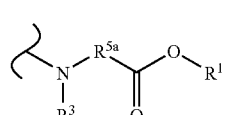
239
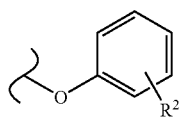
240
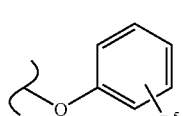
241
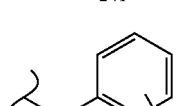
242
TABLE 20.36-continued
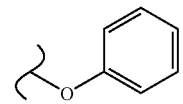
243
TABLE 20.37
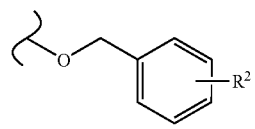
244
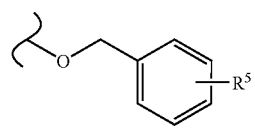
245
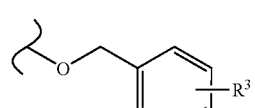
246
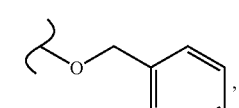
247
Pd$^1$ and Pd$^2$ of the "Sc" structures of Table 1.1 can also be independently selected from Table 30.1, below:
TABLE 30.1
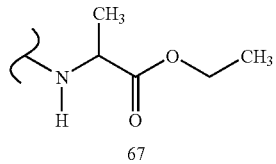
67
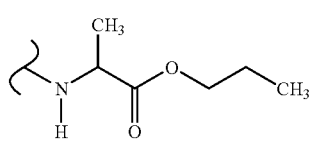
68

TABLE 30.1-continued

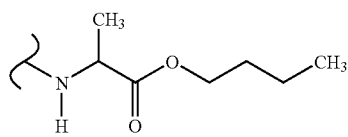
69

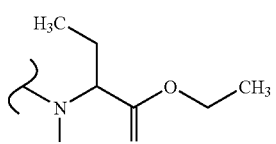
78

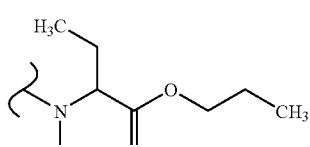
79

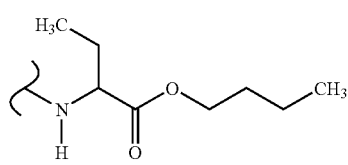
80

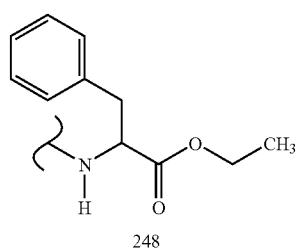
248

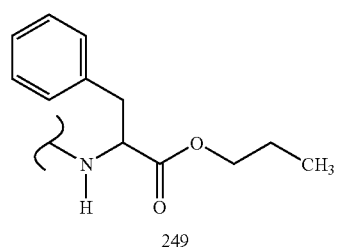
249

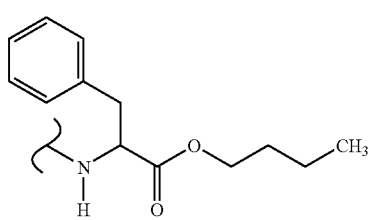
250

TABLE 30.1-continued

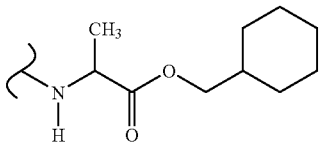
251

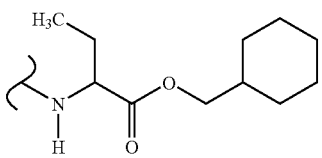
252

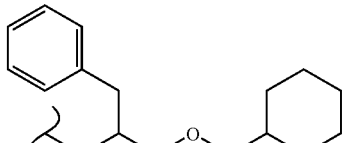
253

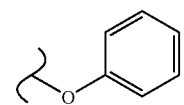
254

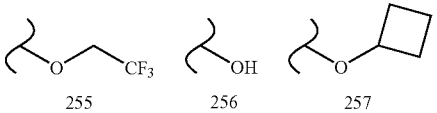
255   256   257

Combinations of "Sc" and $Pd^1$ and $Pd^2$ independently selected from table 30.1 can be expressed in the form of $Sc.Pd^1.Pd^2$, where Sc is represented by the respective letter A-G from Table 1.1 and $Pd^1$ and $Pd^2$ are represented by the respective number from Table 30.1. Thus, A.256.256 represents the following compound:

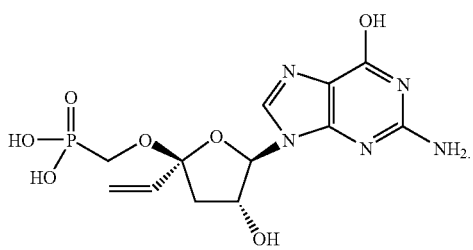

TABLE 7

List of Compounds of MBF

A.254.67, A.254.68, A.254.69, A.254.78, A.254.79, A.254.80,
A.254.248, A.254.249, A.254.250, A.254.251, A.254.252, A.254.253,
B.254.67, B.254.68, B.254.69, B.254.78, B.254.79, B.254.80,

TABLE 7-continued

List of Compounds of MBF

B.254.248, B.254.249, B.254.250, B.254.251, B.254.252, B.254.253,
C.254.67, C.254.68, C.254.69, C.254.78, C.254.79, C.254.80,
C.254.248, C.254.249, C.254.250, C.254.251, C.254.252, C.254.253,
D.254.67, D.254.68, D.254.69, D.254.78, D.254.79, D.254.80,
D.254.248, D.254.249, D.254.250, D.254.251, D.254.252, D.254.253,
E.254.67, E.254.68, E.254.69, E.254.78, E.254.79, E.254.80,
E.254.248, E.254.249, E.254.250, E.254.251, E.254.252, E.254.253,
F.254.67, F.254.68, F.254.69, F.254.78, F.254.79, F.254.80,
F.254.248, F.254.249, F.254.250, F.254.251, F.254.252, F.254.253,
G.254.67, G.254.68, G.254.69, G.254.78, G.254.79, G.254.80,
G.254.248, G.254.249, G.254.250, G.254.251, G.254.252, G.254.253,
A.255.67, A.255.68, A.255.69, A.255.78, A.255.79, A.255.80,
A.255.248, A.255.249, A.255.250, A.255.251, A.255.252, A.255.253,
B.255.67, B.255.68, B.255.69, B.255.78, B.255.79, B.255.80,
B.255.248, B.255.249, B.255.250, B.255.251, B.255.252, B.255.253,
C.255.67, C.255.68, C.255.69, C.255.78, C.255.79, C.255.80,
C.255.248, C.255.249, C.255.250, C.255.251, C.255.252, C.255.253,
D.255.67, D.255.68, D.255.69, D.255.78, D.255.79, D.255.80,
D.255.248, D.255.249, D.255.250, D.255.251, D.255.252, D.255.253,
E.255.67, E.255.68, E.255.69, E.255.78, E.255.79, E.255.80,
E.255.248, E.255.249, E.255.250, E.255.251, E.255.252, E.255.253,
F.255.67, F.255.68, F.255.69, F.255.78, F.255.79, F.255.80,
F.255.248, F.255.249, F.255.250, F.255.251, F.255.252, F.255.253,
G.255.67, G.255.68, G.255.69, G.255.78, G.255.79, G.255.80,
G.255.248, G.255.249, G.255.250, G.255.251, G.255.252, G.255.253,
A.67.67, A.68.68, A.69.69, A.78.78, A.79.79, A.80.80, A.248.248,
A.249.249, A.250.250, A.251.251, A252.252, A.253.253, B.67.67,
B.68.68, B.69.69, B.78.78, B.79.79, B.80.80, B.248.248, B.249.249,
B.250.250, B.251.251, B252.252, B.253.253, C.67.67, C.68.68,
C.69.69, C.78.78, C.79.79, C.80.80, C.248.248, C.249.249,
C.250.250, C.251.251, C252.252, C.253.253, D.67.67, D.68.68,
D.69.69, D.78.78, D.79.79, D.80.80, D.248.248, D.249.249,
D.250.250, D.251.251, D252.252, D.253.253, E.67.67, E.68.68,
E.69.69, E.78.78, E.79.79, E.80.80, E.248.248, E.249.249,
E.250.250, E.251.251, E252.252, E.253.253, F.67.67, F.68.68,
F.69.69, F.78.78, F.79.79, F.80.80, F.248.248, F.249.249, F.250.250,
F.251.251, F252.252, F.253.253, G.67.67, G.68.68, G.69.69,
G.78.78, G.79.79, G.80.80, G.248.248, G.249.249, G.250.250,
G.251.251, G252.252, G.253.253, A.256.257, B.256.257,
C.256.257 ,D.256.257, E.256.257, F.256.257, G.256.257.

Methods of Inhibition of HCV Polymerase

Another aspect of the invention relates to methods of inhibiting the activity of HCV polymerase comprising the step of treating a sample suspected of containing HCV with a composition of the invention.

Compositions of the invention may act as inhibitors of HCV polymerase, as intermediates for such inhibitors or have other utilities as described below. The inhibitors will bind to locations on the surface or in a cavity of HCV polymerase having a geometry unique to HCV polymerase. Compositions binding HCV polymerase may bind with varying degrees of reversibility. Those compounds binding substantially irreversibly are ideal candidates for use in this method of the invention. Once labeled, the substantially irreversibly binding compositions are useful as probes for the detection of HCV polymerase. Accordingly, the invention relates to methods of detecting HCV polymerase in a sample suspected of containing HCV polymerase comprising the steps of: treating a sample suspected of containing HCV polymerase with a composition comprising a compound of the invention bound to a label; and observing the effect of the sample on the activity of the label. Suitable labels are well known in the diagnostics field and include stable free radicals, fluorophores, radioisotopes, enzymes, chemiluminescent groups and chromogens. The compounds herein are labeled in conventional fashion using functional groups such as hydroxyl, carboxyl, sulfhydryl or amino.

Within the context of the invention, samples suspected of containing HCV polymerase include natural or man-made materials such as living organisms; tissue or cell cultures; biological samples such as biological material samples (blood, serum, urine, cerebrospinal fluid, tears, sputum, saliva, tissue samples, and the like); laboratory samples; food, water, or air samples; bioproduct samples such as extracts of cells, particularly recombinant cells synthesizing a desired glycoprotein; and the like. Typically the sample will be suspected of containing an organism which produces HCV polymerase, frequently a pathogenic organism such as HCV. Samples can be contained in any medium including water and organic solvent\water mixtures. Samples include living organisms such as humans, and man made materials such as cell cultures.

The treating step of the invention comprises adding the composition of the invention to the sample or it comprises adding a precursor of the composition to the sample. The addition step comprises any method of administration as described above.

If desired, the activity of HCV polymerase after application of the composition can be observed by any method including direct and indirect methods of detecting HCV polymerase activity. Quantitative, qualitative, and semiquantitative methods of determining HCV polymerase activity are all contemplated. Typically one of the screening methods described above are applied, however, any other method such as observation of the physiological properties of a living organism are also applicable.

Organisms that contain HCV polymerase include the HCV virus. The compounds of this invention are useful in the treatment or prophylaxis of HCV infections in animals or in man.

However, in screening compounds capable of inhibiting human immunodeficiency viruses, it should be kept in mind that the results of enzyme assays may not correlate with cell culture assays. Thus, a cell based assay should be the primary screening tool.

Screens for HCV Polymerase Inhibitors.

Compositions of the invention are screened for inhibitory activity against HCV polymerase by any of the conventional techniques for evaluating enzyme activity. Within the context of the invention, typically compositions are first screened for inhibition of HCV polymerase in vitro and compositions showing inhibitory activity are then screened for activity in vivo. Compositions having in vitro Ki (inhibitory constants) of less then about $200 \times 10^{-6}$ M, typically less than about $100 \times 10^{-7}$ M and preferably less than about $50 \times 10^{-8}$ M are preferred for in vivo use.

Useful in vitro screens have been described in detail and will not be elaborated here. However, the examples describe suitable in vitro assays.

The compounds of the present invention have HCV CC50 values (μM) in the range of about 0.1 to about 1000, or about 0.1 to about 500, or about 0.1 to about 400, or about 0.1 to about 300, or about 0.1 to about 200, or about 0.1 to about 100, or less than about 500, or less than about 400, or less than about 300, or less than about 200, or less than about 100, or less than about 50, or less than about 20, or less than about 10.

The compounds of the present invention have HCV EC50 values (μM) in the range of about 0.1 to about 500, or about 0.1 to about 400, or about 0.1 to about 300, or about 0.1 to about 200, or about 0.1 to about 100, or about 0.1 to about 50, or less than about 500, or less than about 400, or less than about 300, or less than about 200, or less than about 100, or less than about 50, or less than about 20, or less than about 10.

Salts and Hydrates

The compositions of this invention optionally comprise salts of the compounds herein, especially pharmaceutically acceptable non-toxic salts containing, for example, $Na^+$, $Li^+$, $K^+$, $Ca^{+2}$ and $Mg^{+2}$. Such salts may include those derived by combination of appropriate cations such as alkali and alkaline earth metal ions or ammonium and quaternary amino ions with an acid anion moiety, typically a carboxylic acid. Monovalent salts are preferred if a water soluble salt is desired.

Metal salts typically are prepared by treating a metal hydroxide with a compound of this invention. Examples of metal salts which are prepared in this way are salts containing $Li^+$, $Na^+$, and $K^+$. A less soluble metal salt may be precipitated from the solution of a more soluble salt by addition of the suitable metal compound.

In addition, salts may be formed from acid addition of certain organic and inorganic acids, e.g., HCl, HBr, $H_2SO_4$, $H_3PO_4$ or organic sulfonic acids, to basic centers, typically amines, or to acidic groups. Finally, it is to be understood that the compositions herein comprise compounds of the invention in their unionized, as well as zwitterionic form, and combinations with stoichiometric amounts of water as in hydrates.

Also included within the scope of this invention are the salts of the parental compounds with one or more amino acids. Any of the amino acids described above are suitable, especially the naturally-occurring amino acids found as protein components, although the amino acid typically is one bearing a side chain with a basic or acidic group, e.g., lysine, arginine or glutamic acid, or a neutral group such as glycine, serine, threonine, alanine, isoleucine, or leucine.

Pharmaceutical Formulations

The compounds of this invention are formulated with conventional carriers and excipients, which will be selected in accord with ordinary practice. Tablets will contain excipients, glidants, fillers, binders and the like. Aqueous formulations are prepared in sterile form, and when intended for delivery by other than oral administration generally will be isotonic. All formulations will optionally contain excipients such as those set forth in the Handbook of Pharmaceutical Excipients (1986), herein incorporated by reference in its entirety. Excipients include ascorbic acid and other antioxidants, chelating agents such as EDTA, carbohydrates such as dextrin, hydroxyalkylcellulose, hydroxyalkylmethylcellulose, stearic acid and the like. The pH of the formulations ranges from about 3 to about 11, but is ordinarily about 7 to 10.

While it is possible for the active ingredients to be administered alone it may be preferable to present them as pharmaceutical formulations. The formulations of the invention, both for veterinary and for human use, comprise at least one active ingredient, e.g. a compound of the present invention, together with one or more acceptable carriers and optionally other therapeutic ingredients. The carrier(s) must be "acceptable" in the sense of being compatible with the other ingredients of the formulation and physiologically innocuous to the recipient thereof.

The formulations include those suitable for the foregoing administration routes. The formulations may conveniently be presented in unit dosage form and may be prepared by any of the methods well known in the art of pharmacy. Techniques and formulations generally are found in Remington's Pharmaceutical Sciences (Mack Publishing Co., Easton, Pa.), herein incorporated by reference in its entirety. Such methods include the step of bringing into association the active ingredient with the carrier which constitutes one or more accessory ingredients. In general the formulations are prepared by uniformly and intimately bringing into association the active ingredient with liquid carriers or finely divided solid carriers or both, and then, if necessary, shaping the product.

Formulations of the present invention suitable for oral administration may be presented as discrete units such as capsules, cachets or tablets each containing a predetermined amount of the active ingredient; as a powder or granules; as a solution or a suspension in an aqueous or non-aqueous liquid; or as an oil-in-water liquid emulsion or a water-in-oil liquid emulsion. The active ingredient may also be administered as a bolus, electuary or paste.

A tablet is made by compression or molding, optionally with one or more accessory ingredients. Compressed tablets may be prepared by compressing in a suitable machine the active ingredient in a free-flowing form such as a powder or granules, optionally mixed with a binder, lubricant, inert diluent, preservative, surface active or dispersing agent. Molded tablets may be made by molding in a suitable machine a mixture of the powdered active ingredient moistened with an inert liquid diluent. The tablets may optionally be coated or scored and optionally are formulated so as to provide slow or controlled release of the active ingredient.

For administration to the eye or other external tissues e.g., mouth and skin, the formulations are preferably applied as a topical ointment or cream containing the active ingredient(s) in an amount of, for example, 0.075 to 20% w/w (including active ingredient(s) in a range between 0.1% and 20% in increments of 0.1% w/w such as 0.6% w/w, 0.7% w/w, etc.), preferably 0.2 to 15% w/w and most preferably 0.5 to 10% w/w. When formulated in an ointment, the active ingredients may be employed with either a paraffinic or a water-miscible ointment base. Alternatively, the active ingredients may be formulated in a cream with an oil-in-water cream base.

If desired, the aqueous phase of the cream base may include, for example, at least 30% w/w of a polyhydric alcohol, i.e. an alcohol having two or more hydroxyl groups such as propylene glycol, butane 1,3-diol, mannitol, sorbitol, glycerol and polyethylene glycol (including PEG 400) and mixtures thereof. The topical formulations may desirably include a compound which enhances absorption or penetration of the active ingredient through the skin or other affected areas. Examples of such dermal penetration enhancers include dimethyl sulphoxide and related analogs.

The oily phase of the emulsions of this invention may be constituted from known ingredients in a known manner. While the phase may comprise merely an emulsifier (otherwise known as an emulgent), it desirably comprises a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make up the so-called emulsifying wax, and the wax together with the oil and fat make up the so-called emulsifying ointment base which forms the oily dispersed phase of the cream formulations.

Emulgents and emulsion stabilizers suitable for use in the formulation of the invention include Tween® 60, Span® 80, cetostearyl alcohol, benzyl alcohol, myristyl alcohol, glyceryl mono-stearate and sodium lauryl sulfate.

The choice of suitable oils or fats for the formulation is based on achieving the desired cosmetic properties. The cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used, the last three being preferred esters. These may be used alone or in combination depending on the properties required. Alternatively, high melting point lipids such as white soft paraffin and/or liquid paraffin or other mineral oils are used.

Pharmaceutical formulations according to the present invention comprise one or more compounds of the invention together with one or more pharmaceutically acceptable carriers or excipients and optionally other therapeutic agents. Pharmaceutical formulations containing the active ingredient may be in any form suitable for the intended method of administration. When used for oral use for example, tablets, troches, lozenges, aqueous or oil suspensions, dispersible powders or granules, emulsions, hard or soft capsules, syrups or elixirs may be prepared. Compositions intended for oral use may be prepared according to any method known to the art for the manufacture of pharmaceutical compositions and such compositions may contain one or more agents including sweetening agents, flavoring agents, coloring agents and preserving agents, in order to provide a palatable preparation. Tablets containing the active ingredient in admixture with non-toxic pharmaceutically acceptable excipient which are suitable for manufacture of tablets are acceptable. These excipients may be, for example, inert diluents, such as calcium or sodium carbonate, lactose, lactose monohydrate, croscarmellose sodium, povidone, calcium or sodium phosphate; granulating and disintegrating agents, such as maize starch, or alginic acid; binding agents, such as cellulose, microcrystalline cellulose, starch, gelatin or acacia; and lubricating agents, such as magnesium stearate, stearic acid or talc. Tablets may be uncoated or may be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax may be employed.

Formulations for oral use may be also presented as hard gelatin capsules where the active ingredient is mixed with an inert solid diluent, for example calcium phosphate or kaolin, or as soft gelatin capsules wherein the active ingredient is mixed with water or an oil medium, such as peanut oil, liquid paraffin or olive oil.

Aqueous suspensions of the invention contain the active materials in admixture with excipients suitable for the manufacture of aqueous suspensions. Such excipients include a suspending agent, such as sodium carboxymethylcellulose, methylcellulose, hydroxypropyl methylcelluose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycetanol), a condensation product of ethylene oxide with a partial ester derived from a fatty acid and a hexitol anhydride (e.g., polyoxyethylene sorbitan monooleate). The aqueous suspension may also contain one or more preservatives such as ethyl or n-propyl p-hydroxy-benzoate, one or more coloring agents, one or more flavoring agents and one or more sweetening agents, such as sucrose or saccharin.

Oil suspensions may be formulated by suspending the active ingredient in a vegetable oil, such as arachis oil, olive oil, sesame oil or coconut oil, or in a mineral oil such as liquid paraffin. The oral suspensions may contain a thickening agent, such as beeswax, hard paraffin or cetyl alcohol. Sweetening agents, such as those set forth herein, and flavoring agents may be added to provide a palatable oral preparation. These compositions may be preserved by the addition of an antioxidant such as ascorbic acid.

Dispersible powders and granules of the invention suitable for preparation of an aqueous suspension by the addition of water provide the active ingredient in admixture with a dispersing or wetting agent, a suspending agent, and one or more preservatives. Suitable dispersing or wetting agents and suspending agents are exemplified by those disclosed above. Additional excipients, for example sweetening, flavoring and coloring agents, may also be present.

The pharmaceutical compositions of the invention may also be in the form of oil-in-water emulsions. The oily phase may be a vegetable oil, such as olive oil or arachis oil, a mineral oil, such as liquid paraffin, or a mixture of these. Suitable emulsifying agents include naturally-occurring gums, such as gum acacia and gum tragacanth, naturally occurring phosphatides, such as soybean lecithin, esters or partial esters derived from fatty acids and hexitol anhydrides, such as sorbitan monooleate, and condensation products of these partial esters with ethylene oxide, such as polyoxyethylene sorbitan monooleate. The emulsion may also contain sweetening and flavoring agents. Syrups and elixirs may be formulated with sweetening agents, such as glycerol, sorbitol or sucrose. Such formulations may also contain a demulcent, a preservative, a flavoring or a coloring agent.

The pharmaceutical compositions of the invention may be in the form of a sterile injectable preparation, such as a sterile injectable aqueous or oleaginous suspension. This suspension may be formulated according to the known art using those suitable dispersing or wetting agents and suspending agents which have been mentioned herein. The sterile injectable preparation may also be a sterile injectable solution or suspension in a non-toxic parenterally acceptable diluent or solvent, such as a solution in 1,3-butane-diol or prepared as a lyophilized powder. Among the acceptable vehicles and solvents that may be employed are water, Ringer's solution and isotonic sodium chloride solution. In addition, sterile fixed oils may conventionally be employed as a solvent or suspending medium. For this purpose any bland fixed oil may be employed including synthetic mono- or diglycerides. In addition, fatty acids such as oleic acid may likewise be used in the preparation of injectables.

The amount of active ingredient that may be combined with the carrier material to produce a single dosage form will vary depending upon the host treated and the particular mode of administration. For example, a time-release formulation intended for oral administration to humans may contain approximately 1 to 1000 mg of active material compounded with an appropriate and convenient amount of carrier material which may vary from about 5 to about 95% of the total compositions (weight:weight). The pharmaceutical composition can be prepared to provide easily measurable amounts for administration. For example, an aqueous solution intended for intravenous infusion may contain from about 3 to 500 μg of the active ingredient per milliliter of solution in order that infusion of a suitable volume at a rate of about 30 mL/hr can occur.

Formulations suitable for administration to the eye include eye drops wherein the active ingredient is dissolved or suspended in a suitable carrier, especially an aqueous solvent for the active ingredient. The active ingredient is preferably present in such formulations in a concentration of 0.5 to 20%, advantageously 0.5 to 10% particularly about 1.5% w/w.

Formulations suitable for topical administration in the mouth include lozenges comprising the active ingredient in a flavored basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

Formulations for rectal administration may be presented as a suppository with a suitable base comprising for example cocoa butter or a salicylate.

Formulations suitable for intrapulmonary or nasal administration have a particle size for example in the range of 0.1 to 500 µm (including particle sizes in a range between 0.1 and 500 µm in increments such as 0.5 µm, 1 µm, 30 µm, 35 µm, etc.), which is administered by rapid inhalation through the nasal passage or by inhalation through the mouth so as to reach the alveolar sacs. Suitable formulations include aqueous or oily solutions of the active ingredient. Formulations suitable for aerosol or dry powder administration may be prepared according to conventional methods and may be delivered with other therapeutic agents such as compounds heretofore used in the treatment or prophylaxis of infections as described herein.

Formulations suitable for vaginal administration may be presented as pessaries, tampons, creams, gels, pastes, foams or spray formulations containing in addition to the active ingredient such carriers as are known in the art to be appropriate.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents.

The formulations are presented in unit-dose or multi-dose containers, for example sealed ampoules and vials, and may be stored in a freeze-dried (lyophilized) condition requiring only the addition of the sterile liquid carrier, for example water for injection, immediately prior to use. Extemporaneous injection solutions and suspensions are prepared from sterile powders, granules and tablets of the kind previously described. Preferred unit dosage formulations are those containing a daily dose or unit daily sub-dose, as herein above recited, or an appropriate fraction thereof, of the active ingredient.

It should be understood that in addition to the ingredients provided by the present invention the formulations of this invention may include other agents conventional in the art having regard to the type of formulation in question, for example those suitable for oral administration may include flavoring agents.

The invention further provides veterinary compositions comprising at least one active ingredient, e.g., a compound of the present invention together with a veterinary carrier.

Veterinary carriers are materials useful for the purpose of administering the composition and may be solid, liquid or gaseous materials which are otherwise inert or acceptable in the veterinary art and are compatible with the active ingredient. These veterinary compositions may be administered orally, parenterally or by any other desired route.

Compounds of the invention can also be formulated to provide controlled release of the active ingredient to allow less frequent dosing or to improve the pharmacokinetic or toxicity profile of the active ingredient. Accordingly, the invention also provided compositions comprising one or more compounds of the invention formulated for sustained or controlled release.

The effective dose of an active ingredient depends at least on the nature of the condition being treated, toxicity, whether the compound is being used prophylactically (lower doses) or against an active disease or condition, the method of delivery, and the pharmaceutical formulation, and will be determined by the clinician using conventional dose escalation studies. The effective dose can be expected to be from about 0.0001 to about 100 mg/kg body weight per day. Typically, from about 0.01 to about 10 mg/kg body weight per day. More typically, from about 0.01 to about 5 mg/kg body weight per day. More typically, from about 0.05 to about 0.5 mg/kg body weight per day. For example, the daily candidate dose for an adult human of approximately 70 kg body weight will range from 1 mg to 1000 mg, or between 5 mg and 500 mg, and may take the form of single or multiple doses.

In another embodiment, the present application provides pharmaceutical compositions comprising a compound of the present invention, or a pharmaceutically acceptable salt, solvate, and/or ester thereof, and a pharmaceutically acceptable carrier or excipient.

Routes of Administration

One or more compounds of the invention (herein referred to as the active ingredients) are administered by any route appropriate to the condition to be treated. Suitable routes include oral, rectal, nasal, topical (including buccal and sublingual), vaginal and parenteral (including subcutaneous, intramuscular, intravenous, intradermal, intrathecal and epidural), and the like. It will be appreciated that the preferred route may vary with for example the condition of the recipient. An advantage of the compounds of this invention is that they are orally bioavailable and can be dosed orally.

Combination Therapy

In one embodiment, the compounds of the present invention can be used alone, e.g., for inhibiting cytochrome P450 monooxygenase. In another embodiment, the compounds of the present invention are used in combination with other active therapeutic ingredients or agents. Preferably, the other active therapeutic ingredients or agents are interferons, ribavirin analogs, NS3 protease inhibitors, alpha-glucosidase 1 inhibitors, hepatoprotectants, non-nucleoside inhibitors of HCV, and other drugs for treating HCV.

Combinations of the compounds of Formula I-IV are typically selected based on the condition to be treated, cross-reactivities of ingredients and pharmaco-properties of the combination. For example, when treating an infection (e.g., HCV), the compositions of the invention are combined with other active therapeutic agents (such as those described herein).

Suitable active therapeutic agents or ingredients which can be combined with the compounds of Formula I-IV can include interferons, e.g., pegylated rIFN-alpha 2b, pegylated rIFN-alpha 2a, rIFN-alpha 2b, IFN alpha-2b XL, rIFN-alpha 2a, consensus IFN alpha, infergen, rebif, locteron, AVI-005, PEG-infergen, pegylated IFN-beta, oral interferon alpha, feron, reaferon, intermax alpha, r-IFN-beta, infergen+actimmune, IFN-omega with DUROS, and albuferon; ribavirin analogs, e.g., rebetol, copegus, VX-497, and viramidine (taribavirin); NS5a inhibitors, e.g., A-831 and A-689; NS5b polymerase inhibitors, e.g., NM-283, valopicitabine, R1626, PSI-6130 (R1656), HCV-796, BILB 1941, MK-0608, NM-107, R7128, VCH-759, PF-868554, GSK625433, and XTL-2125; NS3 protease inhibitors, e.g., SCH-503034 (SCH-7), VX-950 (Telaprevir), ITMN-191, and BILN-2065; alpha-glucosidase 1 inhibitors, e.g., MX-3253 (celgosivir) and UT-231B; hepatoprotectants, e.g., IDN-6556, ME 3738, MitoQ, and LB-84451; non-nucleoside inhibitors of HCV, e.g., benzimidazole derivatives, benzo-1,2,4-thiadiazine derivatives, and phenylalanine derivatives; and other drugs for treating HCV, e.g., zadaxin, nitazoxanide (alinea), BIVN-401 (virostat), DEBIO-025, VGX-410C, EMZ-702, AVI 4065, bavituximab, oglufanide, PYN-17, KPE02003002, actilon (CPG-10101), KRN-7000, civacir, GI-5005, ANA-975, XTL-6865, ANA 971, NOV-205, tarvacin, EHC-18, and NIM811.

In yet another embodiment, the present application discloses pharmaceutical compositions comprising a compound of the present invention, or a pharmaceutically acceptable salt, solvate, and/or ester thereof, in combination with at least one additional therapeutic agent, and a pharmaceutically acceptable carrier or excipient.

According to the present invention, the therapeutic agent used in combination with the compound of the present invention can be any agent having a therapeutic effect when used in combination with the compound of the present invention. For example, the therapeutic agent used in combination with the compound of the present invention can be interferons, ribavirin analogs, NS3 protease inhibitors, alpha-glucosidase 1 inhibitors, hepatoprotectants, non-nucleoside inhibitors of HCV, and other drugs for treating HCV.

In another embodiment, the present application provides pharmaceutical compositions comprising a compound of the present invention, or a pharmaceutically acceptable salt, solvate, and/or ester thereof, in combination with at least one additional therapeutic agent selected from the group consisting of pegylated rIFN-alpha 2b, pegylated rIFN-alpha 2a, rIFN-alpha 2b, IFN alpha-2b XL, rIFN-alpha 2a, consensus IFN alpha, infergen, rebif, locteron, AVI-005, PEG-infergen, pegylated IFN-beta, oral interferon alpha, feron, reaferon, intermax alpha, r-IFN-beta, infergen+actimmune, IFN-omega with DUROS, albuferon, rebetol, copegus, VX-497, viramidine (taribavirin), A-831, A-689, NM-283, valopicitabine, R1626, PSI-6130 (R1656), HCV-796, BILB 1941, MK-0608, NM-107, R7128, VCH-759, PF-868554, GSK625433, XTL-2125, SCH-503034 (SCH-7), VX-950 (Telaprevir), ITMN-191, and BILN-2065, MX-3253 (celgosivir), UT-231B, IDN-6556, ME 3738, MitoQ, and LB-84451, benzimidazole derivatives, benzo-1,2,4-thiadiazine derivatives, and phenylalanine derivatives, zadaxin, nitazoxanide (alinea), BIVN-401 (virostat), DEBIO-025, VGX-410C, EMZ-702, AVI 4065, bavituximab, oglufanide, PYN-17, KPE02003002, actilon (CPG-10101), KRN-7000, civacir, GI-5005, ANA-975, XTL-6865, ANA 971, NOV-205, tarvacin, EHC-18, and NIM811 and a pharmaceutically acceptable carrier or excipient.

In yet another embodiment, the present application provides a combination pharmaceutical agent comprising:

a) a first pharmaceutical composition comprising a compound of the present invention, or a pharmaceutically acceptable salt, solvate, or ester thereof; and b) a second pharmaceutical composition comprising at least one additional therapeutic agent selected from the group consisting of HIV protease inhibiting compounds, HIV non-nucleoside inhibitors of reverse transcriptase, HIV nucleoside inhibitors of reverse transcriptase, HIV nucleotide inhibitors of reverse transcriptase, HIV integrase inhibitors, gp41 inhibitors, CXCR4 inhibitors, gp120 inhibitors, CCR5 inhibitors, interferons, ribavirin analogs, NS3 protease inhibitors, alpha-glucosidase 1 inhibitors, hepatoprotectants, non-nucleoside inhibitors of HCV, and other drugs for treating HCV, and combinations thereof.

Combinations of the compounds of Formula I-IV and additional active therapeutic agents may be selected to treat patients infected with HCV and other conditions such as HIV infections. Accordingly, the compounds of Formula I-IV may be combined with one or more compounds useful in treating HIV, for example HIV protease inhibiting compounds, HIV non-nucleoside inhibitors of reverse transcriptase, HIV nucleoside inhibitors of reverse transcriptase, HIV nucleotide inhibitors of reverse transcriptase, HIV integrase inhibitors, gp41 inhibitors, CXCR4 inhibitors, gp120 inhibitors, CCR5 inhibitors, interferons, ribavirin analogs, NS3 protease inhibitors, alpha-glucosidase 1 inhibitors, hepatoprotectants, non-nucleoside inhibitors of HCV, and other drugs for treating HCV.

More specifically, one or more compounds of the present invention may be combined with one or more compounds selected from the group consisting of 1) HIV protease inhibitors, e.g., amprenavir, atazanavir, fosamprenavir, indinavir, lopinavir, ritonavir, lopinavir+ritonavir, nelfinavir, saquinavir, tipranavir, brecanavir, darunavir, TMC-126, TMC-114, mozenavir (DMP-450), JE-2147 (AG1776), AG1859, DG35, L-756423, RO0334649, KNI-272, DPC-681, DPC-684, and GW640385X, DG17, PPL-100, 2) a HIV non-nucleoside inhibitor of reverse transcriptase, e.g., capravirine, emivirine, delaviridine, efavirenz, nevirapine, (+) calanolide A, etravirine, GW5634, DPC-083, DPC-961, DPC-963, MIV-150, and TMC-120, TMC-278 (rilpivirine), efavirenz, BILR 355 BS, VRX 840773, UK-453,061, RDEA806, 3) a HIV nucleoside inhibitor of reverse transcriptase, e.g., zidovudine, emtricitabine, didanosine, stavudine, zalcitabine, lamivudine, abacavir, amdoxovir, elvucitabine, alovudine, MIV-210, racivir (±-FTC), D-d4FC, emtricitabine, phosphazide, fozivudine tidoxil, fosalvudine tidoxil, apricitibine (AVX754), amdoxovir, KP-1461, abacavir+lamivudine, abacavir+lamivudine+zidovudine, zidovudine+lamivudine, 4) a HIV nucleotide inhibitor of reverse transcriptase, e.g., tenofovir, tenofovir disoproxil fumarate+emtricitabine, tenofovir disoproxil fumarate+emtricitabine+efavirenz, and adefovir, 5) a HIV integrase inhibitor, e.g., curcumin, derivatives of curcumin, chicoric acid, derivatives of chicoric acid, 3,5-dicaffeoylquinic acid, derivatives of 3,5-dicaffeoylquinic acid, aurintricarboxylic acid, derivatives of aurintricarboxylic acid, caffeic acid phenethyl ester, derivatives of caffeic acid phenethyl ester, tyrphostin, derivatives of tyrphostin, quercetin, derivatives of quercetin, S-1360, zintevir (AR-177), L-870812, and L-870810, MK-0518 (raltegravir), BMS-707035, MK-2048, BA-011, BMS-538158, GSK364735C, 6) a gp41 inhibitor, e.g., enfuvirtide, sifuvirtide, FB006M, TRI-1144, SPC3, DES6, Locus gp41, CovX, and REP 9, 7) a CXCR4 inhibitor, e.g., AMD-070, 8) an entry inhibitor, e.g., SP01A, TNX-355, 9) a gp120 inhibitor, e.g., BMS-488043 and BlockAide/CR, 10) a G6PD and NADH-oxidase inhibitor, e.g., immunitin, 10) a CCR5 inhibitor, e.g., aplaviroc, vicriviroc, INCB9471, PRO-140, INCB15050, PF-232798, CCR5 mAb004, and maraviroc, 11) an interferon, e.g., pegylated rIFN-alpha 2b, pegylated rIFN-alpha 2a, rIFN-alpha 2b, IFN alpha-2b XL, rIFN-alpha 2a, consensus IFN alpha, infergen, rebif, locteron, AVI-005, PEG-infergen, pegylated IFN-beta, oral interferon alpha, feron, reaferon, intermax alpha, r-IFN-beta, infergen+actimmune, IFN-omega with DUROS, and albuferon, 12) ribavirin analogs, e.g., rebetol, copegus, VX-497, and viramidine (taribavirin) 13) NS5a inhibitors, e.g., A-831 and A-689, 14) NS5b polymerase inhibitors, e.g., NM-283, valopicitabine, R1626, PSI-6130 (R1656), HCV-796, BILB 1941, MK-0608, NM-107, R7128, VCH-759, PF-868554, GSK625433, and XTL-2125, 15) NS3 protease inhibitors, e.g., SCH-503034 (SCH-7), VX-950 (Telaprevir), ITMN-191, and BILN-2065, 16) alpha-glucosidase 1 inhibitors, e.g., MX-3253 (celgosivir) and UT-231B, 17) hepatoprotectants, e.g., IDN-6556, ME 3738, MitoQ, and LB-84451, 18) non-nucleoside inhibitors of HCV, e.g., benzimidazole derivatives, benzo-1,2,4-thiadiazine derivatives, and phenylalanine derivatives, 19) other drugs for treating HCV, e.g., zadaxin, nitazoxanide (alinea), BIVN-401 (virostat), DEBIO-025, VGX-410C, EMZ-702, AVI 4065, bavituximab, oglufanide, PYN-17, KPE02003002, actilon (CPG-10101), KRN-7000, civacir, GI-5005, ANA-975, XTL-6865, ANA 971, NOV-205, tarvacin, EHC-18, and NIM811, 19) pharmacokinetic enhancers, e.g., BAS-100 and SPI452, 20)RNAse H inhibitors, e.g., ODN-93 and ODN-112, 21) other anti-HIV agents, e.g., VGV-1, PA-457 (bevirimat), ampligen, HRG214, cytolin, polymun, VGX-410, KD247, AMZ 0026, CYT 99007, A-221 HIV, BAY 50-4798, MDX010 (iplimumab), PBS119, ALG889, and PA-1050040.

It is also possible to combine any compound of the invention with one or more other active therapeutic agents in a unitary dosage form for simultaneous or sequential administration to a patient. The combination therapy may be administered as a simultaneous or sequential regimen. When administered sequentially, the combination may be administered in two or more administrations.

Co-administration of a compound of the invention with one or more other active therapeutic agents generally refers to simultaneous or sequential administration of a compound of the invention and one or more other active therapeutic agents, such that therapeutically effective amounts of the compound of the invention and one or more other active therapeutic agents are both present in the body of the patient.

Co-administration includes administration of unit dosages of the compounds of the invention before or after administration of unit dosages of one or more other active therapeutic agents, for example, administration of the compounds of the invention within seconds, minutes, or hours of the administration of one or more other active therapeutic agents. For example, a unit dose of a compound of the invention can be administered first, followed within seconds or minutes by administration of a unit dose of one or more other active therapeutic agents. Alternatively, a unit dose of one or more other therapeutic agents can be administered first, followed by administration of a unit dose of a compound of the invention within seconds or minutes. In some cases, it may be desirable to administer a unit dose of a compound of the invention first, followed, after a period of hours (e.g., 1-12 hours), by administration of a unit dose of one or more other active therapeutic agents. In other cases, it may be desirable to administer a unit dose of one or more other active therapeutic agents first, followed, after a period of hours (e.g., 1-12 hours), by administration of a unit dose of a compound of the invention.

The combination therapy may provide "synergy" and "synergistic effect", i.e. the effect achieved when the active ingredients used together is greater than the sum of the effects that results from using the compounds separately. A synergistic effect may be attained when the active ingredients are: (1) co-formulated and administered or delivered simultaneously in a combined formulation; (2) delivered by alternation or in parallel as separate formulations; or (3) by some other regimen. When delivered in alternation therapy, a synergistic effect may be attained when the compounds are administered or delivered sequentially, e.g., in separate tablets, pills or capsules, or by different injections in separate syringes. In general, during alternation therapy, an effective dosage of each active ingredient is administered sequentially, i.e. serially, whereas in combination therapy, effective dosages of two or more active ingredients are administered together.

In still yet another embodiment, the present application provides for methods of inhibiting HCV polymerase in a cell, comprising: contacting a cell infected with HCV with an effective amount of a compound of Formula I-IV, or a pharmaceutically acceptable salt, solvate, and/or ester thereof, whereby HCV polymerase is inhibited.

In still yet another embodiment, the present application provides for methods of inhibiting HCV polymerase in a cell, comprising: contacting a cell infected with HCV with an effective amount of a compound of Formula I-IV, or a pharmaceutically acceptable salt, solvate, and/or ester thereof, and at least one additional active therapeutic agent, whereby HCV polymerase is inhibited.

In still yet another embodiment, the present application provides for methods of inhibiting HCV polymerase in a cell, comprising: contacting a cell infected with HCV with an effective amount of a compound of Formula I-IV, or a pharmaceutically acceptable salt, solvate, and/or ester thereof, and at least one additional active therapeutic agent selected from the group consisting of interferons, ribavirin analogs, NS3 protease inhibitors, alpha-glucosidase 1 inhibitors, hepatoprotectants, non-nucleoside inhibitors of HCV, and other drugs for treating HCV.

In still yet another embodiment, the present application provides for methods of treating HCV in a patient, comprising: administering to the patient a therapeutically effective amount of a compound of Formula I-IV, or a pharmaceutically acceptable salt, solvate, and/or ester thereof.

In still yet another embodiment, the present application provides for methods of treating HCV in a patient, comprising: administering to the patient a therapeutically effective amount of a compound of Formula I-IV, or a pharmaceutically acceptable salt, solvate, and/or ester thereof, and at least one additional active therapeutic agent, whereby HCV polymerase is inhibited.

In still yet another embodiment, the present application provides for methods of treating HCV in a patient, comprising: administering to the patient a therapeutically effective amount of a compound of Formula I-IV, or a pharmaceutically acceptable salt, solvate, and/or ester thereof, and at least one additional active therapeutic agent selected from the group consisting of interferons, ribavirin analogs, NS3 protease inhibitors, alpha-glucosidase 1 inhibitors, hepatoprotectants, non-nucleoside inhibitors of HCV, and other drugs for treating HCV.

In still yet another embodiment, the present application provides for the use of a compound of the present invention, or a pharmaceutically acceptable salt, solvate, and/or ester thereof, for the preparation of a medicament for treating an HCV infection in a patient.

EXAMPLES

Exemplary methods for the preparation of the compounds of the invention are provided below. These methods are intended to illustrate the nature of such preparations and are not intended to limit the scope of applicable methods. While the examples specify certain reaction conditions, one skilled in the art will understand how to vary the specific reaction conditions to obtain the full scope of the invention. Exemplary methods for the preparation of the compounds of the invention are illustrated in Schemes 2, 3, 5, 6, 7, 8, 9, 10, 30, 31, and 32.

Certain abbreviations and acronyms are used in describing the experimental details. Although most of these would be understood by one skilled in the art, Table 1E contains a list of many of these abbreviations and acronyms.

TABLE 1E

List of abbreviations and acronyms.

| Abbreviation | Meaning |
|---|---|
| AIBN | 2,2'-azobis(2-methylpropionitrile) |
| BnBr | benzylbromide |
| BSA | bis(trimethylsilyl)acetamide |
| BzCl | benzoyl chloride |
| CDI | carbonyl diimidazole |
| DCA | dichloroacetamide |
| DCC | dicyclohexylcarbodiimide |
| DMAP | 4-dimethylaminopyridine |
| DME | 1,2-dimethoxyethane |
| DMTCl | dimethoxytrityl chloride |
| DMSO | dimethylsulfoxide |
| DMF | dimethylformamide |
| EtOAc | ethyl acetate |
| ESI | electrospray ionization |
| HMDS | hexamethyldisilazane |
| HPLC | High pressure liquid chromatography |
| LDA | lithium diisopropylamide |
| LRMS | low resolution mass spectrum |
| mCPBA | meta-chloroperbenzoic acid |
| MeOH | methanol |
| m/z or m/e | mass to charge ratio |
| MH$^+$ | mass plus 1 |
| MH$^-$ | mass minus 1 |
| MsOH | methanesulfonic acid |
| MS or ms | mass spectrum |
| rt or r.t. | room temperature |
| TMSCl | chlorotrimethylsilane |
| TMSBr | bromotrimethylsilane |
| TMSI | iodotrimethylsilane |
| TEA | triethylamine |
| TBA | tributylamine |
| TBAP | tributylammonium pyrophosphate |
| TBSCl | t-butyldimethylsilyl chloride |
| TEAB | triethylammonium bicarbonate |
| TFA | trifluoroacetic acid |
| TLC or tlc | thin layer chromatography |
| δ | parts per million down field from tetramethylsilane |

Example 1

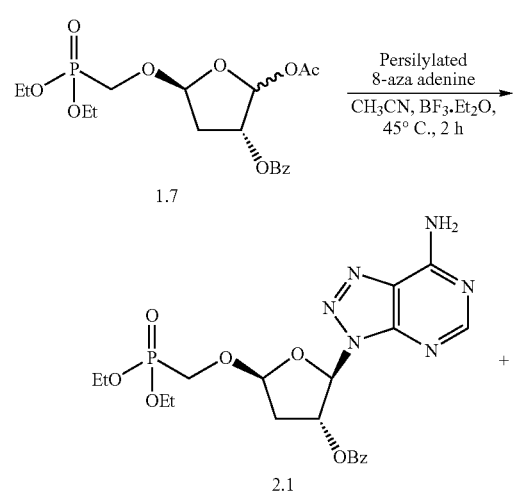

Scheme 2

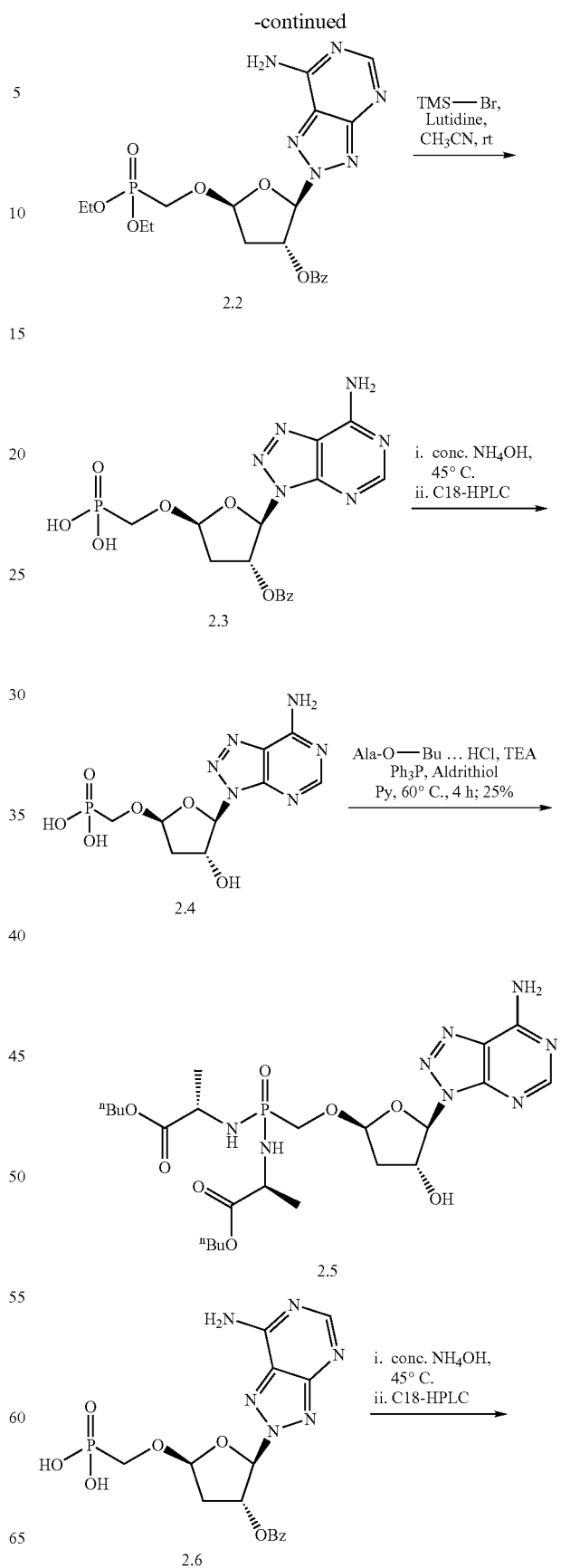

-continued

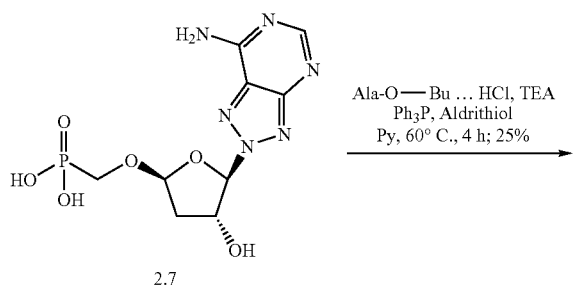

2.7

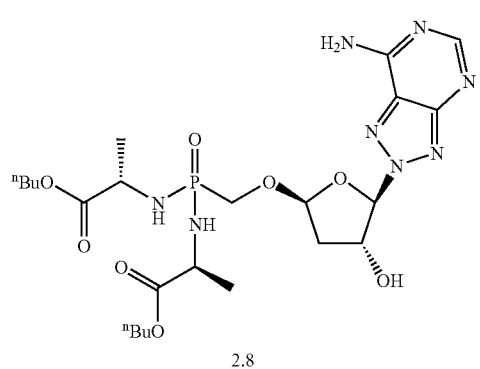

2.8

Benzoic acid 2-(7-amino-[1,2,3]triazolo[4,5-d]pyrimidin-3-yl)-5-(diethoxy-phosphorylmethoxy)-tetrahydrofyran-3-yl ester, (2.1) and benzoic acid 2-(7-amino-[1,2,3]triazolo[4,5-d]pyrimidin-2-yl)-5-(diethoxy-phosphorylmethoxy)-tetrahydrofyran-3-yl ester (2.2)

A 1,1,1,3,3,3-hexamethyldisilazane suspension (10 mL) of 8-azaadenine (0.25 g, 1.8 mmol) and ammonium sulfate (0.16 g, 1.2 mmol) was heated at 140° C. for 1.5 h. The resulting clear solution was concentrated to dryness and azeotroped with acetonitrile twice. The solution of the persilylated 8-azaadenine was added to phosphonate 1.7 (see scheme 1) (0.5 g, 1.2 mmol) in acetonitrile (10 mL), and the resultant solution then treated with $BF_3.Et_2O$ (0.24 mL, 1.8 mmol). The resulting solution was heated at 45° C. for 1.5 h and then concentrated to dryness. The crude residue was purified by C-18 HPLC to afford the title compound 2.1 (0.16 g, 37%) and 2.2 (0.07 g, 12%). Compound 2.1 $^1$H NMR (CDCl$_3$): δ 8.45 (s, 1H), 8.00 (d, 2H, J=8.0), 7.56 (t, 1H, J=7.3), 7.42 (t, 2H, J=7.6), 6.68 (d, 1H, J=1.9), 6.49-6.54 (m, 1H), 5.60-5.70 (m, 1H), 4.01-4.18 (m, 4H), 3.64-3.80 (m, 2H), 3.08-3.17 (m, 1H), 2.64-2.72 (m, 1H), 1.20-1.34 (2t, 6H). $^{31}$P NMR: 20.55 ppm. Compound 2.2 $^1$H NMR (CDCl$_3$): δ 8.48 (s, 1H), 8.00 (d, 2H, J=8.0), 7.59 (t, 1H, J=7.6), 7.42 (t, 2H, J=7.6), 6.65 (d, 1H, J=3.3), 6.15-6.21 (m, 1H), 5.55 (m, 1H), 4.04-4.22 (m, 5H), 3.69 (t, 1H, J=2.4), 2.94-3.01 (m, 1H), 2.49-2.60 (m, 1H), 1.20-1.34 (2t, 6H). $^{31}$P NMR: 20.68 ppm.

[5-(7-Amino-[1,2,3]triazolo[4,5-d]pyrimidin-3-yl)-4-hydroxy-tetrahydrofuran-2-yloxymethyl]-phosphonic acid (2.4)

A solution of compound 2.1 (300 mg, 0.6 mmol) in acetonitrile (5 mL) was treated with bromotrimethylsilane (0.93 g, 6 mmol) and 2,6-lutidine at room temperature for 3.5 h. The mixture was concentrated to dryness and azeotroped with conc. NH$_4$OH twice. The residue was subjected to C-18 HPLC eluting with to give 180 mg (68% yield) diacid 2.3. The diacid 2.3 was then treated with concentrated NH$_4$OH (10 ml) at 45° C. for 30 min. The reaction mixture was concentrated to dryness and purified by C-18 HPLC to afford compound 2.4 (94 mg, 68%). $^1$H NMR (D$_2$O): δ 8.25 (s, 1H), 6.26 (d, 1H, J=2.4), 5.42-5.52 (m, 2H), 3.32 (d, 2H, J=9.1), 2.54-2.61 (m, 1H), 2.33-2.42 (m, 1H); $^{31}$P NMR: 15.39 ppm.

[5-(7-Amino-[1,2,3]triazolo[4,5-d]pyrimidin-2-yl)-4-hydroxy-tetrahydrofuran-2-yloxymethyl]-phosphonic acid (2.7)

Compound 2.7 (76 mg, 71%) was obtained from 2.2 using the procedure described for the preparation of 2.4. $^1$H NMR (D$_2$O): δ 8.21 (s, 1H), 6.25 (d, 1H, J=2.4), 563 (t, 1H, J=4.0), 4.99-5.04 (m, 1H), 3.48-3.56 (m, 1H), 3.32-3.40 (m, 1H), 2.46-2.54 (m, 1H), 2.28-2.37 (m, 1H); $^{31}$P NMR: 13.03 ppm. LRMS (ESI) MH$^+$ C$_9$H$_{13}$N$_6$O$_6$P requires 333.1. Found 332.9.

Bis-amidate prodrug 2.5: Phosphonic acid 2.4 (30 mg, 0.09 mmol) was dissolved in pyridine (0.5 mL) and treated with (S)-Alanine n-butyl ester hydrochloride (98 mg, 0.54 mmol) and TEA (91 mg, 0.90 mmol). A freshly prepared solution of Ph$_3$P (165 mg, 0.63 mmol) and 2-Aldrithiol (140 mg, 0.66 mmol) in pyridine (1 mL) was added. The resulting mixture was heated at 65° C. for 4 h and then concentrated to dryness. The crude residue was purified on silica gel column chromatography (eluting with EtOAc and then 30% Ethanol/70% EtOAc) and repurified on C-18 HPLC to afford 14.5 mg of prodrug 2.4. $^1$H NMR (CD$_3$OD): δ 8.36 (s, 1H), 6.31 (d, 1H, J=3.7), 5.45-5.48 (m, 1H), 5.34-5.40 (m, 1H), 3.92-4.20 (m, 6H), 3.75-3.82 (m, 1H), 3.61-3.70 (m, 1H), 2.64-2.72 (m, 1H), 2.35-2.44 (m, 1H), 1.53-1.70 (m, 4H), 1.30-1.47 (m, 10H), 0.89-1.00 (m, 6H); $^{31}$P NMR: 23.30 ppm. LRMS (ESI) MH$^+$ C$_{23}$H$_{39}$N$_8$O$_8$P requires 587.3. Found 587.2.

Diphosphophosphonate of 2.4: The diphosphophosphonate of 2.4 was prepared as the same manner as the diphosphophosphonate of 5.2 as described below.

Bis-amidate prodrug 2.8: Prepared as described for the synthesis of 2.5. Yield 15 mg (26%). $^1$H NMR (CD$_3$OD): δ 8.31 (s, 1H), 6.27 (d, 1H, J=3.0), 5.52-5.55 (m, 1H), 5.13-5.17 (m, 1H), 3.92-4.20 (m, 7H), 3.69-3.77 (m, 1H), 2.60-2.67 (m, 1H), 2.32-2.40 (m, 1H), 1.53-1.70 (m, 4H), 1.30-1.47 (m, 10H), 0.89-0.98 (2t, 6H); $^{31}$P NMR: 23.19 ppm.

Diphosphophosphonate of 2.7: The diphosphophosphonate of 2.7 was prepared as the same manner as the diphosphophosphonate of 5.2 as described below. $^1$H NMR (CD$_3$OD): δ 2.33-2.38 (m, 1H), 2.54-2.65 (m, 1H), 3.58-3.70 (m, 2H), 5.20-5.30 (m, 1H), 5.57-5.65 (m, 1H), 6.00 (d, 1H, J=3.4). $^{31}$P NMR: 8.11, −10.68, −23.23 ppm.

Example 2
Scheme 3
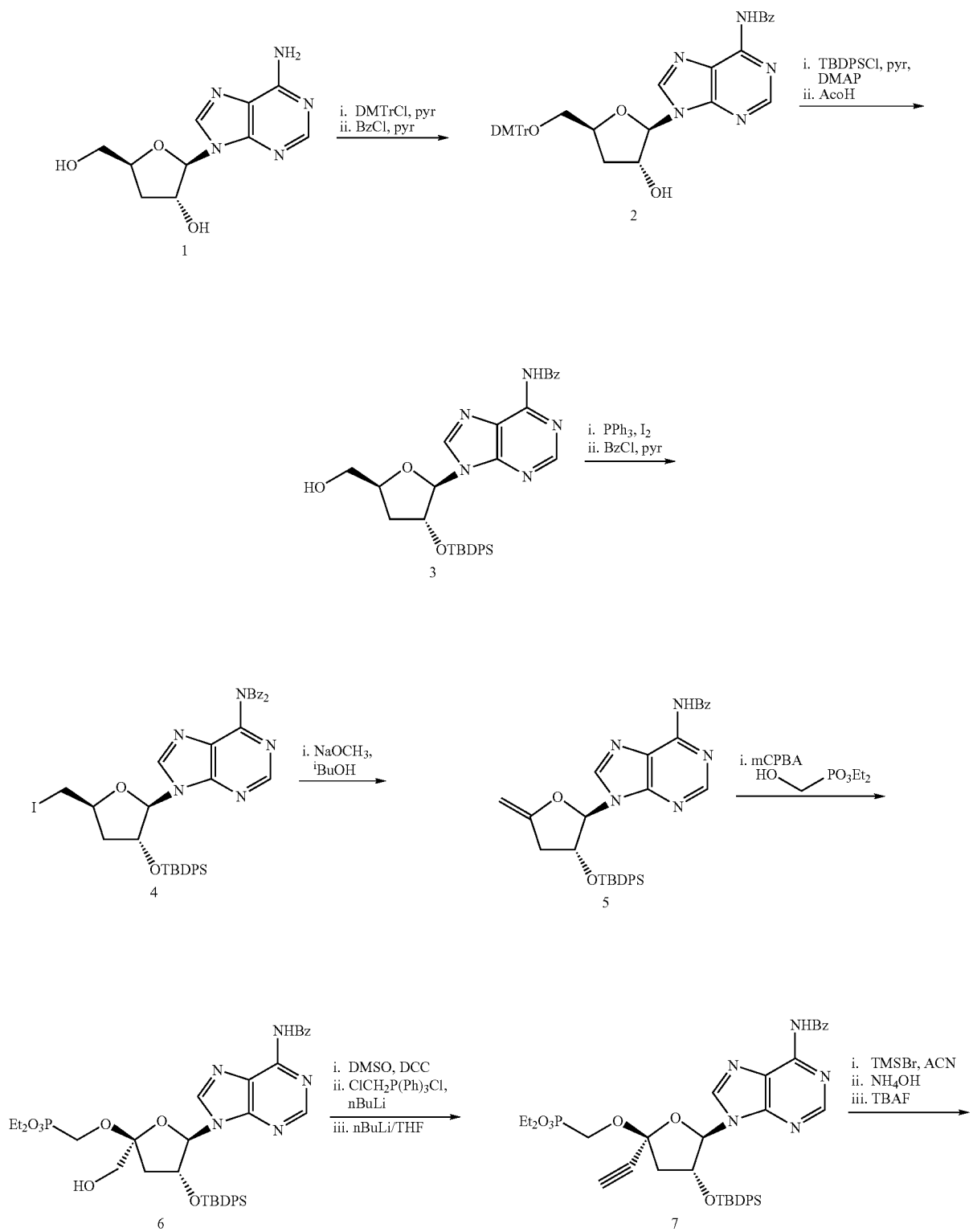

-continued

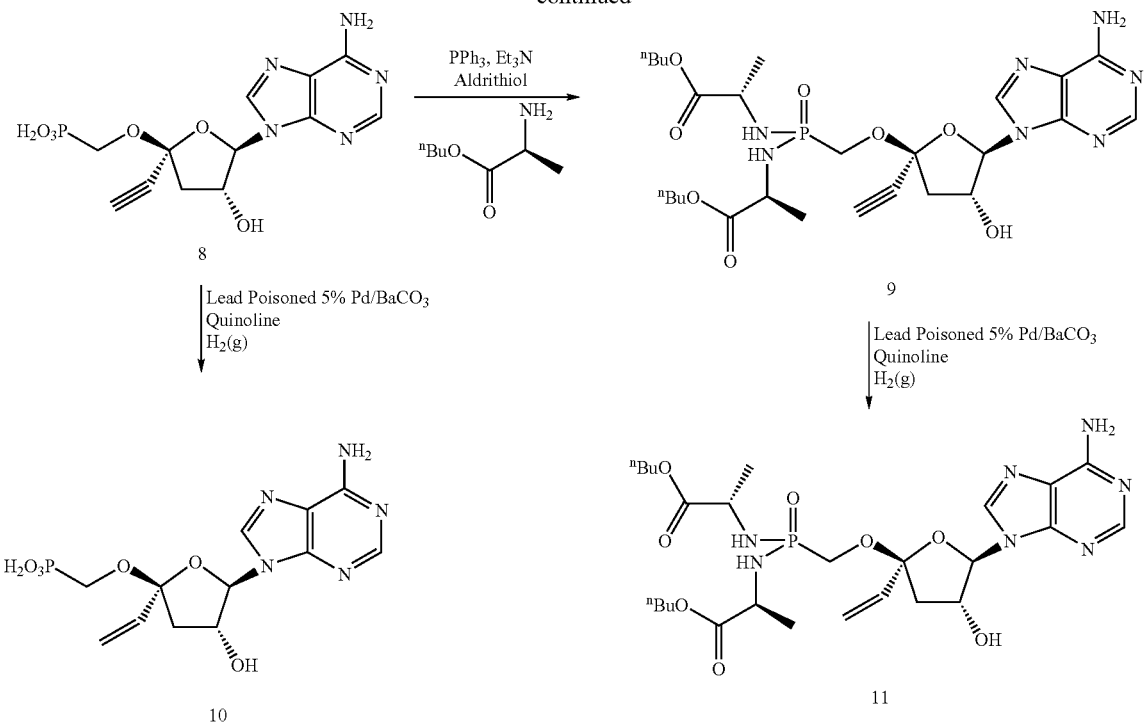

Cordycepin 1 (3' deoxy adenosine) (Sigma Aldrich) is first 5'O protected by treatment with dimethoxy trityl chloride, and then N-6 benzoyl protected according to the procedure of Charubala et al. (Helv. Chim Acta 2002 p 2284, herein incorporated by reference in its entirety), to give 2. Intermediate 2 is then 2'O protected by treatment with TBDMS chloride in the presence of pyridine and silver nitrate (see Tet Lett. 1981, p 4775, herein incorporated by reference in its entirety) and then the 5'O trityl group is removed by treatment with acetic acid to give the intermediate 3. Treatment of 3 with triphenylphosphine and iodine according to the procedure of Maag et al. (J. Med. Chem. 1992, p 1440, herein incorporated by reference in its entirety) introduces the 5' iodine. Further treatment with benzoyl chloride then affords the bis benzoyl protected product 4 (Maag et al J. Med. Chem. 1992 p 1440). Treatment of 4 with sodium methoxide affords exocyclic alkene 5 (Maag et al J. Med. Chem. 1992, p 1440). Treatment of alkene 5 with m-CPBA (m-chloroperbenzoic acid) in the presence of hydroxylmethyl diethylphosphonate afforded the alcohol 6 (see Maag et al J. Med. Chem. 1992 p 1440). Alcohol 6 was then oxidized using Swern conditions, followed by Wittig olefination using (chloromethyl)triphenylphosphonium chloride, and finally treatment with nBuLi at low temperature provided the alkyne 7 (see J. Med. Chem., 2004, p 5041, Siddiqui et al.) both of which are herein incorporated by reference in their entirety. The alkyne 7 is then treated with TMSBr in acetonitrile to remove the phosphonate ester groups, followed by treatment with ammonium hydroxide to remove the benzoyl groups, and finally TBAF to remove the 2'O-silyl group, thereby affording 8 (See scheme 1 and 4 and Greene and Wuts, protecting groups in Organic Chemistry, 3$^{rd}$ Edition, Wiley, herein incorporated by reference in its entirety). Diacid 8 is then converted to the bis amidate prodrug 9 according to the procedure described in Scheme 1. Diacid 8 is then treated with lead poisoned-5% palladium on barium carbonate in the presence of quinoline under about one to five atmospheres of hydrogen gas to give olefin 10. Similar treatment of bis amidate prodrug 9 will give olefin 11.

Example 3

Scheme 5

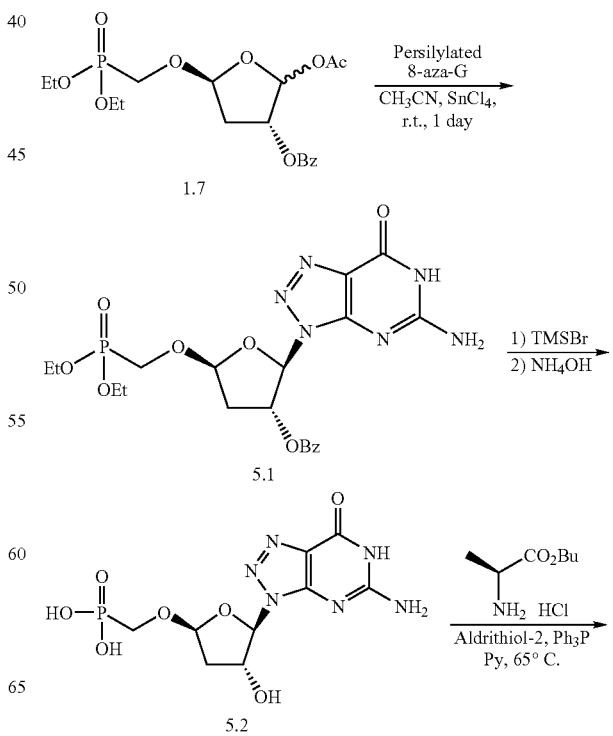

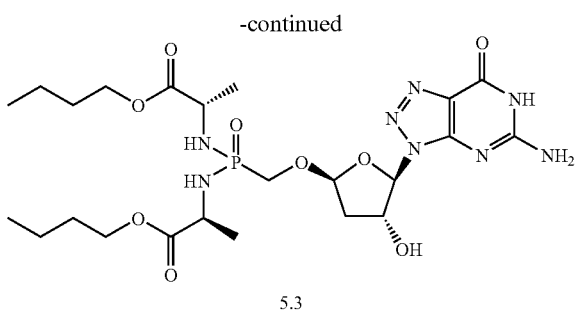

5.3

[5-(2-Amino-6-oxo-1,6-dihydro-purin-9-yl)-4-hydroxy-tetrahydro-furan-2-yloxymethyl]-phosphonic acid (5.2).

8-aza-G was persilylated first using the procedure described for the preparation of compound 2.2. Compound 1.7 (300 mg, 0.7 mmol) and the persilyated 8-aza-G base (1.8 mmol) were dissolved in 5 mL $CH_3CN$, and treated with $SnCl_4$ (1M solution in $CH_2Cl_2$) (2.1 mL, 2.1 mmol). The mixture was stirred at r.t. for 24 h, quenched with $NaHCO_3$ (2 g) and water (3 mL), filtered, and concentrated down under reduced pressure. The residue was subjected to reverse phase HPLC eluting with 5-95% $CH_3CN$ in water (0.1% TFA) to yield crude product 5.1 (45 mg, 14% yield). The crude product was carried on to the next two steps using the procedure described for the preparation of compound 2.4 to yield compound 5.2 (21 mg, 68% yield). $^1H$ NMR (300 MHz, $D_2O$) δ 2.35-2.41 (m, 1H), 2.54-2.63 (m, 1H), 3.29-3.45 (m, 2H), 5.24-5.26 (m, 1H), 5.58 (d, 1H, J=2.7), 6.04 (d, 1H, J=2.7) $^{31}P$ NMR: 24.32 ppm.

Bis-amidate Prodrug 5.3

Compound 5.3 (4.5 mg, 45% yield) was synthesized from compound 5.2 (7 mg, 0.02 mmol) using the procedure described for the preparation of compound 2.5. $^1H$ NMR (300 MHz, $CD_3OD$) δ 0.92-1.00 (m, 6H), 1.36-1.45 (m, 10H), 1.60-1.70 (m, 4H), 2.30-2.40 (m, 1H), 2.60-2.70 (m, 1H), 3.65-3.70 (m, 1H), 3.84-3.90 (m, 1H), 3.90-4.20 (m, 6H), 5.25-5.28 (m, 1H), 5.42 (s, 1H), 6.09 (d, 1H, J=3.5). $^{31}P$ NMR: 24.32. LRMS (ESI) $MH^+$ $C_{23}H_{39}N_8O_9P$ requires 603.3. Found 603.0.

Diphosphophosphonate of 5.2

Compound 5.2 (6.0 mg, 0.0173 mmol) was dissolved in DMSO (0.500 mL) and then treated with tributylamine (0.021 mL, 0.087 mmol) followed by carbonyldiimidazole (28 mg, 0.173 mmol). The mixture was stirred at room temperature for 1 h and then MeOH (0.0063 mL, 0.156 mmol) was added. The mixture was stirred for an additional 30 min. Tributyl ammonium pyrophosphate (95 mg, 0.173 mmol) in DMF (0.4 mL) was added and the reaction mixture stirred for 1 h. The solvent was removed under reduced pressure and the crude product was purified by ion exchange HPLC (0-40% TEAB) to provide the diphosphophosphonate (4.5 mg). $^1H$ NMR (300 MHz, $D_2O$) δ 1.11-1.20 (m, 27H), 2.38-2.45 (m, 1H), 2.60-2.70 (m, 1H), 2.85-3.25 (m, 18H), 3.40-3.60 (m, 2H), 5.38-5.42 (m, 1H), 5.58-5.61 (m, 1H), 6.25 (d, 1H, J=2.8), 8.24 (s, 1H). $^{31}P$ NMR: 8.25, −5.67, −21.46 ppm.

Example 4

Scheme 6

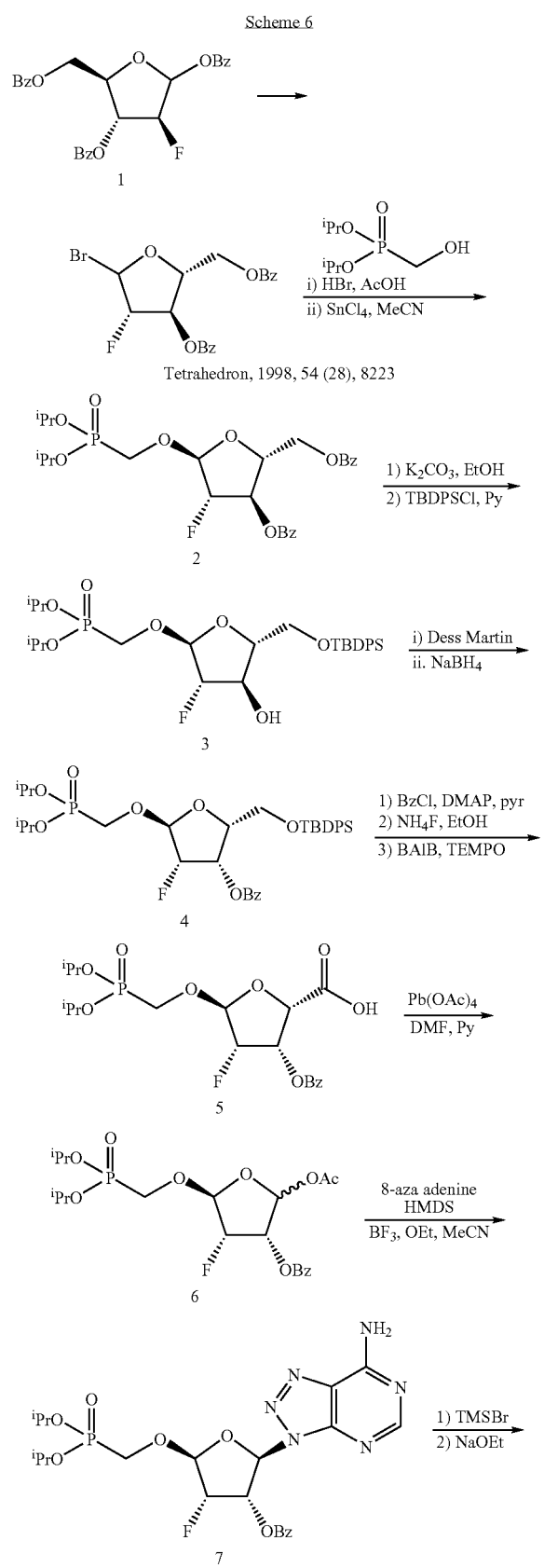

Tetrahedron, 1998, 54 (28), 8223

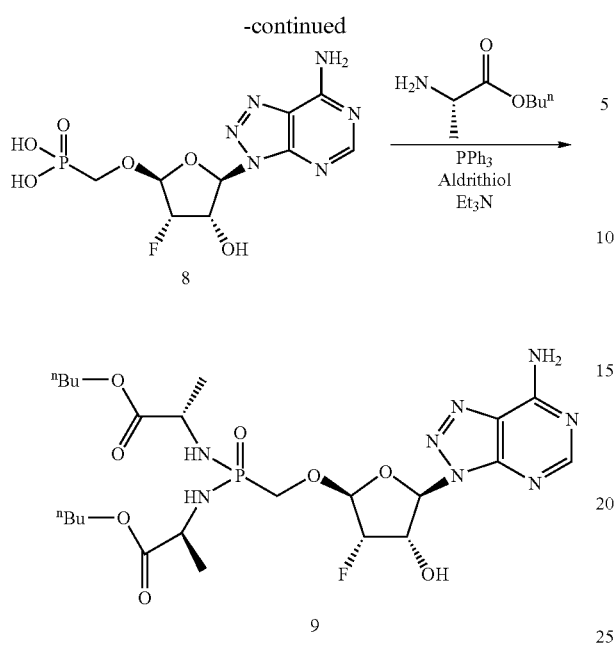

8

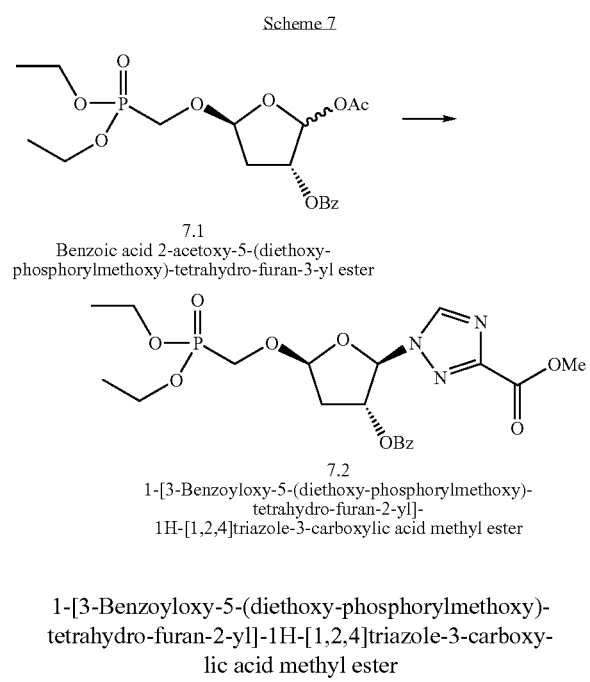

7.1
Benzoic acid 2-acetoxy-5-(diethoxy-phosphorylmethoxy)-tetrahydro-furan-3-yl ester

9

The commercially available benzoate 6.1 (CMS chemicals, UK) is converted to the anomeric bromide according to the method described in J. Org. Chem. 1985, p 3644 (herein incorporated by reference in its entirety). The bromide is then reacted with the diisopropyl phosphonate in the presence of tin(IV) chloride in acetonitrile at reflux according to the procedure described in *Tetrahedron*, 1998, 54 (28), 8223, herein incorporated by reference in its entirety. The product is an approximate 1:1 mixture of anomeric isomers that is carried forward as a mixture of isomers. The isomeric mixture 6.2 is then treated with potassium carbonate in methanol to provide the diol as a mixture of isomers. After purification by silica gel chromatography the diol is then treated with TBDPS chloride in pyridine overnight to afford the 5'O-silyl protected mixture of isomers 6.3. At this stage the anomeric isomers are separated to give the desired beta-isomer 6.3. Protected intermediate 6.3 is then oxidized by treatment with 1.5 eq. of Dess Martine Periodinane reagent, and after work up immediately reduced by dissolution in ethanol and treatment with sodium borohydride (6 eq.) at 0 C to afford 6.4. Compound 6.4 was then treated with benzoyl chloride in the presence of pyridine and DMAP (dimethylamino pyridine) to give the benzoate, which is then treated with pyridine.HF (10 eq.) in dichloromethane to provide the 5'OH intermediate. This intermediate is then oxidized using BAIB and TEMPO (as in Scheme 1) to provide 6.5. Acid 6.5 is then treated with lead tetraacetate in DMF and pyridine overnight to afford the anomeric acetate 6.6 (as in Scheme 2). Acetate 6.6 is then reacted with a silylated nucleobase, for example silylated 8-azaadenine prepared from the treatment of 8-aza adenine with hexamethyldisilazide and ammonium sulfate, in the presence of a Lewis acid e.g. BF₃OEt to afford the nucleoside phosphonate 6.7. Phosphonate 6.7 is then treated with TMSBr (trimethylsilyl bromide) to generate the diacid, followed by sodium ethoxide to afford the desired diacid 6.8. Diacid 6.8 can be converted to the prodrug, e.g. the bis alanine n-butyl amidate 6.9, according to the method described in Scheme 2.

Example 5

7.2
1-[3-Benzoyloxy-5-(diethoxy-phosphorylmethoxy)-tetrahydro-furan-2-yl]-1H-[1,2,4]triazole-3-carboxylic acid methyl ester 1-[3-Benzoyloxy-5-(diethoxy-phosphorylmethoxy)-tetrahydro-furan-2-yl]-1H-[1,2,4]triazole-3-carboxylic acid methyl ester Benzoic acid 2-acetoxy-5-(diethoxy-phosphorylmethoxy)-tetrahydro-furan-3-yl ester (170 mg, 0.4 mmol), 1H-[1,2,4]Triazole-3-carboxylic acid methyl ester (51 mg, 0.4 mmol) and Bis-(p-nitrophenyl)phosphate were reacted according to literature procedure (*J. Med. Chem.* 2000, 43, 1019-1028). The desired product was isolated in 65% yield (150 mg). $^1$H NMR (CDCl₃, 300 MHz) δ 8.60 (s, 1H), 8.00 (d, 2H, J=7.8 Hz), 7.60 (t, 1H, J=7.2 Hz), 7.45 (app t, 2H, J=7.7 Hz), 6.29 (d, 1H, J=1.5 Hz), 5.91-5.98 (m, 1H), 5.67-5.71 (m, 1H), 4.11-4.23 (m, 4H), 3.96-4.04 (m, 4H), 3.85-3.92 (m, 1H), 2.55-2.72 (m, 2H), 1.29-1.37 (m, 6H). $^{31}$P NMR (121.4 MHz, CDCl₃) δ 19.8. LRMS (ESI) MH⁺ C₂₀H₂₇N₃O₉P requires 484.1 Found 483.8.

Example 6

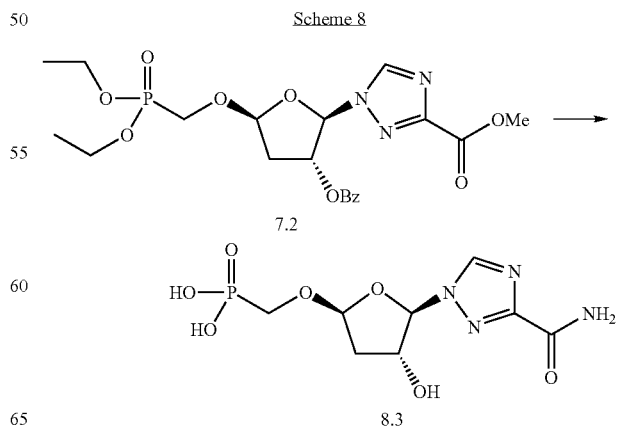

[5-(3-Carbamoyl-[1,2,4]triazol-1-yl)-4-hydroxy-tetrahydro-furan-2-yloxymethyl]-phosphonic acid The 1-[3-benzoyloxy-5-(diethoxy-phosphorylmethoxy)-tetrahydrofuran-2-yl]-1H-[1,2,4]triazole-3-carboxylic acid methyl ester (60 mg. 0.124 mmol) was dissolved in MeCN (1.5 mL). Bromotrimethylsilane (0.164 mL, 1.24 mmol) and 2,6-lutidine (0.043 mL, 0.372 mmol) were added and the mixture stirred at ambient temperature for 10 h. The solvents were removed in vacuo and the product isolated by C-18 HPLC. To this was then added ammonia (7 N in MeOH, 4 mL) and the mixture stirred overnight. The title compound was isolated by C-18 HPLC. $^1$H NMR (300 MHz, D$_2$O) ppm 8.65 (s, 1H), 5.95 (d, 1H, J=2.4 Hz), 5.49-5.52 (m, 1H), 4.81-4.89 (m, 1H), 3.47-3.70 (m, 2H), 2.27-2.32 (m, 2H). $^{31}$P NMR (121.4 MHz, D$_2$O) ppm 15.0. LRMS (ESI) M-H C$_8$H$_{12}$N$_4$O$_7$P requires 307.0 Found 307.0.

Example 7

Scheme 9

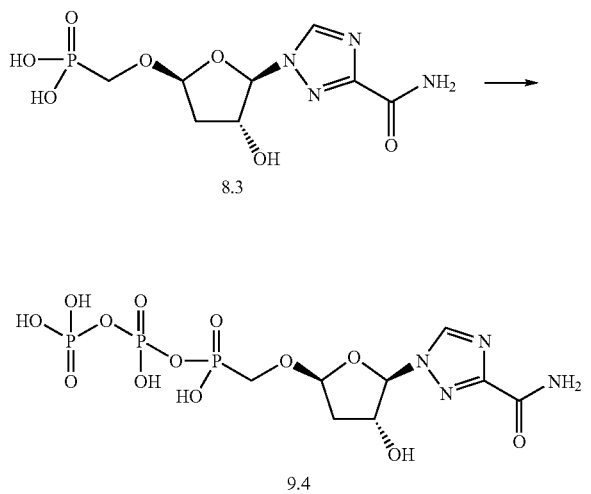

9.4

Diphosphate of [5-(3-Carbamoyl-[1,2,4]triazol-1-yl)-4-hydroxy-tetrahydro-furan-2-yloxymethyl]-phosphonic acid The [5-(3-carbamoyl-[1,2,4]triazol-1-yl)-4-hydroxy-tetrahydro-furan-2-yloxymethyl]-phosphonic acid (20 mg, 0.058 mmol) was dissolved in anhydrous DMF (5 mL) and Bu$_3$N (0.042 mL, 0.175 mmol) was added. The mixture was concentrated in vacuo and then redissolved in anhydrous DMF (5 mL) containing N,N-carbonyldiimidazole (95.0 mg. 0.58 mmol). The mixture was stirred for 30 min and tributylammonium pyrophosphate (excess), predissolved in anhydrous DMF (1 mL) was added. After 2 h, the reaction was complete. Excess aqueous NH$_3$ was added and the mixture concentrated in vacuo. The desired product (9 mg) was isolated by ion exchange chromatography. $^{31}$P NMR (121.4 MHz, D$_2$O) ppm 7.10-7.30 (m), −6.26 (d, J=20.9 Hz), −22.4 (app t, J=21.4 Hz). LRMS (ESI) M-H C$_8$H$_{14}$N$_4$O$_{13}$P$_3$ requires 467.0 Found 466.9.

Example 8

Scheme 10

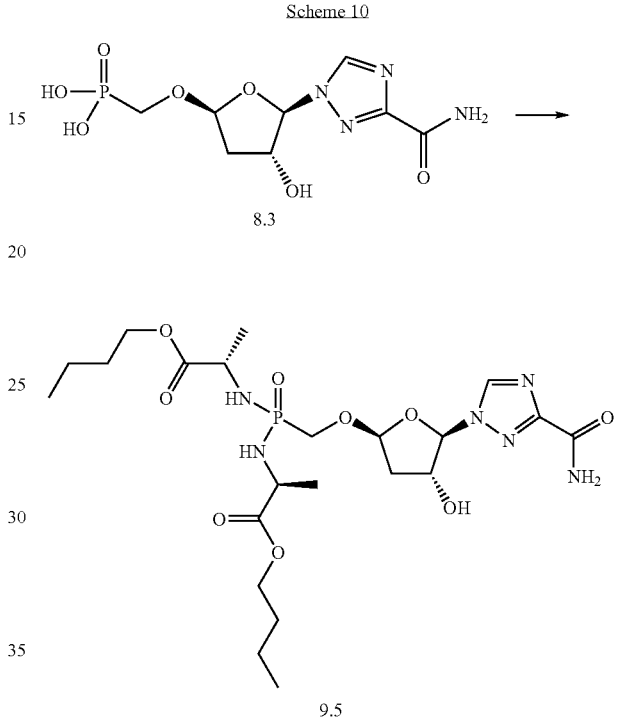

Bis (Alanine-n-butyl ester) phosphonamidate pro drug of [5-(3-carbamoyl-[1,2,4]triazol-1-yl)-4-hydroxy-tetrahydro-furan-2-yloxymethyl]-phosphonic acid The [5-(3-carbamoyl-[1,2,4]triazol-1-yl)-4-hydroxy-tetrahydro-furan-2-yloxymethyl]-phosphonic acid (21.7 mg, 0.057 mmol) was dissolved in anhydrous pyridine (3.2 mL) and the Alanine, n-butyl ester hydrochloride (72.4 mg, 0.40 mmol) was added. The mixture was concentrated in vacuo, redissolved in anhydrous pyridine and concentrated again. The resultant solids were suspended in anhydrous pyridine (2.2 mL) and stirred under Ar (g) at 60° C. A separate flask, PPh$_3$ (104 mg, 0.40 mmol) and Aldrithiol (88.0 mg, 0.40 mmol) were combined in anhydrous pyridine (1 mL) and stirred for 20-30 min. The two mixtures were combined and stirred for 3-4 h at 60° C. under Ar (g). The mixture was concentrated and the product (10.6 mg) isolated by reverse-phase HPLC. $^{31}$P NMR (121.4 MHz, D$_2$O) ppm 21.6. LRMS (ESI) MH$^+$ C$_{22}$H$_{40}$N$_6$O$_9$P requires 563.3 Found 563.0.

Example 9

Scheme 30

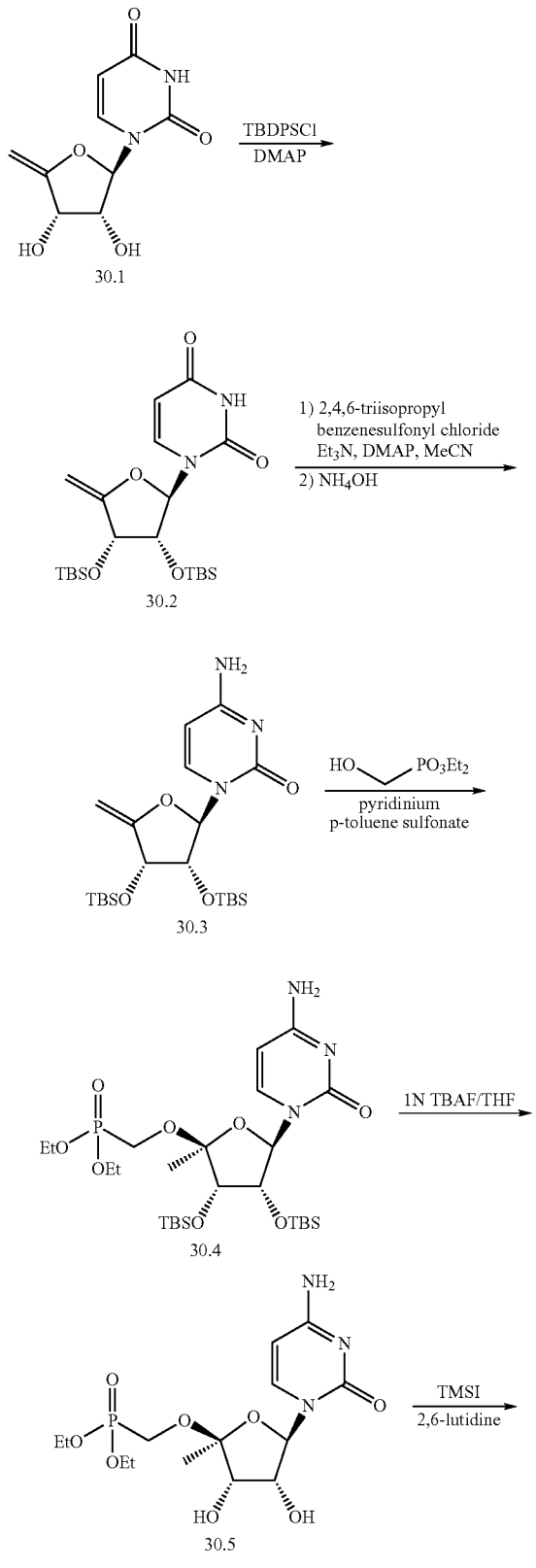

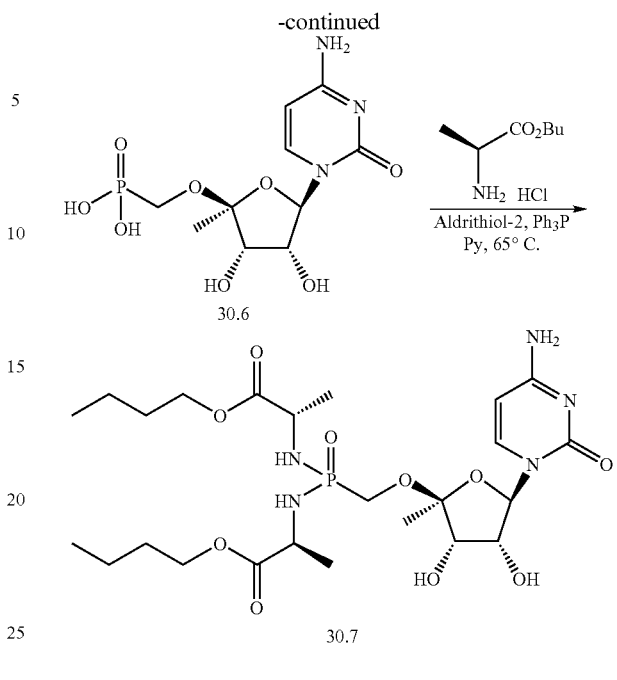

1-((2R,3R,4S)-3,4-bis(tert-butyldimethylsilyloxy)-5-methylene-tetrahydrofuran-2-yl)pyrimidine-2,4(1H,3H)-dione (30.2).

To a solution of compound 30.1 (540 mg, 2.39 mmol) in DMF (20 mL) was added imidazole (1.62 g, 23.9 mmol) and DMAP (290 mg, 2.39 mmol) and finally tert-butyldimethylsilyl chloride (2.15 g, 14.3 mmol). The mixture was heated to 60° C. for 4 h, water was added and the aqueous layer was extracted with ethyl acetate. The organic layer was dried over $MgSO_4$, filtered, and concentrated under reduced pressure. The residue was subjected to a silica gel column chromatography eluting with 40% EtOAc in Hexane to give compound 30.2 (700 mg, 67% yield). $^1$H NMR (300 MHz, $CDCl_3$): δ 0.04 (s, 3H), 0.07 (s, 3H), 0.13 (s, 6H), 0.93 (s, 9H), 1.59 (s, 9H), 4.20 (dd, 1H, J=4.6, 1.0), 4.27 (d, 1H, J=4.3), 4.35 (d, 1H, J=4.3), 4.54 (s, 1H), 5.80 (d, 1H, J=6.1), 6.08 (d, 1H, J=8.3), 7.18 (d, 1H, J=8.0), 8.24 (s, 1H). LCMS [M-H]$^-$ $C_{21}H_{38}N_2O_5Si_2$ requires 453.7. Found 453.3.

1-((2R,3R,4S)-3,4-bis(tert-butyldimethylsilyloxy)-5-methylene-tetrahydrofuran-2-yl)-4-aminopyrimidin-2(1H)-one (30.3).

To a solution of compound 30.2 (940 mg, 2.07 mmol) in acetonitrile (25 mL) was added DMAP (505 mg, 4.14 mmol) and triethylamine (0.58 mL, 4.14 mmol) and 2,4,6 triisopropylbenzene sulfonyl chloride (1.25 g, 4.14 mmol). The mixture was stirred for 1 hour; concentrated ammonia hydroxide (20 mL) was added and stirred for 12 hours. The mixture was then concentrated under reduced pressure and the residue was partitioned between water and EtOAc. The organic layer was dried over $MgSO_4$, filtered, and concentrated under reduced pressure. The residue was subjected to a silica gel column chromatography eluting with 5% methanol in $CH_2Cl_2$ to give compound 30.3 (843 mg, 90% yield). $^1$H NMR (300 MHz, $CDCl_3$): δ 0.04 (s, 3H), 0.07 (s, 3H), 0.13 (s, 6H), 0.93 (s, 9H), 0.98 (s, 9H), 4.22 (s, 1H), 4.27 (d, 1H, J=2.1), 4.35 (d, 1H, J=4.3), 4.58 (s, 1H), 5.78 (d, 1H, J=8.1), 5.95 (d, 1H, J=2.3), 7.22 (d, 1H, J=8.1).

diethyl((2R,3S,4R,5R)-5-(4-amino-2-oxopyrimidin-1(2H)-yl)-3,4-bis(tert-butyldimethylsilyloxy)-2-methyl-tetrahydrofuran-2-yloxy)methylphosphonate (30.4)

To a solution of compound 30.3 (840 mg, 1.85 mmol) in dichloroethane (20 mL) was added diethyl (hydroxymethyl)phosphonate (0.41 mL, 2.87 mmol) and pyridinium p-toluene sulfonate (0.23 g, 0.92 mmol). The mixture was heated to 60° C. for 1 h and then concentrated under reduced pressure. The residue was subjected to a silica gel column chromatography eluting with 10% MeOH in $CH_2Cl_2$ to give compound 30.4 (289 mg, 24% yield). $^1$H NMR (300 MHz, $CDCl_3$): δ⊕ 0.04 (s, 3H), 0.08 (s, 3H), 0.10 (s, 6H), 0.89 (s, 9H), 0.92 (s, 9H), 1.38 (m, 6H), 1.49 (s, 3H), 3.93 (m, 1H), 4.14 (m, 2H), 4.20 (m, 1H), 4.38 (m, 1H), 5.83 (d, 1H, J=7.7), 6.08 (d, 1H, J=4.0), 7.99 (d, 1H, J=7.3). LRMS (ESI) $MH^+$ $C_{26}H_{52}N_3O_8PSi_2$ requires 622.9. Found 622.1.

diethyl((2R,3S,4R,5R)-5-(4-amino-2-oxopyrimidin-1(2H)-yl)-3,4-dihydroxy-2-methyl-tetrahydrofuran-2-yloxy)methylphosphonate (30.5).

To a solution of compound 30.4 (288 mg, 0.46 mmol) in THF (20 mL) was added a 1N solution of tetrabutylammonium fluoride in THF (2.7 mL, 2.8 mmol). The mixture was stirred at r.t. for 1 h and concentrated down under reduced pressure. The residue was subjected to a silica gel column chromatography eluting with 10% MeOH in $CH_2Cl_2$ to give compound 30.5 (114 mg, 63% yield). $^1$H NMR (300 MHz, $CD_3OD$): δ 1.38 (t, 6H, J=7.0), 1.40 (s, 3H), 3.86 (m, 2H), 4.02 (d, 1H, J=4.9), 4.11 (m, 4H), 4.56 (dd, 1H, J=7.0, 6.7), 5.98 (d, 1H, J=7.4), 6.11 (d, 1H, J=7.0), 7.63 (d, 1H, J=7.6). LRMS (ESI) $MH^+$ $C_{14}H_{24}N_3O_8P$ requires 394.4. Found 394.1.

((2R,3S,4R,5R)-5-(4-amino-2-oxopyrimidin-1(2H)-yl)-3,4-dihydroxy-2-methyl-tetrahydrofuran-2-yloxy)methylphosphonic acid (30.6).

To a solution of compound 30.5 (112 mg, 0.29 mmol) in acetonitrile (10 mL) was added 2,6-lutidine (0.20 mL, 1.7 mmol) and then trimethylsilyl iodide (0.41 mL, 2.8 mmol). The mixture was stirred at room temperature for 1 h. After the reaction was done, 0.30 mL of 2,6-lutidine was added to the mixture and the mixture was concentrated under reduced pressure. The residue was then put into solution with water (3 mL) and treated with sodium hydroxide 1N to pH=10. The solution was then acidify to pH=3 using acetic acid and subjected to a reverse phase (YMC-Pack ODS-A) to give compound 30.6 (69 mg, 72% yield). $^1$H NMR (300 MHz, $D_2O$): δ 1.39 (s, 3H), 3.54 (m, 2H), 3.99 (d, 1H, J=4.6), 4.63 (m, 1H), 6.09 (d, 1H, J=7.0), 6.14 (d, 1H, J=7.0), 8.0 (d, 1H, J=7.6). LRMS (ESI) $MH^+$ $C_{10}H_{16}N_3O_8P$ requires 338.2. Found 337.8.

Bis-amidate prodrug 30.7

To a solution of compound 30.6 (31.7 mg, 0.094 mmol) in pyridine (2 mL) was added the bis-alabutylamine (85.0 mg, 0.47 mmol), triphenylphosphine (148 mg, 0.56 mmol), triethylamine (80 uL, 0.47 mmol) and Aldrichthiol-2 (104 mg, 0.47 mmol). The mixture was heated to 60° C. for 3 h and then concentrated down under reduced pressure. The residue was diluted in ethyl acetate and washed with a 1N solution of $NaH_2PO_4$ and then with brine. The organic layer was dried over $Na_2SO_4$, filtered, and concentrated under reduced pressure. The residue was subjected to a silica gel column chromatography eluting with 10% MeOH in $CH_2Cl_2$ to give compound 30.7 (11 mg, 20% yield).

Example 10

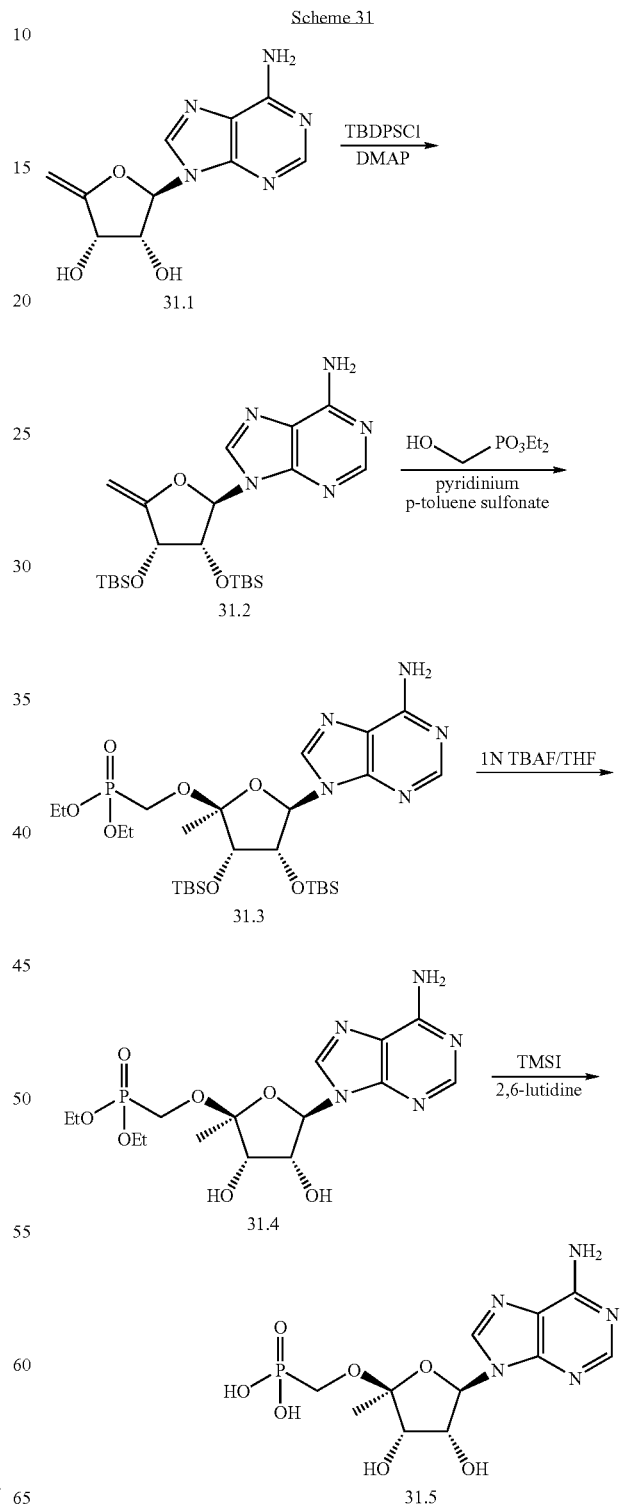

Scheme 31

9-((2R,3R,4S)-3,4-bis(tert-butyldimethylsilyloxy)-5-methylene-tetrahydrofuran-2-yl)-9H-purin-6-amine (31.2).

To a solution of compound 31.1 (276 mg, 2.39 mmol) in DMF (10 mL) was added imidazole (604 mg, 8.9 mmol) and DMAP (135 mg, 1.1 mmol) and finally tert-butyldimethylsilyl chloride (665 mg, 4.4 mmol). The mixture was heated to 60° C. for 4 h, water was added and the aqueous layer was extracted with ethyl acetate. The organic layer was dried over MgSO$_4$, filtered, and concentrated under reduced pressure. The residue was subjected to a silica gel column chromatography eluting with 50% EtOAc in Hexane to give compound 31.2 (280 mg, 63% yield). $^1$H NMR (300 MHz, CDCl$_3$): δ −0.30 (s, 3H), −0.06 (s, 3H), 0.16 (s, 6H), 0.77 (s, 9H), 0.96 (s, 9H), 4.30 (s, 1H), 4.54 (s, 1H), 4.60 (d, 1H, J=4.2), 5.10 (t, 1H), 5.52 (s, 2H), 6.12 (d, 1H, J=5.8), 7.89 (s, 1H), 8.39 (s, 1H). LRMS (ESI) MH$^+$ C$_{22}$H$_{39}$N$_5$O$_3$Si$_2$ requires 478.8. Found 477.9.

diethyl ((2R,3S,4R,5R)-5-(6-amino-9H-purin-9-yl)-3,4-bis(tert-butyldimethylsilyloxy)-2-methyl-tetrahydrofuran-2-yloxy)methylphosphonate (31.3)

To a solution of compound 31.2 (280 mg, 0.59 mmol) in dichloroethane (5 mL) was added diethyl (hydroxymethyl)phosphonate (0.22 mL, 1.47 mmol) and pyridinium p-toluene sulfonate (56 mg, 0.29 mmol). The mixture was heated to 60° C. for 1 h and then concentrated under reduced pressure. The residue was subjected to a silica gel column chromatography eluting with 10% MeOH in CH$_2$Cl$_2$ to give compound 31.3 (102 mg, 16% yield). $^1$H NMR (300 MHz, CDCl$_3$): δ −0.45 (s, 3H), −0.08 (s, 3H), 0.05 (s, 3H), 0.71 (s, 9H), 0.98 (s, 9H), 1.35 (m, 6H), 1.61 (s, 3H), 3.78 (t, 1H), 3.95 (t, 1H), 4.04 (s, 1H), 4.21 (m, 4H), 4.96 (m, 1H), 6.24 (d, 1H, J=6.7), 8.10 (s, 1H), 8.70 (s, 1H). LRMS (ESI) MH$^+$ C$_{27}$H$_{52}$N$_5$O$_7$PSi$_2$ requires 646.9. Found 645.9.

diethyl ((2R,3S,4R,5R)-5-(6-amino-9H-purin-9-yl)-3,4-dihydroxy-2-methyl-tetrahydrofuran-2-yloxy) methylphosphonate (31.4).

To a solution of compound 31.3 (102 mg, 0.16 mmol) in THF (5 mL) was added a 1N solution of tetrabutylammonium fluoride in THF (0.15 mL, 0.5 mmol). The mixture was stirred at r.t. for 1 h and concentrated down under reduced pressure. The residue was subjected to a silica gel column chromatography eluting with 10% MeOH in CH$_2$Cl$_2$ to give compound 31.4 (38 mg, 59% yield). $^1$H NMR (300 MHz, CD$_3$OD): δ 1.28 (m, 6H), 1.52 (s, 3H), 3.62 (m, 1H), 3.80 (m, 2H), 4.02 (m, 4H), 4.11 (m, 1H), 6.15 (d, 1H, J=7.1), 8.1 (s, 1H), 8.75 (s, 1H). LRMS (ESI) MH$^+$ C$_{15}$H$_{24}$N$_5$O$_7$P requires 418.4. Found 417.9.

((2R,3S,4R,5R)-5-(6-amino-9H-purin-9-yl)-3,4-dihydroxy-2-methyl-tetrahydrofuran-2-yloxy)methylphosphonic acid (31.5)

To a solution of compound 31.4 (20 mg, 0.048 mmol) in acetonitrile (2 mL) was added 2,6-lutidine (0.034 mL, 0.29 mmol) and then trimethylsilyl iodide (0.068 mL, 0.48 mmol). The mixture was stirred at room temperature for 1 h. After the reaction was done, 0.08 mL of 2,6-lutidine was added to the mixture and the mixture was concentrated under reduced pressure. The residue was then put into solution with water (2 mL) and treated with sodium hydroxide 1N to pH=10. The solution was then acidify to pH=3 using acetic acid and subjected to a reverse phase (YMC-Pack ODS-A) to give compound 31.5 (69 mg, 72% yield). $^1$H NMR (300 MHz, D$_2$O): δ 1.42 (s, 3H), 3.33 (t, 1H, J=10.7), 3.51 (t, 1H, J=11.9), 4.12 (d, 1H, J=4.6), 5.18 (m, 1H), 6.10 (d, 1H, J=7.1), 8.24 (s, 1H), 8.55 (s, 1H). LRMS (ESI) MH$^+$ C$_{11}$H$_{16}$N$_5$O$_7$P requires 362.3. Found 361.9.

Example 11

Scheme 32

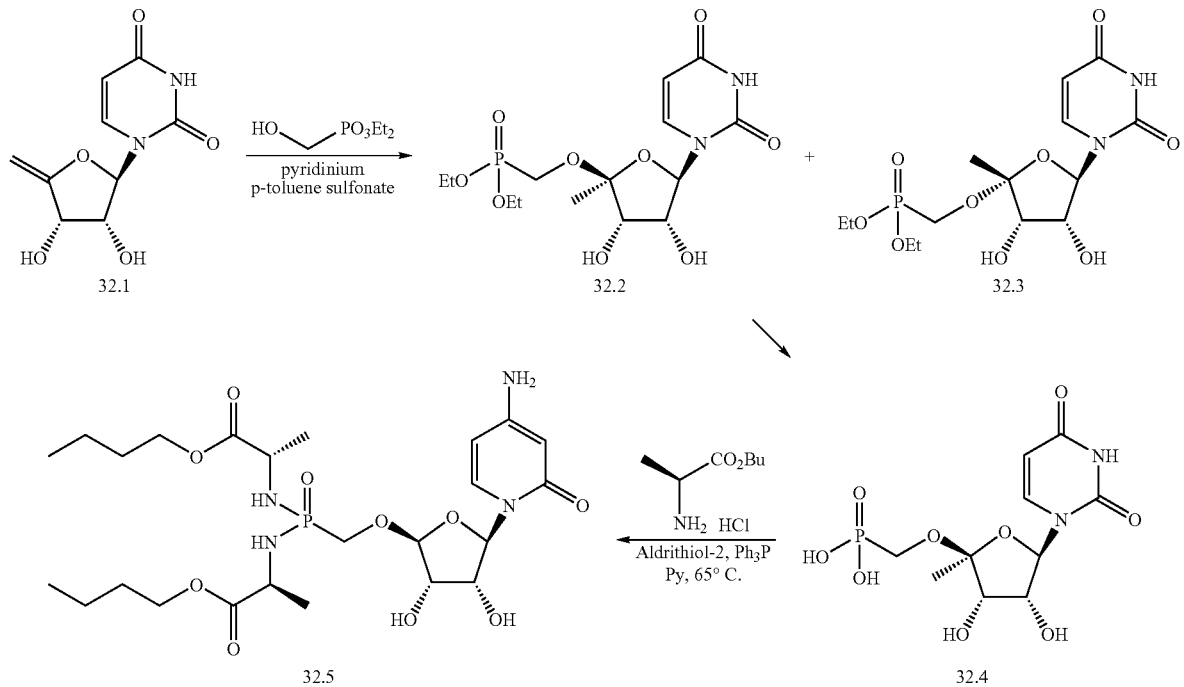

diethyl ((2R,3S,4R,5R)-5-(2,4-dioxo-3,4-dihydropyrimidin-1(2H)-yl)-3,4-dihydroxy-2-methyl-tetrahydrofuran-2-yloxy)methylphosphonate (32.2);

diethyl ((2S,3S,4R,5R)-5-(2,4-dioxo-3,4-dihydropyrimidin-1(2H)-yl)-3,4-dihydroxy-2-methyl-tetrahydrofuran-2-yloxy)methylphosphonate (32.3).

To a solution of compound 32.1 (0.67 g, 2.8 mmol) in dimethyl formamide (15 mL) was added diethyl (hydroxymethyl) phosphonate (0.65 mL, 4.4 mmol) and pyridinium p-toluene sulfonate (0.37 g, 1.5 mmol). The mixture was heated to 80° C. for 1 h and then concentrated under reduced pressure. The residue was subjected to a silica gel column chromatography eluting with 10% MeOH in $CH_2Cl_2$ and then 10% MeOH in EtOAc to give two diastereoisomers, compound 32.2 (80 mg, 7% yield) and compound 32.3 (100 mg, 8.5% yield). Data for compound 32.2: $^1$H NMR (300 MHz, $CD_3OD$): 1.37 (t, 6H), 1.52 (s, 3H), 3.95 (m, 1H), 4.02 (m, 2H), 4.10 (m, 2H), 4.25 (m, 4H), 5.71 (d, 1H, J=8.0), 5.85 (d, 1H, J=2.7), 7.56 (d, 1H, J=8.0). LRMS [M-H]$^-$ $C_{14}H_{23}N_2O_9P$ requires 393.3. Found 393.2.

((2R,3S,4R,5R)-5-(2,4-dioxo-3,4-dihydropyrimidin-1(2H)-yl)-3,4-dihydroxy-2-methyl-tetrahydrofuran-2-yloxy)methylphosphonic acid (32.4).

Compound 32.4 (61 mg, 75% yield) was synthesized from compound 32.2 (95 mg, 0.24 mmol) using the procedure described for the preparation of compound 31.5. $^1$H NMR (300 MHz, $D_2O$) δ 1.38 (s, 3H), 3.50 (m, 2H), 3.98 (d, 1H, J=4.6), 5.84 (d, 1H, J=7.6), 6.08 (d, 1H, J=7.3), 7.81 (d, 1H, J=8.2). LRMS [M-H]$^-$ $C_{10}H_{15}N_2O_9P$ requires 337.2. Found 337.2.

Bisamidate Prodrug 32.5

Compound 32.5 (6.2 mg, 18% yield) was synthesized from compound 32.4 (19.4 mg, 0.057 mmol) using the procedure described for the preparation of compound 30.7. $^1$H NMR (300 MHz, $CD_3OD$): δ 0.98 (t, 6H, J=7.3), 1.34-1.46 (m, 8H), 1.44 (s, 3H), 1.66 (m, 4H), 3.67 (m, 2H), 3.91 (d, 1H, J=4.5), 4.18 (m, 4H), 4.56 (m, 1H), 5.69 (d, 1H, J=8.3), 6.07 (d, 1H, J=7.4), 7.93 (d, 1H, J=8.2).

HCV Replicon and Cytotoxicity Assays

The compounds of the present invention can be evaluated using known HCV replicon assays and cytotoxicity assays, for example those described in Stuyver et al., *Antimicrobial Agents and Chemotherapy* 2003, 47 (1), pp. 244-254, and Lohman et al., *Science* 1999, vol. 285, pp. 110-113, each of which is herein incorporated by reference in its entirety. Exemplary experimental protocols are shown below.

HCV $IC_{50}$ Determination

Assay Protocol: NS5b polymerase assay (40 µL) was assembled by adding 28 µL polymerase mixture (final concentration: 50 mM Tris-HCl at pH 7.5, 10 mM KCL, 5 mM $MgCl_2$, 1 mM DTT, 10 mM EDTA, 4 ng/µL of RNA template, and 75 nM HCV ⓡ 21 NS5b polymerase) to assay plates followed by 4 µL of compound dilution. The polymerase and compound were pre-incubated at 35° C. for 10 minute before the addition of 8 µL of nucleotide substrate mixture (33P-ⓡ-labeled competing nucleotide at $K_M$ and 0.5 mM of the remaining three nucleotides). The assay plates were covered and incubated at 35° C. for 90 min. Reactions were then filtered through 96-well DEAE-81 filter plates via vacuum. The filter plates were then washed under vacuum with multiple volumes of 0.125 M $NaHPO_4$, water, and ethanol to remove unincorporated label. Plates were then counted on TopCount to assess the level of product synthesis over background controls. The IC50 value was determined using Prism fitting program.

Table 2E shows representative examples of the activity of the compounds of the invention at a particular concentration when tested in this assay.

TABLE 2E

Representative activity of compounds in the polymerase assay.

| Compound | Concentration tested (micromolar) | % Inhibition of polymerase |
|---|---|---|
| 9.4 | 200 | 65.5 |
| 2.4 diphosphophosphonate | 200 | 40.2 |

HCV $EC_{50}$ Determination

Replicon cells were seeded in 96-well plates at a density of $8 \times 10^3$ cells per well in 100 µL of culture medium, excluding Geneticin. Compound was serially diluted in 100% DMSO and then added to the cells at a 1:200 dilution, achieving a final concentration of 0.5% DMSO and a total volume of 200 µL. Plates were incubated at 37° C. for 3 days, after which culture medium was removed and cells were lysed in lysis buffer provided by Promega's luciferase assay system. Following the manufacturer's instruction, 100 µL of luciferase substrate was added to the lysed cells and luciferase activity was measured in a TopCount luminometer.

Typically, compounds of the invention that were tested were found to have an EC50 of less than about 1000 µM (Huh7). Some compounds demonstrated an EC50 of less than about 250 µM (Huh7).

Table 3E shows representative examples of the activity of the compounds of the invention at a particular concentration when tested in this assay.

TABLE 3E

Representative activity of compounds in the replicon assay.

| Compound | Concentration tested (micromolar) | % Inhibition of replicon |
|---|---|---|
| 8.3 | 250 | 18.5 |
| 9.5 | 50 | 1.1 |
| 2.5 | 250 | 23.6 |
| 5.2 | 250 | 27.2 |
| 5.3 | 250 | 31.9 |
| 32.4 | 250 | 14.8 |
| 32.5 | 500 | 37.5 |

The cytotoxicity of a compound of the invention can be determined using the following general protocol.

Cytotoxicity Cell Culture Assay (Determination of CC50):

The assay is based on the evaluation of cytotoxic effect of tested compounds using a metabolic substrate.

Assay Protocol for Determination of CC50:
1. Maintain MT-2 cells in RPMI-1640 medium supplemented with 5% fetal bovine serum and antibiotics.
2. Distribute the cells into a 96-well plate (20,000 cell in 100 µl media per well) and add various concentrations of the tested compound in triplicate (100 µl/well). Include untreated control.
3. Incubate the cells for 5 days at 37° C.

4. Prepare XTT solution (6 ml per assay plate) in dark at a concentration of 2 mg/ml in a phosphate-buffered saline pH 7.4. Heat the solution in a water-bath at 55° C. for 5 min. Add 50 μl of N-methylphenazonium methasulfate (5 μg/ml) per 6 ml of XTT solution.
5. Remove 100 μl media from each well on the assay plate and add 100 μl of the XTT substrate solution per well. Incubate at 37° C. for 45 to 60 min in a $CO_2$ incubator.
6. Add 20 μl of 2% Triton X-100 per well to stop the metabolic conversion of XTT.
7. Read the absorbance at 450 nm with subtracting off the background at 650 nm.
8. Plot the percentage absorbance relative to untreated control and estimate the CC50 value as drug concentration resulting in a 50% inhibition of the cell growth. Consider the absorbance being directly proportional to the cell growth.

We claim:
1. A compound having a structure according to Formula I, Formula II, Formula III or Formula IV:

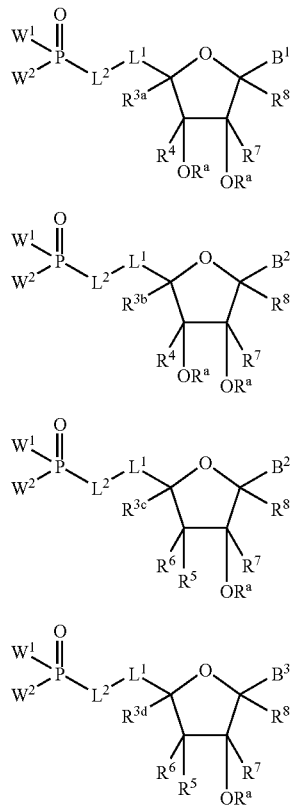

or a pharmaceutically acceptable salt, solvate, and/or ester thereof, wherein:
L$^1$ is —O—, —S—, or —N(R$^{11}$)—;
L$^2$ is —C(R$^{10}$)$_2$—;
each R$^{3a}$ is CH$_2$R$^9$, alkenyl, substituted alkenyl, alkynyl, or substituted alkynyl;
each R$^{3b}$ is CH$_2$R$^9$, alkenyl, substituted alkenyl, alkynyl, or substituted alkynyl wherein R$^9$ is not H;
each R$^{3c}$ is CH$_2$R$^9$, alkenyl, substituted alkenyl, alkynyl, or substituted alkynyl wherein R$^9$ is not H, OH, or F;
each R$^{3d}$ is H, CH$_2$R$^9$, alkenyl, substituted alkenyl, alkynyl, or substituted alkynyl;
each R$^4$ is independently H, CH$_2$R$^9$, alkenyl, substituted alkenyl, alkynyl, or substituted alkynyl;
each R$^5$ and R$^6$ is independently H, N(R$^a$)$_2$, N$_3$, CN, NO$_2$, SR$^a$, halogen, CH$_2$R$^9$, alkenyl, substituted alkenyl, alkynyl, or substituted alkynyl; or R$^5$ and R$^6$ taken together are =O, =NR$^b$, or =CR$^c$R$^d$; or R$^5$ and R$^6$ taken together with the carbon atom to which they are attached form a 3-7 membered heterocyclic ring wherein one carbon atom in the heterocyclic ring can optionally be replaced with —O—, —S— or —NR$^a$—;
each R$^a$ is independently H, alkyl, substituted alkyl, alkenyl, substituted alkenyl, alkynyl, or substituted alkynyl;
each R$^b$ is independently H, alkyl, substituted alkyl, alkenyl, substituted alkenyl, alkynyl, substituted alkynyl, or OR$^a$;
each R$^c$ and R$^d$ are independently H, alkyl, substituted alkyl, alkenyl, substituted alkenyl, alkynyl, substituted alkynyl, or halo;
each R$^7$ is independently H, CH$_2$R$^9$, alkenyl, substituted alkenyl, alkynyl, or substituted alkynyl;
each R$^8$ is independently H, CH$_2$R$^9$, halo, alkyl, substituted alkyl, haloalkyl, —CN, —N$_3$, alkenyl, substituted alkenyl, alkynyl, or substituted alkynyl;
each R$^9$ is independently H, OH, halo, N$_3$, CN, N(R$^a$)$_2$, alkyl, substituted alkyl, alkenyl, substituted alkenyl, alkynyl, or substituted alkynyl, wherein one or more of the non-adjacent carbon atoms in the alkyl or substituted alkyl is optionally replaced with —O—, —S— or —NR$^a$—;
each R$^{10}$ is independently H, alkoxy, alkyl, or halo;
each R$^{11}$ is independently H, alkyl, aryl, or substituted aryl;
B$^1$ is a nucleobase selected from

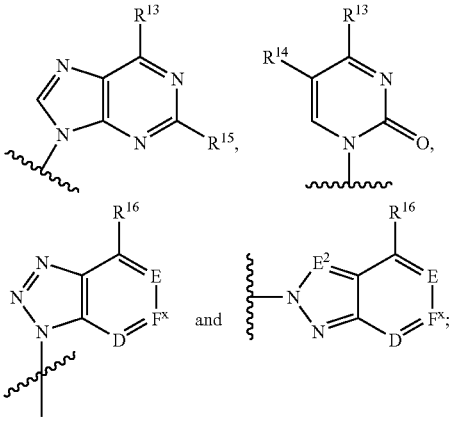

each R$^{13}$ is independently OH or NH$_2$;
R$^{14}$ is H or CH$_3$;
R$^{15}$ is H, amino, or halo;
R$^{16}$ is H, halo, OR$^{17a}$, N(R$^{20}$)(R$^{21}$), N(R$^{28}$)N(R$^{28}$)S(O)$_2$R$^{28}$, alkyl, substituted alkyl, alkenyl, substituted alkenyl, alkynyl, substituted alkynyl, aryl, substituted aryl, heteroaryl, substituted heteroaryl, S(O)$_m$R$^{28}$, or S(O)$_2$NR$^{17a}$R$^{17b}$, NR$^{17a}$R$^{17b}$, N$_3$, NO, NO$_2$, formyl, cyano, —C(O)NR$^{17a}$R$^{17b}$, C(S)NR$^{17a}$R$^{17b}$, or —C(O)OR$^{17a}$;
each R$^{17a}$ and R$^{17b}$ are independently H, alkyl, substituted alkyl, alkenyl, substituted alkenyl, alkynyl, substituted alkynyl, optionally substituted aryl, optionally substituted heteroaryl, or optionally substituted alkanoyl;
R$^{20}$ is H or OR$^{17a}$;

$R^{21}$ is H, alkyl, substituted alkyl, alkenyl, substituted alkenyl, alkynyl, substituted alkynyl, optionally substituted aryl, cycloalkyl, or arylalkyl; or $R^{20}$ and $R^{21}$ together with the nitrogen to which they are attached form an optionally substituted 3-7 membered heterocyclic ring wherein one carbon atom of the heterocyclic ring can optionally be replaced with —O—, —S— or —NR$^a$—;

$E^2$ is >N, >C—$R^{25}$ or >C—$R^{30}$;

D, E, and $F^x$ are each independently >N or >C—$R^{25}$;

each $R^{25}$ is independently H, cyano, nitro, azido, optionally substituted $(C_1-C_6)$alkyl, optionally substituted $(C_1-C_6)$alkenyl, optionally substituted $(C_1-C_6)$alkynyl, —NHCONH$_2$, C(O)NR$^{26}$R$^{27}$, C(S)NR$^{26}$R$^{27}$, C(O)OR$^{28}$, hydroxy, OR$^{28}$, S(O)$_m$R$^{28}$, S(O)$_m$NR$^{26}$R$^{27}$, —NR$^{26}$R$^{27}$, halo, 1,3-oxazol-2-yl, 1,3-oxazol-5-yl, 1,3-thiazol-2-yl, imidazol-2-yl, 2-oxo-[1,3]dithiol-4-yl, furan-2-yl, or 2H-[1,2,3]triazol-4-yl;

each $R^{26}$ and $R^{27}$ is independently H, optionally substituted $(C_1-C_6)$alkyl, optionally substituted $(C_1-C_6)$alkenyl, optionally substituted $(C_1-C_6)$alkynyl, optionally substituted $(C_3-C_8)$cycloalkyl, aryl, heteroaryl, optionally substituted heterocycle, hydroxy, optionally substituted $(C_1-C_6)$alkoxy; or $R^{26}$ and $R^{27}$ together with the nitrogen to which they are attached form an optionally substituted 3-7 membered heterocyclic ring wherein one carbon atom of the heterocyclic ring can optionally be replaced with —O—, —S— or —NR$^a$—;

each $R^{28}$ is independently H, optionally substituted $(C_1-C_6)$alkyl, optionally substituted $(C_1-C_6)$alkenyl, optionally substituted $(C_1-C_6)$alkynyl, optionally substituted $(C_3-C_8)$cycloalkyl, aryl, heteroaryl or heterocycle;

$R^{30}$ is —C≡CR$^{31}$, —CH=CHR$^{32}$, formyl, —CH=NNHR$^{33}$, —CH=N(OR$^{33}$), —CH(OR$^{34}$), or —B(OR$^{33}$);

$R^{31}$ is H, tri$(C_1-C_6)$alkylsilyl, $(C_1-C_6)$alkoxy$(C_1-C_6)$alkyl, optionally substituted heteroaryl, optionally substituted aryl, carboxy, or $(C_1-C_6)$alkoxycarbonyl;

$R^{32}$ is hydrogen or $(C_1-C_6)$alkoxy;

$R^{33}$ is H or $(C_1-C_6)$alkyl;

$R^{34}$ is $(C_1-C_6)$alkyl;

m is 0, 1, or 2;

wherein each aryl or heteroaryl of $R^{26}$, $R^{27}$, $R^{28}$ and $R^{31}$ is independently optionally substituted with one or more $(C_1-C_6)$alkyl, $(C_1-C_6)$alkoxy, $(C_1-C_6)$alkanoyl, $(C_1-C_6)$alkanoyloxy, $(C_1-C_6)$alkoxycarbonyl, NR$^{35}$R$^{36}$, —C(=O)NR$^{35}$R$^{36}$, cyano, halo, hydroxy, nitro, carboxy, $(C_3-C_8)$cycloalkyl, $(C_3-C_8)$cycloalkoxy, guanidino, trifluoromethoxy, mercapto, S(O)$_m$R$^{38}$, S(O)$_m$NR$^{35}$R$^{36}$ or trifluoromethyl;

$R^{35}$ and $R^{36}$ are each independently H, $(C_1-C_6)$alkyl or $(C_1-C_6)$alkanoyl;

$R^{38}$ is H, $(C_1-C_6)$alkyl or $(C_1-C_6)$alkanoyl;

$B^2$ is a nucleobase selected from

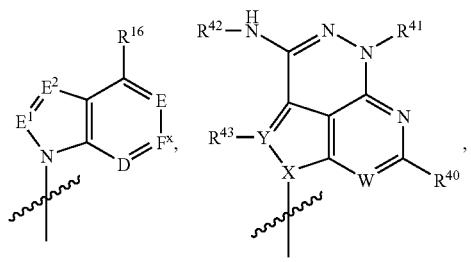

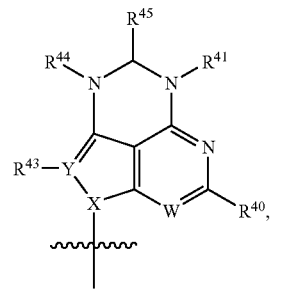

-continued

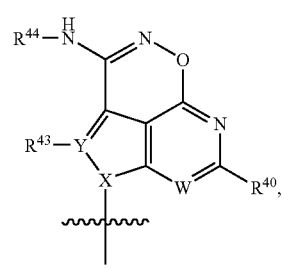

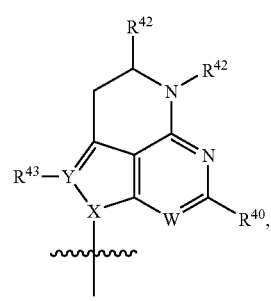

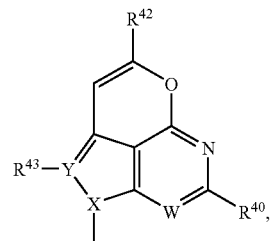

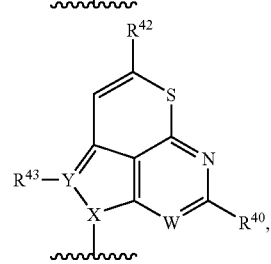

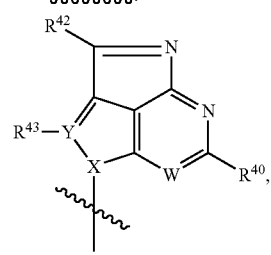

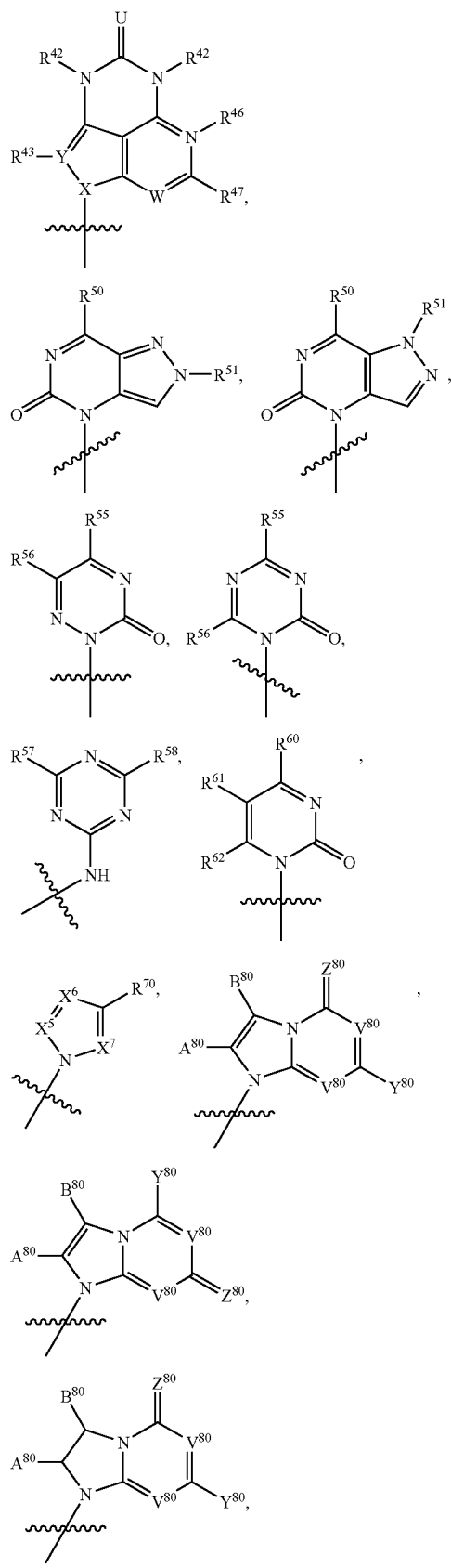
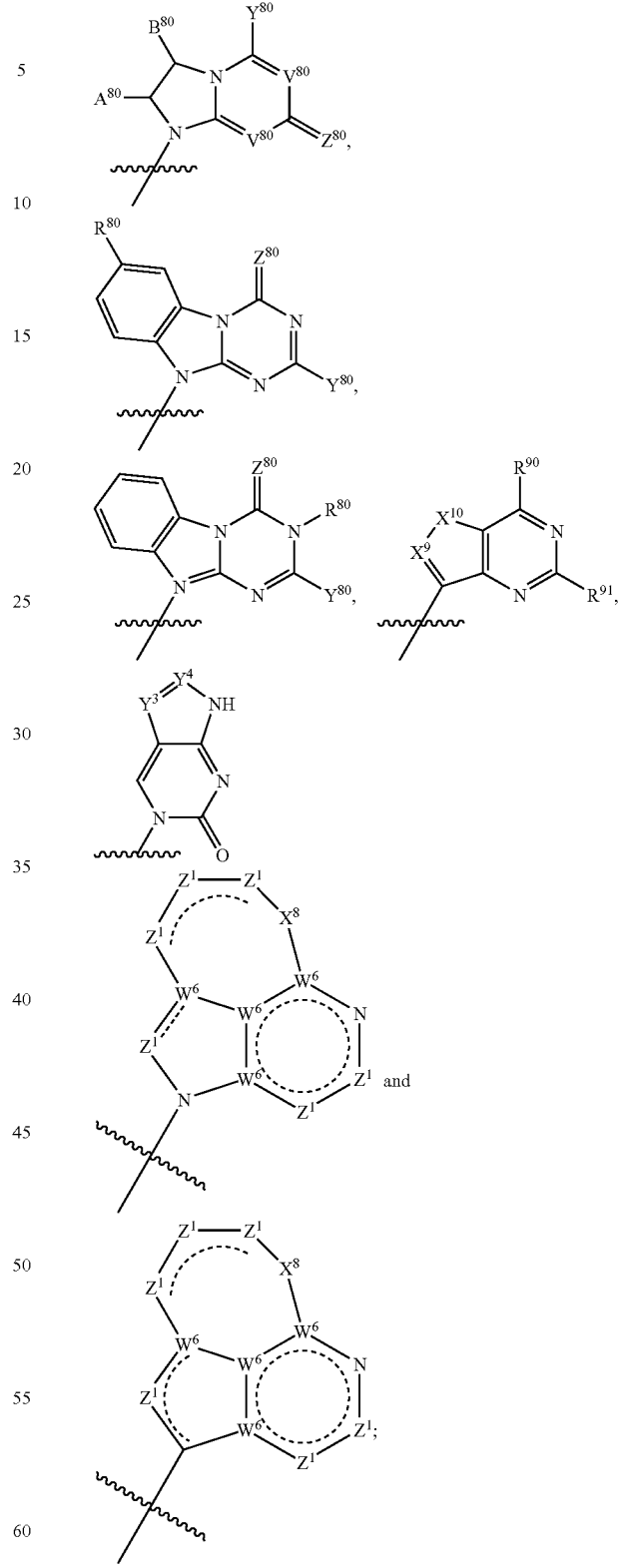
$E^1$ is >N or >C—$R^{25}$;
$E^2$, $R^{16}$, E, $F^x$, and D are defined as for $B^1$;
$R^{40}$ is H, $NR^{4a}R^{4b}$, $NHC(O)R^{4b}$, $(C_1$-$C_6)$alkyl$NR^{4a}R^{4b}$, $NHNH_2$, cyano, $(C_1$-$C_6)$alkyl, $(C_2$-$C_6)$alkenyl, $(C_2$-$C_6)$ alkynyl, aryl($C_1$-$C_6$)alkyl, heterocycle($C_1$-$C_6$)alkyl, halo, ($C_1$-$C_6$)alkylthio, ($C_1$-$C_6$)alkoxy, hydroxy, or mercapto;

$R^{41}$ is H, ($C_1$-$C_6$)alkyl, hydroxy($C_1$-$C_6$)alkyl, ($C_2$-$C_6$)alkenyl, ($C_2$-$C_6$)alkynyl, heterocycle, aryl, aryl($C_1$-$C_6$) alkyl;

each $R^{42}$ is independently H, hydroxy, mercapto, cyano, —SNR$^{4c}$R$^{4d}$, —C(NH)NR$^{4c}$R$^{4d}$, —C(=NH)NHOH, —C(NH)NHOR$^{4c}$, —C(=NH)NHNR$^{4c}$R$^{4d}$, NHCOR$^{4c}$, SR$^{4c}$, OR$^{4c}$, SOR$^{4c}$, SO$_2$R$^{4c}$, —C(O)NR$^{4c}$R$^{4d}$, —C(S)NR$^{4c}$R$^{4d}$, or R$^{4c}$;

$R^{43}$ is H, hydroxy, NR$^{4c}$R$^{4d}$, NHC(O)NR$^{4c}$, NHNHR$^{4c}$, ($C_1$-$C_6$)alkyl, ($C_2$-$C_6$)alkenyl, ($C_2$-$C_6$)alkynyl, heterocycle, aryl, aryl($C_1$-$C_6$)alkyl, halo, C(O)OR$^{4c}$, C(O)NR$^{4c}$R$^{4d}$, or absent when Y is N;

$R^{4a}$ and $R^{4b}$ are each independently hydrogen, ($C_1$-$C_6$) alkyl, ($C_2$-$C_6$)alkenyl, ($C_2$-$C_6$)alkynyl, heterocycle, or aryl;

$R^{4c}$, and $R^{4d}$ are each independently hydrogen, ($C_1$-$C_6$) alkyl, ($C_2$-$C_6$)alkenyl, ($C_2$-$C_6$)alkynyl, heterocycle, or aryl;

X, Y, and W are each independently N, C, CR$^{4c}$, S or P;

each $R^{44}$ and $R^{45}$ is independently H, hydroxy, mercapto, cyano, —SNR$^{4c}$R$^{4d}$, —C(NH)NR$^{4c}$R$^{4d}$, —C(=NH)NHOH, —C(NH)NHOR$_{4c}$, —C(=NH)NHNR$^{4c}$R$^{4d}$, NHCOR$^{4c}$, SR$^{4c}$, OR$^{4c}$, SOR$^{4c}$, SO$_2$R$^{4c}$, —C(O)NR$^{4c}$R$^{4d}$, —C(S)NR$^{4c}$R$^{4d}$, or R$^{4c}$;

$R^{46}$, and $R^{47}$ together with the atoms to which they are attached form a heterocyclic ring;

U is S or O;

wherein each aryl or heterocycle of $R^{40}$, $R^{41}$, $R^{42}$, $R^{43}$, $R^{4a}$, $R^{4b}$, $R^{4c}$, $R^{4d}$, $R^{44}$ and $R^{45}$ is optionally substituted with one or more ($C_1$-$C_6$)alkyl, ($C_1$-$C_6$)alkylthio, ($C_1$-$C_6$) alkoxy, ($C_1$-$C_6$)alkanoyl, ($C_1$-$C_6$)alkanoyloxy, ($C_1$-$C_6$) alkoxycarbonyl, cyano, halo, hydroxy, nitro, carboxy, ($C_3$-$C_8$)cycloalkyl, ($C_3$-$C_8$)cycloalkoxy, trifluoromethoxy, mercapto, or trifluoromethyl;

$R^{50}$ is NR$^{5a}$R$^{5b}$, ONR$^{5a}$R$^{5b}$, NR$^{5a}$NR$^{5a}$R$^{5b}$, SR$^{5b}$, OR$^{5b}$, H, hydroxy, ($C_1$-$C_6$)alkyl, ($C_1$-$C_6$)alkenyl, ($C_1$-$C_6$)alkynyl, or aryl;

$R^{51}$ is ($C_1$-$C_6$)alkyl, ($C_1$-$C_6$)alkanoyl, or aryl;

$R^{55}$ is NR$^{5a}$R$^{5b}$, ONR$^{5a}$R$^{5b}$, NR$^{5a}$NR$^{5a}$R$^{5b}$, SR$^{5b}$, OR$^{5b}$, H, halo, hydroxy, ($C_1$-$C_6$)alkyl, ($C_2$-$C_6$)alkenyl, ($C_2$-$C_6$) alkynyl, or aryl;

$R^{56}$ is H, halo, ($C_1$-$C_6$)alkyl, ($C_2$-$C_6$)alkenyl or ($C_2$-$C_6$) alkynyl;

$R^{57}$ and $R^{58}$ are each independently -L-R$^{5c}$;

each L is independently a direct bond, —N(R$^{5a}$)—, O or S;

each $R^{5a}$ and $R^{5b}$ is independently H, hydroxy, ($C_1$-$C_6$) alkyl, ($C_2$-$C_6$)alkenyl, ($C_2$-$C_6$)alkynyl, or aryl;

each $R^{5c}$ is NR$^{5a}$R$^{5b}$, H, hydroxy, ($C_1$-$C_6$)alkyl, ($C_2$-$C_6$) alkenyl, ($C_2$-$C_6$)alkynyl, or aryl;

wherein each ($C_1$-$C_6$)alkyl, ($C_2$-$C_6$)alkenyl, ($C_2$-$C_6$)alkynyl, or aryl of $R^{50}$, $R^{51}$, $R^{55}$, $R^{56}$, $R^{57}$, $R^{58}$, $R^{5a}$, $R^{5b}$ and $R^{5c}$ is optionally substituted with one or more ($C_1$-$C_6$) alkyl, ($C_1$-$C_6$)alkylthio, ($C_1$-$C_6$)alkoxy, ($C_1$-$C_6$)alkanoyl, ($C_1$-$C_6$)alkanoyloxy, ($C_1$-$C_6$)alkoxycarbonyl, cyano, halo, hydroxy, nitro, carboxy, ($C_3$-$C_8$)cycloalkyl, ($C_3$-$C_8$)cycloalkoxy, trifluoromethoxy, mercapto, or trifluoromethyl;

$R^{60}$, $R^{61}$, and $R^{62}$ are each independently H, halo, NR$^{6b}$R$^{6c}$, hydroxyamino, NR$^{6b}$NR$^{6b}$R$^{6c}$, $N_3$, NO, $NO_2$, formyl, cyano, —C(O)NR$^{6b}$R$^{6c}$, —C(S)NR$^{6b}$R$^{6c}$, —C(O)OR$^{6b}$, R$^{6b}$, OR$^{6b}$ or SR$^{6b}$;

$R^{6b}$, and $R^{6c}$ are each independently H, ($C_1$-$C_6$)alkyl, ($C_2$-$C_6$)alkenyl, ($C_2$-$C_6$)alkynyl, aryl, ($C_1$-$C_6$)alkanoyl, or aryl($C_1$-$C_6$)alkyl;

wherein each ($C_1$-$C_6$)alkyl, ($C_2$-$C_6$)alkenyl, ($C_2$-$C_6$)alkynyl, or aryl of R$^{6b}$ and R$^{6c}$ is optionally substituted with one or more ($C_1$-$C_6$)alkyl, ($C_1$-$C_6$)alkylthio, ($C_1$-$C_6$) alkoxy, ($C_1$-$C_6$)alkanoyl, ($C_1$-$C_6$)alkanoyloxy, ($C_1$-$C_6$) alkoxycarbonyl, cyano, halo, hydroxy, nitro, carboxy, ($C_3$-$C_8$)cycloalkyl, ($C_3$-$C_8$)cycloalkoxy, trifluoromethoxy, mercapto, or trifluoromethyl;

$X^5$, $X^6$, and $X^7$ are each independently N, CH, or C—R$^{7a}$;

$R^{70}$ and $R^{7a}$ are each independently H, halo, NR$^{7b}$R$^{7c}$, hydroxyamino, NR$^{7b}$NR$^{7b}$R$^{7c}$, $N_3$, NO, $NO_2$, formyl, cyano, —C(O)NR$^{7b}$R$^{7c}$, —C(S)NR$^{7b}$R$^{7c}$, —C(O)OR$^{7b}$, R$^{7b}$, OR$^{7b}$, or SR$^{7b}$;

$R^{7b}$, and $R^{7c}$ are each independently H, ($C_1$-$C_6$)alkyl, ($C_2$-$C_6$)alkenyl, ($C_2$-$C_6$)alkynyl, aryl, ($C_1$-$C_6$)alkanoyl, or aryl($C_1$-$C_6$)alkyl;

$A^{80}$, $B^{80}$, and $Y^{80}$ are each independently H, halo, OR$^{80}$, S(O)$_n$R$^{80}$, NR$^{80}$R$^{81}$, cyano, trifluoromethyl, C(W$^{80}$) OR$^{80}$, C(W$^{80}$)SR$^{80}$, C(W$^{80}$)NR$^{80}$R$^{81}$, nitro, azido, carbocyclic, ($C_1$-$C_6$)alkyl, ($C_2$-$C_6$)alkenyl, ($C_2$-$C_6$)alkynyl, aryl, aryl($C_1$-$C_6$)alkyl, or heterocycle; or $A^{80}$ and $B^{80}$ taken together with the carbon atoms to which they are attached from a 4-7 membered carbocyclic or heterocyclic ring;

$W^{80}$ is O, S, NR$^{80}$;

n is 0, 1, or 2;

$Z^{80}$ is O, S, NR$^{80}$, or CR$^{80}$R$^{81}$;

each $V^{80}$ is independently N or CR$^{80}$;

each $R^{80}$ and $R^{81}$ is independently H, carbocycle, ($C_1$-$C_6$) alkyl, ($C_2$-$C_6$)alkenyl, ($C_2$-$C_6$)alkynyl, halo, ($C_1$-$C_6$) alkoxy, amino, methylamino, dimethylamino, cyano, ($C_1$-$C_6$)alkanoyl, aryl, aryl($C_1$-$C_6$)alkyl, an amino acid residue or heterocycle; or R$^{80}$ and R$^{81}$ taken together with the atom(s) to which they are attached form a 3-7 membered carbocyclic or heterocyclic ring;

$X^9$ is CR$^{90a}$ or N;

$X^{10}$ is O, S, or NR$^{91a}$;

$R^{90}$ and $R^{91}$ are each independently H, halo, hydroxy, ($C_1$-$C_6$)alkoxy, NR$^{90b}$R$^{91b}$, aryl, heterocycle; ($C_1$-$C_6$)alkyl, ($C_2$-$C_6$)alkenyl, ($C_2$-$C_6$)alkynyl, ($C_3$-$C_8$)cycloalkyl, aryl($C_1$-$C_6$)alkyl, S(O)$_m$R$^{90b}$, S(O)$_m$(aryl), or S(O)$_m$NR$^{90b}$R$^{91b}$;

$R^{90a}$ is H, halo, methyl, azido, or amino;

$R^{91a}$ is H, ($C_1$-$C_6$)alkyl or ($C_1$-$C_6$) alkanoyl;

$R^{90b}$ and $R^{91b}$ are each independently H, ($C_1$-$C_6$)alkyl, ($C_3$-$C_8$)cycloalkyl, aryl($C_1$-$C_6$)alkyl, aryl, ($C_1$-$C_6$) alkanoyl, or aryl-C(O)—;

wherein each ($C_1$-$C_6$)alkyl, ($C_3$-$C_8$)cycloalkyl, aryl($C_1$-$C_6$)alkyl, aryl, ($C_1$-$C_6$) alkanoyl, aryl-C(O)— and heterocycle of $R^{90}$, $R^{91}$, $R^{91a}$, $R^{90b}$ and $R^{91b}$ are optionally substituted with one to four halo, hydroxy, amino, ($C_1$-$C_6$)alkyl, and ($C_1$-$C_6$)alkoxy;

each $Z^1$ is independently N, C—R$^{9a}$, O, S, NR$^{9b}$, >C=O, >C=S, >C=NR$^{9b}$, >S=O, >S(O)$_2$ or CH—R$^{9a}$; provided that if a $Z^1$ participates in an optional bond represented by a dotted line ▬▬▬ in the formula, then that $Z^1$ is N or C—R$^{9a}$; and provided that if a $Z^1$ does not participate in an optional bond represented by a dotted line ▬▬▬ in the formula, then that $Z^1$ is O, S, NR$^{9b}$, >C=O, >C=S, >C=NR$^{9b}$, >S=O, >S(O)$_2$ or CH—R$^{9a}$;

$X^8$ is O, S, SO, $SO_2$, Se, SeO, $SeO_2$ or NR$^{9b}$;

each $W^6$ is C, CH, or N; wherein if a $W^6$ participates in an optional bond represented by a dotted line ▬▬▬ in the formula, then that $W^6$ is C; and if a $W^6$ does not participate in an optional bond represented by a dotted line ▬▬▬ in the formula, then that $W^6$ is CH, or N;

each $R^{9a}$ is independently H, halo, $NR^{9c}R^{9d}$, hydroxyamino, $NR^{9c}NR^{9c}R^{9d}$, $N_3$, cyano, C(O)$NR^{9c}R^{9d}$, —C(S)$NR^{9c}R^{9d}$, —C(S)$NR^{9c}R^{9d}$, —C(=NH)$OR^{9c}$, $R^{9c}$, $OR^{9c}$, or $SR^{9c}$;

each $R^{9b}$ is independently H, ($C_1$-$C_6$)alkyl, ($C_2$-$C_6$)alkenyl, ($C_2$-$C_6$)alkynyl, aryl, ($C_1$-$C_6$)alkanoyl, or aryl($C_1$-$C_6$)alkyl;

$R^{9c}$ and $R^{9d}$ are each independently H, ($C_1$-$C_6$)alkyl, ($C_2$-$C_6$)alkenyl, ($C_2$-$C_6$)alkynyl, aryl, ($C_1$-$C_6$)alkanoyl, or aryl($C_1$-$C_6$)alkyl;

$Y^3$=$Y^4$ is —N=N—, —CH=N—, —N=$CR^{8a}$—, or —CH=$CR^{8a}$—;

each $R^{8a}$ is independently H, halo, or ($C_1$-$C_6$)alkyl;

$B^3$ is a nucleobase selected from

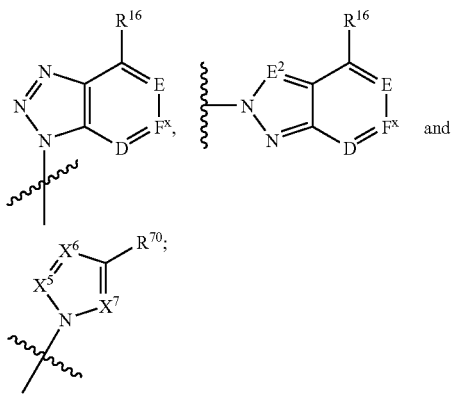

$W^1$ and $W^2$ are each independently a group of the formula:

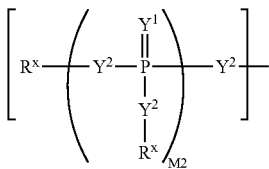

wherein:
each $Y^1$ is independently O, S, NR, $^+$N(O)(R), N(OR), $^+$N(O)(OR), or N—$NR_2$;
each $Y^2$ is independently a bond, O, $CR_2$, NR, $^+$N(O)(R), N(OR), $^+$N(O)(OR), N—$NR_2$, S, S—S, S(O), or S(O)$_2$;
M2 is 0, 1 or 2;
each $R^x$ is independently $R^y$, a protecting group, or the formula:

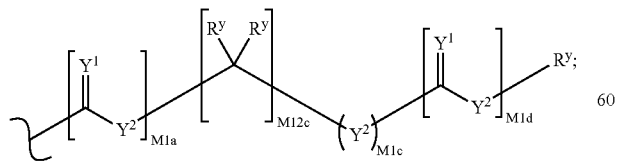

wherein:
M1a, M1c, and M1d are independently 0 or 1;
M12c is 0, 1, 2, 3, 4, 5, 6, 7, 8, 9, 10, 11 or 12; or when taken together, two $R^x$ are optionally substituted $C_2$-$C_4$ alkylene thereby forming a phosphorous-containing heterocycle;

each $R^y$ is independently H, F, Cl, Br, I, OH, R, —C(=$Y^1$)R, —C(=$Y^1$)OR, —C(=$Y^1$)N(R)$_2$, —N(R)$_2$, —$^+$N(R)$_3$, —SR, —S(O)R, —S(O)$_2$R, —S(O)(OR), —S(O)$_2$(OR), —OC(=$Y^1$)R, —OC(=$Y^1$)OR, —OC(=$Y^1$)(N(R)$_2$), —SC(=$Y^1$)R, —SC(=$Y^1$)OR, —SC(=$Y^1$)(N(R)$_2$), —N(R)C(=$Y^1$)R, —N(R)C(=$Y^1$)OR, or —N(R)C(=$Y^1$)N(R)$_2$, amino (—$NH_2$), ammonium (—$NH_3^+$), alkylamino, dialkylamino, trialkylammonium, $C_1$-$C_8$ alkyl, $C_1$-$C_8$ alkylhalide, carboxylate, sulfate, sulfamate, sulfonate, $C_1$-$C_8$ alkylsulfonate, $C_1$-$C_8$ alkylamino, $C_1$-$C_8$ alkylhydroxyl, $C_1$-$C_8$ alkylthiol, alkylsulfone (—$SO_2$R), sulfonamide (—$SO_2NR_2$), alkylsulfoxide (—SOR), ester (—C(=O)OR), amido (—C(=O)$NR_2$), nitrile (—CN), azido (—$N_3$), nitro (—$NO_2$), $C_1$-$C_8$ alkoxy (—OR), $C_1$-$C_8$ alkyl, $C_1$-$C_8$ substituted alkyl, $C_2$-$C_8$ alkenyl, $C_2$-$C_8$ substituted alkenyl, $C_2$-$C_8$ alkynyl, $C_2$-$C_8$ substituted alkynyl, a protecting group, or $W^3$; or when taken together, two $R^y$ on the same carbon atom forms a carbocyclic ring of 3 to 7 carbon atoms;

each R is independently H, halogen, $C_1$-$C_8$ alkyl, $C_1$-$C_8$ substituted alkyl, $C_2$-$C_8$ alkenyl, $C_2$-$C_8$ substituted alkenyl, $C_2$-$C_8$ alkynyl, $C_2$-$C_8$ substituted alkynyl, $C_6$-$C_{20}$ aryl, $C_6$-$C_{20}$ substituted aryl, $C_2$-$C_{20}$ heterocycle, $C_2$-$C_{20}$ substituted heterocycle or a protecting group;

$W^3$ is $W^4$ or $W^5$;
$W^4$ is R, —C($Y^1$)$R^y$, —C($Y^1$)$W^5$, —$SO_2R^y$, or —$SO_2W^5$; and
$W^5$ is a carbocycle or a heterocycle wherein $W^5$ is independently substituted with 0 to 3 $R^y$ groups.

2. A compound according to claim 1 wherein

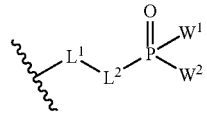

of Formula I, Formula II, Formula III, or Formula IV is

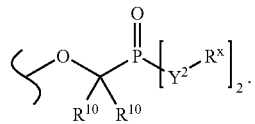

3. A compound according to claim 2 wherein each $Y^2$ is independently —O— or —N(R)—.

4. A compound according to claim 1 wherein

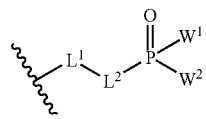

of Formula I, Formula II, Formula III, or Formula IV is

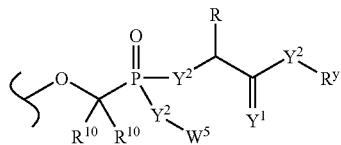

wherein $W^5$ is phenyl or substituted phenyl, and each $Y^2$ is independently —O—, —N(R)— or —S—.

5. A compound according to claim 1 wherein

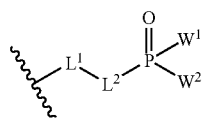

of Formula I, Formula II, Formula III, or Formula IV is

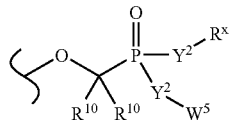

wherein $W^5$ is a carbocycle.

6. A compound according to claim 1 wherein

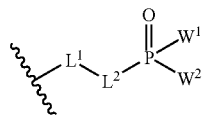

of Formula I, Formula II, Formula III, or Formula IV is

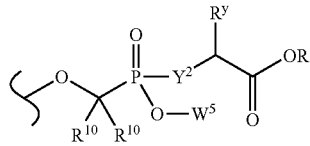

wherein $W^5$ is phenyl or phenyl substituted with 0 to 3 $R^y$ and $Y^2$ is —O— or —N(R)—.

7. A compound according to claim 1 wherein

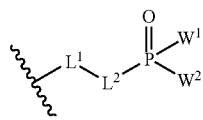

of Formula I, Formula II, Formula III, or Formula IV is

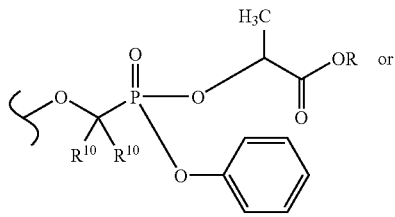

8. A compound according to claim 1 wherein

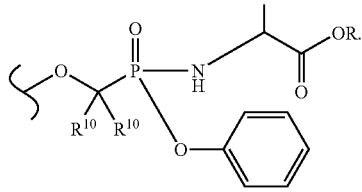

of Formula I, Formula II, Formula III, or Formula IV is

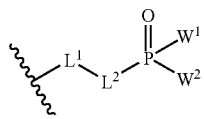

wherein $Y^1$ is O or S and each $Y^2$ is —O— or —N(R)—.

9. A compound according to claim 1 wherein

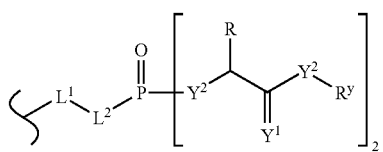

of Formula I, Formula II, Formula III, or Formula IV is

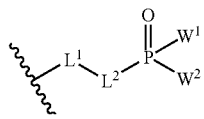

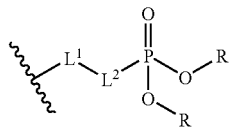

wherein each R is independently $C_1$-$C_8$ alkyl, $C_6$-$C_{20}$ aryl or $C_6$-$C_{20}$ substituted aryl.

10. A compound of claim 1 according to Formula I.

11. A compound according to claim 10 wherein the nucleobase is

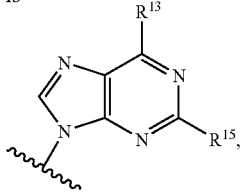

each $R^{10}$ is H, $L^1$ is O, and each $R^a$ is H.

12. A compound according to claim 11 wherein $R^{13}$ is $NH_2$ and $R^{15}$ is H or $R^{13}$ is OH and $R^{15}$ is $NH_2$.

13. A compound according to claim 12 wherein each $W^1$ and $W^2$ is independently $Y^2$—$R^x$ wherein each $Y^2$ is independently —O— or —N(R)— and $R^x$ is not H.

14. A compound according to claim 10 wherein the nucleobase is

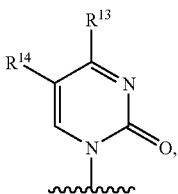

each $R^{10}$ is H, $L^1$ is O, and each $R^a$ is H.

15. A compound according to claim 14 wherein $R^{14}$ is H and $R^{13}$ is $NH_2$ or OH.

16. A compound according to claim 15 wherein each $W^1$ and $W^2$ is independently $Y^2$—$R^x$ wherein each $Y^2$ is independently —O— or —N(R)— and $R^x$ is not H.

17. A compound according to claim 10 wherein the nucleobase is

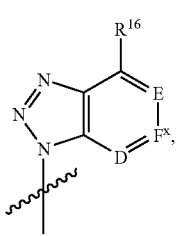

each $R^{10}$ is H, $L^1$ is O, and each $R^a$ is H.

18. A compound according to claim 17 wherein each E and D is >N and $F^x$ is >C—$R^{25}$.

19. A compound according to claim 18 wherein each $W^1$ and $W^2$ is independently $Y^2$—$R^x$ wherein each $Y^2$ is independently —O— or —N(R)— and $R^x$ is not H.

20. A compound according to claim 10 wherein the nucleobase is

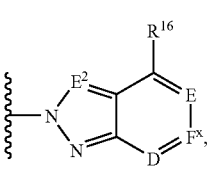

each $R^{10}$ is H, $L^1$ is O, and each $R^a$ is H.

21. A compound of claim 1 according to Formula II.

22. A compound according to claim 21 wherein the nucleobase is

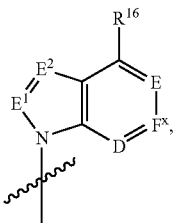

each $R^{10}$ is H, $L^1$ is O, and each $R^a$ is H.

23. A compound according to claim 22 wherein each $E^2$, E, and D is >N and each $E^1$ and $F^x$ is independently >C—$R^{25}$.

24. A compound according to claim 23 wherein each $W^1$ and $W^2$ is independently $Y^2$—$R^x$ wherein each $Y^2$ is independently —O— or —N(R)— and $R^x$ is not H.

25. A compound according to claim 22 wherein each $E^1$, $E^2$, E, and D is >N and $F^x$ is >C—$R^{25}$.

26. A compound according to claim 25 wherein each $W^1$ and $W^2$ is independently $Y^2$—$R^x$ wherein each $Y^2$ is independently —O— or —N(R)— and $R^x$ is not H.

27. A compound according to claim 22 wherein each $E^1$, E, and D is >N and each $E^2$ and $F^x$ is independently >C—$R^{25}$.

28. A compound according to claim 27 wherein each $W^1$ and $W^2$ is independently $Y^2$—$R^x$ wherein each $Y^2$ is independently —O— or —N(R)— and $R^x$ is not H.

29. A compound according to claim 22 wherein each E and D is >N, each $E^1$ and $F^x$ is independently >C—$R^{25}$, and $E^2$ is >C—$R^{30}$.

30. A compound according to claim 29 wherein each $W^1$ and $W^2$ is independently $Y^2$—$R^x$ wherein each $Y^2$ is independently —O— or —N(R)— and $R^x$ is not H.

31. A compound according to claim 21 wherein the nucleobase is

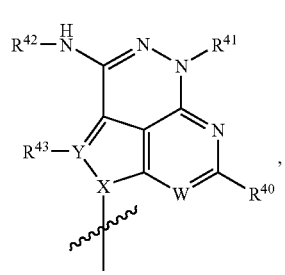

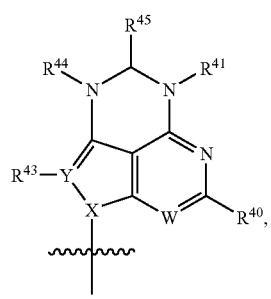

-continued

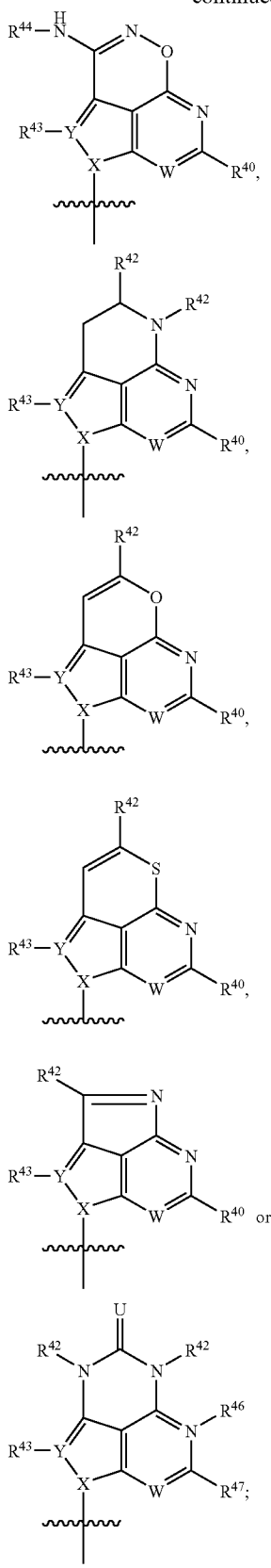

wherein each $R^{10}$ is H, $L^1$ is O, and each $R^a$ is H.

32. A compound according to claim 21 wherein the nucleobase is

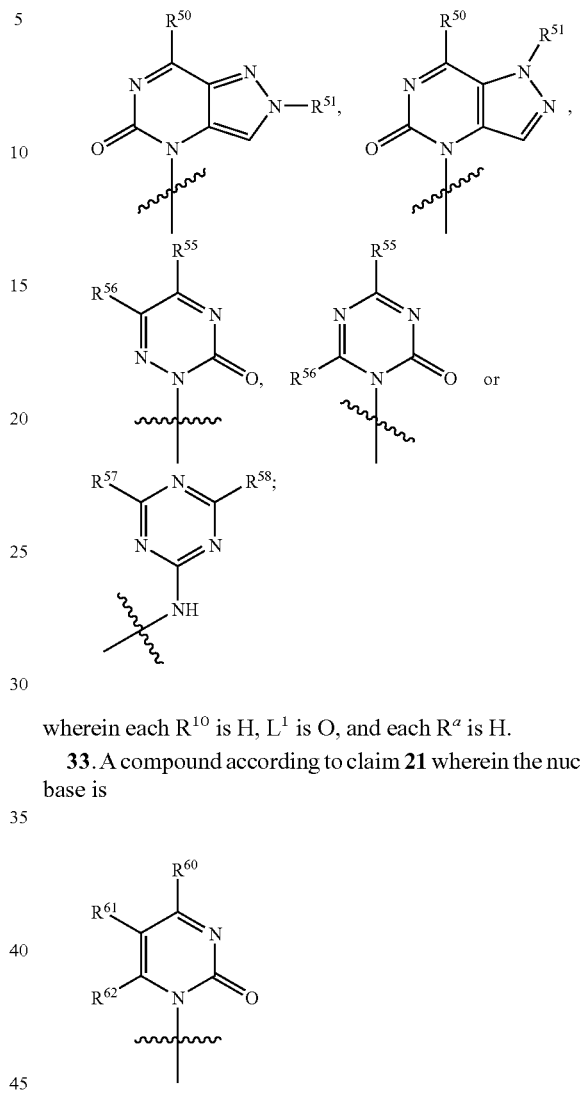

wherein each $R^{10}$ is H, $L^1$ is O, and each $R^a$ is H.

33. A compound according to claim 21 wherein the nucleobase is

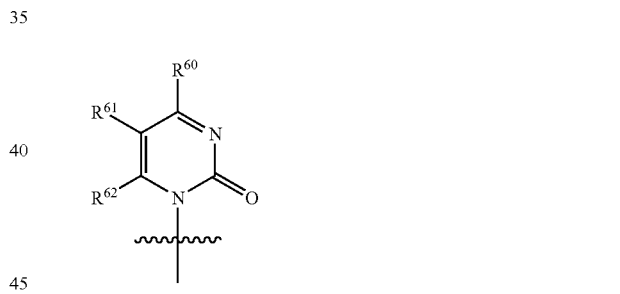

wherein each $R^{10}$ is H, $L^1$ is O, and each $R^a$ is H.

34. A compound according to claim 33 wherein each $W^1$ and $W^2$ is independently $Y^2$—$R^x$ wherein each $Y^2$ is independently —O— or —N(R)— and $R^x$ is not H.

35. A compound according to claim 21 wherein the nucleobase is

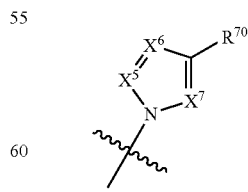

wherein each $R^{10}$ is H, $L^1$ is O, and each $R^a$ is H.

36. A compound according to claim 35 wherein each $W^1$ and $W^2$ is independently $Y^2$—$R^x$ wherein each $Y^2$ is independently —O— or —N(R)— and $R^x$ is not H.

37. A compound according to claim 21 wherein the nucleobase is

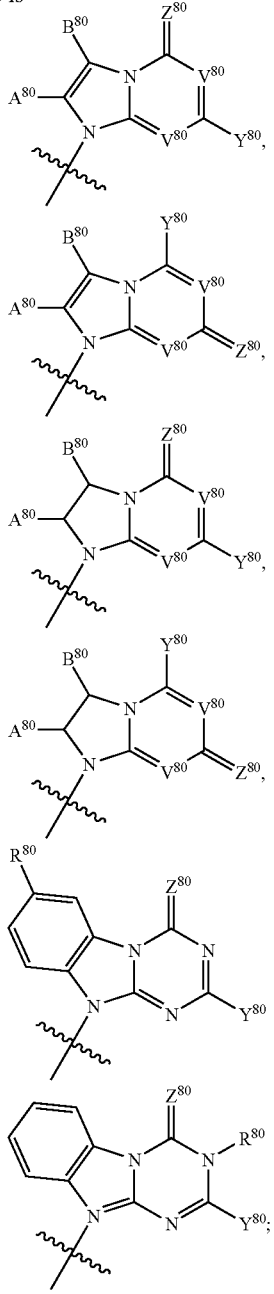

wherein each $R^{10}$ is H, $L^1$ is O, and each $R^a$ is H.

38. A compound according to claim 21 wherein the nucleobase is

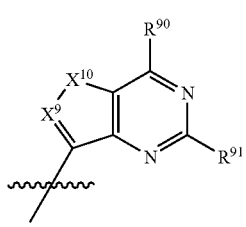

wherein each $R^{10}$ is H, $L^1$ is O, and each $R^a$ is H.

39. A compound according to claim 38 wherein each $W^1$ and $W^2$ is independently $Y^2$—$R^x$ wherein each $Y^2$ is independently —O— or —N(R)— and $R^x$ is not H.

40. A compound according to claim 21 wherein the nucleobase is

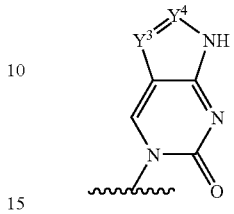

wherein each $R^{10}$ is H, $L^1$ is O, and each $R^a$ is H.

41. A compound according to claim 21 wherein the nucleobase is

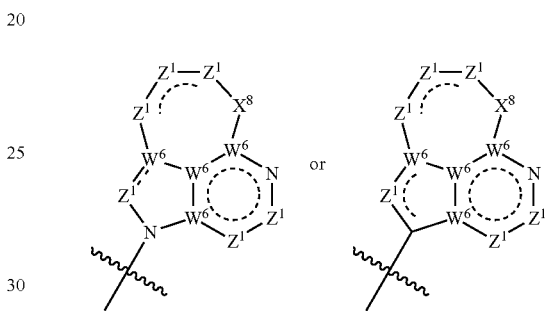

wherein each $R^{10}$ is H, $L^1$ is O, and each $R^a$ is H.

42. A compound according to claim 41 wherein each $W^1$ and $W^2$ is independently $Y^2$—$R^x$ wherein each $Y^2$ is independently —O— or —N(R)— and $R^x$ is not H.

43. A compound of claim 1 according to Formula III.

44. A compound according to claim 43 wherein the nucleobase is

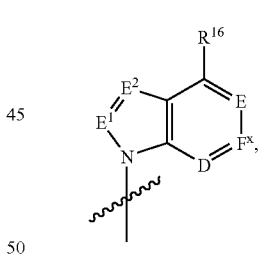

each $R^{10}$ is H, $L^1$ is O, and each $R^a$ is H.

45. A compound according to claim 44 wherein each $E^2$, E, and D is >N and each $E^1$ and $F^x$ is independently >C—$R^{25}$.

46. A compound according to claim 45 wherein each $R^5$ and $R^6$ is H.

47. A compound according to claim 45 wherein $R^5$ and $R^6$ taken together are =$CR^cR^d$.

48. A compound according to claim 45 wherein each $W^1$ and $W^2$ is independently $Y^2$—$R^x$ wherein each $Y^2$ is independently —O— or —N(R)— and $R^x$ is not H.

49. A compound according to claim 44 wherein each $E^1$, $E^2$, E, and D is >N and $F^x$ is >C—$R^{25}$.

50. A compound according to claim 49 wherein each $R^5$ and $R^6$ is H.

51. A compound according to claim 49 wherein $R^5$ and $R^6$ taken together are =$CR^cR^d$.

52. A compound according to claim 49 wherein each $W^1$ and $W^2$ is independently $Y^2—R^x$ wherein each $Y^2$ is independently —O— or —N(R)— and $R^x$ is not H.

53. A compound according to claim 44 wherein each $E^1$, E, and D is >N and each $E^2$ and $F^x$ is independently >C—$R^{25}$.

54. A compound according to claim 53 wherein each $R^5$ and $R^6$ is H.

55. A compound according to claim 53 wherein $R^5$ and $R^6$ taken together are =$CR^cR^d$.

56. A compound according to claim 53 wherein each $W^1$ and $W^2$ is independently $Y^2—R^x$ wherein each $Y^2$ is independently —O— or —N(R)— and $R^x$ is not H.

57. A compound according to claim 44 wherein each E and D is >N, each $E^1$ and $F^x$ is independently >C—$R^{25}$, and $E^2$ is >C—$R^{30}$.

58. A compound according to claim 57 wherein each $R^5$ and $R^6$ is H.

59. A compound according to claim 57 wherein $R^5$ and $R^6$ taken together are =$CR^cR^d$.

60. A compound according to claim 57 wherein each $W^1$ and $W^2$ is independently $Y^2—R^x$ wherein each $Y^2$ is independently —O— or —N(R)— and $R^x$ is not H.

61. A compound according to claim 43 wherein the nucleobase is

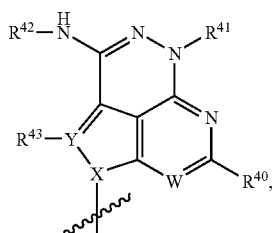

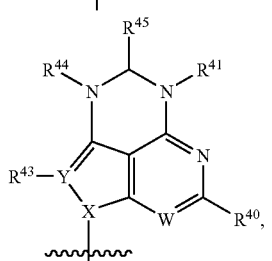

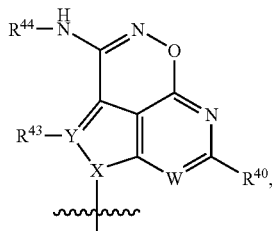

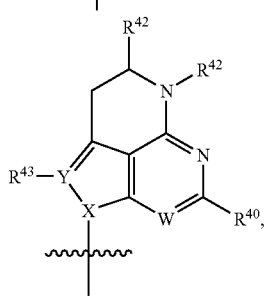

-continued

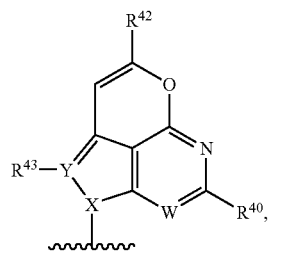

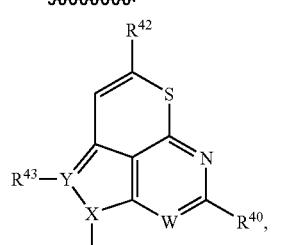

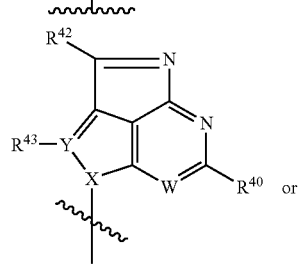

or

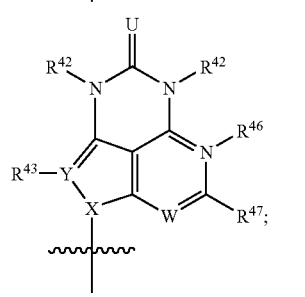

wherein each $R^{10}$ is H, $L^1$ is O, and each $R^a$ is H.

62. A compound according to claim 43 wherein the nucleobase is

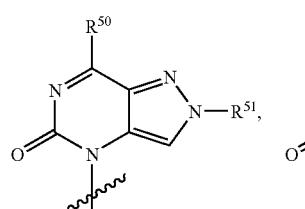

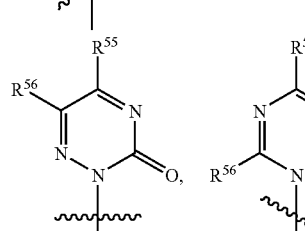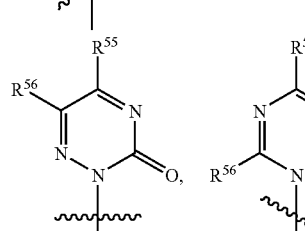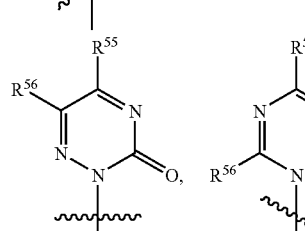

or

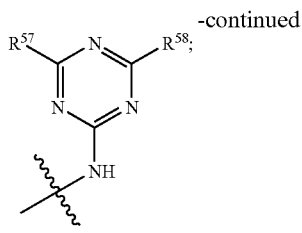

wherein each $R^{10}$ is H, $L^1$ is O, and each $R^a$ is H.

63. A compound according to claim 43 wherein the nucleobase is

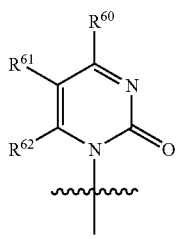

wherein each $R^{10}$ is H, $L^1$ is O, and each $R^a$ is H.

64. A compound according to claim 63 wherein each $R^5$ and $R^6$ is H.

65. A compound according to claim 63 wherein $R^5$ and $R^6$ taken together are $=CR^cR^d$.

66. A compound according to claim 63 wherein each $W^1$ and $W^2$ is independently $Y^2$—$R^x$ wherein each $Y^2$ is independently —O— or —N(R)— and $R^x$ is not H.

67. A compound according to claim 43 wherein the nucleobase is

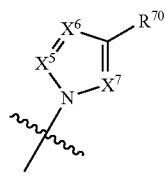

wherein each $R^{10}$ is H, $L^1$ is O, and each $R^a$ is H.

68. A compound according to claim 67 wherein each $R^5$ and $R^6$ is H.

69. A compound according to claim 67 wherein $R^5$ and $R^6$ taken together are $=CR^cR^d$.

70. A compound according to claim 67 wherein each $W^1$ and $W^2$ is independently $Y^2$—$R^x$ wherein each $Y^2$ is independently —O— or —N(R)— and $R^x$ is not H.

71. A compound according to claim 43 wherein the nucleobase is

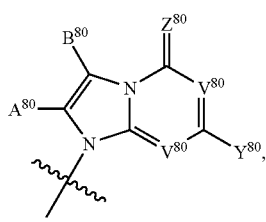

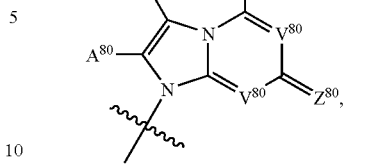

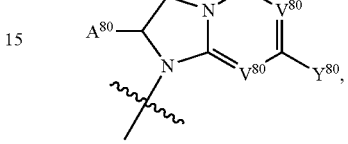

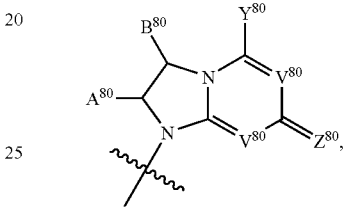

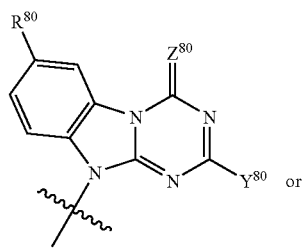

or

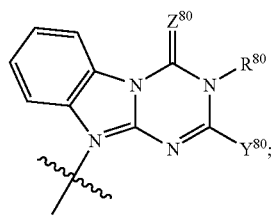

wherein each R10 is H, $L^1$ is O, and each $R^a$ is H.

72. A compound according to claim 43 wherein the nucleobase is

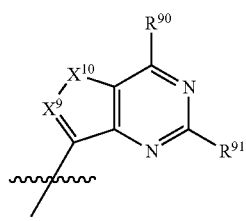

wherein each $R^{10}$ is H, $L^1$ is O, and each $R^a$ is H.

73. A compound according to claim 72 wherein each $W^1$ and $W^2$ is independently $Y^2$—$R^x$ wherein each $Y^2$ is independently —O— or —N(R)— and $R^x$ is not H.

74. A compound according to claim 50 wherein the nucleobase is

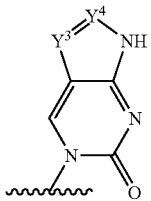

wherein each $R^{10}$ is H, $L^1$ is O, and each $R^a$ is H.

75. A compound according to claim 43 wherein the nucleobase is

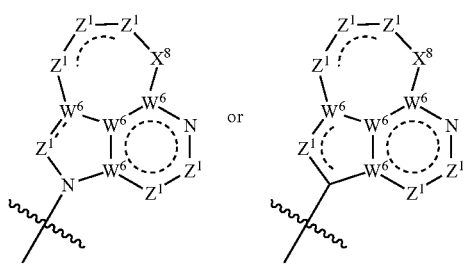

wherein each $R^{10}$ is H, $L^1$ is O, and each $R^a$ is H.

76. A compound according to claim 75 wherein each $R^5$ and $R^6$ is H.

77. A compound according to claim 75 wherein $R^5$ and $R^6$ taken together are $=CR^cR^d$.

78. A compound according to claim 75 wherein each $W^1$ and $W^2$ is independently $Y^2$—$R^x$ wherein each $Y^2$ is independently —O— or —N(R)— and $R^x$ is not H.

79. A compound of claim 1 according to Formula IV.

80. A compound according to claim 79 wherein the nucleobase is

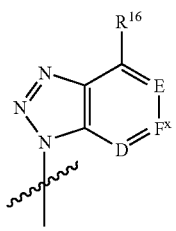

wherein each $R^{10}$ is H, $L^1$ is O, and each $R^a$ is H.

81. A compound according to claim 80 wherein each E and D is >N and $F^x$ is >C—$R^{25}$.

82. A compound according to claim 81 wherein each $R^5$ and $R^6$ is H.

83. A compound according to claim 81 wherein $R^5$ and $R^6$ taken together are $=CR^cR^d$.

84. A compound according to claim 81 wherein each $W^1$ and $W^2$ is independently $Y^2$—$R^x$ wherein each $Y^2$ is independently —O— or —N(R)— and $R^x$ is not H.

85. A compound according to claim 79 wherein the nucleobase is

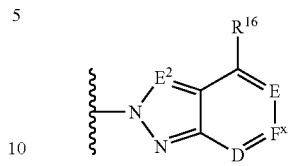

wherein each $R^{10}$ is H, $L^1$ is O, and each $R^a$ is H.

86. A compound according to claim 79 wherein the nucleobase is

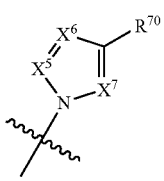

wherein each $R^{10}$ is H, $L^1$ is O, and each $R^a$ is H.

87. A compound according to claim 86 wherein each $R^5$ and $R^6$ is H.

88. A compound according to claim 86 wherein $R^5$ and $R^6$ taken together are $=CR^cR^d$.

89. A compound according to claim 86 wherein each $W^1$ and $W^2$ is independently $Y^2$—$R^x$ wherein each $Y^2$ is independently —O— or —N(R)— and $R^x$ is not H.

90. A compound selected from the group consisting of:

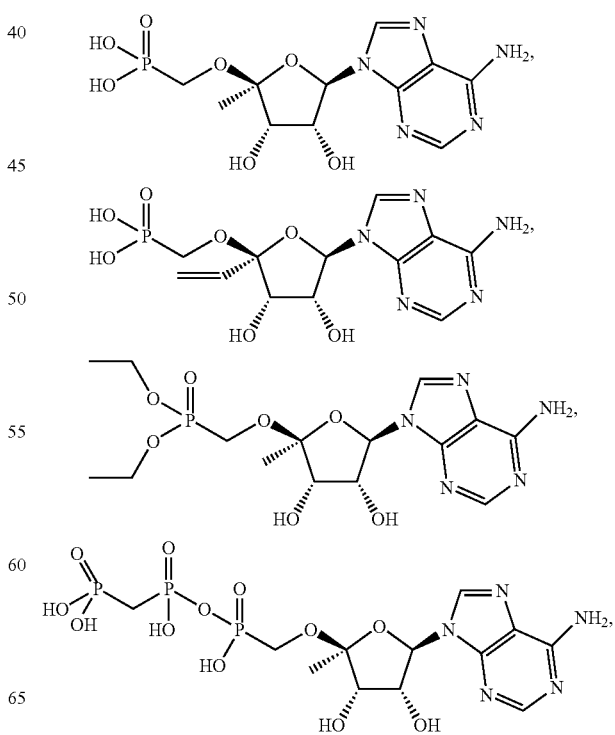

237 238
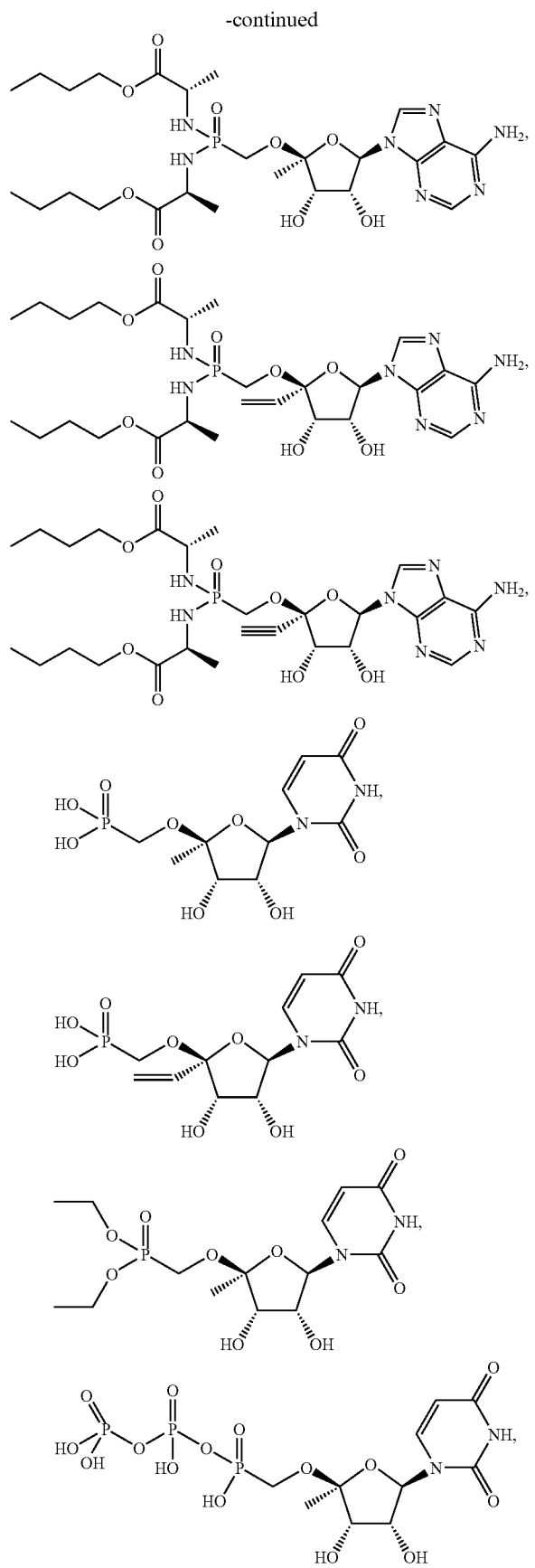
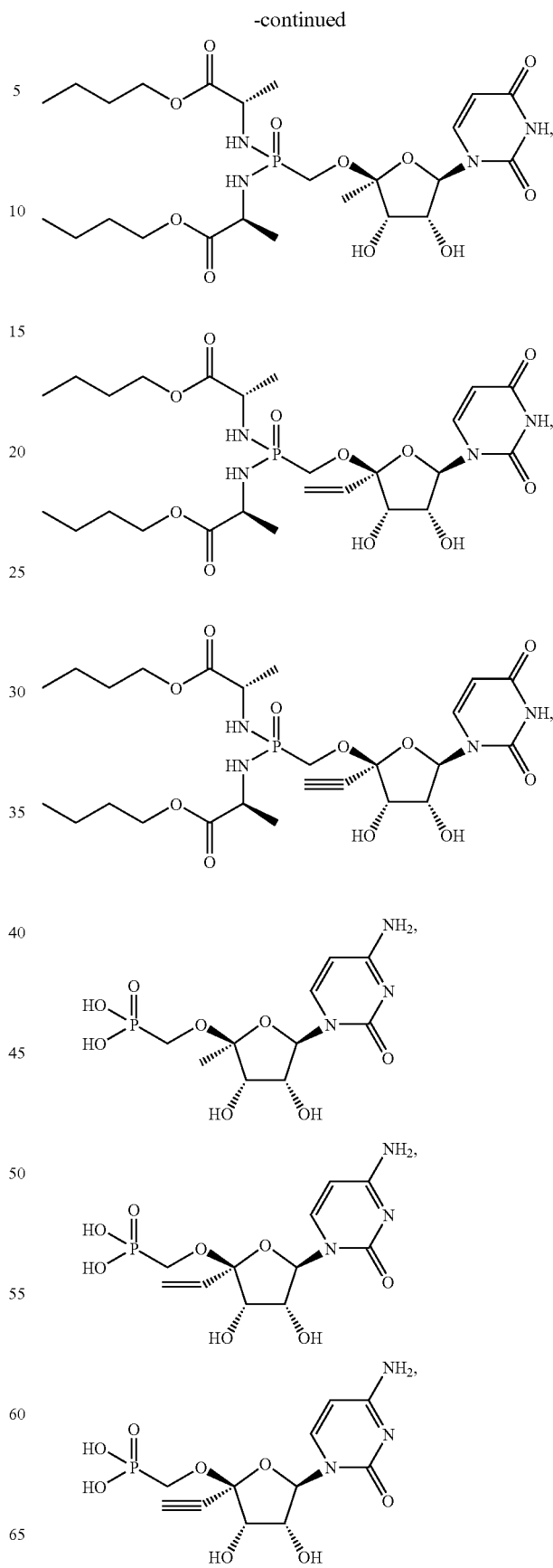

-continued
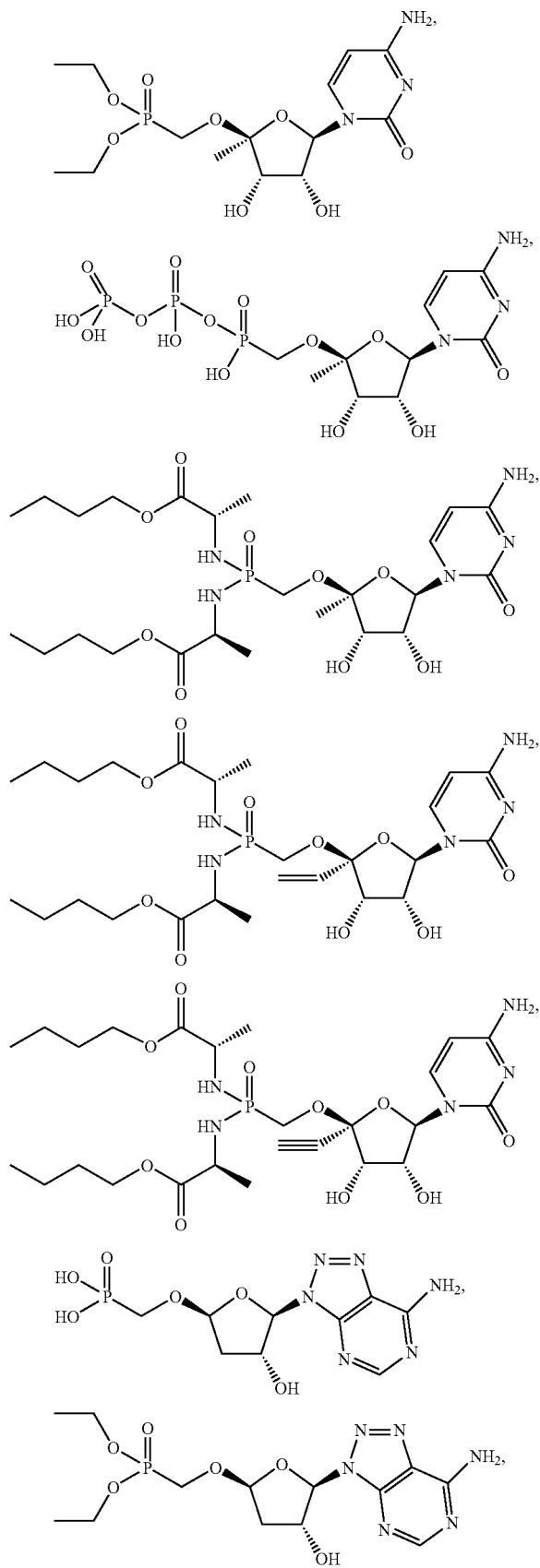
-continued
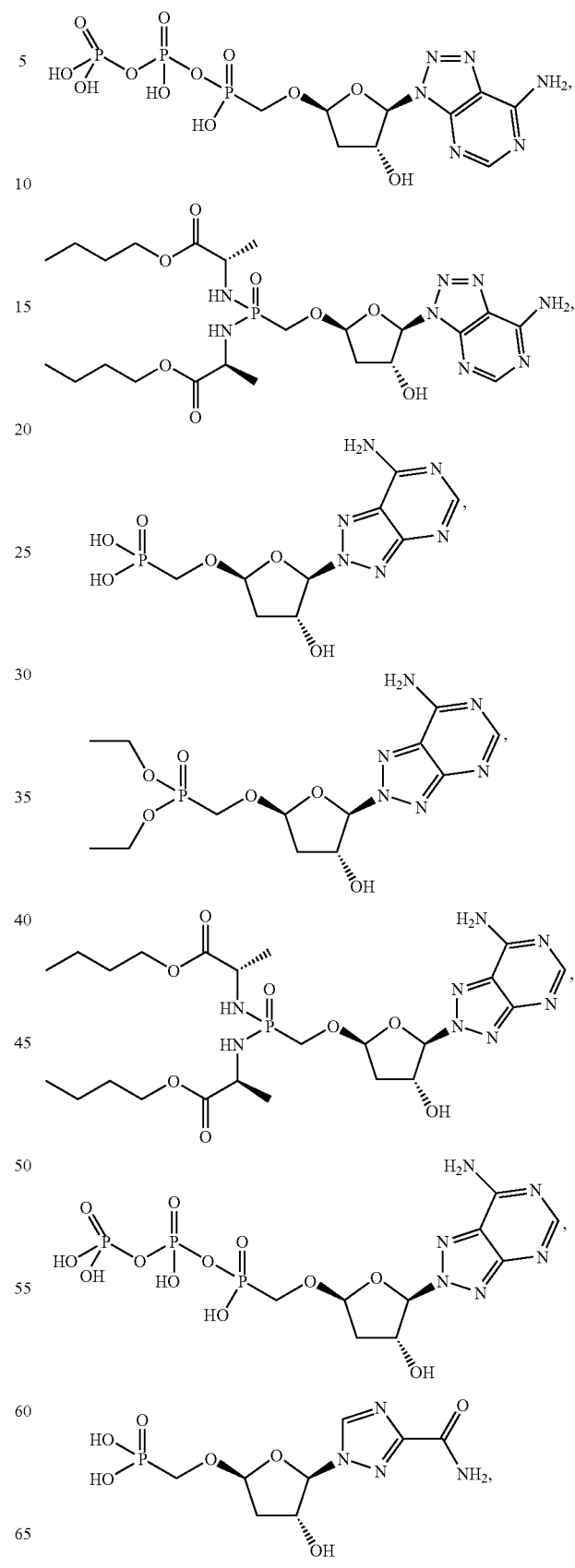

-continued
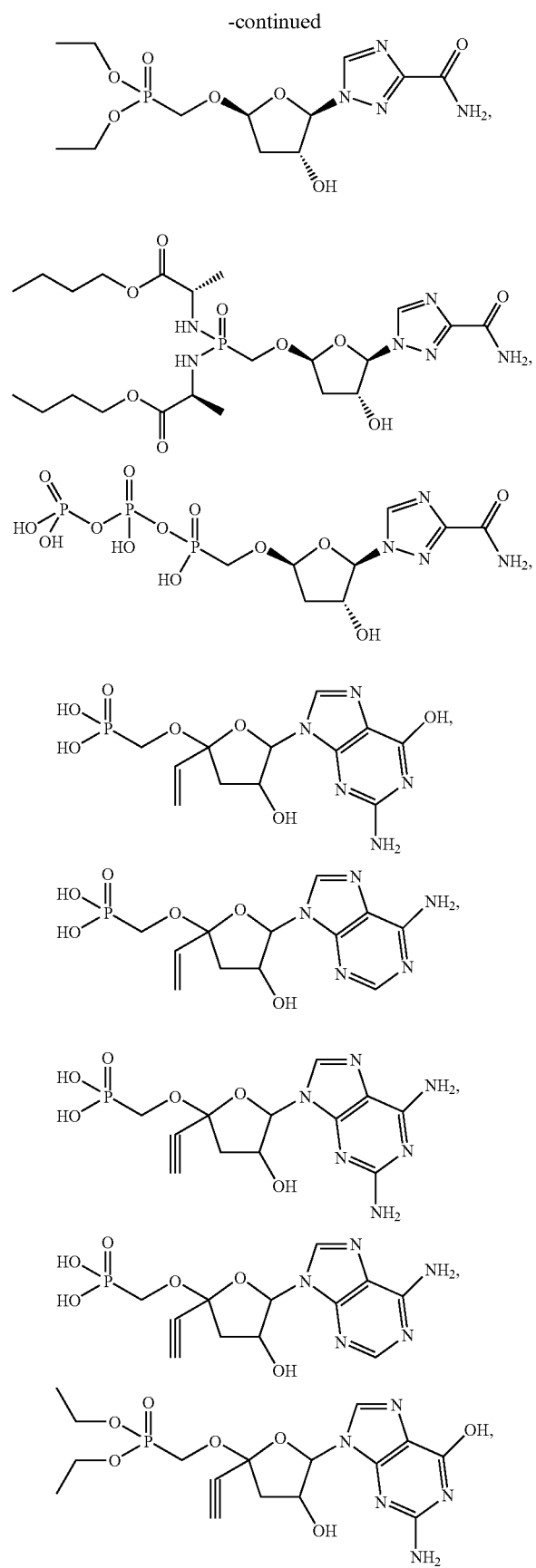
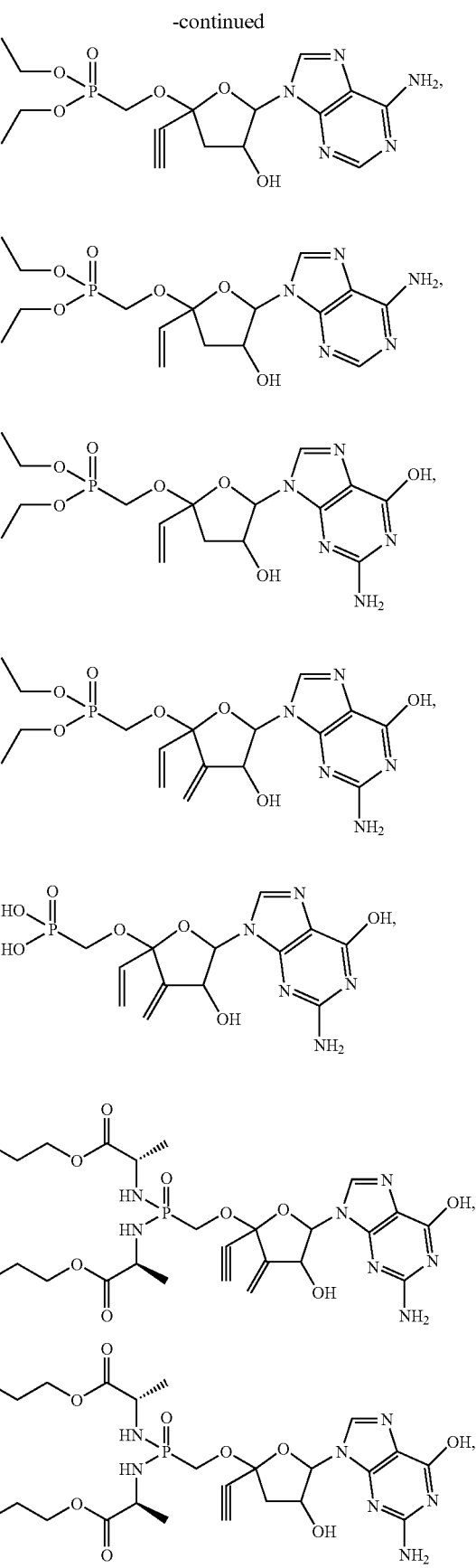

-continued

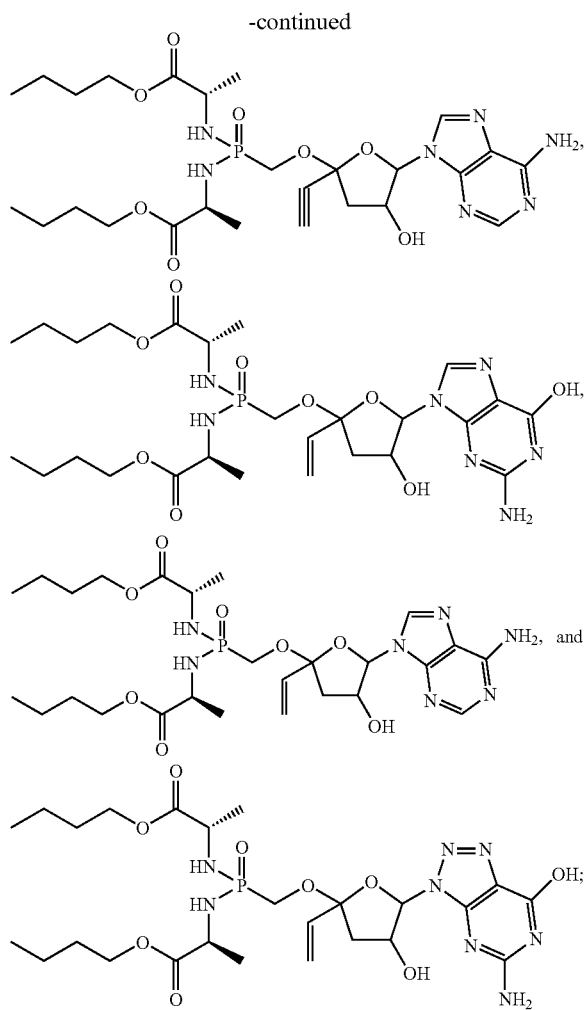

or pharmaceutically acceptable salts, solvates, and/or esters thereof.

91. A pharmaceutical composition comprising a compound of claim 1, or a pharmaceutically acceptable salt, solvate, and/or ester thereof, and a pharmaceutically acceptable carrier or excipient.

92. The pharmaceutical composition of claim 91, further comprising at least one additional therapeutic agent.

93. The pharmaceutical composition of claim 92, wherein said at least one additional therapeutic agent is selected from the group consisting of interferons, ribavirin analogs, NS3 protease inhibitors, NS5b polymerase inhibitors, alpha-glucosidase 1 inhibitors, hepatoprotectants, non-nucleoside inhibitors of HCV, and other drugs for treating HCV.

94. The pharmaceutical composition of claim 93, wherein said interferon is selected from the group consisting of pegylated rIFN-alpha 2b, pegylated rIFN-alpha 2a, rIFN-alpha 2b, rIFN-alpha 2a, consensus IFN alpha, feron, reaferon, intermax alpha, rIFN-beta, infergen+actimmune, IFN-omega with DUROS, and albuferon; said ribavirin analog is selected from the group consisting of rebetol, copegus, and viramidine (taribavirin); said NS5b polymerase inhibitor is selected from the group consisting of NM-283, valopicitabine, R1626, PSI-6130 (R1656), HCV-796, BILB 1941, and XTL-2125; said NS3 protease inhibitor is selected from the group consisting of SCH-503034 (SCH-7), VX-950, and BILN-2065; said alpha-glucosidase 1 inhibitor is selected from the group consisting of MX-3253 (celgosivir) and UT-231B; said hepatoprotectant is selected from the group consisting of IDN-6556, ME 3738, and LB-84451; and said non-nucleoside inhibitor of HCV is selected from the group consisting of benzimidazole derivatives, benzo-1,2,4-thiadiazine derivatives, and phenylalanine derivatives; and 17) other drugs for treating HCV, e.g., zadaxin, nitazoxanide (alinea), BIVN-401 (virostat), PYN-17, KPE02003002, actilon (CPG-10101), KRN-7000, civacir, GI-5005, ANA-975, XTL-6865, ANA 971, NOV-205, tarvacin, EHC-18, and NIM811.

95. A combination pharmaceutical agent comprising:
    a) a first pharmaceutical composition comprising a compound of claim 1, or a pharmaceutically acceptable salt, solvate, or ester thereof; and
    b) a second pharmaceutical composition comprising at least one additional therapeutic agent selected from the group consisting of interferons, ribavirin analogs, NS3 protease inhibitors, NS5b polymerase inhibitors, alpha-glucosidase 1 inhibitors, hepatoprotectants, non-nucleoside inhibitors of HCV, and other drugs for treating HCV.

96. A method of inhibiting HCV polymerase, comprising: contacting a cell infected with HCV with an effective amount of a compound of claim 1, or a pharmaceutically acceptable salt, solvate, and/or ester thereof, whereby HCV polymerase is inhibited.

97. The method of claim 96, further comprising contacting said cell infected with HCV with at least one additional therapeutic agent.

98. The method of claim 97, wherein said at least one additional therapeutic agent is selected from the group consisting of interferons, ribavirin analogs, NS3 protease inhibitors, NS5b polymerase inhibitors, alpha-glucosidase 1 inhibitors, hepatoprotectants, non-nucleoside inhibitors of HCV, and other drugs for treating HCV.

99. A method of treating HCV in a patient, comprising: administering to said patient a therapeutically effective amount of a compound of claim 1, or a pharmaceutically acceptable salt, solvate, and/or ester thereof.

100. The method of claim 99, further comprising: administering at least one additional therapeutic agent.

101. The method of claim 100, wherein said at least one additional therapeutic agent is selected from the group consisting of interferons, ribavirin analogs, NS3 protease inhibitors, NS5b polymerase inhibitors, alpha-glucosidase 1 inhibitors, hepatoprotectants, non-nucleoside inhibitors of HCV, and other drugs for treating HCV.

102. The method of claim 101, wherein said interferon is selected from the group consisting of pegylated rIFN-alpha 2b, pegylated rIFN-alpha 2a, rIFN-alpha 2b, rIFN-alpha 2a, consensus IFN alpha, feron, reaferon, intermax alpha, r-IFN-beta, infergen+actimmune, IFN-omega with DUROS, and albuferon; said ribavirin analog is selected from the group consisting of rebetol, copegus, and viramidine (taribavirin); said NS5b polymerase inhibitor is selected from the group consisting of NM-283, valopicitabine, R1626, PSI-6130 (R1656), HCV-796, BILB 1941, and XTL-2125; said NS3 protease inhibitor is selected from the group consisting of SCH-503034 (SCH-7), VX-950, and BILN-2065; said alpha-glucosidase 1 inhibitor is selected from the group consisting of MX-3253 (celgosivir) and UT-231B; said hepatoprotectant is selected from the group consisting of IDN-6556, ME 3738, and LB-84451; and said non-nucleoside inhibitor of HCV is selected from the group consisting of benzimidazole derivatives, benzo-1,2,4-thiadiazine derivatives, and phenylalanine derivatives; and 17) other drugs for treating HCV, e.g., zadaxin, nitazoxanide (alinea), BIVN-401 (virostat), PYN-17, KPE02003002, actilon (CPG-10101), KRN-7000, civacir, GI-5005, ANA-975, XTL-6865, ANA 971, NOV-205, tarvacin, EHC-18, and NIM811.

103. The use of a compound of claim 1 for the manufacture of a medicament for treating infection by HCV in a patient.

104. A compound as described in Table 6 or Table 7.

105. A new compound, substantially as described herein.

106. A new pharmaceutical composition or use for the preparation of a medicament, substantially as described herein.

107. A compound of claim 1 as a therapeutic substance.

* * * * *